United States Patent
Mizutani et al.

(10) Patent No.: US 9,963,456 B2
(45) Date of Patent: May 8, 2018

(54) PYRROLOPYRIMIDINE COMPOUND OR SALT THEREOF AND COMPOSITIONS CONTAINING THE PYRROLOPYRIMIDINE COMPOUND OR SALT THEREOF

(71) Applicant: TAIHO PHARMACEUTICAL CO., LTD., Tokyo (JP)

(72) Inventors: Takashi Mizutani, Tsukuba (JP); Chihoko Yoshimura, Tsukuba (JP); Hitomi Kondo, Tsukuba (JP); Makoto Kitade, Saitama (JP); Shuichi Ohkubo, Tsukuba (JP)

(73) Assignee: Taiho Pharmaceutical Co., Ltd, Tokyo (JP)

( * ) Notice: Subject to any disclaimer, the term of this patent is extended or adjusted under 35 U.S.C. 154(b) by 0 days. days.

(21) Appl. No.: 15/122,863

(22) PCT Filed: Jun. 24, 2015

(86) PCT No.: PCT/JP2015/068218
§ 371 (c)(1),
(2) Date: Aug. 31, 2016

(87) PCT Pub. No.: WO2015/199136
PCT Pub. Date: Dec. 30, 2015

(65) Prior Publication Data
US 2017/0066772 A1 Mar. 9, 2017

(30) Foreign Application Priority Data

Jun. 24, 2014 (JP) .................. 2014-129740
Feb. 10, 2015 (JP) .................. 2015-024785

(51) Int. Cl.
*C07D 487/04* (2006.01)
*A61K 31/519* (2006.01)
*C07D 519/00* (2006.01)
*A61P 35/00* (2006.01)
*A61P 35/04* (2006.01)

(52) U.S. Cl.
CPC .......... *C07D 487/04* (2013.01); *A61K 31/519* (2013.01); *C07D 519/00* (2013.01)

(58) Field of Classification Search
CPC ....................... C07D 487/04; A61K 31/519
USPC ....................... 544/280; 514/265.1
See application file for complete search history.

(56) References Cited

U.S. PATENT DOCUMENTS

2007/0191293 A1 8/2007 Langston et al.
2013/0345194 A1 12/2013 Schou et al.
2014/0343035 A1 11/2014 Sagara et al.

FOREIGN PATENT DOCUMENTS

| JP | 2008-530027 A | 8/2008 |
|---|---|---|
| RU | 2013 136 906 A | 2/2015 |
| WO | 2006084281 A1 | 8/2006 |
| WO | 2007067559 A2 | 6/2007 |
| WO | 2007092213 A2 | 8/2007 |
| WO | 2012061551 A1 | 5/2012 |
| WO | 2013108809 A1 | 7/2013 |

OTHER PUBLICATIONS

International Search Report issued for International Patent Application No. PCT/JP2015/068218 dated Sep. 15, 2015 (2 pages).
Kielkowski, P. et al., "7-Aryl-7-deazaadenine 2'-Deoxyribonucleoside Triphosphates (dNTPs): Better Substrates for DNA Polymerases than dATP in Competitive Incorporations," Angewandte Chemie International Edition, 2014, vol. 53, No. 29, pp. 7552-7555.
Schulman, B. A. et al., "Ubiquitin-like protein activation by El enzymes: the apex for downstream signalling pathways," Nature Reviews Molecular Cell Biology, 2009, vol. 10, No. 5, pp. 319-331.
Lee J. et al., "Cullins and Cancer," Genes & Cancer, 2010, vol. 1, No. 7, pp. 690-699.
Slingerland J., et al., "Regulation of the Cdk Inhibitor p27 and Its Deregulation in Cancer," Journal of Cellular Physiology, 2000, vol. 183, pp. 10-17.
Soucy, T. A., et al., "An inhibitor of NEDD8-activating enzyme as a new approach to treat cancer," Nature, 2009, vol. 458, pp. 732-736.
Garcia, K., et al., "Nedd8-Activating Enzyme Inhibitor MLN4924 Provides Synergy with Mitomycin C through Interactions with ATR, BRCA1/BRCA2, and Chromatin Dynamics Pathways," Molecular Cancer Therapeutics, 2014, vol. 13, No. 6, pp. 1625-1635.

(Continued)

*Primary Examiner* — Susanna Moore
(74) *Attorney, Agent, or Firm* — Rothwell, Figg, Ernst & Manbeck, P.C.

(57) ABSTRACT

A pyrrolopyrimidine compound or a salt thereof and compositions, NAE inhibitors and anti-tumor agents containing the pyrrolopyrimidine compound or a salt thereof. The pyrrolopyrimidine compound or a salt thereof has an NAE inhibitory action and a cell growth inhibitory effect and is represented by Formula (A):

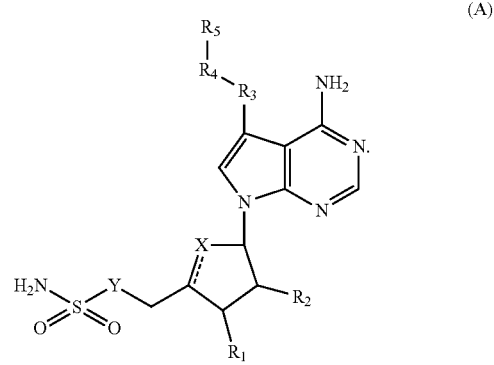

4 Claims, 3 Drawing Sheets

(56) References Cited

OTHER PUBLICATIONS

McMillin, D. W., "Molecular and Cellular Effects of NEDD8-Activating enzyme Inhibition in Myeloma," Molecular Cancer Therapeutics, 2012, vol. 11, No. 4, pp. 942-951.

Xia, C. Q., "Mechanistic RBC Partitioning Studies of MLN4924, a Nedd8-Activating Enzyme inhibitor," 9th International ISSX Meeting Abstract, p. 108.

Nesher, R., "Switching from Systemic to the Topical Carbonic Anhydrase Inhibitor Dorzolamide: Effect on the Quality of Life of Glaucoma Patients with Drug-Related Side Effects," The Israel Medical Association Journal, 2003, vol. 5, pp. 260-263.

Office Action cited in corresponding RU Patent Application No. 2016149319 dated Dec. 2017, English translation (13 pgs).

Office Action cited in Chinese Patent Application No. 201580034466.6 dated Feb. 1, 2018, 14 pages.

PYRROLOPYRIMIDINE COMPOUND OR SALT THEREOF AND COMPOSITIONS CONTAINING THE PYRROLOPYRIMIDINE COMPOUND OR SALT THEREOF

CROSS REFERENCE TO RELATED APPLICATIONS

This application is a 35 U.S.C. 371 National Phase Entry Application from PCT/JP2015/068218, filed Jun. 24, 2015, which claims priority to the specification of Japan Patent Application No. 2014-129740 filed on Jun. 24, 2014, and the specification of Japan Patent Application No. 2015-024785 filed on Feb. 10, 2015 the disclosures of which are incorporated herein in their entirety by reference. The present invention relates to a novel pyrrolopyrimidine compound or a salt thereof, and a pharmaceutical composition comprising the pyrrolopyrimidine compound, in particular, a prophylactic agent and/or a therapeutic agent for tumors etc. based on an NAE inhibitory action.

TECHNICAL FIELD

Background Art

A protein group called ubiquitin-like protein (Ubl), typified by ubiquitin, binds to corresponding activating enzyme E1 and transferase E2 to be added to a target protein through a covalent bond, thereby exerting influences on various characteristics such as target enzyme activity, stability, intracellular localization, and the like (Non-patent Document 1).

Nedd8, a kind of Ubl, is activated by APPBP1-UBA3 heterodimer, which is a Nedd8-activating enzyme (NAE), in an ATP-dependent manner. The activated Nedd8 is subsequently transferred to E2 (Ubc12), and is then added to a series of target proteins called cullin. It is called neddylation that Nedd8 is conjugated to a target protein. The neddylation with respect to cullin promotes the activity (ability to add ubiquitin to a ligase substrate) of cullin-RING ligases (CRL), which function by forming a complex with cullin family protein and adaptor protein. The protein group ubiquitinated by CRL is degraded in the proteasome. Many proteins are known as CRL substrates that regulate cell cycles and conduct intracellular signal transduction, and that are reported to be decreased expression in tumors; examples of such proteins include p27, p21, and phosphorylated IκB (Non-patent Documents 2 and 3). More specifically, NAE contributes to tumor cell growth and survival by facilitating ubiquitination and degradation by proteasome of the CRL substrate protein group through Nedd8 activation.

Because of the physiological function of NAE, an NAE inhibitor has a characteristic property of simultaneously affecting a plurality of signaling pathways involved in the survival and growth of tumors. Thus, NAE inhibitors are expected to serve as a therapeutic agent having broad and effective antitumor actions. N-[(1S)-1-indanyl]-7-[(1R)-3α-hydroxy-4α-(sulfamoyloxymethyl)cyclopentyl]-7H-pyrrolo[2,3-d]pyrimidin-4-amine (hereinafter referred to as "MLN4924") and the like have been known as a compound that inhibits the Nedd8-activating function of NAE (Patent Document 1). MLN4924 is a compound having a pyrrolopyrimidine skeleton, and is characterized by having a substituted amino group at 4-position. MLN4924 causes accumulation of the CRL substrate protein group through neddylation inhibition, thereby inducing cell growth arrest and apoptosis (Non-patent Document 4). Currently, the development of MLN4924 as an antitumor agent has been advanced (Patent Document 2); and, in addition to the use of MLN4924 alone, tests using a combination of MLN4924 and other various anticancer drugs have also been conducted (Non-patent Documents 5 and 6). However, a great deal of the MLN4924 administered is transferred to red blood cells in the blood; thus, an issue of decrease in plasma concentration from the concentration required for ensuring the original medicinal effects of MLN4924 has been identified (Non-patent Document 6). Further, since MLN4924 inhibits carbonic anhydrase II, which is highly expressed even in normal organs, such as red blood cells, kidneys, brain, and eyes, there is a concern that MLN4924 induces side effects, specifically, electrolyte abnormality, hypotonia bulbi, metabolic acidosis, polyuria, urinary calculus, and dysesthesia (Non-patent Document 8). Under such circumstances, a new NAE inhibitor that ensures NAE inhibitory activity, but that has a smaller carbonic anhydrase II inhibitory effect, has been desired.

CITATION LIST

Patent Documents

Patent Document 1: International Publication No. WO2006084281
Patent Document 2: International Publication No. WO2012061551

Non-Patent Documents

Non-patent Document 1: Nature Rev Mol Cell Biol, 2009, 10 (5): 319-31.
Non-patent Document 2: Genes & Cancer, 20101; 1 (7): 690-699
Non-patent Document 3: Journal of Cellular Physiology, 2000, 183, 10-17
Non-patent Document 4: Nature, 2009, 9; 458 (7239): 732-6
Non-patent Document 5: Mol Cancer Ther, 2014, 13 (6); 1623-1635
Non-patent Document 6: Mol Cancer Ther, 2012, 11 (4): 942-951
Non-patent Document 7: 9th International ISSX Meeting Abstract, p. 108
Non-patent Document 8: Israel Medical Association Journal, 2003, 5 Apr., 260-263

SUMMARY OF INVENTION

Technical Problem

An object of the present invention is to provide a novel pyrrolopyrimidine compound or a salt thereof having NAE inhibitory action, a cell growth inhibitory effect, and attenuated carbonic anhydrase II inhibitory activity. Another object of the present invention is to provide a pharmaceutical preparation useful for preventing and/or treating NAE-related diseases, particularly tumors, based on its NAE inhibitory action.

Solution to Problem

The present inventors conducted extensive research on compounds having an NAE inhibitory action, and found that a novel compound represented by Formula (A) below, which is characterized by comprising a vinylene group, an ethynylene group, an arylene group, or a heteroarylene group at 5-position ($R_3$ in Formula (A)) of the pyrrolopyrimidine skeleton, or a salt thereof, has superior NAE inhibitory action as well as a superior cell growth inhibitory effect against tumor cell lines. The inventors further found that the compound or a salt thereof has attenuated carbonic anhydrase II inhibitory activity. With these findings, the inventors completed the present invention.

(A)

$$\text{[structure]}$$

wherein:

⋯⋯ is a single bond or a double bond;

X is —O—, —CH$_2$—, or —CH═;

Y is —NH— or —O—;

$R_1$ is hydrogen, fluorine, a hydroxy group, a cyano group, or an amino group;

$R_2$ is hydrogen, fluorine, a hydroxy group, a cyano group, or an amino group;

$R_3$ is a vinylene group, an ethynylene group, a C6-C14 arylene group, or a monocyclic or bicyclic heteroarylene group having at least one heteroatom selected from the group consisting of N, S and O;

$R_4$ is a bond, a methylene group, or a C3-C7 cycloalkylidene group;

$R_5$ is a C3-C7 saturated cycloalkyl group that may have one or more $R_6$, a C6-C10 unsaturated cycloalkyl group that may have one or more $R_6$, or a monocyclic or bicyclic unsaturated heterocycloalkyl group that has at least one heteroatom selected from the group consisting of N, S, and O, and that may have one or more $R_6$;

$R_6$ is
halogen,
a hydroxy group,
a cyano group,
a C1-C6 alkyl group that may have one or more phenoxy group as a substituent,
a carbamoyl group,
a C1-C6 alkoxycarbonyl group,
a monocyclic or bicyclic unsaturated heterocycloalkyl group having at least one heteroatom selected from the group consisting of N, S and O,
a monocyclic or bicyclic saturated heterocycloalkyl group that has at least one heteroatom selected from the group consisting of N, S, and O, and that may have, one or more of either halogen, hydroxy group, carboxyl group, or C1-C6 alkyl group, as a substituent,
an amino group,
a mono- or di-(C1-C4 alkyl) amino group that may have one or more hydroxy group or phenyl group as a substituent,
a C1-C6 alkoxy group that may have one or more of either halogen, C3-C7 saturated cycloalkyl group, or monocyclic or bicyclic unsaturated heterocycloalkyl group having at least one heteroatom selected from the group consisting of N, S and O as a substituent, a benzyloxy group that may have one or more carbamoyl group as a substituent,
a C1-C6 alkylthio group,
a C1-C6 alkylsulfonyl group, or
an aminosulfonyl group,
when two or more $R_6$ are present, the plurality of $R_6$ may be the same or different.

Advantageous Effects of Invention

The present invention provides a novel compound or a salt thereof represented by Formula (A) above. The novel compound is useful as an NAE inhibitor.

It was clarified that the compound of the present invention or a salt thereof has superior NAE inhibitory activity, and inhibits growth of tumor cells. Further, since the carbonic anhydrase II inhibitory activity of the compound of the present invention or a salt thereof is attenuated, the effect of the decrease in plasma concentration due to the transfer to the red blood cells will not occur. Therefore, the compound of the present invention or a salt thereof is significantly useful as an agent for preventing and/or treating Tumors.

DESCRIPTION OF EMBODIMENTS

Figure 1:
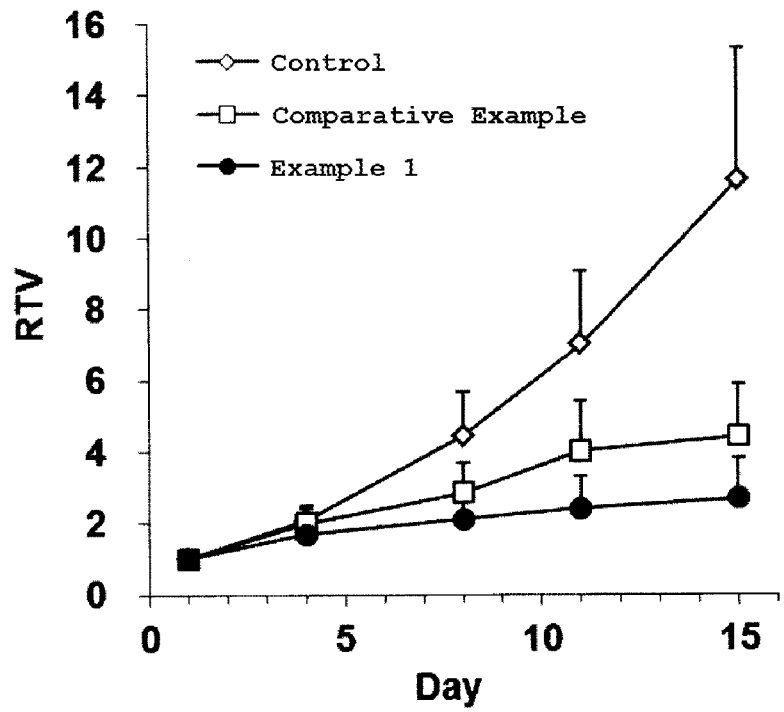
FIG. 1 shows the growth inhibitory effects of the compound obtained in Example 1 on HCT-116.

The groups in the composition represented by Formula (A) are described below.

In Formula (A), the "C6-C14 arylene group" represented by $R_3$ is a monocyclic or polycyclic bivalent aromatic hydrocarbon group having 6 to 14 carbon atoms. More specifically, examples of C6-C14 arylene group include phenylene group, naphthylene group, and tetrahydronaphthylene group. A phenylene group or naphthylene group is preferable.

In Formula (A), "a monocyclic or bicyclic heteroarylene group having at least one heteroatom selected from the group consisting of N, S and O" represented by $R_3$ is a monocyclic or bicyclic heteroarylene group having 1 to 3 of at least one kind of heteroatom selected from the group consisting of N, S and O. Examples include thiazolylene group, pyrazolylene group, imidazolylene group, thienylene group, furylene group, pyrrolylene group, oxazolylene group, isoxazolylene group, isothiazolylene group, thiadiazolylene group, triazolylene group, tetrazolylene group, pyridylene group, pyrazylene group, pyrimidinylene group, pyridazinylene group, indolylene group, isoindolylene group, indazolylene group, triazolopyridilene group, benzimidazolilene group, benzoxazolylene group, benzothiazolylene group, benzothienylene group, benzofuranylene group, purinylene group, quinolylene group, isoquinolylene group, quinazolinylene group, quinoxalylene group, methylenedioxy phenylene group, ethylenedioxy phenylene group, dihydro benzofuranylene group, benzoxazinylene group, dihydrobenzoxazinylene group, chromanylene group, thiochromanylene group, 1,1-dioxythiochromanylene group, dihydro benzothienylene group, and 1,1-dioxydihydro benzothienylene group. Preferable examples include a monocyclic heteroarylene group having 1 to 3 of at least one kind of heteroatom selected from the group consisting of N, S, and O. More preferable examples include a monocyclic 5-membered heteroarylene group having 1 or 2 of at least one kind of heteroatom selected from the group consisting of N, S, and O. Particularly preferable examples include thiazolylene group, pyrazolylene group, imidazolylene group, thienylene group, and oxazolylene group.

In Formula (A), the "C3-C7 cycloalkylidene group" is a monocyclic saturated alkylidene group having 3 to 7 carbon atoms. Examples include the compounds below.

Cyclopropylidene group

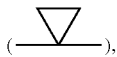

Cyclobutylidene group

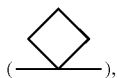

Cyclopentylidene group

Cyclohexylidene group

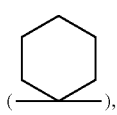

Cycloheptylidene group

Preferable examples include a cyclopropylidene group.

In the present specification, the "cycloalkyl group" refers to a saturated or unsaturated monovalent cyclic hydrocarbon group. Unless otherwise specified, the term "cycloalkyl" encompasses a monocyclic cycloalkyl, and a polycyclic cycloalkyl such as bicyclic or tricyclic cycloalkyl.

In the present specification, the "heterocycloalkyl group" refers to a saturated or unsaturated monovalent heterocyclic group. Unless otherwise specified, the term "heterocycloalkyl" encompasses a monocyclic heterocycloalkyl, and a polycyclic heterocycloalkyl such as bicyclic or tricyclic heterocycloalkyl.

In Formula (A), the C3-C7 saturated cycloalkyl group of the "C3-C7 saturated cycloalkyl group that may have one or more $R_6$" represented by $R_5$ refers to a cyclic saturated hydrocarbon group having 3 to 7 carbon atoms. Examples include cyclopropyl group, cyclobutyl group, cyclopentyl group, cyclohexyl group, and cycloheptyl group. Preferable examples include cyclohexyl group.

In Formula (A), the C6-C10 unsaturated cycloalkyl group of the "C6-C10 unsaturated cycloalkyl group that may have one or more $R_6$" represented by $R_5$ is a monocyclic or bicyclic unsaturated hydrocarbon group having 6 to 10 carbon atoms. Examples include phenyl group, naphthyl group, tetrahydronaphthyl group, and 2,3-dihydroindenyl group. Preferable examples include phenyl group, naphthyl group, and 2,3-dihydroindenyl group.

In Formula (A), examples of the monocyclic or bicyclic unsaturated heterocycloalkyl group having at least one heteroatom selected from the group consisting of N, S, and O of the "monocyclic or bicyclic unsaturated heterocycloalkyl group that has at least one heteroatom selected from the group consisting of N, S, and O, and that may have one or more $R_6$" represented by $R_5$ include hexamethyleneimino group, imidazolyl group, thienyl group, furyl group, pyrrolyl group, oxazolyl group, isooxazolyl group, triazolyl group, isothiazolyl group, pyrazolyl group, triazolyl group, tetrazolyl group, pyridyl group, pyrazyl group, pyrimidinyl group, pyridazinyl group, indolyl group, isoindolyl group, indazolyl group, methylenedioxy phenyl group, ethylene dioxyphenyl group, benzofuranyl group, dihydro benzofuranyl group, benzimidazolyl group, benzooxazolyl group, benzothiazolyl group, purinyl group, quinolyl group, isoquinolyl group, quinazolinyl group, quinoxalinyl group, 1H-pyrazolo[4,3-b]pyridin-5-yl group, 2,3-dihydro-1,4-benzoxazino group, 1,1-dioxo-3,4-dihydro-2H-thiochromen-8-yl group, 2,3-dihydro benzothiophen-7-yl group, and 1,1-dioxo-2,3-dihydro benzothiophen-7-yl group. Preferable examples include a monocyclic or bicyclic 5 to 10-membered unsaturated heterocycloalkyl group having 1 to 3 of at least one kind of heteroatom selected from the group consisting of N, S, and O. More preferable examples include thienyl group, pyridyl group, pyrazyl group, quinolyl group, isoquinolyl group, 1H-pyrazolo[4,3-b]pyridin-5-yl group, 2,3-dihydro-1,4-benzoxazino group, 1,1-dioxo-3,4-dihydro-2H-thiochromen-8-yl group, 2,3-dihydro benzothiophen-7-yl group, and 1,1-dioxo-2,3-dihydro benzothiophen-7-yl group.

In Formula (A), examples of the "halogen" represented by $R_6$ include fluorine, chlorine, bromine, and iodine. Preferable examples include fluorine and chlorine.

In Formula (A), the C1-C6 alkyl group of the "C1-C6 alkyl group that may have one or more phenoxy group as a substituent" represented by $R_6$ refers to a linear or branched alkyl group having 1 to 6 carbon atoms. Examples include methyl, ethyl, n-propyl, isopropyl, n-butyl, isobutyl, sec-butyl, tert-butyl, pentyl, and hexyl. Methyl is preferable.

In Formula (A), the C1-C6 alkoxy group of the "C1-C6 alkoxy group that may have one or more of either halogen, C3-C7 saturated cycloalkyl group, or monocyclic or bicyclic unsaturated heterocycloalkyl group having at least one heteroatom selected from the group consisting of N, S, and O as a substituent" represented by $R_6$ refers to a linear or branched alkoxy group having 1 to 6 carbon atoms. Examples include methoxy group, ethoxy group, n-propoxy group, isopropoxy group, n-butoxy group, isobutoxy group, and tert-butoxy group. Methoxy group, ethoxy group, n-propoxy group, and isopropoxy group are preferable.

In Formula (A), the halogen of the "C1-C6 alkoxy group that may have one or more of either halogen, C3-C7 saturated cycloalkyl group, or monocyclic or bicyclic unsaturated heterocycloalkyl group having at least one heteroatom selected from the group consisting of N, S, and O as a substituent" represented by $R_6$ refers to the halogens listed above, and is preferably fluorine. The number of substituted halogens is 1 to 3, preferably 2 or 3.

In Formula (A), the C3-C7 saturated cycloalkyl group of the "C1-C6 alkoxy group that may have one or more of either halogen, C3-C7 saturated cycloalkyl group, or monocyclic or bicyclic unsaturated heterocycloalkyl group having at least one heteroatom selected from the group consisting of N, S, and O, as a substituent" represented by $R_6$ refers to a saturated cycloalkyl group having 3 to 7 carbon atoms. Examples include cyclopropyl group, cyclobutyl group, cyclopentyl group, cyclohexyl group, and cycloheptyl group. Cyclopropyl group is preferable. The number of substituted saturated cycloalkyl groups is preferably 1.

In Formula (A), the monocyclic or bicyclic unsaturated heterocycloalkyl group having at least one heteroatom selected from the group consisting of N, S, and O of the "C1-C6 alkoxy group that may have one or more of either halogen, C3-C7 saturated cycloalkyl group, or monocyclic or bicyclic unsaturated heterocycloalkyl group having at least one heteroatom selected from the group consisting of N, S, and O, as a substituent" represented by $R_6$ refers to the unsaturated heterocycloalkyl group described above. Preferable examples include a monocyclic unsaturated heterocycloalkyl group having 1 to 3 of at least one kind of heteroatom selected from the group consisting of N, S, and O. More preferable examples include a monocyclic 5 or 6-membered unsaturated heterocycloalkyl group having 1 or 2 of at least one kind of heteroatom selected from the group consisting of N, S, and O. Particularly preferable examples include pyrazolyl group, triazolyl group, and pyridyl group. The number of substituted unsaturated heterocycloalkyl groups is preferably 1.

In Formula (A), preferable examples of the "C1-C6 alkoxy group that may have one or more of either halogen, C3-C7 saturated cycloalkyl group, or monocyclic or bicyclic unsaturated heterocycloalkyl group having at least one heteroatom selected from the group consisting of N, S, and O, as a substituent" represented by $R_6$ include methoxy group, difluoro methoxy group, trifluoro methoxy group, cyclopropyl methoxy group, 3-pyridyl methoxy group, pyrazol-1-ylmethoxy group, ethoxy group, 2,2,2-trifluoro ethoxy group, n-propoxy group, and isopropoxy group.

In Formula (A), preferable examples of the "benzyloxy group that may have one or more carbamoyl groups as a substituent" represented by $R_6$ include benzyloxy group, and 3-carbamoyl benzyloxy group.

In Formula (A), the mono- or di-(C1-C4 alkyl) amino group of the "mono- or di-(C1-C4 alkyl) amino group that may have one or more hydroxy group or phenyl group as a substituent" represented by $R_6$ refers to, among the above C1-C6 alkyl groups, an amino group monosubstituted or disubstituted with a C1-C4 alkyl group. Examples include methylamino group, ethylamino group, diethylamino group, methylethylamino group, isopropylamino group, cyclobutylmethylamino group, and dimethylamino group. Preferably examples include methylamino group, ethylamino group, dimethylamino group, and isopropylamino group.

In Formula (A), the "mono- or di-(C1-C4 alkyl) amino group that may have one or more hydroxy group or phenyl group as a substituent" represented by $R_6$ is preferably methylamino group, ethylamino group, isopropylamino group, hydroxyethylamino group, dimethylamino group, or phenylmethylamino group (benzylamino group).

In Formula (A), the "C1-C6 alkoxycarbonyl group" represented by $R_6$ refers to a carbonyl group substituted with the above alkoxy group. Examples include methoxycarbonyl group, ethoxycarbonyl group, n-propoxycarbonyl group, isopropoxycarbonyl group, 1-methylpropoxycarbonyl group, n-butoxycarbonyl group, isobutoxycarbonyl group, tert-butoxycarbonyl group, 2-methyl-butoxycarbonyl group, neopentyloxycarbonyl group, and pentan-2-yloxycarbonyl group. Methoxycarbonyl group is preferable.

In Formula (A), the "monocyclic or bicyclic unsaturated heterocycloalkyl group having at least one heteroatom selected from the group consisting of N, S, and O" represented by $R_6$ refers to the unsaturated heterocycloalkyl group described above, preferably a monocyclic 5 or 6-membered unsaturated heterocycloalkyl group having 1 or 2 of at least one kind of heteroatom selected from the group consisting of N, S and O, and more preferably pyridyl group.

In Formula (A), examples of the monocyclic or bicyclic saturated heterocycloalkyl group that has at least one heteroatom selected from the group consisting of N, S, and O of the "monocyclic or bicyclic saturated heterocycloalkyl group that has at least one heteroatom selected from the group consisting of N, S, and O, and that may have one or more of either halogen, hydroxy group, carboxyl group or C1-C6 alkyl group as a substituent" represented by $R_6$ include azetidinyl group, pyrrolidinyl group, piperidinyl group, 2-oxo-1-pyrrolidinyl group, 4-oxo-1-piperidinyl group, piperazinyl group, hexamethyleneimino group, morpholino group, thiomorpholino group, 1,1-dioxo-thiomorpholino group, homopiperazinyl group, tetrahydrofuranyl group, tetrahydropyranyl group, 9-oxa-3-azabicyclo[3.3.1]nonan-3-yl group, and 3-oxa-8-azabicyclo[3.2.1]octan-8-yl group. Preferable examples include a monocyclic or bicyclic 5 to 10-membered saturated heterocycloalkyl group having 1 to 4 of at least one kind of heteroatom selected from the group consisting of N, S, and O. More preferable examples include azetidinyl group, pyrrolidinyl group, piperidinyl group, piperazinyl group, 2-oxo-1-pyrrolidinyl group, 4-oxo-1-piperidinyl group, morpholino group, thiomorpholino group, 1,1-dioxo-thiomorpholino group, 9-oxa-3-azabicyclo[3.3.1]nonan-3-yl group, and 3-oxa-8-azabicyclo[3.2.1]octan-8-yl group.

In Formula (A), the halogen of the "monocyclic or bicyclic saturated heterocycloalkyl group that has at least one heteroatom selected from the group consisting of N, S, and O, and that may have one or more of either halogen, hydroxy group, carboxyl group or C1-C6 alkyl group as a substituent" represented by $R_6$ refers to the halogen listed above, preferably fluorine, chlorine, etc., and more preferably fluorine.

In Formula (A), examples of the C1-C6 alkyl group of the "monocyclic or bicyclic saturated heterocycloalkyl group that has at least one heteroatom selected from the group consisting of N, S, and O, and that may have one or more of either halogen, hydroxy group, carboxyl group or C1-C6 alkyl group as a substituent" represented by $R_6$ include, among the above alkyl groups, an alkyl group having 1 to 6 carbon atoms, preferably a methyl group.

In Formula (A), preferable examples of the "monocyclic or bicyclic saturated heterocycloalkyl group that has at least one heteroatom selected from the group consisting of N, S, and O, and that may have one or more of either halogen, hydroxy group, carboxyl group or C1-C6 alkyl group as a substituent" represented by $R_6$ include azetidinyl group, 3-hydroxy azetidin-1-yl group, pyrrolidinyl group, 3-fluoropyrrolidin-1-yl group, 3-hydroxy pyrrolidin-1-yl group, 3-carboxy-1-pyrrolidin-1-yl group, piperidinyl group, 4-oxo-1-piperidinyl group, 3-hydroxy-1-piperidinyl group, piperazinyl group, 4-methyl piperazin-1-yl group, 4-oxo-1-piperidinyl group, morpholino group, thiomorpholino group, 1,1-dioxo-thiomorpholino group, 9-oxa-3-azabicyclo[3.3.1]nonan-3-yl group, and 3-oxa-8-azabicyclo[3.2.1]octan-8-yl group.

In Formula (A), the "C1-C6 alkylthio group" represented by $R_6$ refers to a thio group having the above C1-C6 alkyl group, preferably a C1-C4 alkylthio group, more preferably a methylthio group or an ethylthio group.

In Formula (A), the "C1-C6 alkylsulfonyl group" represented by $R_6$ refers to a sulfonyl group having the above C1-C6 alkyl group, preferably a C1-C4 alkylsulfonyl group, more preferably a methyl sulfonyl group or an ethyl sulfonyl group.

Y in Formula (A) is —NH— or —O—, preferably —NH—.

$R_1$ in Formula (A) is hydrogen, fluorine, a hydroxy group, a cyano group or an amino group, preferably hydrogen, fluorine or a hydroxy group, further preferably a hydroxy group.

$R_2$ in Formula (A) is hydrogen, fluorine, a hydroxy group, a cyano group or an amino group, preferably hydrogen, fluorine, or a hydroxy group, further preferably hydrogen or a hydroxy group, particularly preferably a hydroxy group.

$R_3$ in Formula (A) is preferably an ethynylene group, or a monocyclic heteroarylene group having 2 of at least one kind of heteroatom selected from the group consisting of N, S, and O, more preferably an ethynylene group.

$R_4$ in Formula (A) is preferably a bond.

$R_5$ in Formula (A) is preferably a C3-C7 saturated cycloalkyl group that may have one or more $R_6$, a C6-C10 unsaturated cycloalkyl group that may have one or more $R_6$, or a monocyclic or bicyclic unsaturated heterocycloalkyl group that has at least one heteroatom selected from the group consisting of N, S, and O, and that may have one or more $R_6$.

More preferably, $R_5$ is a phenyl group or a naphthyl group that may be substituted with one or more $R_6$, or a monocyclic or bicyclic unsaturated heterocycloalkyl group that has at least one heteroatom selected from the group consisting of N, S and O, and that may have one or more $R_6$.

Further preferably, $R_5$ is a unsaturated heterocycloalkyl group or a phenyl group that may be substituted with one or more $R_6$, particularly preferably a phenyl group, thienyl group, pyridyl group, pyrazyl group, quinolyl group, isoquinolyl group, 1H-pyrazolo[4,3-b]pyridin-5-yl group, 2,3-dihydro-1,4-benzoxazino group, 1,1-dioxo-3,4-dihydro-2H-thiochromen-8-yl group, 2,3-dihydro benzothiophen-7-yl group, or 1,1-dioxo-2,3-dihydro benzothiophen-7-yl group that may be substituted with one or more $R_6$.

When $R_5$ is an unsaturated heterocycloalkyl group, $R_5$ is preferably a 2,3-dihydro-1,4-benzoxazinyl group, a 3,4-dihydro-2H-thiochromen-8-yl group, a 2,3-dihydro benzothiophen-7-yl group or the like, more preferably a 2,3-dihydro-1,4-benzoxazinyl group.

The unsaturated heterocycloalkyl groups listed above may be substituted with one or more $R_6$.

When $R_5$ has $R_6$, the number of $R_6$ is, for example, 1 to 5, preferably 1 to 3.

When $R_5$ has one or more $R_6$, $R_6$ is one of:
(i-1) halogen,
(i-2) hydroxy group,
(i-3) cyano group,
(i-4) C1-C6 alkyl group that may have one or more phenoxy group as a substituent,
(i-5) carbamoyl group,
(i-6) C1-C6 alkoxycarbonyl group,
(i-7) monocyclic or bicyclic unsaturated heterocycloalkyl group having at least one heteroatom selected from the group consisting of N, S, and O,
(i-8) monocyclic or bicyclic saturated heterocycloalkyl group that has at least one heteroatom selected from the group consisting of N, S, and O, and that may have one or more of either halogen, hydroxy group, carboxyl group, or C1-C6 alkyl group as a substituent,
(i-9) amino group,
(i-10) mono- or di-(C1-C4 alkyl) amino group that may have one or more hydroxy group or phenyl group as a substituent,
(i-11) C1-6 alkoxy group that may have one or more of either halogen, C3-C7 saturated cycloalkyl group, or monocyclic or bicyclic unsaturated heterocycloalkyl group having at least one heteroatom selected from the group consisting of N, S, and O as a substituent,
(i-12) benzyloxy group that may have one or more carbamoyl group as a substituent,
(i-13) C1-C6 alkylthio group,
(i-14) C1-C6 alkylsulfonyl group,
(i-15) aminosulfonyl group.

When $R_5$ has one or more $R_6$, $R_6$ in Formula (A) is more preferably one of:
(ii-1) halogen,
(ii-2) hydroxy group,
(ii-3) cyano group,
(ii-4) C1-C6 alkyl group that may have one or more phenoxy group as a substituent,
(ii-5) carbamoyl group,
(ii-6) C1-C6 alkoxycarbonyl group,
(ii-7) monocyclic 5 or 6-membered unsaturated heterocycloalkyl group having 1 or 2 of at least one kind of heteroatom selected from the group consisting of N, S, and O,
(ii-8) monocyclic or bicyclic 5 to 10-membered saturated heterocycloalkyl group that has 1 to 4 of at least one kind of heteroatom selected from the group consisting of N, S, and O, and that may have one or more of either halogen, hydroxy group, carboxyl group, or C1-C6 alkyl group as a substituent,
(ii-9) amino group,
(ii-10) mono- or di-(C1-C4 alkyl) amino group that may have one or more hydroxy group or phenyl group, as a substituent,
(ii-11) C1-6 alkoxy group that may have one or more of either halogen, C3-C7 saturated cycloalkyl group, or monocyclic or bicyclic unsaturated heterocycloalkyl group having at least one heteroatom selected from the group consisting of N, S, and O as a substituent,
(ii-12) benzyloxy group that may have one or more carbamoyl group as a substituent
(ii-13) C1-C4 alkylthio group,
(ii-14) C1-C4 alkylsulfonyl group, or
(ii-15) aminosulfonyl group.

When $R_5$ has one or more $R_6$, $R_6$ in Formula (A) is more preferably one of:
(iii-1) fluorine, chlorine
(iii-2) hydroxy group,
(iii-3) cyano group,
(iii-4) C1-C6 alkyl group that may have one or more phenoxy group as a substituent,
(iii-5) carbamoyl group, (iii-6) C1-C6 alkoxycarbonyl group,
(iii-7) pyridinyl group,
(iii-8) azetidinyl group, hydroxy azetidinyl group, thiomorpholinyl group, dioxide thiomorpholinyl group, methyl piperazinyl group, hydroxy piperidinyl group, oxopiperidinyl group, piperidinyl group, hydroxy pyrrolidinyl group, oxopyrrolidinyl group, pyrrolidinyl group, carboxyl pyrrolidinyl group, fluoro pyrrolidinyl group, morpholinyl group, 9-oxa-3-azabicyclo[3.3.1]nonan-3-yl group, 3-oxa-8-azabicyclo[3.2.1]octan-8-yl group,
(iii-9) amino group,
(iii-10) methylamino group, ethylamino group, isopropylamino group, hydroxyethylamino group, dimethylamino group, phenyl methylamino group,
(iii-11) C1-C6 alkoxy group that may have one or more of either halogen, C3-C7 saturated cycloalkyl group, or monocyclic or bicyclic unsaturated heterocycloalkyl group having at least one heteroatom selected from the group consisting of N, S, and O as a substituent,
(iii-12) benzyloxy group that may have one or more carbamoyl group as a substituent
(iii-13) C1-C4 alkylthio group,
(iii-14) C1-C4 alkylsulfonyl group, or
(iii-15) aminosulfonyl group.

When $R_5$ has one or more $R_6$, $R_6$ in Formula (A) is more preferably one of:
(iv-1) fluorine, chlorine
(iv-2) hydroxy group,
(iv-3) cyano group,
(iv-4) methyl group,
(iv-7) 3-fluoro pyrrolidinyl group, morpholinyl group, thiomorpholinyl group, 3-hydroxy azetidinyl group, azetidinyl group,
(iv-9) amino group,
(iv-10) methylamino group,
(iv-11) C1-C6 alkoxy group that may have one or more of either halogen or C3-C7 saturated cycloalkyl group as a substituent, or
(iv-13) C1-C4 alkylthio group.

When $R_5$ has one or more $R_6$, $R_6$ in Formula (A) is more preferably one of:
(v-1) fluorine,
(v-4) methyl group,
(v-7) saturated heterocycloalkyl group selected from the group consisting of 3-fluoro pyrrolidinyl, 3-hydroxy azetidinyl, and azetidinyl,
(v-9) amino group,
(v-10) methylamino group,
(v-11) C1-C6 alkoxy group that may have one or more cyclopropyl group, or
(v-13) C1-C4 alkylthio group.

When two or more $R_6$ are present, the plurality of $R_6$ may be the same or different.

The compound represented by Formula (A) is preferably a compound having high enzyme inhibitory activity against NAE that can generally be tested by a known method, more preferably, a compound such that the concentration ($IC_{50}$) of the compound by which 50% of the enzyme can be inhibited is 0.03 μM or less, further preferably a compound having an $IC_{50}$ of 0.01 μM or less, particularly preferably a compound having an $IC_{50}$ of 0.003 μM or less.

The compound represented by Formula (A) is preferably a compound having high tumor growth inhibitory activity that can generally be tested by a known method, more preferably a compound such that the concentration ($IC_{50}$) of the compound by which 50% of tumor growth can be inhibited is 0.01 μM or less, particularly preferably a compound having an $IC_{50}$ of 0.003 μM or less.

The compound represented by Formula (A) is preferably a compound having a weak enzyme inhibitory activity against carbonic anhydrase II, and said activity can generally be tested by a known method. More preferably, the compound represented by Formula (A) is such that the concentration ($IC_{50}$) of the compound by which 50% of the enzyme is inhibited is 0.03 μM or more, further preferably a compound having an $IC_{50}$ of 0.1 μM or more, further more preferably a compound having an $IC_{50}$ of 0.3 μM or more, and particular preferably a compound having $IC_{50}$ of 1.0 μM or more.

Further preferable examples of the compound of the present invention include a compound wherein in Formula (A),
$R_1$ is hydrogen, fluorine, or a hydroxy group;
$R_2$ is hydrogen, fluorine, or a hydroxy group; and
$R_3$ is an ethynylene group, or a monocyclic or bicyclic heteroarylene group having 1 to 4 of at least one kind of heteroatom selected from the group consisting of N, S, and O, or a salt thereof.

Further preferable examples of the compound of the present invention include a compound wherein in Formula (A),
$R_1$ is a hydroxy group;
$R_2$ is hydrogen or a hydroxy group;
$R_3$ is an ethynylene group, or a monocyclic heteroarylene group having 2 of at least one kind of heteroatom selected from the group consisting of N, S and O;
$R_5$ is a C3-C7 saturated cycloalkyl group that may have one or more $R_6$; a C6-C10 unsaturated cycloalkyl group that may have one or more $R_6$; or a monocyclic or bicyclic unsaturated heterocycloalkyl group that has at least one heteroatom selected from the group consisting of N, S and O, and that may be substituted with one or more $R_6$;
$R_6$ is
halogen,
a hydroxy group,
a cyano group,
a C1-C6 alkyl group that may have one or more phenoxy group as a substituent,
a carbamoyl group,
a C1-C6 alkoxycarbonyl group,
a monocyclic or bicyclic unsaturated heterocycloalkyl group having at least one heteroatom selected from the group consisting of N, S and O,
a monocyclic or bicyclic saturated heterocycloalkyl group that has at least one heteroatom selected from the group consisting of N, S, and O, and that may have one or more of either halogen, hydroxy group, carboxyl group, or C1-C6 alkyl group as a substituent,
an amino group,
a mono- or di-(C1-C4 alkyl) amino group that may have one or more hydroxy group or phenyl group,
a C1-6 alkoxy group that may have, as a substituent, one or more of either halogen, C3-C7 saturated cycloalkyl group, or monocyclic or bicyclic unsaturated heterocycloalkyl group having at least one heteroatom selected from the group consisting of N, S, and O as a substituent,
a benzyloxy group that may have one or more carbamoyl group as a substituent,
a C1-C4 alkylthio group,
a C1-C4 alkylsulfonyl group, or
an aminosulfonyl group,
(when two or more $R_6$ are present, the plurality of $R_6$ may be the same or different), or a salt thereof.

Further preferable examples of the compound of the present invention include a compound wherein, in Formula (A), $R_1$ is a hydroxy group;
$R_2$ is hydrogen or a hydroxy group;
$R_3$ is an ethynylene group, or a monocyclic heteroarylene group having 2 of at least one kind of heteroatom selected from the group consisting of N, S, and O;
$R_5$ is a C3-C7 saturated cycloalkyl group that may have one or more $R_6$; a C6-C10 unsaturated cycloalkyl group that may have one or more $R_6$; or a monocyclic or bicyclic unsaturated heterocycloalkyl group that has at least one heteroatom selected from the group consisting of N, S, and O, and that may have one or more $R_6$;
$R_6$ is fluorine, chlorine, a hydroxy group, a cyano group, a C1-C6 alkyl group that may have one or more phenoxy group as a substituent,
a carbamoyl group, a C1-C6 alkoxycarbonyl group,
a pyridinyl group that may have at least one substituent selected from the group consisting of halogen, hydroxy group, and C1-C4 alkyl group,
a saturated heterocycloalkyl group selected from the group consisting of azetidinyl group, hydroxy azetidinyl group, thiomorpholinyl group, dioxide thiomorpholinyl group, methyl piperazinyl group, hydroxy piperidinyl group, oxopiperidinyl group, piperidinyl group, hydroxy pyrrolidinyl group, oxopyrrolidinyl group, pyrrolidinyl group, carboxyl pyrrolidinyl group, fluoro pyrrolidinyl group and morpholinyl group, amino group, methylamino group, ethylamino group, isopropylamino group, hydroxyethylamino group, dimethylamino group, phenyl methylamino group,
9-oxa-3-azabicyclo[3.3.1]nonan-3-yl group,
3-oxa-8-azabicyclo[3.2.1]octan-8-yl group,
a C1-C6 alkoxy group that may have one or more of either halogen, C3-C7 saturated cycloalkyl group, or monocyclic or bicyclic unsaturated heterocycloalkyl group having at least one heteroatom selected from the group consisting of N, S, and O, as a substituent,
a benzyloxy group that may have one or more carbamoyl group as a substituent,
a C1-C4 alkylthio group,
a C1-C4 alkylsulfonyl group, or
an aminosulfonyl group
(when two or more $R_6$ are present, the plurality of $R_6$ may be the same or different), or a salt thereof.

Further preferable examples of the compound of the present invention include a compound wherein in Formula (A),
$R_1$ is a hydroxy group;
$R_2$ is a hydroxy group;
$R_3$ is an ethynylene group;
$R_4$ is a bond;
$R_5$ is a C6-C10 unsaturated cycloalkyl group that may have one or more $R_6$, or
a monocyclic or bicyclic unsaturated heterocycloalkyl group that has at least one heteroatom selected from the group consisting of N, S and O, and that may have one or more $R_6$; and
$R_6$ is
fluorine,
chlorine,
a hydroxy group,
a cyano group,
a methyl group,
a 3-fluoro pyrrolidinyl group,
a morpholinyl group,
a thiomorpholinyl group,
a 3-hydroxy azetidinyl group,
an azetidinyl group,
an amino group,
a methylamino group,
a C1-C6 alkoxy group that may have one or more of either halogen, C3-C7 saturated cycloalkyl group, or
a C1-C4 alkylthio group as a substituent
(when two or more $R_6$ are present, the plurality of $R_6$ may be the same or different), or a salt thereof.

Further preferable examples of the compound of the present invention include a compound wherein, in Formula (A), Y is —NH—;
$R_1$ is a hydroxy group;
$R_2$ is a hydroxy group;
$R_3$ is an ethynylene group;
$R_4$ is a bond;
$R_5$ is a phenyl group or a naphthyl group having one or more $R_6$, or a monocyclic or bicyclic unsaturated heterocycloalkyl group that has at least one heteroatom selected from the group consisting of N, S, and O, and that may have one or more $R_6$; and $R_6$ is fluorine,
a methyl group,
3-fluoro pyrrolidinyl,
3-hydroxy azetidinyl,
azetidinyl,
an amino group,
a methylamino group,
a C1-C6 alkoxy group that may have a cyclopropyl group, or a C1-C4 alkylthio group
(when two or more $R_6$ are present, the plurality of $R_6$ may be the same or different), or a salt thereof.

Specifically, preferable examples of the compound of the present invention include:
4-amino-5-[2-(2,6-difluoro phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-5-[2-(4-amino-2,6-difluoro-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-5-[2-[2,6-difluoro-4-(methylamino)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-5-[2-[2,6-difluoro-4-[(3R)-3-fluoro pyrrolidin-1-yl]phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-[4-[2-[4-amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-3-ethoxy-5-fluoro-phenyl]morpholine;
4-amino-7-[(2R,3R,4S,5R)-3,4-dihydroxy-5-[(sulfamoylamino)methyl]tetrahydrofuran-2-yl]-5-[2-(2-ethoxy-4,6-difluoro-phenyl)ethynyl]pyrrolo[2,3-d]pyrimidine;
4-[4-[2-[4-amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-3,5-difluoro-phenyl]thio morpholine;
4-amino-5-[2-[2,6-difluoro-4-(3-hydroxy azetidin-1-yl)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-5-[2-[4-(azetidin-1-yl)-2,6-difluoro-phenyl]ethynyl]-7-[(1R,2S,3R,4R)-2,3-dihydroxy-4-[(sulfamoylamino)methyl]cyclopentyl]pyrrolo[2,3-d]pyrimidine;
4-amino-7-[(2R,3R,4S,5R)-3,4-dihydroxy-5-[(sulfamoylamino)methyl]tetrahydrofuran-2-yl]-5-[2-(2-ethoxy-6-fluoro-phenyl)ethynyl]pyrrolo[2,3-d]pyrimidine;

4-amino-7-[(2R,3R,4S,5R)-3,4-dihydroxy-5-[(sulfamoylamino)methyl]tetrahydrofuran-2-yl]-5-[2-(2-fluoro-6-propoxy-phenyl)ethynyl]pyrrolo[2,3-d]pyrimidine;
4-amino-7-[(2R,3R,4S,5R)-3,4-dihydroxy-5-[(sulfamoylamino)methyl]tetrahydrofuran-2-yl]-5-[2-[2-fluoro-6-(2,2,2-trifluoro ethoxy)phenyl]ethynyl]pyrrolo[2,3-d]pyrimidine;
8-[2-[4-amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-7-fluoro-4-methyl-2,3-dihydro-1,4-benzoxazine;
4-amino-7-[(2R,3R,4S,5R)-3,4-dihydroxy-5-[(sulfamoylamino)methyl]tetrahydrofuran-2-yl]-5-[2-(2-ethylsulfanyl-6-fluoro-phenyl)ethynyl]pyrrolo[2,3-d]pyrimidine;
4-amino-5-[2-[2-(cyclopropyl methoxy)-6-fluoro-phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-7-[(1R,2S,3R,4R)-2,3-dihydroxy-4-[(sulfamoylamino)methyl]cyclopentyl]-5-[2-(2-ethoxy-6-fluoro-phenyl)ethynyl]pyrrolo[2,3-d]pyrimidine;
4-amino-7-[(1R,2S,3R,4R)-2,3-dihydroxy-4-[(sulfamoylamino)methyl]cyclopentyl]-5-[2-(2-fluoro-6-methylsulfanyl-phenyl)ethynyl]pyrrolo[2,3-d]pyrimidine;
8-[2-[4-amino-7-[(1R,2S,3R,4R)-2,3-dihydroxy-4-[(sulfamoylamino)methyl]cyclopentyl]pyrrolo[2,3-d]pyrimidin-5-yl]ethynyl]-7-fluoro-4-methyl-2,3-dihydro-1,4-benzoxazine;
4-amino-7-[(1R,4R,5S)-4,5-dihydroxy-3-[(sulfamoylamino)methyl]cyclopent-2-en-1-yl]-5-[2-(2-ethoxy-6-fluoro-phenyl)ethynyl]pyrrolo[2,3-d]pyrimidine;
4-amino-7-[(1R,4R,5S)-4,5-dihydroxy-3-[(sulfamoylamino)methyl]cyclopent-2-en-1-yl]-5-[2-(2-fluoro-6-methylsulfanyl-phenyl)ethynyl]pyrrolo[2,3-d]pyrimidine;
[(2R,3S,4R,5R)-5-[4-amino-5-[2-(2,6-difluoro phenyl)ethynyl]pyrrolo[2,3-d]pyrimidin-7-yl]-3,4-dihydroxy-tetrahydrofuran-2-yl]methyl sulfamate; and salts of these compounds, further preferably,
4-amino-5-[2-(2,6-difluoro phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-5-[2-(4-amino-2,6-difluoro-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-5-[2-[2,6-difluoro-4-(methylamino)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-5-[2-[2,6-difluoro-4-[(3R)-3-fluoro pyrrolidin-1-yl]phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-7-[(2R,3R,4S,5R)-3,4-dihydroxy-5-[(sulfamoylamino)methyl]tetrahydrofuran-2-yl]-5-[2-(2-ethoxy-4,6-difluoro-phenyl)ethynyl]pyrrolo[2,3-d]pyrimidine;
4-amino-5-[2-[2,6-difluoro-4-(3-hydroxy azetidin-1-yl)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-5-[2-[4-(azetidin-1-yl)-2,6-difluoro-phenyl]ethynyl]-7-[(1R,2S,3R,4R)-2,3-dihydroxy-4-[(sulfamoylamino)methyl]cyclopentyl]pyrrolo[2,3-d]pyrimidine;
4-amino-7-[(2R,3R,4S,5R)-3,4-dihydroxy-5-[(sulfamoylamino)methyl]tetrahydrofuran-2-yl]-5-[2-(2-ethoxy-6-fluoro-phenyl)ethynyl]pyrrolo[2,3-d]pyrimidine;
4-amino-7-[(2R,3R,4S,5R)-3,4-dihydroxy-5-[(sulfamoylamino)methyl]tetrahydrofuran-2-yl]-5-[2-(2-fluoro-6-propoxy-phenyl)ethynyl]pyrrolo[2,3-d]pyrimidine;
8-[2-[4-amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-7-fluoro-4-methyl-2,3-dihydro-1,4-benzoxazine;
4-amino-7-[(2R,3R,4S,5R)-3,4-dihydroxy-5-[(sulfamoylamino)methyl]tetrahydrofuran-2-yl]-5-[2-(2-ethylsulfanyl-6-fluoro-phenyl)ethynyl]pyrrolo[2,3-d]pyrimidine;
4-amino-5-[2-[2-(cyclopropyl methoxy)-6-fluoro-phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine;
4-amino-7-[(1R,2S,3R,4R)-2,3-dihydroxy-4-[(sulfamoylamino)methyl]cyclopentyl]-5-[2-(2-fluoro-6-methylsulfanyl-phenyl)ethynyl]pyrrolo[2,3-d]pyrimidine;
8-[2-[4-amino-7-[(1R,2S,3R,4R)-2,3-dihydroxy-4-[(sulfamoylamino)methyl]cyclopentyl]pyrrolo[2,3-d]pyrimidin-5-yl]ethynyl]-7-fluoro-4-methyl-2,3-dihydro-1,4-benzoxazine;
4-amino-7-[(1R,4R,5S)-4,5-dihydroxy-3-[(sulfamoylamino)methyl]cyclopent-2-en-1-yl]-5-[2-(2-ethoxy-6-fluoro-phenyl)ethynyl]pyrrolo[2,3-d]pyrimidine;
4-amino-7-[(1R,4R,5S)-4,5-dihydroxy-3-[(sulfamoylamino)methyl]cyclopent-2-en-1-yl]-5-[2-(2-fluoro-6-methylsulfanyl-phenyl)ethynyl]pyrrolo[2,3-d]pyrimidine; and salts of these compounds.

The method for producing the compound of the present invention is described below.

The compounds of the present invention may be produced, for example, through the production methods below or the methods described in the Examples. However, the method for producing the compounds of the present invention is not limited to these reaction examples.

Production Method A

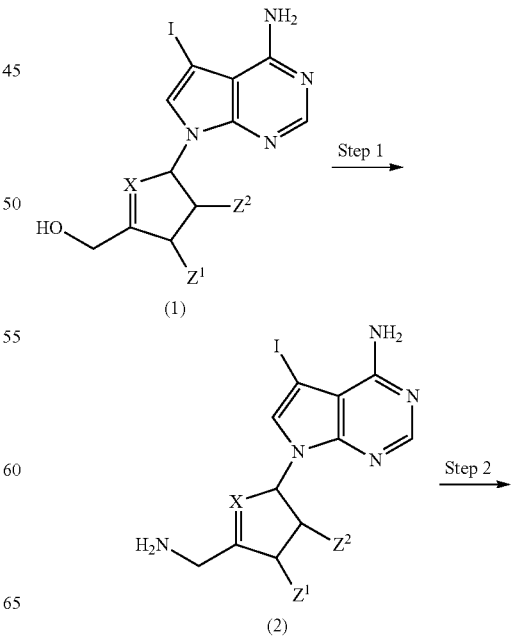

(3)

(4)

(5)

In the formula, $Z^1$ and $Z^2$ are the same or different, and each represents hydrogen, fluorine, a hydroxy group, an amino group, a cyano group or a protector thereof.
$P_1$ is a protecting group of an amino group.
$R_3$ represents a vinylene group, an ethynylene group, a C6-C14 arylene group, or a monocyclic or bicyclic heteroarylene group having at least one heteroatom selected from the group consisting of N, S, and O.
$R_4$ represents a single bond, a methylene group, or a C3-C7 cycloalkylidene.
$R_5$ is a C3-C7 saturated cycloalkyl group that may be substituted with one or more $R_6$;
a C6-C10 unsaturated cycloalkyl group that may be substituted with one or more $R_6$; or
a monocyclic or bicyclic unsaturated heterocycloalkyl group that has at least one heteroatom selected from the group consisting of N, S, O, and that may be substituted with one or more $R_6$.
$R_6$ is
halogen;
a hydroxy group;
a cyano group;
a C1-C6 alkyl group that may have one or more phenoxy group as a substituent;
a carbamoyl group, a C1-C6 alkoxycarbonyl group;
a C4-C7 unsaturated cycloalkyl group that may have one or more of either halogen, hydroxy group, C1-C4 alkyl group, or carbamoyl group as a substituent;

a monocyclic or bicyclic unsaturated heterocycloalkyl group having at least one heteroatom selected from the group consisting of N, S, and O;
a monocyclic or bicyclic saturated heterocycloalkyl group that has at least one heteroatom selected from the group consisting of N, S, and O, and that may have one or more of either halogen, hydroxy group, oxo group, carboxyl group, dioxide group, or C1-C6 alkyl group as a substituent;
an amino group;
a mono- or di-(C1-C4 alkyl) amino group that may have one or more hydroxy group or phenyl group as a substituent;
a C1-C6 alkoxy group having one or more of either halogen, C3-C7 saturated cycloalkyl group, or monocyclic or bicyclic unsaturated heterocycloalkyl group having at least one heteroatom selected from the group consisting of N, S, and O as a substituent; a benzyloxy group that may have one or more carbamoyl group as a substituent;
a C1-C4 alkylthio group;
a C1-C4 alkylsulfonyl group; or
an aminosulfonyl group.

when two or more $R_6$ are present, the plurality of $R_6$ may be the same or different.

represents —O—, —CH$_2$— or =CH.

Step 1

This step produces Compound (2) using a compound represented by Formula (1) (in this specification, the compound represented by Formula (1) may be simply referred to as Compound (1); similarly, compounds represented by Formulas 2 to 30 may be simply referred to as Compounds (2) to (30)) as a raw material, through a Mitsunobu reaction using a nitrogen nucleophile, and a subsequent deprotection reaction.

In Compound (1), when $Z^1$ and/or $Z^2$ represents a protector of a hydroxy group, examples of the protector include dimethyl acetal group, benzylidene acetal group, benzoyl group, and tert-butyl dimethyl silyloxy group. $Z^1$ and $Z^2$ may form the structure below, or the like, (wherein Ra are the same or different, and each represents hydrogen, methyl, ethyl, phenyl, cyclohexyl or cyclopentyl) together with the carbon atoms bound thereto. Examples of nitrogen nucleophile include phthalimide. When phthalimide is used as a nitrogen nucleophile, the amount of phthalimide used is 1 to 10 moles, preferably 1 to 5 moles, per mole of Compound (1).

The Mitsunobu reaction can generally be performed by a known method, such as, for example, the method described in Synthesis, p. 1 (1981); or a similar method.

Examples of azodicarboxylic acid esters used for the Mitsunobu reaction include diethyl azodicarboxylate and diisopropyl azodicarboxylate. Such an azodicarboxylic acid ester can be used in an amount of 1 to 10 moles, and preferably 1 to 5 moles, per mole of Compound (1).

Examples of phosphine compounds used in the Mitsunobu reaction include triphenylphosphine and tributylphosphine, and the amount of phosphine compound used is 1 to 10 moles, preferably 1 to 5 moles, per mole of Compound (1).

Examples of the solvent include tetrahydrofuran, 1,2-dimethoxyethane, 1,4-dioxane, toluene, N,N-dimethyl formamide, N,N-dimethylacetamide, dimethyl sulfoxide, and N-methylpyrrolidin-2-one. These solvents may be used alone, or in a mixture. The reaction time ranges from 0.1 to 100 hours, preferably 0.1 to 24 hours. The reaction temperature ranges from 0° C. to the boiling temperature of the solvent, preferably 0° C. to 100° C. The removal of the protecting group of a nitrogen nucleophile can generally be performed by a known method, such as the method described in Protective Groups in Organic Synthesis, T. W. Greene, John Wiley & Sons (1981); or a similar method.

The removal of the phthalimide group can be performed by using an isolated phthalimide intermediate or by directly using the Mitsunobu reaction solution, with hydrazine, hydroxylamine, methylamine, ethylamine, n-butylamine, etc., as a deprotection reagent. The amount of the deprotection reagent is typically an equimolar to excessive molar amount per mole of Compound (1).

Examples of the solvent include alcohol solvents (ethanol, methanol, etc.), acetonitrile, dichloromethane, chloroform, tetrahydrofuran, 1,2-dimethoxyethane, 1,4-dioxane, toluene, N,N-dimethylformamide, N,N-dimethylacetamide, and N-methylpyrrolidin-2-one. These solvents may be used alone, or in a mixture. The reaction time ranges from 0.1 to 100 hours, preferably 0.1 to 24 hours. The reaction temperature ranges from 0° C. to the boiling temperature of the solvent, preferably 0° C. to 100° C.

Step 2

This step produces Compound (3) by reacting a sulfamoyl-introducing reagent with Compound (2).

The sulfamoyl-introducing reagent can be obtained from commercial suppliers, or can be produced through a known method using, for example, sulfamoyl chloride, 1-aza-4-azoniabicyclo [2.2.2]octane-4-ylsulphonyl(tert-butoxycarbonyl)azanide or the like. The amount of the sulfamoyl-introducing reagent used is 1 to 10 moles, preferably 1 to 5 moles, per mole of Compound (2).

Examples of the protecting group of an amino group include C1-C6 alkyl group, tert-butoxycarbonyl group, benzyloxycarbonyl group, acetyl group, and propionyl group.

Examples of bases include triethylamine, diisopropylethylamine, pyridine, imidazole, and DBU. When a base is used, the amount of the base is generally 1 to 30 moles, preferably 1 to 10 moles, per mole of Compound (2).

Examples of the solvent include acetonitrile, dichloromethane, chloroform, tetrahydrofuran, 1,2-dimethoxyethane, 1,4-dioxane, toluene, N,N-dimethyl formamide, N,N-dimethylacetamide, and N-methylpyrrolidin-2-one. These solvents may be used alone, or in a mixture. The reaction time ranges from 0.1 to 100 hours, preferably 0.1 to 24 hours. The reaction temperature ranges from 0° C. to the boiling temperature of the solvent, and preferably from 0° C. to 100° C.

Step 3

Using Compound (3) as a raw material, this step produces Compound (4) through a coupling reaction (Sonogashira coupling, Suzuki-Miyaura coupling, etc.). This step may be performed through multiple steps as necessary, and may suitably be combined with a protection reaction, a deprotection reaction.

For example, among various Compounds (4), a compound in which $R_3$ has an alkynylene group may be obtained through a coupling (Sonogashira) reaction, using Compound (3) and a compound: H—C≡C—$R_4$—$R_5$ (wherein $R_4$ and $R_5$ are as defined above).

In this case, the compound: H—C≡C—$R_4$—$R_5$ (wherein $R_4$ and $R_5$ are as defined above) can be obtained from commercial suppliers, or can be produced through a known method. The amount of this compound is 1 to 10 mole, preferably 1 to 3 mole, per mole of Compound (3).

This step can generally be performed by a known method, for example, the method disclosed in Chemical Reviews, Vol. 107, p. 874 (2007). For example, this step can be performed in the presence of a transition metal catalyst and a base in a solvent that does not adversely affect the reaction.

Examples of transition metal catalyst usable in this step include palladium catalysts (e.g., palladium acetate, tris(dibenzylideneacetone)dipalladium, 1,1'-bis(diphenylphosphino)ferrocene-palladium(II) dichloride-dichloromethane complex, etc.). As necessary, a ligand (e.g., triphenylphosphine, tri-tert-butylphosphine, etc.) is added, and a copper reagent (e.g., copper iodide, copper acetate, etc.) is used as a cocatalyst. The amount of the transition metal catalyst varies depending on the type of catalyst. For example, the amount of the transition metal catalyst used is generally 0.0001 to 1 mole, preferably 0.01 to 0.5 moles, per mole of Compound (4). The amount of the ligand used is generally 0.0001 to 4 moles, preferably 0.01 to 2 moles, per mole of Compound (4). The amount of the cocatalyst used is generally 0.0001 to 4 moles, preferably 0.001 to 2 moles, per mole of Compound (4).

Further, a base may be added during the above reaction as necessary. Examples of bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, or butyl lithium; and inorganic bases such as sodium hydrogen carbonate, sodium carbonate, potassium carbonate, cesium carbonate, sodium hydroxide, and sodium hydride. Among these, organic bases such as triethylamine and diisopropylethylamine are preferable. The amount of the base used is generally 0.1 to 50 moles, and preferably 1 to 20 moles, per mole of Compound (4).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, 1,4-dioxane, etc.), alcohols (e.g., methanol, ethanol, etc.), aprotic polar solvents (e.g., dimethylformamide, dimethylsulfoxide, hexamethyl phosphoramide, etc.), water, and mixtures thereof. The reaction time ranges from 0.1 to 100 hours, preferably 0.5 to 24 hours. The reaction temperature ranges from 0° C. to the boiling temperature of the solvent, preferably 0 to 150° C.

Further, this step may also be performed through Suzuki-Miyaura coupling using Compound (3) and an organic boron compound (boric-acid compound, boric-acid ester, etc.) having a substituent —$R_3$—$R_4$—$R_5$ (wherein $R_3$, $R_4$, and $R_5$ are as defined above).

In this method, the organic boron compound can be obtained from commercial suppliers, or can be produced through a known method. The amount of the organic boron compound used is 1 to 10 moles, preferably 1 to 3 moles, per mole of Compound (3).

In this method, the Suzuki-Miyaura coupling can generally be performed by a known method, such as the method described in Chemical Reviews, Vol. 95, p. 2457 (1995); or a similar method.

Examples of reaction catalyst used for the Suzuki-Miyaura coupling include tetrakis triphenylphosphine palladium (0), bis (triphenylphosphine)palladium(II) dichloride, and 1,1'-bis (diphenyl phosphino)ferrocene-palladium(II) dichloride-dichloromethane complex. The amount of the reaction catalyst used depends on the type of the catalyst. The amount of the catalyst used is generally 0.0001 to 1 mole, preferably 0.01 to 0.5 moles, per mole of Compound (3).

Examples of the solvent include hydrocarbons (e.g., benzene, toluene, and xylene), nitriles (e.g., acetonitrile), ethers (e.g., dimethoxyethane, tetrahydrofuran, 1,4-dioxane, etc.), alcohols (e.g., methanol, ethanol, etc.), aprotic polar solvents (e.g., dimethylformamide, dimethylsulfoxide, etc.), and water. These solvents may be used alone, or in a mixture. The reaction time ranges from 0.1 to 100 hours, preferably 0.1 to 24 hours. The reaction temperature ranges from 0° C. to the boiling temperature of the solvent, preferably 0° C. to 100° C.

Step 4

This step produces Compound (5) by deprotecting the protected amino group of Compound (4). The deprotection can generally be performed by a known method, such as the method described in Protective Groups in Organic Synthesis, T. W. Greene, John Wiley & Sons (1981); or a similar method. An example of the protecting group is tert-butyloxycarbonyl. When a tert-butyl oxycarbonyl group is used as a protecting group, the deprotection is preferably performed under acidic conditions. Examples of acids that can be used include hydrochloric acid, acetic acid, trifluoroacetic acid, sulfuric acid, methanesulfonic acid, tosic acid, and the like. The amount of the acid used is preferably 1 to 100 moles per mole of Compound (4).

Any solvent that does not adversely affect the reaction may be used for the reaction. Examples of the solvent include alcohols (e.g., methanol), hydrocarbons (e.g., benzene, toluene, and xylene), halogenated hydrocarbons (e.g., methylene chloride, chloroform, 1,2-dichloroethane, etc.), nitriles (e.g., acetonitrile), ethers (e.g., dimethoxyethane, tetrahydrofuran, etc.), aprotic polar solvents (e.g., N,N-dimethylformamide, dimethylsulfoxide, hexamethyl phosphoramide, etc.), and mixtures thereof. The reaction time ranges 0.1 to 100 hours, preferably 0.5 to 24 hours. The reaction temperature ranges from 0 to 120° C., preferably 0 to 90° C.

Compound (1) used as a raw material in Production Method A can be obtained from commercial suppliers, or can be produced through a known method. For example, Compound (7) in which $Z^1$ and $Z^2$ in Formula 1 represent a specific protector of a hydroxy group may be produced through Production Method B below.

Production Method B

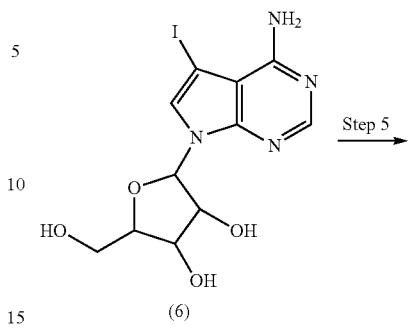

(6)

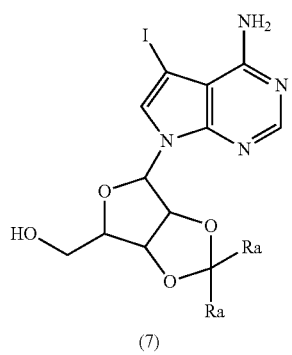

(7)

wherein Ra are the same or different, and each represents hydrogen, methyl, ethyl, phenyl, cyclohexyl, or cyclopentyl.

Step 5

This step produces Compound (7) by protecting two hydroxy groups among the hydroxy groups of Compound (6). Examples of the protection reagent include dialkoxy alkane and the like. The amount of the protection reagent used is 1 to 100 moles, preferably 1 to 10 moles, per mole of Compound (6).

The protection can generally be performed by a known method, such as the method described in Protective Groups in Organic Synthesis, T. W. Greene, John Wiley & Sons (1981); or a similar method.

Examples of the reaction catalyst include p-toluenesulfonic acid, methanesulfonic acid, pyridinium p-toluenesulfonates, perchloric acid, and sulfuric acid. When a reaction catalyst is used, the amount of the reaction catalyst depends on the type of the catalyst. For example, the amount of the reaction catalyst is generally 0.0001 to 1 mole, preferably 0.01 to 0.5 moles, per mole of Compound (6).

Examples of the solvent include acetonitrile, dichloromethane, chloroform, tetrahydrofuran, 1,2-dimethoxyethane, 1,4-dioxane, toluene, N,N-dimethylformamide, N,N-dimethylacetamide, and N-methylpyrrolidin-2-one. These solvents may be used alone, or in a mixture. The reaction time ranges from 0.1 to 100 hours, preferably 0.1 to 24 hours. The reaction temperature ranges from 0° C. to the boiling temperature of the solvent, preferably 0° C. to 100° C.

Further, Compound (15) in which $Z^1$ and $Z^2$ in Formula 1 represent a specific protector of a hydroxy group may be produced through Production Method C below.

Production Method C

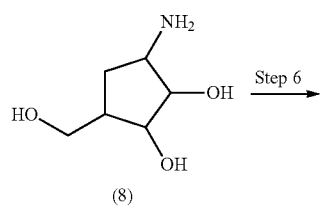
(8)

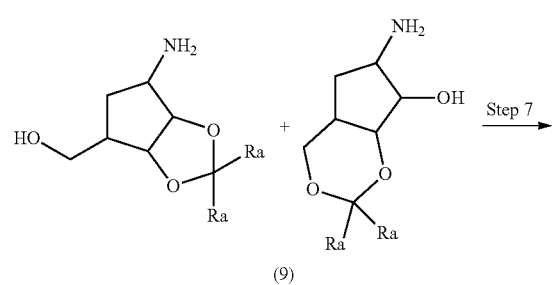
(9)

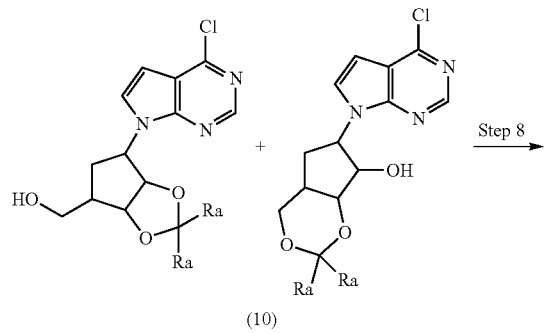
(10)

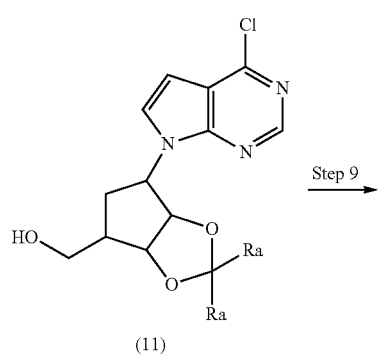
(11)

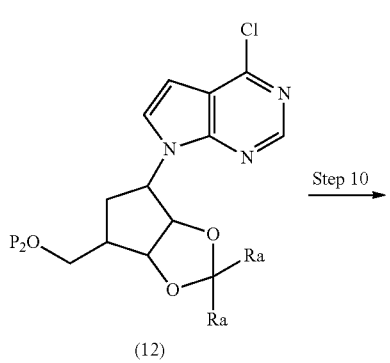
(12)

-continued

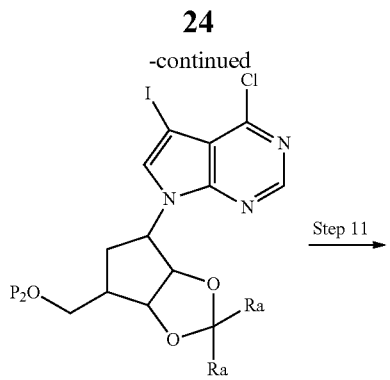
(13)

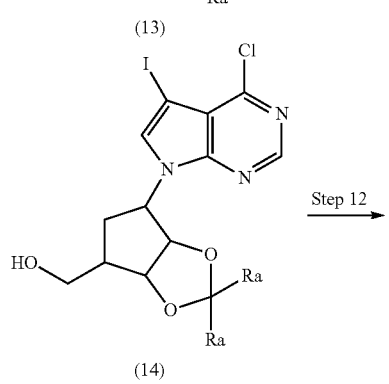
(14)

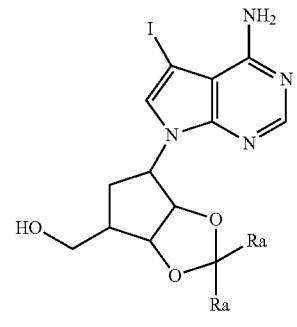
(15)

wherein P$_2$ is a protecting group of a hydroxy group. Ra is as defined above.

Step 6

This step produces Compound (9) by protecting two hydroxy groups among the hydroxy groups of Compound (8). The protection reaction may be performed in the same manner as in Step 5.

Step 7 This step produces an isomer mixture of Compound (10), which is a pyrrolopyrimidine compound, by reacting an isomer mixture of Compound (9) and 2-(4,6-dichloro pyrimidin-5-yl)acetaldehyde in the presence of a base.

The amount of the 2-(4,6-dichloro pyrimidin-5-yl)acetaldehyde is 1 to 10 moles, preferably 1 to 3 moles, per mole of Compound (9).

The reaction can generally be performed by a known method, for example, the method disclosed in Tetrahedron Letters, 26 (16), 2001-2 (1985).

Examples of bases include triethylamine, diisopropylethylamine, pyridine, lutidine, collidine, and DBU. When a base is used, the amount of the base is generally 1 to 100 moles, preferably 1 to 20 moles, per mole of Compound (9).

Examples of the solvent include ethanol, 2-propanol, 2-butanol, acetonitrile, tetrahydrofuran, 1,2-dimethoxyethane, 1,4-dioxane, N,N-dimethylformamide, N,N-dimethylacetamide, and N-methylpyrrolidin-2-one. These solvents may be used alone, or in a mixture. The reaction time ranges from 0.1 to 100 hours, preferably 0.1 to 24 hours. The reaction temperature ranges from 0° C. to the boiling temperature of the solvent, preferably 0° C. to 100° C.

Step 8

This step converts the isomer mixture of Compound (10) into Compound (11) consisting of only one of the isomers, in the presence of an acid catalyst.

Examples of acids include p-toluenesulfonic acid, methanesulfonic acid, pyridinium p-toluene sulfonate, perchloric acid, and sulfuric acid. The amount of the acid is generally 0.001 to 10 moles, preferably 0.01 to 2 moles, per mole of Compound (10).

Examples of the solvent include acetone, 2-butanone, acetonitrile, dichloromethane, chloroform, tetrahydrofuran, 1,2-dimethoxyethane, 1,4-dioxane, toluene, N,N-dimethylformamide, N,N-dimethylacetamide, and N-methylpyrrolidin-2-one. These solvents may be used alone, or in a mixture. The reaction time ranges from 0.1 to 100 hours, preferably 1 to 48 hours. The reaction temperature ranges from 0° C. to the boiling temperature of the solvent, preferably 0° C. to 100° C.

Step 9

This step protects the hydroxy group of Compound (11) using Compound $P_2$—Cl (wherein $P_2$ is a protecting group of a hydroxy group).

The reaction can generally be performed by a known method, such as the method described in Protective Groups in Organic Synthesis, T. W. Greene, John Wiley & Sons (1981); or a similar method.

The protecting group of a hydroxy group represented by $P_2$ in Compound $P_2$—Cl is not particularly limited insofar as it has a protecting function. Examples include lower alkyl groups such as methyl, ethyl, propyl, isopropyl, and tert-butyl; lower alkylsilyl groups such as trimethylsilyl and tert-butyldimethylsilyl; lower alkoxymethyl groups such as methoxymethyl and 2-methoxyethoxymethyl; tetrahydropyranyl; trimethylsilylethoxymethyl; aralkyl groups such as benzyl, p-methoxybenzyl, 2,3-dimethoxybenzyl, o-nitrobenzyl, p-nitrobenzyl, and trityl; and acyl groups such as formyl, acetyl, and trifluoroacetyl. In particular, methyl, methoxymethyl, tetrahydropyranyl, trimethylsilylethoxymethyl, tert-butyldimethylsilyl, and acetyl are preferable.

The compound can be obtained from commercial suppliers, or can be produced through a known method. The amount of the compound is 1 to 20 moles, preferably 1 to 5 moles, per mole of Compound (11).

Examples of the base include triethylamine, diisopropylethylamine, pyridine, lutidine, collidine, and DBU. The amount of the base is generally 1 to 20 moles, preferably 1 to 5 moles, per mole of Compound (11).

Examples of the solvent include acetonitrile, dichloromethane, chloroform, tetrahydrofuran, 1,2-dimethoxyethane, 1,4-dioxane, toluene, N,N-dimethylformamide, N,N-dimethylacetamide, and N-methylpyrrolidin-2-one. These solvents may be used alone, or in a mixture. The reaction time ranges from 0.1 to 100 hours, preferably 0.1 to 24 hours. The reaction temperature ranges from 0° C. to the boiling temperature of the solvent, preferably 0° C. to 100° C.

Step 10

This step produces Compound (13) by reacting Compound (12) with iodosuccinimide, thereby introducing an iodine atom.

The iodination may be performed according to the method disclosed in International Publication WO2006/102079, or a similar method. The amount of the iodosuccinimide is 1 to 20 moles, preferably 1 to 5 moles, per mole of Compound (12).

Examples of the solvent include acetone, acetonitrile, ethyl acetate, dichloromethane, chloroform, tetrahydrofuran, 1,2-dimethoxyethane, 1,4-dioxane, toluene, N,N-dimethylformamide, N,N-dimethylacetamide, and N-methylpyrrolidin-2-one. These solvents may be used alone, or in a mixture. The reaction time ranges from 0.1 to 100 hours, preferably 0.1 to 24 hours. The reaction temperature ranges from 0° C. to the boiling temperature of the solvent, preferably 0° C. to 100° C.

Step 11

This step produces Compound (14) by deprotecting the protected hydroxy group of Compound (13).

The deprotection can generally be performed by a known method, such as the method described in Protective Groups in Organic Synthesis, T. W. Greene, John Wiley & Sons (1981); or a similar method.

When a tert-butyl dimethylsilyl group is used as a protecting group, tetrabutylammonium fluoride, for example, is used as a deprotection reagent. The amount of the reagent is preferably 1 to 10 moles, per mole of Compound (13).

Any solvent that does not adversely affect the reaction may be used for the reaction. Examples of the solvent include ethers (e.g., 1,2-dimethoxyethane, tetrahydrofuran, etc.), aprotic polar solvents (e.g., N,N-dimethylformamide, dimethylsulfoxide, hexamethyl phosphoryl amide), etc.), and mixtures thereof. The reaction time ranges from 0.1 to 100 hours, preferably 0.5 to 24 hours. The reaction temperature ranges from 0 to 80° C., preferably 0 to 50° C.

Step 12

This step produces Compound (15) by reacting Compound (14) with ammonia or a salt thereof.

The amount of the ammonia or a salt thereof used in this step is typically an equimolar to excessive molar amount per mole of Compound (14).

The reaction solvent is not particularly limited, and any solvent that does not adversely affect the reaction can be used. Examples of the solvent include water, methanol, ethanol, isopropanol, tert-butyl alcohol, tetrahydrofuran, 1,2-dimethoxyethane, 1,4-dioxane, N,N-dimethylformamide, N-methylpyrrolidin-2-one, dimethylsulfoxide, and mixtures thereof.

The reaction temperature is generally 0° C. to 200° C., preferably from room temperature to 150° C. The reaction time is generally 5 minutes to 7 days, preferably 30 minutes to 72 hours.

Production Method D

Further, Compound (19), which is a compound in which $Z^1$ in Formula 1 is a hydroxy group, $Z^2$ is hydrogen, and X is $CH_2$, may be produced through Production Method D below.

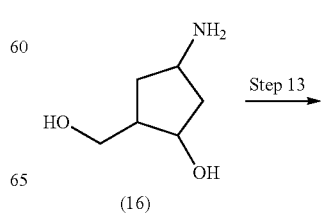

(16)

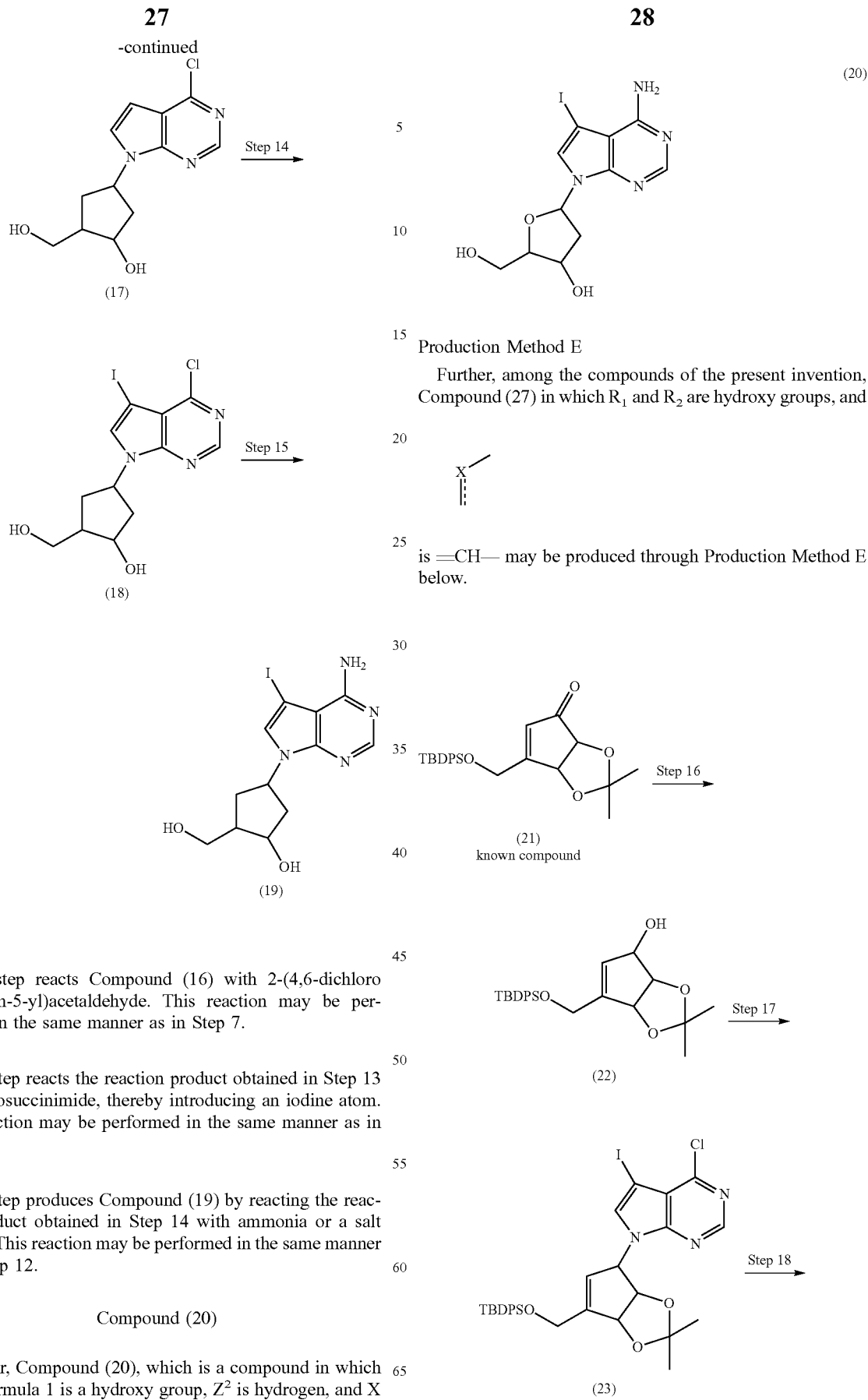

Production Method E

Further, among the compounds of the present invention, Compound (27) in which $R_1$ and $R_2$ are hydroxy groups, and is =CH— may be produced through Production Method E below.

Step 13

This step reacts Compound (16) with 2-(4,6-dichloro pyrimidin-5-yl)acetaldehyde. This reaction may be performed in the same manner as in Step 7.

Step 14

This step reacts the reaction product obtained in Step 13 with iodosuccinimide, thereby introducing an iodine atom. This reaction may be performed in the same manner as in Step 10.

Step 15

This step produces Compound (19) by reacting the reaction product obtained in Step 14 with ammonia or a salt thereof. This reaction may be performed in the same manner as in Step 12.

Compound (20)

Further, Compound (20), which is a compound in which $Z^1$ in Formula 1 is a hydroxy group, $Z^2$ is hydrogen, and X is O, is a publicly known compound.

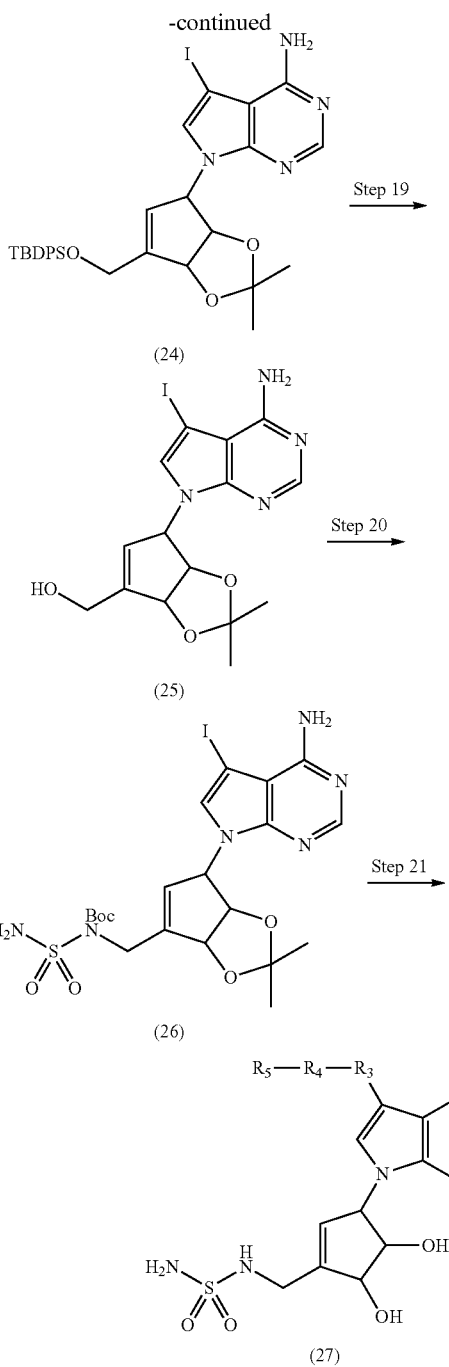

wherein $R_3$, $R_4$, and $R_5$ are as defined above.

Step 16

This step produces Compound (22) by reducing the carboxyl group of Compound (21). This step is performed in the presence of a reducing agent. In this step, the amount of the reducing agent is 1 to 20 moles, preferably 1 to 5 moles, per mole of Compound (21). Examples of the reducing agent include sodium borohydride, lithium aluminum hydride, borane reagent (e.g., diborane), and diisobutylaluminum hydride.

Examples of the solvent include methanol, ethanol, diethylether, tetrahydrofuran, 1,2-dimethoxyethane, 1,4-dioxane, and toluene. These solvents may be used alone, or in a mixture. The reaction time ranges from 0.1 to 100 hours, preferably 0.1 to 24 hours. The reaction temperature ranges from 0° C. to the boiling temperature of the solvent, preferably 0° C. to 100° C.

Step 17

This step produces Compound (23) through a Mitsunobu reaction using Compound (22) as a raw material, and 4-chloro-5-iodo-7H-pyrrolo[2,3-d]pyrimidine as a nucleophilic agent.

This reaction may be performed in the same manner as in Step 1.

Step 18

This step produces Compound (24) by reacting Compound (23) with ammonia or a salt thereof. This reaction may be performed in the same manner as in Step 12.

Step 19

This step produces Compound (25) by deprotecting the protected hydroxy group of Compound (24). This reaction may be performed in the same manner as in Step 11.

Step 20

This step produces Compound (26) through a Mitsunobu reaction using Compound (25) as a raw material, and tert-butyl sulfamoyl carbamate as a nucleophilic agent.

This reaction may be performed in the same manner as in Step 1.

Step 21

This step produces Compound (27) using Compound (26) as a raw material, by deprotecting the protected amino group after a coupling reaction (Sonogashira coupling, Suzuki-Miyaura coupling, etc.). This reaction may be performed in the same manner as in Step 3 and Step 4.

Production Method F

Further, among the compounds of the present invention, Compound (29) in which $R_1$ and $R_2$ are the same or different, and each represent hydrogen, fluorine, a hydroxy group, an amino group, a cyano group, or a protector thereof may be produced through Production Method F below.

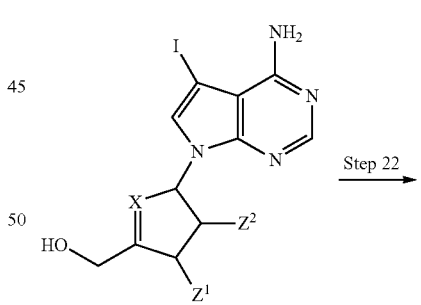

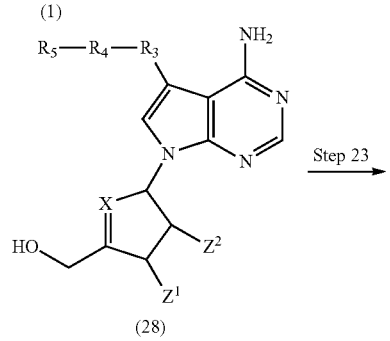

-continued

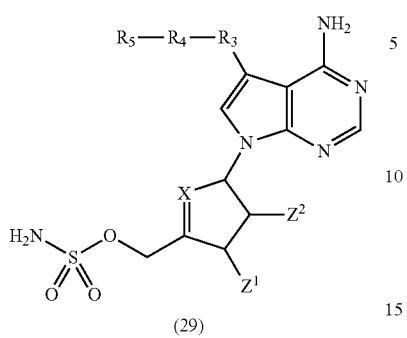

wherein X, $R_3$, $R_4$, $R_5$, $Z^1$, and $Z^2$ are as defined above.

Step 22

This step produces Compound (28) through a coupling reaction (Sonogashira coupling, Suzuki-Miyaura coupling, etc.) using Compound (1) as a raw material. This reaction may be performed in the same manner as in Step 3.

Step 23

This step produces Compound (29) by reacting Compound (28) with a sulfamoyl-introducing reagent.

This reaction may be performed in the same manner as in Step 2. This step may be performed through multiple steps as necessary, and may suitably be combined with a deprotection reaction.

Production Method G

Further, among the compounds of the present invention, Compound (32) may be produced through Production Method G below.

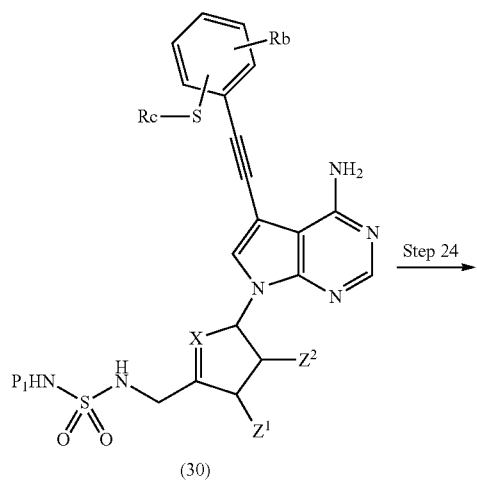

-continued

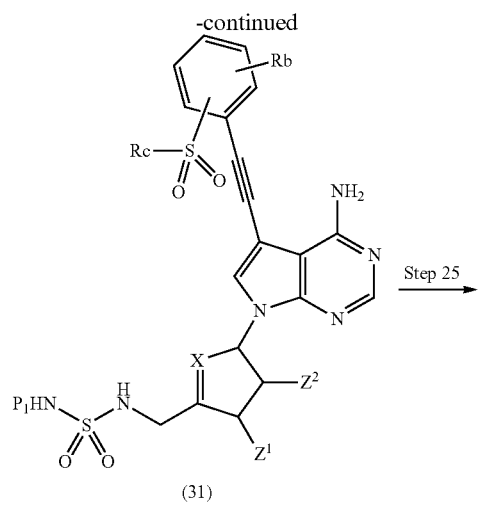

wherein P1, $Z^1$, and $Z^2$ are as defined above. Rb is the same as $R_6$ above. Rc represents a substituted or unsubstituted alkyl group.

Step 24

This step produces Compound (31) by oxidizing Compound (30). This step is performed in the presence of an oxidant. The amount of the oxidant used in this step is 1 to 20 moles, preferably 1 to 5 moles, per mole of Compound (30). Examples of the oxidant include oxone, m-chloroperbenzoic acid, hydrogen peroxide, and potassium permanganate.

Examples of the solvent include water, acetone, 2-butanone, acetonitrile, ethyl acetate, dichloromethane, chloroform, tetrahydrofuran, 1,2-dimethoxyethane, 1,4-dioxane, toluene, N,N-dimethylformamide, N,N-dimethylacetamide, and N-methylpyrrolidin-2-one. These solvents may be used alone, or in a mixture. The reaction time ranges from 0.1 to 100 hours, preferably 0.1 to 24 hours. The reaction temperature ranges from 0° C. to the boiling temperature of the solvent, preferably 0° C. to 100° C.

Step 25

This step produces Compound (32) by deprotecting the protected amino group of Compound (31). This reaction may be performed in the same manner as in Step 4.

The compounds thus-obtained through Production Methods A to G can be subjected to the subsequent step after or without isolation and purification by known separation and purification means, such as concentration, vacuum concentration, crystallization, solvent extraction, reprecipitation, and chromatography.

When the compound of the present invention has isomers such as optical isomers, stereoisomers, regioisomers, and rotational isomers, any of the isomers and mixtures thereof is included within the scope of the compound of the present invention. For example, when the compound has optical isomers, the optical isomer separated from a racemic mixture is also included within the scope of the compound of the present invention. Each of such isomers can be obtained as a single compound by known synthesis and separation means (e.g., concentration, solvent extraction, column chromatography, recrystallization, etc.).

The compound of the present invention can be isolated and purified by usual isolation and purification means. Examples of such means include solvent extraction, recrystallization, preparative reversed-phase high-performance liquid chromatography, column chromatography, preparative thin-layer chromatography, and the like.

The compound or a salt thereof of the present invention may be in the form of crystals. Single crystals and polymorphic mixtures are included within the scope of the compound or a salt thereof of the present invention. Such crystals can be produced by crystallization according to a crystallization method known per se in the art. The compound or a salt thereof of the present invention may be a solvate (e.g., a hydrate) or a non-solvate. Any of such forms are included within the scope of the compound or a salt thereof of the present invention. Compounds labeled with an isotope (e.g., $^3$H, $^{14}$C, $^{35}$S, $^{125}$I) are also included within the scope of the compound or a salt thereof of the present invention.

A prodrug of the compound of the present invention or of a salt thereof refers to a compound that can be converted to the compound or a salt thereof of the present invention through a reaction with an enzyme, gastric acid, or the like, under physiological conditions in vivo, i.e., a compound that can be converted to the compound or a salt thereof of the present invention by enzymatic oxidation, reduction, hydrolysis, or the like; or a compound that can be converted to the compound or a salt thereof of the present invention by hydrolysis with gastric acid or the like. Further, the prodrug of the compound or a salt thereof of the present invention may be compounds that can be converted to the compound or a salt thereof of the present invention under physiological conditions, such as those described in "*Iyakuhin no Kaihatsu* [Development of Pharmaceuticals]," Vol. 7, Molecular Design, published in 1990 by Hirokawa Shoten Co., pp. 163-198.

The salt of the compound of the present invention refers to a common salt used in the field of organic chemistry. Examples of such salts include base addition salts to carboxyl group when the compound has carboxyl group, and acid addition salts to an amino or basic heterocycloalkyl group when the compound has an amino or basic heterocycloalkyl group.

Examples of base addition salts include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts such as hydrochlorides, sulfates, nitrates, phosphates, and perchlorates; organic acid salts such as acetates, formates, maleates, fumarates, tartrates, citrates, ascorbates, and trifluoroacetates; and sulfonates such as methanesulfonates, isethionates, benzenesulfonates, and p-toluenesulfonates. Hydrochlorides are preferable.

The compound or a salt thereof of the present invention has superior NAE inhibitory activity and is useful as an antitumor agent. The type of malignant tumor to be treated by the compound or a salt thereof of the present invention is not particularly limited. Examples of malignant tumors include epithelial cancers (e.g., respiratory system cancers, digestive system cancers, reproductive system cancers, secretion system cancers, and the like), sarcomas, hematopoietic tumors, central nervous system tumors, and peripheral nerve tumors.

Preferable examples include epithelial cancers, sarcomas, and hematopoietic tumors. More preferable examples include digestive system cancers, sarcomas, and hematopoietic tumors. Further, the organ from which the tumor is developed is not particularly limited. Examples include head and neck cancers, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, multiple myeloma, skin cancer, brain tumor, and mesothelioma. Preferably, the target cancer is colon cancer, rectum cancer, pancreatic cancer, lung cancer, prostate cancer, breast cancer, osteosarcoma, soft-tissue sarcoma, or skin cancer.

Further, examples of hematopoietic tumors include bone marrow tumors (e.g., lymphocytic leukemia, myelogenous leukemia, acute leukemia, chronic leukemia, and the like), and lymphoid tumors.

Examples of bone marrow tumors include myeloproliferative neoplasm (MPN), acute myelogenous leukemia (AML), related precursor neoplasm, acute lymphocytic leukemia, chronic myelogenous leukemia (CML), and myelodysplastic syndrome (MDS). Preferable examples include acute leukemia. Particularly preferable examples include acute myelogenous leukemia.

Examples of lymphoid tumors include precursor lymphoid tumor, mature B-cell tumor, mature T-cell tumor and NK-cell tumor, and Hodgkin's lymphoma. Preferable examples include precursor lymphoid tumors, mature B-cell tumor, mature T-cell tumor and NK-cell tumor. Lymphoid tumors that are not regarded as Hodgkin's lymphoma may be collectively referred to as non-Hodgkin's lymphoma.

Examples of precursor lymphoid tumors include B-lymphoblastic leukemia/lymphoma, T-lymphoblastic leukemia/lymphoma (ALL), blastic NK-cell lymphoma, and like blastic lymphoma. T-lymphoblastic leukemia/lymphoma is preferable.

Examples of mature B-cell tumor include chronic lymphocytic leukemia/small lymphocytic lymphoma (CLL/SLL), B-cell prolymphocytic leukemia (B-PLL), splenic marginal zone lymphoma (SMZL), hairy cell leukemia (HCL), Waldenstrom's macroglobulinemia (WM), plasma cell tumor, MALT lymphoma, follicular lymphoma, mantle cell lymphoma (MCL), B-cell lymphoma (diffuse large B-cell lymphoma (DLBCL), and Burkitt's lymphoma). Plasma cell tumor and B-cell lymphoma are preferable.

Preferable examples of plasma cell tumor include multiple myeloma.

Examples of mature T-cell tumor and NK-cell tumor include T-cell prolymphocytic leukemia (T-PLL), aggressive NK-cell leukemia/lymphoma, adult T-cell leukemia/lymphoma, and peripheral T-cell lymphoma not otherwise specified (PTCL-NOS).

Examples of Hodgkin's lymphoma include nodular lymphocyte-predominant Hodgkin's lymphoma, classical Hodgkin's lymphoma, nodular sclerosis classical Hodgkin's lymphoma, and mixed cellularity classical Hodgkin's lymphoma.

FAB classification has been hitherto known for use in the diagnosis and classification of hematopoietic tumors. In recent years, WHO classification has also been used. The compound of the present invention or a salt thereof is useful for the various hematopoietic tumors classified by both FAB classification and WHO classification.

When the compound or a salt thereof of the present invention is used as a pharmaceutical preparation, a pharmaceutical carrier can be added, if required, thereby forming a suitable dosage form according to prevention and treatment purposes. Examples of the dosage form include oral preparations, injections, suppositories, ointments, patches, eye-drops, and the like. Of these, injections (intravenous injections etc.) are preferable. Such dosage forms can be formed by methods conventionally known to persons skilled in the art.

As the pharmaceutical carrier, various conventional organic or inorganic carrier materials used as preparation materials may be blended as an excipient, binder, disintegrant, lubricant, or coating agent in solid preparations; or as a solvent, solubilizing agent, suspending agent, isotonizing agent, pH adjuster/buffer, or soothing agent in liquid preparations. Moreover, pharmaceutical preparation additives, such as antiseptics, antioxidants, colorants, sweeteners, and stabilizers, may also be used, if required.

When a liquid preparation for oral administration is prepared, a taste-masking agent, a buffer, a stabilizer, a flavoring agent, and the like, may be added to the compound of the present invention; and the resulting mixture may be formulated into an oral liquid preparation, syrup, elixir, etc., according to an ordinary method.

When a suppository is prepared, pharmaceutically acceptable carriers known in the art, such as polyethylene glycol, lanolin, cacao butter, and fatty acid triglyceride; and as necessary, surfactants such as Tween 80®, may be added to the compound of the present invention, and the resulting mixture may be formulated into a suppository according to an ordinary method.

When an ointment is prepared, a commonly used base, stabilizer, wetting agent, preservative, and the like, may be blended into the compound of the present invention, as necessary; and the obtained mixture may be mixed and formulated into an ointment according to an ordinary method.

Examples of the base include liquid paraffin, white petrolatum, white beeswax, octyl dodecyl alcohol, paraffin, and the like.

Examples of excipients include lactose, sucrose, D-mannitol, starch, crystalline cellulose, calcium silicate, and the like.

Examples of binders include hydroxypropyl cellulose, methyl cellulose, polyvinylpyrrolidone, candy powder, hypromellose, and the like.

Examples of disintegrators include sodium starch glycolate, carmellose calcium, croscarmellose sodium, crospovidon, low-substituted hydroxy propyl cellulose, partially pregelatinized starch, and the like.

Examples of lubricants include talc, magnesium stearate, sucrose fatty acid ester, stearic acid, sodium stearyl fumarate, and the like.

Examples of coating agents include ethyl cellulose, aminoalkyl methacrylate copolymer RS, hypromellose, sucrose, and the like.

Examples of solvents include water, propylene glycol, physiological saline, and the like.

Examples of solubilizing agents include polyethylene glycol, ethanol, α-cyclodextrin, macrogol 400, polysorbate 80, and the like.

Examples of suspending agents include carrageenan, crystalline cellulose/carmellose sodium, polyoxyethylene hydrogenated castor oil, and the like.

Examples of isotonizing agents include sodium chloride, glycerin, potassium chloride, and the like.

Examples of pH adjuster/buffer include sodium citrate, hydrochloric acid, lactic acid, phosphoric acid, sodium dihydrogen phosphate, and the like.

Examples of soothing agents include procaine hydrochloride, lidocaine, and the like.

Examples of antiseptics include ethyl parahydroxybenzoate, cresol, benzalkonium chloride, and the like.

Examples of antioxidants include sodium sulfite, ascorbic acid, natural vitamin E, and the like.

Examples of coloring agents include titanium oxide, iron sesquioxide, Food Blue No. 1, copper chlorophyll, and the like.

Examples of sweeteners include aspartame, saccharins, sucralose, 1-menthol, mint flavor, and the like.

Examples of stabilizers include sodium pyrosulfite, edetate sodium, erythorbic acid, magnesium oxide, dibutylhydroxytoluene, and the like.

Examples of preservatives include methyl parahydroxybenzoate, ethyl parahydroxybenzoate, propyl parahydroxybenzoate, and the like.

When a patch is prepared, the above-described ointment, cream, gel, paste, or the like, may be applied to an ordinary substrate according to an ordinary method.

As the substrate, woven fabrics or non-woven fabrics comprising cotton, staple fibers, or chemical fibers; and films or foam sheets of soft vinyl chloride, polyethylene, polyurethane, etc., are suitable.

The amount of the compound of the present invention to be incorporated in each of such dosage unit forms depends on the condition of the patient to whom the compound is administered, the dosage form, etc. In general, in the case of an oral agent, an injection, and a suppository, the amount of the compound of the present invention is preferably 10 mg/m$^2$ to 1000 mg/m$^2$ per dosage unit form.

The daily dose of the medicine in such a dosage form depends on the condition, body weight, age, gender, etc., of the patient, and cannot be generalized. For example, the daily dose of the compound of the present invention for an adult (body weight: 50 kg) may be generally 13.9 to 1500 mg, and preferably 50 to 1000 mg; and is preferably administered in one dose, or in two to three divided doses, per day.

EXAMPLES

The following describes the present invention in more detail with reference to Examples. However, the scope of the present invention is not limited to these Examples.

Commercially available reagents were used in the Examples, unless otherwise specified.

For silica gel column chromatography, Purif-Pack (registered trademark) SI produced by Moritex Corp., KP-Sil (registered trademark) Silica prepacked column produced by Biotage, or HP-Sil (registered trademark) Silica prepacked column produced by Biotage was used.

For basic silica gel column chromatography, Purif-Pack (registered trademark) NH produced by Moritex Corp or KP-NH (registered trademark) prepacked column produced by Biotage was used.

For preparative thin-layer chromatography, Kieselgel™ 60F 254, Art. 5744 produced by Merck or $NH_2$ Silica Gel 60F254 Plate produced by Wako was used.

NMR spectra were measured by using AL400 (400 MHz; produced by JEOL), Mercury 400 (400 MHz; produced by Agilent Technologies, Inc.) model spectrometer, or Inova 400 (400 MHz; produced by Agilent Technologies, Inc.) model spectrometer equipped with an OMNMR probe (produced by Protasis). The measurement was carried out using tetramethylsilane as an internal standard when tetramethylsilane was contained in a deuterated solvent; otherwise, an NMR solvent was used as an internal standard. All the δ values are shown by ppm.

The microwave reaction was performed using Discover S-class produced by CEM Corporation, or Initiator produced by Biot age.

LCMS spectra were measured using an Acquity SQD (quadrupole) produced by Waters Corporation under the following conditions.
Column: YMC-Triart C18, 2.0×50 mm, 1.9 µm (produced by YMC)
MS detection: ESI positive
UV detection: 254 and 210 nm
Column flow rate: 0.5 mL/min
Mobile phase: Water/acetonitrile (0.1% formic acid)
Injection volume: 1 µL

TABLE 1

| Gradient | | |
| --- | --- | --- |
| Time (min) | Water (%) | Acetonitrile (%) |
| 0 | 95 | 5 |
| 0.1 | 95 | 5 |
| 2.1 | 5 | 95 |
| 3.0 | STOP | |

Preparative reversed-phase HPLC purification was performed using a preparative separation system available from Waters Corporation.
Column: Connected YMC-Actus Triart C18, 20×50 mm, 5 µm (produced by YMC) and YMC-Actus Triart C18, 20×10 mm, 5 µm (produced by YMC)
UV detection: 254 nm
MS detection: ESI positive
Column flow rate: 25 mL/min
Mobile phase: Water/acetonitrile (0.1% formic acid)
Injection volume: 0.1 to 0.5 mL Abbreviations s: Singlet
d: Doublet
t: Triplet
q: Quartet
m: Multiplet
brs: Broad Singlet
brm: Broad Multiplet
dd: Double Doublet
dt: Double Triplet
dq: Double Quartet
ddd: Double Double Doublet
DMSO-$d_6$: Deuterated dimethyl sulfoxide
$CDCl_3$: Deuterated chloroform
$CD_3OD$: Deuterated methanol
$PdCl_2$ (dppf) $CH_2Cl_2$: 1,1'-bis(diphenylphosphino)ferrocene-palladium(II) dichloride-dichloromethane complex
n-butyllithium: normal butyl lithium Example 1

4-Amino-5-[2-(2,6-difluorophenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of [(3aR,4R,6R,6aR)-4-(4-amino-5-iodo-pyrrolo[2,3-d]pyrimidin-7-yl)-2,2-dimethyl-3a,4,6,6a-tetrahydrofuro[3,4-d][1,3]dioxol-6-yl]methanol (2R,3R,4S,5R)-2-(4-Amino-5-iodo-pyrrolo[2,3-d]pyrimidin-7-yl)-5-(hydroxymethyl)tetrahydrofuran-3,4-diol (15 g, 34.8 mmol) was suspended at room temperature in acetone (120 mL) and 2,2-dimethoxypropane (24.4 mL). Thereafter, boron trifluoride diethyl etherate (27.8 mL, 6.3 eq) was added thereto dropwise in an ice bath with stirring so as to keep the internal temperature at 10° C. or lower. The obtained mixture was stirred for 75 minutes in an ice bath, and a 5 M aqueous sodium hydroxide solution (60 mL) was then slowly added thereto dropwise so as to keep the internal temperature at 15° C. or lower. After acetone was distilled off under reduced pressure, chloroform and water were added thereto, followed by stirring for about 5 minutes. The reaction solution was filtered through a celite bed to remove the generated insoluble matter. Thereafter, the aqueous layer was separated and extracted twice with chloroform. All of the organic layers were combined, washed with water and saturated saline, and dried over sodium sulfate, followed by distilling off the solvent. The brown oil residue was suspended in hexane (50 mL), and stirred for 2 hours. The formed solid was then collected by filtration, followed by drying, thereby obtaining the title compound (10.7 g, 71%) as a light-brown solid.
$^1$H-NMR ($CDCl_3$) δ: 8.23 (1H, s), 7.12 (1H, s), 6.40 (1H, d, J=11.5 Hz), 5.76-5.74 (2H, brs), 5.69 (1H, d, J=5.1 Hz), 5.24-5.22 (1H, m), 5.10-5.08 (1H, m), 4.49 (1H, s), 3.97-3.94 (1H, m), 3.78 (1H, t, J=11.5 Hz), 1.63 (3H, s), 1.36 (3H, s). LCMS (ESI) m/z 433 [M+H]$^+$ Step 2: Synthesis of 7-((3aR,4R,6R,6aR)-6-(aminomethyl)-2,2-dimethyltetrahydrofuro[3,4-d][1,3]dioxol-4-yl)-5-iodo-7H-pyrrolo[2,3-d]pyrimidin-4-amine

[(3aR,4R,6R,6aR)-4-(4-Amino-5-iodo-pyrrolo[2,3-d]pyrimidin-7-yl)-2,2-dimethyl-3a,4,6,6a-tetrahydrofuro[3,4-d][1,3]dioxol-6-yl]methanol (3.2 g, 7.4 mmol) and phthalimide (2.18 g, 14.8 mmol) were dissolved in tetrahydrofuran (30 mL), and triphenylphosphine (2.9 g, 11.1 mmol) was added thereto with stirring under ice-cooling. After triphenylphosphine was dissolved, diisopropyl azodicarboxylate (2.2 mL, 11.1 mmol) was added thereto dropwise with stirring under ice-cooling. After the reaction solution was stirred for 1.5 h under ice-cooling, the reaction solution was distilled off under reduced pressure, and ethanol (30 mL), water (9 mL), and hydrazine monohydrate (1.2 mL, 24.7 mmol) were added at room temperature to the residue. After being stirred under reflux overnight, the reaction solution was distilled off under reduced pressure. The residue was partitioned between ethyl acetate and saturated sodium bicarbonate solution. Then, the aqueous layer was separated and extracted with ethyl acetate. All of the organic layers were combined and dried over sodium sulfate, followed by distilling off the solvent. The residue was then purified by basic silica gel column chromatography (developing solvent: methanol/chloroform), thereby obtaining the title compound (3.23 g, quantitative) as a yellow solid.

$^1$H-NMR (CDCl$_3$) δ: 8.28 (1H, s), 7.19 (1H, s), 6.13 (1H, d, J=3.2 Hz), 5.65-5.63 (2H, brs), 5.23 (1H, dd, J=6.7, 3.2 Hz), 4.93 (1H, dd, J=6.7, 4.0 Hz), 4.18-4.14 (1H, m), 3.04 (1H, dd, J=13.4, 4.3 Hz), 2.93 (1H, dd, J=13.4, 5.9 Hz), 1.61 (3H, s), 1.37 (3H, s). LCMS (ESI) m/z 432 [M+H]$^+$ Step 3: Synthesis of tert-butyl N-(((3aR,4R,6R,6aR)-6-(4-amino-5-iodo-7H-pyrrolo[2,3-d]pyrimidin-7-yl)-2,2-dimethyltetrahydrofuro[3,4-d][1,3]dioxol-4-yl)methyl)sulfamoyl carbamate 7-((3aR,4R,6R,6aR)-6-(Aminomethyl)-2,2-dimethyltetrahydrofuro[3,4-d][1,3]dioxol-4-yl)-5-iodo-7H-pyrrolo[2,3-d]pyrimidin-4-amine (3.23 g) was dissolved in chloroform (40 mL), and 1-aza-4-azoniabicyclo[2.2.2]octan-4-ylsulfonyl(tert-butoxycarbonyl)azanido: 1,4-diazabicyclo[2.2.2]octane monohydrochloride (Reference: Organic Letters, 2012, 10, 2626-2629) (6.2 g, 14.1 mmol) was added thereto at room temperature. After the reaction solution was stirred for 2 hours at room temperature, the precipitate was filtered off and washed with chloroform. After the filtrate was concentrated, the residue was purified by silica gel column chromatography (developing solvent: chloroform/methanol), thereby obtaining the title compound (4.0 g, 88%) as a milky-white solid.

$^1$H-NMR (CDCl$_3$) δ: 9.27-9.25 (1H, brs), 8.50 (1H, s), 7.08 (1H, s), 6.04-6.02 (2H, brs), 5.65 (1H, d, J=4.7 Hz), 5.28 (1H, dd, J=6.3, 4.7 Hz), 5.07 (1H, dd, J=6.3, 2.2 Hz), 4.50 (1H, d, J=2.2 Hz), 3.63-3.49 (2H, m), 1.61 (3H, s), 1.44 (9H, s), 1.35 (3H, s). LCMS (ESI) m/z 611 [M+H]$^+$ Step 4: Synthesis of Example Compound 1 tert-Butyl N-(((3aR,4R,6R,6aR)-6-(4-amino-5-iodo-7H-pyrrolo[2,3-d]pyrimidin-7-yl)-2,2-dimethyltetrahydrofuro[3,4-d][1,3]dioxol-4-yl)methyl)sulfamoyl carbamate (20 mg, 0.033 mmol), 2-ethynyl-1,3-difluorobenzene (9.0 mg, 0.066 mmol), bis(triphenylphosphine)palladium (II) dichloride (3 mg, 0.0043 mmol), copper iodide (1 mg, 0.0053 mmol), and diisopropylethylamine (0.011 mL, 0.066 mmol) were suspended in tetrahydrofuran (0.20 mL). After the reaction solution was stirred at 70° C. for 2 hours, a mixed solution (0.60 mL) of trifluoroacetic acid/water=4/1 was added thereto at room temperature, followed by stirring at room temperature overnight. After the solvent was distilled off, the residue was purified by basic silica gel column chromatography (developing solvent: methanol/chloroform), thereby obtaining the title compound (14 mg, 91%) as a yellow powder.

$^1$H-NMR (CD$_3$OD) δ: 8.25 (1H, s), 7.68 (1H, s), 7.45-7.37 (1H, m), 7.10-7.04 (2H, m), 5.86 (1H, d, J=7.3 Hz), 4.86-4.81 (1H, m), 4.31-4.29 (1H, m), 4.27-4.25 (1H, m), 3.40-3.35 (2H, m). LCMS (ESI) m/z 481 [M+H]$^+$

Step 5: Synthesis of 4-amino-5-[2-(2,6-difluorophenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine hydrochloride tert-Butyl N-(((3aR,4R,6R,6aR)-6-(4-amino-5-((2,6-difluorophenyl)ethynyl)-7H-pyrrolo[2,3-d]pyrimidin-7-yl-2,2-dimethyltetrahydrofuro[3,4-d][1,3]dioxol-4-yl)methyl)sulfamoyl carbamate (8.05 g, 12.9 mmol) was dissolved in acetonitrile (120 mL), and concentrated hydrochloric acid (10.8 mL, 129 mmol) was added thereto at room temperature. After the mixture was stirred at room temperature for 6 hours, acetonitrile (80 mL) was added thereto, followed by stirring at room temperature overnight. The precipitate was collected by filtration and washed with acetonitrile (80 mL), followed by drying, thereby obtaining the title compound hydrochloride (5.93 g, 88%) as a white solid.

$^1$H-NMR (DMSO-D$_6$) δ: 8.42 (1H, s), 8.25 (1H, s), 7.55 (1H, tt, J=8.1, 7.7 Hz), 7.28 (2H, dd, J=8.4, 8.1 Hz), 7.02 (1H, brs), 6.61 (1H, brs), 6.03 (1H, d, J=6.6 Hz), 4.48 (1H, dd, J=6.6, 5.1 Hz), 4.12-4.10 (1H, m), 4.06-4.03 (1H, m), 3.22 (1H, dd, J=13.9, 5.5 Hz), 3.12 (1H, dd, J=13.2, 5.5 Hz). LCMS (ESI) m/z 481 [M+H]$^+$.

Example 2

4-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]-2-(o-tolyl)thiazole tert-Butyl N-(((3aR,4R,6R,6aR)-6-(4-amino-5-iodo-7H-pyrrolo[2,3-d]pyrimidin-7-yl)-2,2-dimethyltetrahydrofuro[3,4-d][1,3]dioxol-4-yl)methyl)sulfamoyl carbamate (300 mg, 0.491 mmol), 1,1'-bis(diphenylphosphino)ferrocene-palladium (II) dichloride-dichloromethane complex (40.1 mg, 0.049 mmol), and 4-(4,4,5,5-tetramethyl-1,3,2-dioxaborolan-2-yl)-2-(o-tolyl)thiazole (295 mg, 0.982 mmol) were suspended in a 2 M aqueous sodium carbonate solution (1.23 mL) and dimethoxyethane (5 mL), followed by stirring at 70° C. for 17 hours. The reaction solution was partitioned between ethyl acetate and water, and the organic layer was washed with water and concentrated. The residue was dissolved in acetonitrile (1 mL), trifluoroacetic acid (0.5 mL), and water (0.1 mL), followed by stirring at room temperature overnight. After the reaction liquid was concentrated, the residue was purified by basic silica gel column chromatography (developing solvent: methanol/chloroform), thereby obtaining the target product (110 mg, 43%) as a yellowish white solid.

$^1$H-NMR (DMSO-D$_6$) δ: 8.10 (1H, s), 8.08 (1H, s), 8.06 (1H, s), 7.70 (1H, d, J=7.3 Hz), 7.46-7.35 (3H, m), 6.60 (2H, s), 5.97 (1H, d, J=6.6 Hz), 5.40 (1H, d, J=6.6 Hz), 5.20 (1H, d, J=4.8 Hz), 4.60 (1H, dt, J=6.6, 5.5 Hz), 4.14-4.11 (1H, m), 4.08-4.04 (1H, m), 2.53 (3H, s). LCMS (ESI) m/z 518 [M+H]$^+$.

Example 3

4-Amino-5-[2-(4-benzyloxyphenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine The title compound was obtained as in step 4 of Example 1, except that 1-(benzyloxy)-4-ethynylbenzene was used in place of 2-ethynyl-1,3-difluorobenzene.

$^1$H-NMR (CDCl$_3$) δ: 8.29 (1H, s), 7.44-7.27 (8H, m), 6.96 (2H, d, J=8.8 Hz), 5.69 (1H, d, J=6.8 Hz), 5.10 (2H, s), 4.87-4.84 (1H, m), 4.36-4.33 (2H, m), 3.46-3.40 (4H, m). LCMS (ESI) m/z 551 [M+H]⁺.

Example 4

4-Amino-7-[(2R,3R,4S,5R)-3,4-dihydroxy-5-[(sulfamoylamino)methyl]tetrahydrofuran-2-yl]-5-[2-[5-(2-pyridyl)-2-thienyl]ethynyl]pyrrolo[2,3-d]pyrimidine The title compound was obtained as in step 4 of Example 1, except that 2-(5-ethynylthiophen-2-yl)pyridine was used in place of 2-ethynyl-1,3-difluorobenzene.

$^1$H-NMR (CD$_3$OD) δ: 8.49 (1H, d, J=5.1 Hz), 8.25 (1H, s), 7.84-7.82 (2H, m), 7.64 (1H, s), 7.64 (1H, d, J=4.1 Hz), 7.35 (1H, d, J=4.1 Hz), 7.30-7.27 (1H, m), 5.87 (1H, d, J=6.8 Hz), 4.87-4.84 (1H, m), 4.32-4.30 (1H, m), 4.28-4.25 (1H, m), 3.39-3.30 (2H, m). LCMS (ESI) m/z 528 [M+H]⁺.

Example 5

4-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]-2-(2-methoxyphenyl)thiazole The title compound was obtained as in Example 2, except that 2-(2-methoxyphenyl)-4-(4,4,5,5-tetramethyl-1,3,2-dioxaborolan-2-yl)thiazole was used in place of 4-(4,4,5,5-tetramethyl-1,3,2-dioxaborolan-2-yl)-2-(o-tolyl)thiazole.

$^1$H-NMR (CD$_3$OD) δ: 8.20 (1H, s), 8.17 (1H, dd, J=7.7, 1.8 Hz), 7.88 (1H, s), 7.84 (1H, s), 7.49 (1H, dt, J=1.1, 8.8 Hz), 7.24 (1H, d, J=8.8 Hz), 7.15 (1H, t, J=7.7 Hz), 5.98 (1H, d, J=6.6 Hz), 4.84-4.80 (1H, m), 4.36 (1H, dd, J=5.5, 2.9 Hz), 4.29-4.26 (1H, m), 4.08 (3H, s), 3.47-3.37 (2H, m). LCMS (ESI) m/z 534 [M+H]⁺.

Example 6

4-Amino-7-[(2R,3R,4S,5R)-3,4-dihydroxy-5-[(sulfamoylamino)methyl]tetrahydrofuran-2-yl]-5-[2-(1-naphthyl)ethynyl]pyrrolo[2,3-d]pyrimidine The title compound was obtained as in step 4 of Example 1, except that 1-ethynylnaphthalene was used in place of 2-ethynyl-1,3-difluorobenzene.

$^1$H-NMR (CD$_3$OD) δ: 8.36 (1H, d, J=8.0 Hz), 8.26 (1H, s), 7.93-7.90 (2H, m), 7.77 (1H, d, J=7.6 Hz), 7.73 (1H, s), 7.64-7.47 (3H, m), 5.90 (1H, d, J=6.8 Hz), 4.87-4.84 (1H, m), 4.34-4.32 (1H, m), 4.30-4.25 (1H, m), 3.39-3.30 (2H, m). LCMS (ESI) m/z 495 [M+H]⁺.

Example 7

4-Amino-7-[(2R,3R,4S,5R)-3,4-dihydroxy-5-[(sulfamoylamino)methyl]tetrahydrofuran-2-yl]-5-(3-phenylprop-1-ynyl)pyrrolo[2,3-d]pyrimidine The title compound was obtained as in step 4 of Example 1, except that prop-2-yn-1-yl benzene was used in place of 2-ethynyl-1,3-difluorobenzene.

$^1$H-NMR (CD$_3$OD) δ: 8.18 (1H, s), 7.43 (1H, s), 7.40 (2H, d, J=7.6 Hz), 7.33 (2H, dd, J=7.6, 7.3 Hz), 7.24 (1H, t, J=7.3 Hz), 5.80 (1H, d, J=6.8 Hz), 4.87-4.80 (1H, m), 4.30-4.25 (1H, m), 4.24-4.20 (1H, m), 3.88 (2H, s), 3.39-3.30 (2H, m). LCMS (ESI) m/z 459 [M+H]⁺.

Example 8

4-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]quinoline The title compound was obtained as in step 4 of Example 1, except that 4-ethynylquinoline was used in place of 2-ethynyl-1,3-difluorobenzene.

$^1$H-NMR (CD$_3$OD) δ: 8.83 (1H, d, J=4.4 Hz), 8.40 (1H, d, J=9.5 Hz), 8.28 (1H, s), 8.06 (1H, d, J=8.0 Hz), 7.91 (1H, s), 7.84 (1H, dd, J=8.8, 8.0 Hz), 7.76-7.73 (2H, m), 5.93 (1H, d, J=6.6 Hz), 4.87-4.80 (1H, m), 4.35-4.30 (1H, m), 4.29-4.26 (1H, m), 3.40-3.30 (2H, m). LCMS (ESI) m/z 496 [M+H]⁺.

Example 9

4-Amino-7-[(2R,3R,4S,5R)-3,4-dihydroxy-5-[(sulfamoylamino)methyl]tetrahydrofuran-2-yl]-5-[2-[4-(phenoxymethyl)phenyl]ethynyl]pyrrolo[2,3-d]pyrimidine The title compound was obtained as in step 4 of Example 1, except that 1-ethynyl-4-(phenoxymethyl)benzene was used in place of 2-ethynyl-1,3-difluorobenzene.

$^1$H-NMR (CD$_3$OD) δ: 8.25 (1H, s), 7.61 (1H, s), 7.57 (2H, d, J=8.3 Hz), 7.49 (2H, d, J=8.3 Hz), 7.28 (2H, dd, J=8.0, 7.8 Hz), 7.00 (2H, d, J=7.8 Hz), 6.94 (1H, t, J=8.0 Hz), 5.86 (1H, d, J=6.8 Hz), 5.12 (2H, s), 4.85-4.75 (1H, m), 4.35-4.30 (1H, m), 4.28-4.25 (1H, m), 3.40-3.30 (2H, m). LCMS (ESI) m/z 551 [M+H]⁺.

Example 10

4-Amino-7-[(2R,3R,4S,5R)-3,4-dihydroxy-5-[(sulfamoylamino)methyl]tetrahydrofuran-2-yl]-5-[2-(1-phenylcyclopropyl)ethynyl]pyrrolo[2,3-d]pyrimidine The title compound was obtained as in step 4 of Example 1, except that (1-ethynylcyclopropyl)benzene was used in place of 2-ethynyl-1,3-difluorobenzene.

$^1$H-NMR (CD$_3$OD) δ: 8.21 (1H, s), 7.46 (1H, s), 7.43-7.40 (2H, m), 7.32 (2H, d, J=8.0 Hz), 7.23-7.19 (1H, m), 5.82 (1H, d, J=6.8 Hz), 4.82-4.79 (1H, m), 4.30-4.28 (1H, m), 4.25-4.21 (1H, m), 3.37-3.34 (2H, m), 1.54-1.50 (2H, m), 1.40-1.37 (2H, m). LCMS (ESI) m/z 485 [M+H]⁺.

Example 11

1-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]isoquinoline The title compound was obtained as in step 4 of Example 1, except that 1-ethynylisoquinoline was used in place of 2-ethynyl-1,3-difluorobenzene.

$^1$H-NMR (DMSO-D$_6$) δ: 8.56 (1H, d, J=8.0 Hz), 8.45 (1H, d, J=8.0 Hz), 8.23 (1H, s), 8.19 (1H, s), 8.07 (1H, d, J=8.0 Hz), 7.90 (1H, d, J=8.0 Hz), 7.88-7.78 (2H, m), 7.38-7.34 (1H, brs), 6.64 (2H, s), 5.99 (1H, d, J=6.8 Hz), 5.48-5.46 (1H, brs), 5.29-5.25 (1H, brs), 4.63-4.59 (1H, m), 4.15-4.11 (1H, m), 4.10-4.06 (1H, m), 3.25-3.21 (1H, m), 3.18-3.12 (1H, m). LCMS (ESI) m/z 496 [M+H]+.

Example 12

4-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]-2-phenyl-oxazol The title compound was obtained as in Example 2, except that 2-phenyl-5-(4,4,5,5-tetramethyl-1,3,2-dioxaborolan-2-yl)oxazol was used in place of 4-(4,4,5,5-tetramethyl-1,3,2-dioxaborolan-2-yl)-2-(o-tolyl)thiazole.

$^1$H-NMR (CD$_3$OD) δ: 8.28 (1H, s), 8.07-8.00 (2H, m), 7.93 (1H, s), 7.51-7.49 (3H, m), 7.48 (1H, s), 6.05 (1H, d, J=6.3 Hz), 4.77-4.71 (2H, m), 4.33 (1H, dd, J=5.4, 3.2 Hz), 4.26-4.22 (1H, m), 3.45-3.35 (2H, m). LCMS (ESI) m/z 488 [M+H]+.

Example 13

5-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]quinoline The title compound was obtained as in step 4 of Example 1, except that 5-ethynylquinoline was used in place of 2-ethynyl-1,3-difluorobenzene.

$^1$H-NMR (CD$_3$OD) δ: 8.91 (1H, dd, J=4.4, 1.7 Hz), 8.84-8.78 (1H, m), 8.26 (1H, s), 8.04 (1H, d, J=8.5 Hz), 7.89 (1H, dd, J=7.9, 1.1 Hz), 7.81 (1H, s), 7.80-7.76 (1H, m), 7.67 (1H, dd, J=8.5, 4.4 Hz), 5.92 (1H, d, J=6.8 Hz), 4.87-4.82 (1H, m), 4.35-4.33 (1H, m), 4.29-4.26 (1H, m), 3.45-3.36 (2H, m). LCMS (ESI) m/z 496 [M+H]+.

Example 14

4-Amino-7-[(2R,3R,4S,5R)-3,4-dihydroxy-5-[(sulfamoylamino)methyl]tetrahydrofuran-2-yl]-5-[2-[2-(trifluoromethoxy)phenyl]ethynyl]pyrrolo[2,3-d]pyrimidine The title compound was obtained as in step 4 of Example 1, except that 1-ethynyl-2-(trifluoromethoxy)benzene was used in place of 2-ethynyl-1,3-difluorobenzene.

$^1$H-NMR (CD$_3$OD) δ: 8.26 (1H, s), 7.68-7.62 (1H, m), 7.65 (1H, s), 7.50-7.46 (1H, m), 7.42-7.38 (2H, m), 5.86 (1H, d, J=7.1 Hz), 4.86-4.81 (1H, m), 4.31-4.29 (1H, m), 4.27-4.25 (1H, m), 3.40-3.35 (2H, m). LCMS (ESI) m/z 529 [M+H]+.

Example 15

4-Amino-7-[(2R,3R,4S,5R)-3,4-dihydroxy-5-[(sulfamoylamino)methyl]tetrahydrofuran-2-yl]-5-[2-(2-methoxy-1-naphthyl)ethynyl]pyrrolo[2,3-d]pyrimidine The title compound was obtained as in step 4 of Example 1, except that 1-ethynyl-2-methoxynaphthalene was used in place of 2-ethynyl-1,3-difluorobenzene.

$^1$H-NMR (CD$_3$OD) δ: 8.23 (1H, s), 7.89-7.80 (2H, m), 7.66-7.57 (1H, m), 7.64 (1H, s), 7.58-7.54 (1H, m), 7.42-7.36 (2H, m), 5.90 (1H, d, J=8.0 Hz), 4.83-4.81 (1H, m), 4.37-4.33 (1H, m), 4.27-4.25 (1H, m), 4.06 (3H, s), 3.40-3.35 (2H, m). LCMS (ESI) m/z 525 [M+H]+.

Example 16

4-Amino-7-[(2R,3R,4S,5R)-3,4-dihydroxy-5-[(sulfamoylamino)methyl]tetrahydrofuran-2-yl]-5-[2-(2,6-dimethoxyphenyl)ethynyl]pyrrolo[2,3-d]pyrimidine The title compound was obtained as in step 4 of Example 1, except that 2-ethynyl-1,3-dimethoxybenzene was used in place of 2-ethynyl-1,3-difluorobenzene.

$^1$H-NMR (CD$_3$OD) δ: 8.22 (1H, s), 7.50 (1H, s), 7.28 (1H, t, J=8.5 Hz), 6.69 (2H, d, J=8.5 Hz), 5.86 (1H, d, J=6.8 Hz), 4.83-4.81 (1H, m), 4.32-4.30 (1H, m), 4.27-4.25 (1H, m), 3.91 (6H, s), 3.40-3.35 (2H, m). LCMS (ESI) m/z 505 [M+H]+.

Example 17

8-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]quinoline The title compound was obtained as in step 4 of Example 1, except that 8-ethynylquinoline was used in place of 2-ethynyl-1, 3-difluorobenzene.

$^1$H-NMR (CD$_3$OD) δ: 8.99 (1H, dd, 4.1, 1.7 Hz), 8.33 (1H, dd, 8.5, 1.7 Hz), 8.22 (1H, s), 7.91 (1H, s), 7.90-7.82 (2H, m), 7.58-7.52 (2H, m), 5.86 (1H, d, J=6.8 Hz), 4.87-4.85 (1H, m), 4.32-4.30 (1H, m), 4.27-4.25 (1H, m), 3.40-3.35 (2H, m). LCMS (ESI) m/z 496 [M+H]+.

Example 18

4-Amino-5-[2-[2-(difluoromethoxy)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine The title compound was obtained as in step 4 of Example 1, except that 1-(difluoromethoxy)-2-ethynylbenzene was used in place of 2-ethynyl-1,3-difluorobenzene.

$^1$H-NMR (CD$_3$OD) δ: 8.24 (1H, s), 7.62 (1H, s), 7.58 (1H, d, J=7.8, 1.7 Hz), 7.43-7.39 (1H, m), 7.28-7.23 (2H, m), 7.01 (1H, t, J=7.2 Hz), 5.86 (1H, d, J=6.8 Hz), 4.87-4.85 (1H, m), 4.32-4.30 (1H, m), 4.27-4.25 (1H, m), 3.40-3.35 (2H, m). LCMS (ESI) m/z 511 [M+H]+.

Example 19

4-Amino-7-[(2R,3R,4S,5R)-3,4-dihydroxy-5-[(sulfamoylamino)methyl]tetrahydrofuran-2-yl]-5-[2-(1H-pyrazolo[4,3-b]pyridin-5-yl)ethynyl]pyrrolo[2,3-d]pyrimidine The title compound was obtained as in step 4 of Example 1, except that 5-ethynyl-1H-pyrazolo[4,3-b]pyridine was used in place of 2-ethynyl-1,3-difluorobenzene.

$^1$H-NMR (CD$_3$OD) δ: 8.25 (1H, s), 8.23 (1H, s), 8.06 (1H, d, J=8.8 Hz), 7.75 (1H, s), 7.64 (1H, d, J=8.8 Hz), 5.89 (1H, d, J=6.8 Hz), 4.87-4.85 (1H, m), 4.34-4.30 (1H, m), 4.27-4.25 (1H, m), 3.40-3.35 (2H, m). LCMS (ESI) m/z 486 [M+H]+.

Example 20

4-Amino-5-[2-(4-amino-2-fluoro-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine The title compound was obtained as in step 4 of Example 1, except that 4-ethynyl-3-fluoroaniline was used in place of 2-ethynyl-1,3-difluorobenzene.

$^1$H-NMR (CD$_3$OD) δ: 8.22 (1H, s), 7.48 (1H, s), 7.21-7.17 (1H, m), 6.46-6.41 (2H, m), 5.84 (1H, d, J=6.8 Hz), 4.87-4.85 (1H, m), 4.32-4.28 (1H, m), 4.27-4.24 (1H, m), 3.40-3.35 (2H, m). LCMS (ESI) m/z 478 [M+H]$^+$.

Example 21

4-Amino-7-[(2R,3R,4S,5R)-3,4-dihydroxy-5-[(sulfamoylamino)methyl]tetrahydrofuran-2-yl]-5-(2-indan-1-ylethynyl)pyrrolo[2,3-d]pyrimidine The title compound was obtained as in step 4 of Example 1, except that 1-ethynyl-2,3-dihydro-1H-indene was used in place of 2-ethynyl-1,3-difluorobenzene.

$^1$H-NMR (CD$_3$OD) δ: 8.19 (1H, s), 7.42 (1H, s), 7.42-7.38 (1H, m), 7.26-7.18 (3H, m), 5.81 (1H, d, J=7.1 Hz), 4.84-4.79 (1H, m), 4.30-4.18 (3H, m), 3.40-3.35 (2H, m), 3.04-2.91 (2H, m), 2.62-2.54 (1H, m), 2.19-2.11 (1H, m). LCMS (ESI) m/z 485 [M+H]$^+$.

Example 22

4-Amino-7-[(2R,3R,4S,5R)-3,4-dihydroxy-5-[(sulfamoylamino)methyl]tetrahydrofuran-2-yl]-5-[2-(2-methylsulfonylphenyl)ethynyl]pyrrolo[2,3-d]pyrimidine The title compound was obtained as in step 4 of Example 1, except that 1-ethynyl-2-(methylsulfonyl)benzene was used in place of 2-ethynyl-1,3-difluorobenzene.

$^1$H-NMR (CD$_3$OD) δ: 8.24 (1H, s), 8.07 (1H, dd, J=7.7, 1.3 Hz), 7.79 (1H, dd, J=7.7, 1.3 Hz), 7.77 (1H, s), 7.75-7.70 (1H, m), 7.62-7.57 (1H, m), 5.89 (1H, d, J=6.8 Hz), 4.85-4.81 (1H, m), 4.33-4.29 (1H, m), 4.28-4.24 (1H, m), 3.40-3.35 (2H, m), 3.30 (3H, s). LCMS (ESI) m/z 523 [M+H]$^+$.

Example 23

4-[4-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-3,5-difluorophenyl]morpholine

Step 1: Synthesis of 4-(4-ethynyl-3,5-difluorophenyl)morpholine

2-Ethynyl-1,3,5-trifluorobenzene (52 mg, 0.33 mmol) and cesium carbonate (163 mg, 0.50 mmol) were dissolved in N,N-dimethylformamide (0.50 mL). Morpholine (0.044 mL, 0.50 mmol) was added thereto at room temperature, followed by stirring at 80° C. overnight. After the resulting mixture was air-cooled to room temperature, ethyl acetate (2.0 mL) and a saturated aqueous ammonium chloride solution (1.0 mL) were sequentially added thereto, and the mixture was partitioned into an aqueous layer and an organic layer. The organic layer was then sequentially washed with water and saturated saline, and dried over anhydrous sodium sulfate, followed by distilling off the solvent. The residue was purified by silica gel column chromatography (developing solvent: ethyl acetate/hexane), thereby obtaining 4-(4-ethynyl-3,5-difluorophenyl)morpholine (40 mg, 54%) as a white solid.

$^1$H-NMR (CDCl$_3$) δ: 6.37 (2H, d, J=10.7 Hz), 3.83 (4H, dd, J=5.7, 4.2 Hz), 3.40 (1H, s), 3.19 (4H, dd, J=5.7, 4.2 Hz). LCMS (ESI) m/z 224 [M+H]$^+$

Step 2: Synthesis of Example Compound 23

The title compound was obtained as in step 4 of Example 1, except that 4-(4-ethynyl-3,5-difluorophenyl)morpholine was used in place of 2-ethynyl-1,3-difluorobenzene.

$^1$H-NMR (CD$_3$OD) δ: 8.23 (1H, s), 7.56 (1H, s), 6.63 (2H, d, J=11.5 Hz), 5.85 (1H, d, J=7.1 Hz), 4.85-4.79 (1H, m), 4.30 (1H, dd, J=5.6, 2.4 Hz), 4.27-4.23 (1H, m), 3.80 (4H, t, J=4.9 Hz), 3.42-3.32 (2H, m), 3.27-3.22 (4H, m). LCMS (ESI) m/z 566 [M+H]$^+$.

Example 24

4-Amino-5-[2-(4-amino-2,6-difluoro-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine The title compound was obtained as in step 4 of Example 1, except that 4-ethynyl-3,5-difluoroaniline was used in place of 2-ethynyl-1,3-difluorobenzene.

$^1$H-NMR (CD$_3$OD) δ: 8.23 (1H, s), 7.52 (1H, s), 6.26 (2H, d, J=10.2 Hz), 5.85 (1H, d, J=6.8 Hz), 4.85-4.81 (1H, m), 4.33-4.29 (1H, m), 4.26-4.23 (1H, m), 3.40-3.34 (2H, m). LCMS (ESI) m/z 496 [M+H]$^+$.

Example 25

4-Amino-5-[2-[2,6-difluoro-4-(methylamino)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine

Step 1: Synthesis of 4-ethynyl-3,5-difluoro-N-methylaniline

The title compound was obtained as in step 1 of Example 23, except that methylamine was used in place of morpholine.

$^1$H-NMR (CDCl$_3$) δ: 6.11 (2H, d, J=10.6 Hz), 4.22-4.14 (1H, brm), 3.39 (1H, s), 2.84 (3H, s). LRMS (ESI) m/z 168 [M+H]$^+$

Step 2: Synthesis of Example Compound 25

The title compound was obtained as in step 4 of Example 1, except that 4-ethynyl-3,5-difluoro-N-methylaniline was used in place of 2-ethynyl-1,3-difluorobenzene.

$^1$H-NMR (CD$_3$OD) δ: 8.24 (1H, s), 8.18 (1H, brs), 8.03 (1H, dd, J=7.7, 1.1 Hz), 7.53 (1H, s), 7.48 (1H, t, J=7.7 Hz), 6.22 (2H, d, J=11.0 Hz), 5.86 (1H, d, J=7.0 Hz), 4.86-4.81 (1H, m), 4.32 (1H, dd, J=5.5, 2.2 Hz), 4.27-4.25 (1H, m), 3.43-3.34 (2H, m), 2.79 (3H, s). LCMS (ESI) m/z 510 [M+H]$^+$.

Example 26

4-Amino-7-[(2R,3R,4S,5R)-3,4-dihydroxy-5-[(sulfamoylamino)methyl]tetrahydrofuran-2-yl]-5-[2-[4-(ethylamino)-2,6-difluoro-phenyl]ethynyl]pyrrolo[2,3-d]pyrimidine

Step 1: Synthesis of N-ethyl-4-ethynyl-3,5-difluoroaniline

The title compound was obtained as in step 1 of Example 23, except that ethylamine was used in place of morpholine.

$^1$H-NMR (CDCl$_3$) δ: 6.10 (2H, d, J=10.3 Hz), 4.07-4.00 (1H, brm), 3.38 (1H, s), 3.18-3.11 (2H, m), 1.27 (5H, t, J=7.3 Hz). LRMS (ESI) m/z 182 [M+H]$^+$

Step 2: Synthesis of Example Compound 26

The title compound was obtained as in step 4 of Example 1, except that N-ethyl-4-ethynyl-3,5-difluoroaniline was used in place of 2-ethynyl-1,3-difluorobenzene.

$^1$H-NMR (CD$_3$OD) δ: 8.24 (1H, s), 8.07-8.00 (1H, m), 7.59-7.45 (1H, m), 7.57 (1H, s), 6.23 (2H, d, J=11.0 Hz), 5.89 (1H, d, J=7.0 Hz), 4.80 (1H, dd, J=7.0, 5.5 Hz), 4.32 (1H, dd, J=5.5, 2.6 Hz), 4.26 (1H, ddd, J=4.0, 3.7, 2.6 Hz), 3.41 (1H, dd, J=13.2, 3.7 Hz), 3.36 (1H, dd, J=13.2, 4.0 Hz), 3.13 (2H, q, J=7.3 Hz), 1.25 (3H, t, J=7.3 Hz). LCMS (ESI) m/z 524 [M+H]$^+$

Example 27

4-Amino-7-[(2R,3R,4S,5R)-3,4-dihydroxy-5-[(sulfamoylamino)methyl]tetrahydrofuran-2-yl]-5-[2-[3-(isopropylamino)phenyl]ethynyl]pyrrolo[2,3-d]pyrimidine The title compound was obtained as in step 4 of Example 1, except that 3-ethynyl-N-isopropylaniline was used in place of 2-ethynyl-1,3-difluorobenzene.

$^1$H-NMR (CD$_3$OD) δ: 8.24 (1H, s), 7.55 (1H, s), 7.11 (1H, t, J=8.3 Hz), 6.79-6.76 (2H, m), 6.67-6.65 (1H, m), 5.86 (1H, d, J=6.8 Hz), 4.84-4.79 (1H, m), 4.31 (1H, dd, J=5.6, 2.4 Hz), 4.25 (1H, q, J=3.2 Hz), 3.67-3.54 (1H, m), 3.39-3.35 (2H, m), 1.20 (6H, d, J=6.3 Hz). LCMS (ESI) m/z 502 [M+H]$^+$.

Example 28

4-Amino-5-[2-(5-amino-2-fluoro-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine The title compound was obtained as in step 4 of Example 1, except that 3-ethynyl-4-fluoroaniline was used in place of 2-ethynyl-1,3-difluorobenzene.

$^1$H-NMR (DMSO-D$_6$) δ: 8.18 (1H, s), 7.90 (1H, s), 7.38-7.33 (1H, m), 6.99 (1H, t, J=9.3 Hz), 6.70 (1H, dd, J=6.1, 2.9 Hz), 6.62-6.56 (3H, m), 5.92 (1H, d, J=7.1 Hz), 5.40 (1H, d, J=6.3 Hz), 5.23 (1H, d, J=4.4 Hz), 5.16 (2H, s), 4.57 (1H, dd, J=12.1, 6.7 Hz), 4.12-4.08 (1H, m), 4.07-4.03 (1H, m), 3.24-3.08 (2H, m).
LCMS (ESI) m/z 478 [M+H]$^+$.

Example 29

4-Amino-5-[2-[2,6-difluoro-4-[(3R)-3-fluoropyrrolidin-1-yl]phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine

Step 1: Synthesis of (3R)-1-(4-ethynyl-3,5-difluorophenyl)-3-fluoropyrrolidine The title compound was obtained as in step 1 of Example 23, except that (R)-3-fluoropyrrolidine was used in place of morpholine.

$^1$H-NMR (CDCl$_3$) δ: 6.07 (2H, d, J=10.3 Hz), 5.38 (1H, d, J=52.8 Hz), 3.59-3.38 (5H, m), 2.47-2.36 (1H, m), 2.27-2.06 (1H, m).
LCMS (ESI) m/z 226 [M+H]$^+$

Step 2: Synthesis of Example Compound 29

The title compound was obtained as in step 4 of Example 1, except that (3R)-1-(4-ethynyl-3,5-difluorophenyl)-3-fluoropyrrolidine was used in place of 2-ethynyl-1,3-difluorobenzene.

$^1$H-NMR (DMSO-D$_6$) δ: 8.16 (1H, s), 7.84 (1H, s), 7.35-7.30 (1H, m), 6.58 (2H, s), 6.42 (2H, d, J=11.2 Hz), 5.91 (1H, d, J=7.1 Hz), 5.45 (1H, d, J=52.7 Hz), 5.37 (1H, d, J=6.3 Hz), 5.20 (1H, d, J=4.4 Hz), 4.56 (1H, dd, J=12.1, 6.7 Hz), 4.11-4.07 (1H, m), 4.06-4.01 (1H, m), 3.61-3.45 (3H, m), 3.41-3.33 (1H, m), 3.24-3.16 (1H, m), 3.14-3.06 (1H, m), 2.30-2.10 (2H, m). LCMS (ESI) m/z 568 [M+H]$^+$.

Example 30

4-Amino-5-[2-[2,6-difluoro-4-[(3R)-3-hydroxypyrrolidin-1-yl]phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine

Step 1: Synthesis of (3R)-1-(4-ethynyl-3,5-difluorophenyl)-pyrrolidin-3-ol

The title compound was obtained as in step 1 of Example 23, except that (R)-pyrrolidin-3-ol was used in place of morpholine.

$^1$H-NMR (CDCl$_3$) δ: 6.02 (2H, d, J=10.5 Hz), 4.63-4.60 (1H, m), 3.50-3.43 (2H, m), 3.40-3.38 (1H, m), 3.33 (1H, dt, J=3.3, 9.0 Hz), 3.22 (1H, d, J=10.7 Hz), 2.22-2.11 (1H, m), 2.11-2.06 (1H, m). LCMS (ESI) m/z 224 [M+H]$^+$

Step 2: Synthesis of Example Compound 30

The title compound was obtained as in step 4 of Example 1, except that (3R)-1-(4-ethynyl-3,5-difluorophenyl)-pyrrolidin-3-ol was used in place of 2-ethynyl-1,3-difluorobenzene.

$^1$H-NMR (DMSO-D$_6$) δ: 8.17 (1H, s), 7.85 (1H, s), 7.36 (1H, dd, J=7.7, 4.8 Hz), 6.60 (2H, s), 6.35 (2H, d, J=11.0 Hz), 5.91 (1H, d, J=7.0 Hz), 5.39 (1H, d, J=6.2 Hz), 5.23 (1H, d, J=4.4 Hz), 5.06 (1H, d, J=3.7 Hz), 4.60-4.55 (1H, m), 4.42-4.37 (1H, m), 4.11-4.07 (1H, m), 4.06-4.02 (1H, m), 3.45-3.37 (2H, m), 3.24-3.18 (2H, m), 3.16-3.09 (2H, m), 2.07-1.99 (1H, m), 1.94-1.86 (1H, m). LCMS (ESI) m/z 566.3 [M+H]$^+$.

Example 31

4-Amino-5-[3-(2,6-difluorophenyl)prop-1-ynyl]-7-[(2R,3R,4S,5R)-3,4-dihydroxy-5-[(sulfamoylamino)methyl]tetrahydrofuran-2-yl]pyrrolo[2,3-d]pyrimidine The title compound was obtained as in step 4 of Example 1, except that 1,3-difluoro-2-(prop-2-yn-1-yl)benzene was used in place of 2-ethynyl-1,3-difluorobenzene.

$^1$H-NMR (CD$_3$OD) δ: 8.20 (1H, s), 7.40 (1H, s), 7.36-7.30 (1H, m), 7.04-6.99 (2H, m), 5.79 (1H, d, J=6.8 Hz), 4.80-4.69 (1H, m), 4.28-4.25 (1H, m), 4.22-4.20 (1H, m), 3.88 (2H, s), 3.39-3.32 (2H, m). LCMS (ESI) m/z 495 [M+H].

Example 32

4-Amino-5-[2-[2,6-difluoro-4-(2-hydroxyethylamino)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine 2-((4-Ethynyl-3,5-difluorophenyl)amino)ethanol was obtained as in step 1 of Example 23, except that 2-aminoethanol was used in place of morpholine, and the title compound was then obtained as in step 4 of Example 1, except that the thus-obtained 2-((4-ethynyl-3,5-difluorophenyl)amino)ethanol was used in place of 2-ethynyl-1,3-difluorobenzene.

$^1$H-NMR (DMSO-D$_6$) δ: 8.20 (1H, s), 7.91 (1H, s), 7.38 (1H, s), 7.03 (2H, t, J=9.5 Hz), 6.61 (2H, brs), 5.93 (1H, d, J=6.6 Hz), 5.47-5.36 (1H, m), 5.34-5.18 (1H, m), 4.60 (1H, t, J=10.0 Hz), 4.13-4.08 (1H, m), 4.08-4.04 (1H, m), 3.26-3.19 (1H, m), 3.16-3.08 (1H, m), 2.55 (2H, s). LCMS (ESI) m/z 540.3 [M+H]$^+$.

Example 33

4-Amino-5-[2-[2,6-difluoro-4-(2-oxopyrrolidin-1-yl)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine

Step 1: Synthesis of 1-(4-ethynyl-3,5-difluorophenyl)pyrrolidin-2-one

The title compound was obtained as in step 1 of Example 23, except that pyrrolidin-2-one was used in place of morpholine.

$^1$H-NMR (CDCl$_3$) δ: 7.35 (2H, d, J=10.0 Hz), 3.82 (2H, t, J=7.2 Hz), 3.47 (1H, s), 2.65 (2H, t, J=8.2 Hz), 2.23-2.15 (2H, m).

LCMS (ESI) m/z 222 [M+H]$^+$

Step 2: Synthesis of Example Compound 33

The title compound was obtained as in step 4 of Example 1, except that 1-(4-ethynyl-3,5-difluorophenyl)pyrrolidin-2-one was used in place of 2-ethynyl-1,3-difluorobenzene.

$^1$H-NMR (DMSO-D$_6$) δ: 8.18 (1H, s), 7.97 (1H, s), 7.64 (2H, d, J=10.5 Hz), 7.33-7.30 (1H, brs), 6.58 (2H, s), 5.92 (1H, d, J=7.3 Hz), 5.38 (1H, d, J=6.8 Hz), 5.21 (1H, d, J=4.1 Hz), 4.60-4.54 (1H, m), 4.08-4.07 (1H, m), 4.05-4.02 (1H, m), 3.84 (2H, t, J=7.2 Hz), 3.27-3.18 (1H, m), 3.15-3.08 (1H, m), 2.56 (2H, t, J=8.2 Hz), 2.10-2.02 (2H, m). LCMS (ESI) m/z 564 [M+H].

Example 34

4-[4-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-3-ethoxy-5-fluoro-phenyl]morpholine

Step 1: Synthesis of 4-(3-ethoxy-4-ethynyl-5-fluorophenyl)morpholine 4-(4-ethynyl-3,5-difluorophenyl)morpholine (100 mg, 0.448 mmol) was dissolved in ethanol (3 mL). Sodium ethoxide (a 21 wt % ethanol solution, 0.168 mL, 0.448 mmol) was added thereto, followed by stirring for 0.5 hours in a sealed container at 160° C. After the resulting mixture was air-cooled to room temperature, ethyl acetate (5.0 mL) and a saturated ammonium chloride solution (2.0 mL) were sequentially added thereto, and the mixture was partitioned into an aqueous layer and an organic layer. The organic layer was then sequentially washed with water and saturated saline, and dried over anhydrous sodium sulfate, followed by distilling off the solvent. The residue was purified by silica gel column chromatography (developing solvent: hexane/ethyl acetate), thereby obtaining 4-(3-ethoxy-4-ethynyl-5-fluorophenyl)morpholine (60 mg, 54%) as a green solid.

$^1$H-NMR (CDCl$_3$) δ: 6.20 (1H, dd, J=12.1, 2.2 Hz), 6.13 (1H, s), 4.12-4.07 (2H, m), 3.85-3.82 (4H, m), 3.41 (1H, s), 3.20-3.15 (4H, m), 1.46 (3H, t, J=7.1 Hz). LCMS (ESI) m/z 250 [M+H]$^+$

Step 2: Synthesis of Example Compound 34

The title compound was obtained as in Example 1, except that 4-(3-ethoxy-4-ethynyl-5-fluorophenyl)morpholine was used in place of 2-ethynyl-1,3-difluorobenzene.

$^1$H-NMR (DMSO-D$_6$) δ: 8.17 (1H, s), 7.77 (1H, s), 7.41-7.36 (1H, m), 6.60 (2H, s), 6.48 (1H, d, J=13.6 Hz), 6.42 (1H, s), 5.90 (1H, d, J=7.0 Hz), 5.37 (1H, d, J=6.6 Hz), 5.21 (1H, d, J=4.4 Hz), 4.60-4.55 (1H, m), 4.20 (2H, q, J=7.0 Hz), 4.12-4.07 (1H, m), 4.06-4.02 (1H, m), 3.74-3.69 (4H, m), 3.27-3.05 (6H, m), 1.36 (3H, t, J=7.0 Hz). LCMS (ESI) m/z 592 [M+H]$^+$.

Example 35

4-Amino-7-[(2R,3R,4S,5R)-3,4-dihydroxy-5-[(sulfamoylamino)methyl]tetrahydrofuran-2-yl]-5-[2-(2-ethoxy-4,6-difluoro-phenyl)ethynyl]pyrrolo[2,3-d]pyrimidine

Step 1: Synthesis of 1-ethoxy-2-ethynyl-3,5-difluorobenzene

The title compound was obtained as in step 1 of Example 34, except that 2-ethynyl-1,3,5-trifluorobenzene was used in place of 4-(4-ethynyl-3,5-difluorophenyl)morpholine.

$^1$H-NMR (CDCl$_3$) δ: 6.48-6.39 (2H, m), 4.09 (2H, q, J=7.0 Hz), 3.45 (1H, s), 1.47 (3H, t, J=7.0 Hz).

Step 2: Synthesis of Example Compound 35

The title compound was obtained as in Example 1, except that 1-ethoxy-2-ethynyl-3,5-difluorobenzene was used in place of 2-ethynyl-1,3-difluorobenzene.

$^1$H-NMR (DMSO-D$_6$) δ: 8.18 (1H, s), 7.90 (1H, s), 7.36 (1H, s), 7.02-6.97 (2H, m), 6.61-6.58 (2H, m), 5.92 (1H, d,

J=7.1 Hz), 5.41-5.36 (1H, m), 5.24-5.21 (1H, m), 4.61-4.55 (1H, m), 4.24 (2H, q, J=7.0 Hz), 4.11-4.08 (1H, m), 4.07-4.03 (1H, m), 3.25-3.07 (2H, m), 1.38 (3H, t, J=7.0 Hz). LCMS (ESI) m/z 525 [M+H]$^+$.

Example 36

4-Amino-7-[(2R,3R,4S,5R)-3,4-dihydroxy-5-[(sulfamoylamino)methyl]tetrahydrofuran-2-yl]-5-[3-(2-fluorophenyl)prop-1-ynyl]pyrrolo[2,3-d]pyrimidine The title compound was obtained as in Example 1, except that 1-fluoro-2-(prop-2-yn-1-yl)benzene was used in place of 2-ethynyl-1,3-difluorobenzene.
$^1$H-NMR (CD$_3$OD) δ: 8.20 (1H, s), 7.54 (1H, t, J=8.0 Hz), 7.45 (1H, s), 7.33-7.25 (1H, m), 7.20-7.16 (1H, m), 7.13-7.08 (1H, m), 5.82 (1H, d, J=6.8 Hz), 4.80-4.77 (1H, m), 4.30-4.28 (1H, m), 4.24-4.23 (1H, m), 3.90 (2H, s), 3.40-3.31 (2H, m). LCMS (ESI) m/z 477 [M+H].

Example 37

4-[4-[2-[4-Amino-7-[(2R,3R,4S,5R)-3,4-dihydroxy-5-[(sulfamoylamino)methyl]tetrahydrofuran-2-yl] pyrrolo[2,3-d]pyrimidin-5-yl]ethynyl]-3,5-difluorophenyl]thiomorpholine Step 1: Synthesis of 4-(4-ethynyl-3,5-difluorophenyl)thiomorpholine The title compound was obtained as in step 1 of Example 23, except that thiomorpholine was used in place of morpholine.
$^1$H-NMR (CDCl$_3$) δ: 6.32 (2H, d, J=11.0 Hz), 3.69-3.66 (4H, m), 3.38 (1H, s), 2.69-2.66 (4H, m). LCMS (ESI) m/z 240 [M+H]$^+$ Step 2: Synthesis of Example Compound 37

The title compound was obtained as in Example 1, except that 4-(4-ethynyl-3,5-difluorophenyl)thiomorpholine was used in place of 2-ethynyl-1,3-difluorobenzene.
$^1$H-NMR (DMSO-D$_6$) δ: 8.18 (1H, s), 7.87 (1H, s), 7.36-7.32 (1H, m), 6.78 (2H, d, J=12.1 Hz), 6.59 (2H, s), 5.92 (1H, d, J=7.0 Hz), 5.46-5.32 (1H, m), 5.30-5.16 (1H, m), 4.59-4.55 (1H, m), 4.11-4.07 (1H, m), 4.06-4.02 (1H, m), 3.78-3.72 (4H, m), 3.24-3.06 (2H, m), 2.63-2.58 (4H, m). LCMS (ESI) m/z 582 [M+H]$^+$.

Example 38

4-Amino-5-[2-[2,6-difluoro-4-(3-hydroxy-1-piperidyl)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of 1-(4-ethynyl-3,5-difluorophenyl)piperidin-3-ol The title compound was obtained as in step 1 of Example 23, except that piperidin-3-ol was used in place of morpholine.
$^1$H-NMR (CDCl$_3$) δ: 6.39 (2H, dt, J=17.2, 3.2 Hz), 3.91-3.83 (1H, m), 3.49 (1H, dd, J=12.7, 3.4 Hz), 3.38 (1H, s), 3.31-3.28 (1H, m), 3.12-3.00 (2H, m), 1.98-1.82 (3H, m), 1.68-1.56 (2H, m). LCMS (ESI) m/z 238 [M+H]$^+$ Step 2: Synthesis of Example Compound 38

The title compound was obtained as in Example 1, except that 1-(4-ethynyl-3,5-difluorophenyl)piperidin-3-ol was used in place of 2-ethynyl-1,3-difluorobenzene.
$^1$H-NMR (DMSO-D$_6$) δ: 8.20 (1H, s), 7.86 (1H, s), 7.36-7.32 (1H, m), 6.72 (2H, d, J=12.1 Hz), 6.59 (2H, s), 5.92 (1H, d, J=7.0 Hz), 5.38 (1H, d, J=6.2 Hz), 5.22 (1H, d, J=3.3 Hz), 4.88-4.83 (1H, m), 4.60-4.54 (1H, m), 4.11-4.08 (1H, m), 4.06-4.03 (1H, m), 3.68-3.51 (3H, m), 3.25-3.17 (1H, m), 3.15-3.07 (1H, m), 3.01-2.94 (1H, m), 2.84 (1H, dd, J=12.6, 8.6 Hz), 1.89-1.83 (1H, m), 1.75-1.69 (1H, m), 1.48-1.34 (2H, m). LCMS (ESI) m/z 580 [M+H]$^+$.

Example 39

4-Amino-5-[2-[2,6-difluoro-4-(3-hydroxyazetidin-1-yl)phenyl]ethynyl]-7-[(2R,3R,4S,5R)-3,4-dihydroxy-5-[(sulfamoylamino)methyl]tetrahydrofuran-2-yl] pyrrolo[2,3-d]pyrimidine Step 1: Synthesis of 1-(4-ethynyl-3,5-difluorophenyl)azetidin-3-ol The title compound was obtained as in step 1 of Example 23, except that azetidin-3-ol was used in place of morpholine.
$^1$H-NMR (CDCl$_3$) δ: 5.90 (2H, dq, J=19.2, 3.4 Hz), 4.83-4.76 (1H, m), 4.17 (2H, dd, J=8.4, 7.0 Hz), 3.75 (2H, dd, J=8.4, 4.2 Hz), 3.38 (1H, s), 2.21 (1H, d, J=6.2 Hz). LCMS (ESI) m/z 210 [M+H]$^+$ Step 2: Synthesis of Example Compound 39

The title compound was obtained as in Example 1, except that 1-(4-ethynyl-3,5-difluorophenyl)azetidin-3-ol was used in place of 2-ethynyl-1,3-difluorobenzene.
$^1$H-NMR (DMSO-D$_6$) δ: 8.17 (1H, s), 7.85 (1H, s), 7.37-7.32 (1H, m), 6.59 (2H, s), 6.24 (2H, d, J=9.9 Hz), 5.91 (1H, d, J=7.0 Hz), 5.75 (1H, d, J=6.6 Hz), 5.38 (1H, d, J=6.6 Hz), 5.22 (1H, d, J=4.4 Hz), 4.60-4.54 (2H, m), 4.16-4.07 (3H, m), 4.06-4.02 (1H, m), 3.64 (2H, dd, J=8.6, 4.6 Hz), 3.25-3.17 (1H, m), 3.14-3.05 (1H, m). LCMS (ESI) m/z 552 [M+H]$^+$.

Example 40

4-Amino-5-[2-[2,6-difluoro-4-[(3R)-3-hydroxy-1-piperidyl]phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of (3R)-1-(4-ethynyl-3,5-difluorophenyl)piperidin-3-ol The title compound was obtained as in step 1 of Example 23, except that (R)-piperidin-3-ol was used in place of morpholine.
$^1$H-NMR (CDCl$_3$) δ: 6.39 (2H, d, J=11.0 Hz), 3.91-3.84 (1H, m), 3.49 (1H, dd, J=12.5, 3.3 Hz), 3.38 (1H, s), 3.33-3.27 (1H, m), 3.12-3.01 (2H, m), 1.98-1.85 (2H, m), 1.80 (1H, d, J=6.2 Hz), 1.69-1.60 (1H, m). LCMS (ESI) m/z 238 [M+H]$^+$ Step 2: Synthesis of Example Compound 40

The title compound was obtained as in Example 1, except that (3R)-1-(4-ethynyl-3,5-difluorophenyl)piperidin-3-ol was used in place of 2-ethynyl-1,3-difluorobenzene.

¹H-NMR (DMSO-D₆) δ: 8.17 (1H, s), 7.86 (1H, s), 7.36-7.32 (1H, m), 6.72 (2H, d, J=12.1 Hz), 6.59 (2H, s), 5.92 (1H, d, J=7.0 Hz), 5.38 (1H, d, J=6.6 Hz), 5.22 (1H, d, J=4.4 Hz), 4.86 (1H, d, J=4.4 Hz), 4.57 (1H, dd, J=12.3, 6.8 Hz), 4.11-4.08 (1H, m), 4.06-4.03 (1H, m), 3.68-3.50 (3H, m), 3.23-3.18 (1H, m), 3.15-3.07 (1H, m), 3.01-2.94 (1H, m), 2.84 (1H, dd, J=12.6, 8.6 Hz), 1.89-1.83 (1H, m), 1.75-1.69 (1H, m), 1.47-1.37 (2H, m). LCMS (ESI) m/z 580 [M+H]⁺.

Example 41

1-[4-[2-[4-amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-3,5-difluorophenyl]pyrrolidine-3-carboxylic acid Step 1: Synthesis of 1-(4-ethynyl-3,5-difluorophenyl)pyrrolidine-3-carboxylic acid The title compound was obtained as in step 1 of Example 23, except that pyrrolidine-3-carboxylic acid was used in place of morpholine.
¹H-NMR (CDCl₃) δ: 6.06 (2H, d, J=10.3 Hz), 3.61-3.52 (2H, m), 3.46-3.25 (4H, m), 2.38-2.33 (2H, m). LCMS (ESI) m/z 252 [M+H]⁺

Step 2: Synthesis of Example Compound 41

The title compound was obtained as in step 4 of Example 1, except that 1-(4-ethynyl-3,5-difluorophenyl)pyrrolidine-3-carboxylic acid was used in place of 2-ethynyl-1,3-difluorobenzene.
¹H-NMR (DMSO-D₆) δ: 12.59 (1H, s), 8.17 (1H, s), 7.85 (1H, s), 7.36-7.32 (1H, m), 6.59 (2H, s), 6.39 (2H, d, J=11.0 Hz), 5.91 (1H, d, J=7.0 Hz), 5.38 (1H, d, J=6.2 Hz), 5.22 (1H, d, J=4.4 Hz), 4.59-4.55 (1H, m), 4.12-4.08 (1H, m), 4.06-4.02 (1H, m), 3.54-3.42 (2H, m), 3.24-3.07 (5H, m), 2.27-2.11 (2H, m). LCMS (ESI) m/z 594 [M+H]⁺.

Example 42

4-Amino-5-[2-[2,6-difluoro-4-(4-oxo-1-piperidyl)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of 1-(4-ethynyl-3,5-difluorophenyl)piperidin-4-one The title compound was obtained as in step 1 of Example 23, except that piperidin-4-one was used in place of morpholine.
¹H-NMR (CDCl₃) δ: 6.40 (2H, d, J=11.0 Hz), 3.66 (4H, t, J=6.0 Hz), 3.41 (1H, s), 2.57 (4H, t, J=6.0 Hz). LCMS (ESI) m/z 236 [M+H]⁺

Step 2: Synthesis of Example Compound 42

The title compound was obtained as in step 4 of Example 1, except that 1-(4-ethynyl-3,5-difluorophenyl)piperidin-4-one was used in place of 2-ethynyl-1,3-difluorobenzene.
¹H-NMR (DMSO-D₆) δ: 8.18 (1H, s), 7.88 (1H, s), 7.37-7.32 (1H, m), 6.86 (2H, d, J=11.7 Hz), 6.60 (2H, s), 5.92 (1H, d, J=7.0 Hz), 5.40 (1H, d, J=6.2 Hz), 5.24 (1H, d, J=4.0 Hz), 4.60-4.55 (1H, m), 4.11-4.08 (1H, m), 4.06-4.03 (1H, m), 3.73 (4H, t, J=5.9 Hz), 3.25-3.18 (1H, m), 3.14-3.07 (1H, m), 2.44 (4H, t, J=5.9 Hz). LCMS (ESI) m/z 578 [M+H]⁺.

Example 43

4-amino-5-[2-[4-(azetidin-1-yl)-2,6-difluoro-phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of 1-(4-ethynyl-3,5-difluorophenyl)azetidine The title compound was obtained as in step 1 of Example 23, except that azetidine was used in place of morpholine.
¹H-NMR (CDCl₃) δ: 5.86 (2H, d, J=9.5 Hz), 3.93-3.89 (4H, m), 3.37 (1H, s), 2.45-2.37 (2H, m). LCMS (ESI) m/z 194 [M+H]⁺

Step 2: Synthesis of Example Compound 43

The title compound was obtained as in step 4 of Example 1, except that 1-(4-ethynyl-3,5-difluorophenyl)azetidine was used in place of 2-ethynyl-1,3-difluorobenzene.
¹H-NMR (DMSO-D₆) δ: 8.17 (1H, s), 7.85 (1H, s), 7.36-7.33 (1H, m), 6.60 (2H, s), 6.20 (2H, d, J=9.9 Hz), 5.91 (1H, d, J=7.0 Hz), 5.38 (1H, d, J=6.6 Hz), 5.22 (1H, d, J=4.4 Hz), 4.57 (1H, q, J=6.2 Hz), 4.11-4.07 (1H, m), 4.05-4.03 (1H, m), 3.91 (4H, t, J=7.3 Hz), 3.25-3.17 (1H, m), 3.14-3.07 (1H, m), 2.37-2.30 (2H, m). LCMS (ESI) m/z 536 [M+H]⁺.

Example 44

4-Amino-7-[(2R,3R,4S,5R)-3,4-dihydroxy-5-[(sulfamoylamino)methyl]tetrahydrofuran-2-yl]-5-[2-(2-pyridyl)ethynyl]pyrrolo[2,3-d]pyrimidine The title compound was obtained as in step 4 of Example 1, except that 2-ethynylpyridine was used in place of 2-ethynyl-1, 3-difluorobenzene.
¹H-NMR (DMSO-D₆) δ: 8.12 (1H, s), 7.90 (1H, s), 7.78 (1H, t, J=7.6 Hz), 7.60 (1H, d, J=7.6 Hz), 7.33 (1H, dd, J=7.6, 5.1 Hz), 7.28 (1H, dd, J=7.6, 5.1 Hz), 6.53 (2H, s), 5.86 (1H, d, J=7.0 Hz), 4.52 (1H, dd, J=7.0, 5.7 Hz), 4.04 (1H, dd, J=5.1, 2.5 Hz), 4.01-3.97 (1H, brm), 3.18-3.02 (2H, m). LCMS (ESI) m/z 446 [M+H]⁺.

Example 45

4-Amino-5-[2-(2-chlorophenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine The title compound was obtained as in step 4 of Example 1, except that 1-chloro-2-ethynylbenzene was used in place of 2-ethynyl-1,3-difluorobenzene.
¹H-NMR (DMSO-D₆) δ: 8.12 (1H, s), 7.88 (1H, s), 7.63-7.52 (1H, m), 7.54-7.53 (1H, m), 7.38-7.32 (2H, m), 7.27 (1H, dd, J=7.6, 5.1 Hz), 6.53 (2H, s), 5.86 (1H, d, J=7.0

Hz), 4.51 (1H, dd, J=7.0, 5.1 Hz), 4.03 (1H, dd, J=5.1, 2.5 Hz), 4.00-3.97 (1H, brm), 3.19-3.02 (2H, m). LCMS (ESI) m/z 479 [M+H]$^+$.

Example 46

4-Amino-7-[(2R,3R,4S,5R)-3,4-dihydroxy-5-[(sulfamoylamino)methyl]tetrahydrofuran-2-yl]-5-[2-(2-fluorophenyl)ethynyl]pyrrolo[2,3-d]pyrimidine The title compound was obtained as in step 4 of Example 1, except that 1-ethynyl-2-fluorobenzene was used in place of 2-ethynyl-1,3-difluorobenzene.
$^1$H-NMR (DMSO-D$_6$) δ: 8.11 (1H, s), 7.86 (1H, s), 7.58 (1H, t, J=7.6 Hz), 7.43-7.37 (1H, m), 7.30-7.26 (2H, m), 7.21 (1H, t, J=7.6 Hz), 6.52 (2H, s), 5.86 (1H, d, J=7.0 Hz), 4.51 (1H, dd, J=7.0, 5.1 Hz), 4.03 (1H, t, J=2.5 Hz), 4.00-3.97 (1H, m), 3.17-3.02 (2H, m). LCMS (ESI) m/z 463 [M+H]$^+$.

Example 47

4-Amino-7-[(2R,3R,4S,5R)-3,4-dihydroxy-5-[(sulfamoylamino)methyl]tetrahydrofuran-2-yl]-5-[2-(2-methoxyphenyl)ethynyl]pyrrolo[2,3-d]pyrimidine The title compound was obtained as in step 4 of Example 1, except that 1-ethynyl-2-methoxybenzene was used in place of 2-ethynyl-1,3-difluorobenzene.
$^1$H-NMR (DMSO-D$_6$) δ: 8.10 (1H, s), 7.73 (1H, s), 7.36-7.29 (3H, m), 7.04 (1H, d, J=8.2 Hz), 6.92 (1H, t, J=7.6 Hz), 6.53 (2H, s), 5.84 (1H, d, J=7.0 Hz), 4.50 (1H, dd, J=7.0, 5.1 Hz), 4.03 (1H, dd, J=5.1, 2.5 Hz), 3.84-3.84 (1H, brm), 4.00 (3H, s), 3.21-3.01 (2H, m). LCMS (ESI) m/z 475 [M+H]$^+$.

Example 48

4-Amino-7-[(2R,3R,4S,5R)-3,4-dihydroxy-5-[(sulfamoylamino)methyl]tetrahydrofuran-2-yl]-5-[2-(4-dimethylaminophenyl)ethynyl]pyrrolo[2,3-d]pyrimidine The title compound was obtained as in step 4 of Example 1, except that 4-ethynyl-N,N-dimethylaniline was used in place of 2-ethynyl-1,3-difluorobenzene.
$^1$H-NMR (DMSO-D$_6$) δ: 8.10 (1H, s), 7.73 (1H, s), 7.36-7.29 (3H, m), 7.04 (1H, d, J=8.2 Hz), 6.92 (1H, t, J=7.6 Hz), 6.53 (2H, s), 5.84 (1H, d, J=7.0 Hz), 4.50 (1H, dd, J=7.0, 5.1 Hz), 4.03 (1H, dd, J=5.1, 2.5 Hz), 3.84-3.84 (1H, brm), 4.00 (3H, s), 3.21-3.01 (2H, m). LCMS (ESI) m/z 475 [M+H]$^+$.

Example 49

4-Amino-5-[2-(2-cyanophenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine The title compound was obtained as in step 4 of Example 1, except that 2-ethynylbenzonitrile was used in place of 2-ethynyl-1,3-difluorobenzene.
$^1$H-NMR (DMSO-D$_6$) δ: 8.12 (1H, s), 7.93 (1H, s), 7.87 (1H, d, J=7.5 Hz), 7.74-7.68 (2H, m), 7.52 (1H, dt, J=1.4, 7.5 Hz), 7.29 (1H, m), 6.53 (2H, s), 5.87 (1H, d, J=6.8 Hz), 5.40 (1H, brs), 5.23 (1H, brs), 4.53 (1H, t, J=5.5 Hz), 4.04 (2H, dd, J=5.5, 2.7 Hz), 4.01-3.98 (2H, brm), 3.19-3.03 (2H, m). LCMS (ESI) m/z 470 [M+H]$^+$.

Example 50

4-Amino-5-(3-cyclohexylprop-1-ynyl)-7-[(2R,3R,4S,5R)-3,4-dihydroxy-5-[(sulfamoylamino)methyl]tetrahydrofuran-2-yl]pyrrolo[2,3-d]pyrimidine The title compound was obtained as in step 4 of Example 1, except that prop-2-yn-1-yl cyclohexane was used in place of 2-ethynyl-1,3-difluorobenzene.
$^1$H-NMR (DMSO-D$_6$) δ: 8.05 (1H, s), 7.56 (1H, s), 7.27 (1H, dd, J=7.5, 4.1 Hz), 6.51 (2H, s), 5.79 (1H, d, J=6.8 Hz), 4.46 (1H, dd, J=6.8, 5.5 Hz), 4.01 (1H, dd, J=5.5, 2.1 Hz), 3.97-3.94 (1H, brm), 3.17-2.99 (2H, m), 2.32 (2H, d, J=6.2 Hz), 1.76-1.72 (2H, brm), 1.65-1.60 (2H, brm), 1.58-1.54 (1H, brm), 1.49-1.41 (1H, brm), 1.23-0.93 (5H, m). LCMS (ESI) m/z 465 [M+H]$^+$.

Example 51

4-Amino-7-[(2R,3R,4S,5R)-3,4-dihydroxy-5-[(sulfamoylamino)methyl]tetrahydrofuran-2-yl]-5-[2-(2-fluoro-6-methoxy-phenyl)ethynyl]pyrrolo[2,3-d]pyrimidine Step 1: Synthesis of 2-ethynyl-1-fluoro-3-methoxybenzene 2-Fluoro-6-methoxybenzaldehyde (2.0 g, 13 mmol) was dissolved in methanol (20 mL). Then, potassium carbonate (3.6 g, 26 mmol) was added thereto at room temperature, and dimethyl(1-diazo-2-oxopropyl)phosphonate (2.3 mL, 16 mmol) was added thereto under ice-cooling, followed by stirring under ice-cooling for 1 hour and at room temperature for another 1 hour. The reaction solution was partitioned with the addition of ethyl acetate, a saturated aqueous sodium hydrogen carbonate solution, and water, and the organic layer was washed with saturated saline. After being dried over sodium sulfate, the resulting product was filtered and concentrated, and the residue was purified by silica gel column chromatography (developing solvent: ethyl acetate/hexane), thereby obtaining 2-ethynyl-1-fluoro-3-methoxybenzene (1.6 g, 11 mmol, 81%) as a reddish brown solid.
$^1$H-NMR (CDCl$_3$) δ: 7.31-7.22 (1H, m), 6.76-6.65 (2H, m), 3.92 (3H, s), 3.53 (1H, s).

Step 2: Synthesis of Example Compound 51

The title compound was obtained as in step 4 of Example 1, except that 2-ethynyl-1-fluoro-3-methoxybenzene was used in place of 2-ethynyl-1,3-difluorobenzene.
$^1$H-NMR (CD$_3$OD) δ: 8.23 (1H, s), 7.57 (1H, s), 7.37-7.30 (1H, m), 6.90 (1H, d, J=8.5 Hz), 6.82-6.78 (1H, m), 5.86 (1H, d, J=6.8 Hz), 4.87-4.85 (1H, m), 4.32-4.27 (1H, m), 4.26-4.24 (1H, m), 3.97 (3H, s), 3.40-3.35 (2H, m). LCMS (ESI) m/z 493 [M+H]$^+$.

Example 52

4-Amino-5-[2-(5-benzyloxy-2-pyridyl)ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of 5-(benzyloxy)-2-ethynylpyridine The title compound was obtained as in step 1 of Example 51, except that 5-(benzyloxy)picolinaldehyde was used in place of 2-fluoro-6-methoxybenzaldehyde.

¹H-NMR (CDCl₃) δ: 8.36 (1H, d, J=2.9 Hz), 7.44-7.34 (5H, m), 7.20 (2H, dd, 8.8, 2.9 Hz), 5.13 (2H, s), 3.07 (1H, s). LCMS (ESI) m/z 210 [M+H]⁺

Step 2: Synthesis of Example Compound 52

The title compound was obtained as in step 4 of Example 1, except that 5-(benzyloxy)-2-ethynylpyridine was used in place of 2-ethynyl-1,3-difluorobenzene.

¹H-NMR (CD₃OD) δ: 8.29 (1H, d, J=2.9 Hz), 8.22 (1H, s), 7.65 (1H, s), 7.56 (1H, d, J=8.0 Hz), 7.50-7.30 (6H, m), 5.86 (1H, d, J=6.8 Hz), 5.20 (2H, s), 4.85-4.75 (1H, m), 4.35-4.20 (2H, m), 3.40-3.30 (2H, m). LCMS (ESI) m/z 552 [M+H]⁺.

Example 53

4-Amino-5-[2-(4-benzyloxy-2-methoxy-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of 4-(benzyloxy)-1-ethynyl-2-methoxybenzene The title compound was obtained as in step 1 of Example 51, except that 4-(benzyloxy)-2-methoxybenzaldehyde was used in place of 2-fluoro-6-methoxybenzaldehyde.

¹H-NMR (CDCl₃) δ: 7.48-7.32 (6H, m), 6.50-6.55 (2H, m), 5.07 (2H, s), 3.87 (3H, s), 3.24 (1H, s). LCMS (ESI) m/z 239 [M+H]⁺

Step 2: Synthesis of Example Compound 53

The title compound was obtained as in step 4 of Example 1, except that 4-(benzyloxy)-1-ethynyl-2-methoxybenzene was used in place of 2-ethynyl-1,3-difluorobenzene.

¹H-NMR (DMSO-D₆) δ: 8.16 (1H, s), 7.74 (1H, s), 7.46-7.32 (7H, m), 6.78-6.76 (1H, brs), 6.67 (1H, d, J=8.0 Hz), 6.63-6.59 (2H, brs), 5.90 (1H, d, J=6.3 Hz), 5.39 (1H, d, J=6.1 Hz), 5.23 (1H, d, J=4.1 Hz), 5.16 (2H, s), 4.61-4.55 (1H, m), 4.12-4.08 (1H, m), 4.06-4.04 (1H, m), 3.89 (3H, s), 3.26-3.15 (1H, m), 3.15-3.03 (1H, m). LCMS (ESI) m/z 581 [M+H]⁺.

Example 54

4-Amino-5-[2-(2,6-difluoro-4-hydroxy-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of 4-ethynyl-3,5-difluorophenol The title compound was obtained as in step 1 of Example 51, except that 2,6-difluoro-4-hydroxybenzaldehyde was used in place of 2-fluoro-6-methoxybenzaldehyde.

¹H-NMR (CDCl₃) δ: 6.43 (2H, d, J=8.0 Hz), 5.60-5.40 (1H, brs.), 3.42 (1H, s).

Step 2: Synthesis of Example Compound 54

The title compound was obtained as in step 4 of Example 1, except that 4-ethynyl-3,5-difluorophenol was used in place of 2-ethynyl-1,3-difluorobenzene.

¹H-NMR (CD₃OD) δ: 8.23 (1H, s), 7.58 (1H, s), 6.48 (2H, d, J=9.5 Hz), 5.86 (1H, d, J=6.8 Hz), 4.85-4.81 (1H, m), 4.33-4.29 (1H, m), 4.26-4.23 (1H, m), 3.40-3.34 (2H, m). LCMS (ESI) m/z 497 [M+H]⁺.

Example 55

4-Amino-7-[(2R,3R,4S,5R)-3,4-dihydroxy-5-[(sulfamoylamino)methyl]tetrahydrofuran-2-yl]-5-[2-(2-ethoxy-6-fluoro-phenyl)ethynyl]pyrrolo[2,3-d]pyrimidine Step 1: Synthesis of 2-ethoxy-6-fluorobenzaldehyde 2-Fluoro-6-hydroxybenzaldehyde (50 g, 360 mmol) was dissolved in N,N-dimethylformamide (500 mL), and potassium carbonate (74 g, 540 mmol) and iodoethane (86 mL, 1.1 mol) were added thereto at room temperature, followed by stirring at room temperature overnight. The reaction solution was partitioned with the addition of ethyl acetate and water, and extracted with ethyl acetate. The organic layer was washed with water and brine and dried over sodium sulfate, followed by filtration and concentration. The residue was purified by silica gel column chromatography (developing solvent: ethyl acetate/hexane), thereby obtaining 2-ethoxy-6-fluorobenzaldehyde (59 g, 98%) as a white solid.

¹H-NMR (CDCl₃) δ: 10.47 (1H, s), 7.50-7.41 (1H, m), 6.77-6.67 (2H, m), 4.16 (2H, q, J=6.8 Hz), 1.48 (3H, t, J=6.8 Hz). LCMS (ESI) m/z 169 [M+H]⁺

Step 2: Synthesis of 1-ethoxy-2-ethynyl-3-fluorobenzene

The title compound was obtained as in step 1 of Example 51, except that 2-ethoxy-6-fluorobenzaldehyde was used in place of 2-fluoro-6-methoxybenzaldehyde.

¹H-NMR (CDCl₃) δ: 7.28-7.20 (1H, m), 6.74-6.63 (2H, m), 4.13 (2H, q, J=7.1 Hz), 3.50 (1H, s), 1.47 (3H, t, J=7.1 Hz).

Step 3: Synthesis of Example Compound 55

The title compound was obtained as in step 4 of Example 1, except that 1-ethoxy-2-ethynyl-3-fluorobenzene was used in place of 2-ethynyl-1,3-difluorobenzene.

¹H-NMR (CD₃OD) δ: 8.24 (1H, s), 7.58 (1H, s), 7.34-7.28 (1H, m), 6.88 (1H, d, J=8.0 Hz), 6.82-6.74 (1H, m), 5.86 (1H, d, J=7.0 Hz), 4.85-4.81 (1H, m), 4.33-4.29 (1H, m), 4.27-4.21 (3H, m), 3.40-3.34 (2H, m), 1.47 (3H, t, J=7.0 Hz). LCMS (ESI) m/z 507 [M+H]⁺.

Step 4: Synthesis of 4-amino-7-[(2R,3R,4S,5R)-3,4-dihydroxy-5-[(sulfamoylamino)methyl]tetrahydrofuran-2-yl]-5-[2-(2-ethoxy-6-fluoro-phenyl)ethynyl]pyrrolo[2,3-d]pyrimidine hydrochloride The title compound hydrochloride was obtained as in step 5 of Example 1.

¹H-NMR (DMSO-D6) δ: 8.38 (1H, s), 8.13 (1H, s), 7.44-7.38 (1H, m), 7.01-6.91 (3H, m), 6.80-6.40 (1H, brs), 6.01 (1H, d, J=6.8 Hz), 4.51-4.48 (1H, m), 4.24 (2H, q, J=7.0 Hz), 4.11-4.09 (1H, m), 4.06-4.02 (1H, m), 3.24-3.19 (1H, m), 3.14-3.09 (1H, m), 1.38 (3H, t, J=7.0 Hz). LCMS (ESI) m/z 507 [M+H]⁺

Example 56

4-Amino-7-[(2R,3R,4S,5R)-3,4-dihydroxy-5-[(sulfamoylamino)methyl]tetrahydrofuran-2-yl]-5-[2-(2-fluoro-6-isopropoxy-phenyl)ethynyl]pyrrolo[2,3-d]pyrimidine

Step 1: Synthesis of 2-fluoro-6-isopropoxybenzaldehyde

The title compound was obtained as in step 1 of Example 55, except that 2-iodopropane was used in place of iodoethane.

$^1$H-NMR (CDCl$_3$) δ: 10.44 (1H, s), 7.44 (1H, dt, J=6.3, 8.5 Hz), 6.77 (1H, d, J=8.5 Hz), 6.68 (1H, dd, J=10.2, 8.5 Hz), 4.72-4.62 (1H, m), 1.41 (6H, d, J=6.1 Hz).

Step 2: Synthesis of 2-ethynyl-1-fluoro-3-isopropoxybenzene

The title compound was obtained as in step 1 of Example 51, except that 2-fluoro-6-isopropoxybenzaldehyde was used in place of 2-fluoro-6-methoxybenzaldehyde.

$^1$H-NMR (CDCl$_3$) δ: 7.22 (1H, dt, J=6.6, 8.4 Hz), 6.71-6.65 (2H, m), 4.64-4.56 (1H, m), 3.47 (1H, s), 1.39 (6H, d, J=6.2 Hz).

Step 3: Synthesis of Example Compound 56

The title compound was obtained as in step 4 of Example 1, except that 2-ethynyl-1-fluoro-3-isopropoxybenzene was used in place of 2-ethynyl-1,3-difluorobenzene.

$^1$H-NMR (CD$_3$OD) δ: 8.24 (1H, s), 7.57 (1H, s), 7.32-7.26 (1H, m), 6.89 (1H, d, J=9.0 Hz), 6.78-6.73 (1H, m), 5.87 (1H, d, J=6.8 Hz), 4.85-4.81 (1H, m), 4.79-4.71 (1H, m), 4.33-4.31 (1H, m), 4.27-4.24 (1H, m), 3.42-3.33 (2H, m), 1.41 (6H, d, J=5.9 Hz).

LCMS (ESI) m/z 521 [M+H]$^+$.

Example 57

4-Amino-5-[2-(4-cyano-2,6-difluoro-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine

Step 1: Synthesis of 4-ethynyl-3,5-difluorobenzonitrile

The title compound was obtained as in step 1 of Example 51, except that 3,5-difluoro-4-formylbenzonitrile was used in place of 2-fluoro-6-methoxybenzaldehyde.

$^1$H-NMR (CDCl$_3$) δ: 7.25 (2H, d, J=8.0 Hz), 3.73 (1H, s).

Step 2: Synthesis of Example Compound 57

The title compound was obtained as in step 4 of Example 1, except that 4-ethynyl-3,5-difluorobenzonitrile was used in place of 2-ethynyl-1,3-difluorobenzene.

$^1$H-NMR (CD$_3$OD) δ: 8.26 (1H, s), 7.78 (1H, s), 7.58 (2H, d, J=7.1 Hz), 5.88 (1H, d, J=6.8 Hz), 4.85-4.78 (1H, m), 4.33-4.30 (1H, m), 4.27-4.24 (1H, m), 3.42-3.33 (2H, m). LCMS (ESI) m/z 506 [M+H]$^+$.

Example 58

Methyl 4-[2-[4-amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-3,5-difluoro-benzoate

Step 1: Synthesis of methyl 4-ethynyl-3,5-difluorobenzimidate 3,5-Difluoro-4-formylbenzonitrile (200 mg, 1.2 mmol) was dissolved in methanol (3 mL). Then, potassium carbonate (331 mg, 24 mmol) was added thereto at room temperature, and dimethyl(1-diazo-2-oxopropyl)phosphonate (0.22 mL, 1.4 mmol) was added thereto under ice-cooling, followed by stirring under ice-cooling for 30 minutes and at room temperature for additional 2 hours and 30 minutes. The reaction solution was partitioned with the addition of ethyl acetate, a saturated aqueous sodium hydrogen carbonate solution, and water, and the organic layer was washed with saturated saline. After being dried over sodium sulfate, the resulting product was filtered and concentrated, and the residue was purified by silica gel column chromatography (developing solvent: ethyl acetate/hexane), thereby obtaining methyl 4-ethynyl-3,5-difluorobenzimidate (172 mg).

LCMS (ESI) m/z 196 [M+H]$^+$

Step 2: Synthesis of Example Compound 58

The title compound was obtained as in step 4 of Example 1, except that methyl 4-ethynyl-3,5-difluorobenzimidate was used in place of 2-ethynyl-1,3-difluorobenzene.

$^1$H-NMR (CD$_3$OD) δ: 8.27 (1H, s), 7.76 (1H, s), 7.69 (2H, d, J=7.8 Hz), 5.88 (1H, d, J=6.6 Hz), 4.85-4.78 (1H, m), 4.33-4.31 (1H, m), 4.27-4.24 (1H, m), 3.94 (3H, s), 3.42-3.33 (2H, m). LCMS (ESI) m/z 539 [M+H]$^+$.

Example 59

4-Amino-7-[(2R,3R,4S,5R)-3,4-dihydroxy-5-[(sulfamoylamino)methyl]tetrahydrofuran-2-yl]-5-[2-(2-fluoro-6-methylsulfanyl-phenyl)ethynyl]pyrrolo[2,3-d]pyrimidine

Step 1: Synthesis of (2-ethynyl-3-fluorophenyl)(methyl)sulfane

The title compound was obtained as in step 1 of Example 51, except that 2-fluoro-6-(methylthio)benzaldehyde was used in place of 2-fluoro-6-methoxybenzaldehyde.

$^1$H-NMR (CDCl$_3$) δ: 7.32-7.25 (1H, m), 6.94 (1H, d, J=8.1 Hz), 6.89-6.64 (1H, m), 3.70 (1H, s), 2.51 (3H, s).

Step 2: Synthesis of Example Compound 59

The title compound was obtained as in step 4 of Example 1, except that (2-ethynyl-3-fluorophenyl)(methyl)sulfane was used in place of 2-ethynyl-1,3-difluorobenzene.

$^1$H-NMR (CD$_3$OD) δ: 8.24 (1H, s), 7.65 (1H, s), 7.37-7.31 (1H, m), 7.11 (1H, d, J=8.0 Hz), 6.99-6.94 (1H, m), 5.88 (1H, d, J=6.8 Hz), 4.85-4.78 (1H, m), 4.33-4.31 (1H, m), 4.27-4.24 (1H, m), 3.42-3.33 (2H, m), 2.56 (3H, s). LCMS (ESI) m/z 509 [M+H]$^+$.

Example 60

4-Amino-7-[(2R,3R,4S,5R)-3,4-dihydroxy-5-[(sulfamoylamino)methyl]tetrahydrofuran-2-yl]-5-[2-(2-fluoro-6-propoxy-phenyl)ethynyl]pyrrolo[2,3-d]pyrimidine

Step 1: Synthesis of 2-fluoro-6-propoxybenzaldehyde

The title compound was obtained as in step 1 of Example 55, except that 1-iodopropane was used in place of iodoethane.

$^1$H-NMR (CDCl$_3$) δ: 10.48 (1H, s), 7.46 (1H, dt, J=6.3, 8.5 Hz), 6.76 (1H, d, J=8.5 Hz), 6.71 (1H, dd, J=10.4, 8.5 Hz), 4.04 (2H, t, J=6.3 Hz), 1.93-1.83 (2H, m), 1.56 (1H, s), 1.07 (3H, t, J=7.3 Hz). LCMS (ESI) m/z 183 [M+H]$^+$

Step 2: Synthesis of 2-ethynyl-1-fluoro-3-propoxybenzene

The title compound was obtained as in step 1 of Example 51, except that 2-fluoro-6-propoxybenzaldehyde was used in place of 2-fluoro-6-methoxybenzaldehyde.

$^1$H-NMR (CDCl$_3$) δ: 7.27-7.20 (1H, m), 6.72-6.63 (2H, m), 4.01 (2H, t, J=6.5 Hz), 3.49 (1H, s), 1.81-1.91 (2H, m), 1.07 (3H, t, J=8.0 Hz).

Step 3: Synthesis of Example Compound 60

The title compound was obtained as in step 4 of Example 1, except that 2-ethynyl-1-fluoro-3-propoxybenzene was used in place of 2-ethynyl-1,3-difluorobenzene.

$^1$H-NMR (CD$_3$OD) δ: 8.24 (1H, s), 7.57 (1H, s), 7.34-7.28 (1H, m), 6.88 (1H, d, J=8.0 Hz), 6.80-6.74 (1H, m), 5.86 (1H, d, J=6.8 Hz), 4.85-4.78 (1H, m), 4.33-4.31 (1H, m), 4.27-4.24 (1H, m), 4.13 (2H, t, J=6.7 Hz), 3.42-3.33 (2H, m), 1.92-1.82 (2H, m), 1.07 (3H, t, 7.4 Hz). LCMS (ESI) m/z 521 [M+H]$^+$.

Example 61

4-Amino-7-[(2R,3R,4S,5R)-3,4-dihydroxy-5-[(sulfamoylamino)methyl]tetrahydrofuran-2-yl]-5-[2-[2-fluoro-6-(2,2,2-trifluoroethoxy)phenyl]ethynyl]pyrrolo[2,3-d]pyrimidine

Step 1: Synthesis of 2-fluoro-6-(2,2,2-trifluoroethoxy)benzaldehyde

The title compound was obtained as in step 1 of Example 55, except that 1,1,1-trifluoro-2-iodoethane was used in place of iodoethane.

$^1$H-NMR (CDCl$_3$) δ: 10.45 (1H, s), 7.53 (1H, dt, J=6.1, 8.6 Hz), 6.89 (1H, dd, J=9.8, 8.6 Hz), 6.77 (1H, d, J=8.6 Hz), 4.48 (2H, q, J=8.0 Hz). LCMS (ESI) m/z 223 [M+H]$^+$

Step 2: Synthesis of 2-ethynyl-1-fluoro-3-(2,2,2-trifluoroethoxy)benzene

The title compound was obtained as in step 1 of Example 51, except that 2-fluoro-6-(2,2,2-trifluoroethoxy)benzaldehyde was used in place of 2-fluoro-6-methoxybenzaldehyde.

$^1$H-NMR (CDCl$_3$) δ: 7.32-7.24 (1H, m), 6.88-6.81 (1H, m), 6.72 (1H, d, J=8.0 Hz), 4.45 (2H, q, J=8.0 Hz), 3.53 (1H, s).

Step 3: Synthesis of Example Compound 61

The title compound was obtained as in step 4 of Example 1, except that 2-ethynyl-1-fluoro-3-(2,2,2-trifluoroethoxy)benzene was used in place of 2-ethynyl-1,3-difluorobenzene.

$^1$H-NMR (CD$_3$OD) δ: 8.24 (1H, s), 7.60 (1H, s), 7.39-7.33 (1H, m), 6.98 (1H, d, J=8.5 Hz), 6.93-6.89 (1H, m), 5.86 (1H, d, J=7.1 Hz), 4.84-4.82 (1H, m), 4.76 (2H, q, J=8.4 Hz), 4.33-4.29 (1H, m), 4.27-4.25 (1H, m), 3.40-3.37 (2H, m). LCMS (ESI) m/z 561 [M+H]$^+$.

Example 62

4-Amino-7-[(2R,3R,4S,5R)-3,4-dihydroxy-5-[(sulfamoylamino)methyl]tetrahydrofuran-2-yl]-5-[2-(2-ethoxy-6-methoxy-phenyl)ethynyl]pyrrolo[2,3-d]pyrimidine

Step 1: Synthesis of 2-ethoxy-6-methoxybenzaldehyde

The title compound was obtained as in step 1 of Example 55, except that 2-hydroxy-6-methoxybenzaldehyde was used in place of 2-fluoro-6-hydroxybenzaldehyde.

$^1$H-NMR (CDCl$_3$) δ: 10.53 (1H, s), 7.42 (1H, t, J=8.5 Hz), 6.56 (2H, d, J=8.5 Hz), 4.15-4.08 (2H, q, J=7.0 Hz), 3.90 (3H, s), 1.46 (3H, t, J=7.0 Hz). LCMS (ESI) m/z 181 [M+H]$^+$

Step 2: Synthesis of 1-ethoxy-2-ethynyl-3-methoxybenzene

The title compound was obtained as in step 1 of Example 51, except that 2-ethoxy-6-methoxybenzaldehyde was used in place of 2-fluoro-6-methoxybenzaldehyde.

$^1$H-NMR (CDCl$_3$) δ: 7.23 (1H, t, J=8.4 Hz), 6.55-6.50 (2H, m), 4.12 (2H, q, J=7.0 Hz), 3.90 (3H, s), 3.53 (1H, s), 1.46 (3H, t, J=7.0 Hz). LCMS (ESI) m/z 177 [M+H]$^+$

Step 3: Synthesis of Example Compound 62

The title compound was obtained as in step 4 of Example 1, except that 1-ethoxy-2-ethynyl-3-methoxybenzene was used in place of 2-ethynyl-1,3-difluorobenzene.

$^1$H-NMR (CD$_3$OD) δ: 8.22 (1H, s), 7.48 (1H, s), 7.27-7.23 (1H, m), 6.67-6.64 (2H, m), 5.85 (1H, d, J=6.5 Hz), 4.88-4.80 (1H, m), 4.32-4.30 (1H, m), 4.26-4.23 (1H, m), 4.18 (2H, q, J=7.0 Hz), 3.91 (3H, s), 3.42-3.31 (2H, m), 1.45 (3H, t, J=7.0 Hz). LCMS (ESI) m/z 519 [M+H]$^+$.

Example 63

8-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-7-methoxyquinoline

Step 1: Synthesis of 8-ethynyl-7-methoxyquinoline

The title compound was obtained as in step 1 of Example 51, except that 7-methoxyquinoline-8-carbaldehyde was used in place of 2-fluoro-6-methoxybenzaldehyde.

$^1$H-NMR (CDCl$_3$) δ: 9.03 (1H, dd, J=4.2, 1.8 Hz), 8.12 (1H, dd, J=8.3, 1.8 Hz), 7.83 (1H, d, J=9.2 Hz), 7.35 (1H, d,

J=9.2 Hz), 7.33 (1H, dd, J=8.3, 4.2 Hz), 4.10 (3H, s), 3.87 (1H, s).
LCMS (ESI) m/z 184 [M+H]⁺

Step 2: Synthesis of Example Compound 63

The title compound was obtained as in step 4 of Example 1, except that 8-ethynyl-7-methoxyquinoline was used in place of 2-ethynyl-1,3-difluorobenzene.
¹H-NMR (CD₃OD) δ: 8.92 (1H, dd, J=4.3, 1.7 Hz), 8.29 (1H, dd, J=8.3, 1.7 Hz), 8.22 (1H, s), 7.92 (1H, d, J=9.0 Hz), 7.59 (1H, s), 7.54 (1H, d, J=9.0 Hz), 7.43 (1H, dd, J=8.3, 4.3 Hz), 5.89 (1H, d, J=6.8 Hz), 4.61-4.59 (1H, m), 4.33 (1H, dd, J=5.4, 2.7 Hz), 4.29-4.26 (1H, m), 4.11 (3H, s), 3.44-3.34 (2H, m).
LCMS (ESI) m/z 526 [M+H]⁺.

Example 64

8-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-7-fluoro-4-methyl-2,3-dihydro-1,4-benzoxazine Step 1: Synthesis of 7-fluoro-4-methyl-2,3-dihydro-1,4-benzoxazine 7-Fluoro-2,3-dihydro-1,4-benzoxazine (1.50 g, 9.79 mmol) was dissolved in N,N-dimethylformamide (15 mL), and potassium carbonate (2.98 g, 21.5 mmol) and methyl iodide (1.67 g, 11.8 mmol) were added thereto at room temperature. After the resulting mixture was stirred at room temperature for 3 days, water (60 mL) and ethyl acetate (60 mL) were sequentially added thereto to partition the mixture into an aqueous layer and an organic layer, followed by separation of each layer. The aqueous layer was extracted with ethyl acetate (60 mL), and the obtained organic layers were combined. The combined organic layer was sequentially washed with water (60 mL) and saturated saline (60 mL), and dried over anhydrous sodium sulfate, followed by distilling off the solvent. The residue was purified by silica gel column chromatography (developing solvent: ethyl acetate/hexane), thereby obtaining 7-fluoro-4-methyl-2,3-dihydro-1,4-benzoxazine (1.09 g) as a light-yellow oil.
¹H-NMR (CDCl₃) δ: 6.58-6.51 (3H, m), 4.31 (2H, t, J=4.4 Hz), 3.20 (2H, t, J=4.4 Hz), 2.84 (3H, s). LCMS (ESI) m/z 168.1 [M+H]⁺

Step 2: Synthesis of 7-fluoro-4-methyl-2,3-dihydro-1,4-benzoxazine-8-carbaldehyde 7-Fluoro-4-methyl-2,3-dihydro-1,4-benzoxazine (1.07 g, 6.40 mmol) was dissolved in tetrahydrofuran (17.1 mL), and n-butyllithium (a 1.6 M hexane solution, 4.83 mL) was added thereto dropwise with stirring at −78° C. After the mixture was stirred at −78° C. for 3 hours, N,N-dimethylformamide (702 mg, 9.60 mmol) was added thereto dropwise, and the temperature was increased to 0° C. A saturated aqueous ammonium chloride solution (40 mL) and ethyl acetate (40 mL) were sequentially added thereto, followed by separation of each layer. The aqueous layer was extracted twice with ethyl acetate (40 mL), and the obtained organic layers were combined. The combined organic layer was sequentially washed with a saturated aqueous ammonium chloride solution (100 mL), water (100 mL), and saturated saline (100 mL), and dried over anhydrous sodium sulfate, followed by distilling off the solvent. The residue was purified by silica gel column chromatography (developing solvent: ethyl acetate/hexane), thereby obtaining 7-fluoro-4-methyl-2,3-dihydro-1,4-benzoxazine-8-carbaldehyde (1.13 g) as a bright yellow solid.
¹H-NMR (CDCl₃) δ: 10.38 (1H, d, J=2.2 Hz), 6.78-6.73 (1H, m), 6.62-6.57 (1H, m), 4.45-4.42 (2H, m), 3.28-3.25 (2H, m), 2.87 (3H, d, J=1.8 Hz). LCMS (ESI) m/z 196.2 [M+H]⁺

Step 3: Synthesis of 8-ethynyl-7-fluoro-4-methyl-2,3-dihydro-1,4-benzoxazine

The title compound was obtained as in step 1 of Example 51, except that 7-fluoro-4-methyl-2,3-dihydro-1,4-benzoxazine-8-carbaldehyde was used in place of 2-fluoro-6-methoxybenzaldehyde.
¹H-NMR (CDCl₃) δ: 6.59-6.56 (2H, m), 4.43 (2H, t, J=4.4 Hz), 3.49 (1H, s), 3.22 (2H, t, J=4.4 Hz), 2.84 (3H, s). LCMS (ESI) m/z 192.4 [M+H]⁺

Step 4: Synthesis of Example Compound 64

The title compound was obtained as in step 4 of Example 1, except that 8-ethynyl-7-fluoro-4-methyl-2,3-dihydro-1,4-benzoxazine was used in place of 2-ethynyl-1,3-difluorobenzene.
¹H-NMR (DMSO-D₆) δ: 8.17 (1H, s), 7.88 (1H, s), 7.38 (1H, dd, J=7.3, 4.8 Hz), 6.78-6.69 (2H, m), 6.60 (2H, s), 5.91 (1H, d, J=7.3 Hz), 5.40 (1H, s), 5.24 (1H, s), 4.58 (1H, t, J=6.2 Hz), 4.43 (2H, t, J=4.2 Hz), 4.12-4.07 (1H, m), 4.07-4.02 (1H, m), 3.26 (2H, t, J=4.2 Hz), 3.23-3.16 (1H, m), 3.15-3.07 (1H, m), 2.82 (3H, s). LCMS (ESI) m/z 534.3 [M+H]⁺.

Step 5: Synthesis of 8-[2-[4-amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-7-fluoro-4-methyl-2,3-dihydro-1,4-benzoxazine hydrochloride The title compound hydrochloride was obtained as in step 5 of Example 1.
¹H-NMR (DMSO-D₆) δ: 8.47 (1H, s), 8.23 (1H, s), 6.82-6.76 (2H, m), 6.06 (1H, d, J=6.8 Hz), 4.49-4.45 (3H, m), 4.12 (1H, dd, J=5.2, 2.8 Hz), 4.05 (1H, dt, J=5.6, 2.8 Hz), 3.28 (2H, t, J=4.4 Hz), 3.23 (1H, dd, J=14.0, 6.0 Hz), 3.13 (1H, dd, J=14.0, 6.0 Hz), 2.84 (3H, s). LCMS (ESI) m/z 534.3 [M+H]⁺

Example 65

4-Amino-7-[(2R,3R,4S,5R)-3,4-dihydroxy-5-[(sulfamoylamino)methyl]tetrahydrofuran-2-yl]-5-[2-(2,4-dimethoxy-3-pyridyl)ethynyl]pyrrolo[2,3-d]pyrimidine Step 1: Synthesis of 3-ethynyl-2,4-dimethoxypyridine The title compound was obtained as in step 1 of Example 51, except that 2,4-dimethoxynicotinaldehyde was used in place of 2-fluoro-6-methoxybenzaldehyde.
¹H-NMR (CDCl₃) δ: 8.05 (1H, d, J=6.1 Hz), 6.54 (1H, d, J=6.1 Hz), 4.02 (3H, s), 3.95 (3H, s), 3.58 (1H, s). LCMS (ESI) m/z 164 [M+H]⁺

Step 2: Synthesis of Example Compound 65

The title compound was obtained as in step 4 of Example 1, except that 3-ethynyl-2,4-dimethoxypyridine was used in place of 2-ethynyl-1,3-difluorobenzene.

$^1$H-NMR (DMSO-D$_6$) δ: 8.18 (1H, s), 8.08 (1H, d, J=6.1 Hz), 7.85 (1H, d, J=2.0 Hz), 7.35 (1H, s), 6.89 (1H, d, J=6.1 Hz), 6.59 (2H, s), 5.91 (1H, d, J=7.1 Hz), 4.58 (1H, t, J=5.7 Hz), 4.11-4.08 (1H, m), 4.06-4.03 (1H, m), 3.95 (6H, d, J=2.7 Hz), 3.35 (2H, s), 3.22-3.10 (2H, m). LCMS (ESI) m/z 506 [M+H]$^+$.

Example 66

4-Amino-7-[(2R,3R,4S,5R)-3,4-dihydroxy-5-[(sulfamoylamino)methyl]tetrahydrofuran-2-yl]-5-[2-(2-ethylsulfanyl-6-fluoro-phenyl)ethynyl]pyrrolo[2,3-d]pyrimidine

Step 1: Synthesis of 2-(ethylthio)-6-fluorobenzaldehyde

Ethyl (3-fluorophenyl)sulfane (2.0 g, 12.8 mmol) was dissolved in tetrahydrofuran (30 mL), and n-butyllithium (a 2.69 M hexane solution, 5.71 mL) was added thereto dropwise while being stirred with cooling at −78° C. After the resulting mixture was stirred at −78° C. for 30 minute, N,N-dimethylformamide (2.95 mL, 38.4 mmol) was added thereto, followed by stirring for 1 hour. A saturated aqueous ammonium chloride solution was added to the reaction liquid, followed by extraction with ethyl acetate. After the solvent was distilled off, the residue was purified by column chromatography (developing solvent: hexane/ethyl acetate), thereby obtaining 2-(ethylthio)-6-fluorobenzaldehyde (430 mg, 18%) as a light-yellow solid.

$^1$H-NMR (CDCl$_3$) δ: 10.52 (1H, s), 7.51-7.46 (1H, m), 7.13 (1H, d, J=8.8 Hz), 6.91 (1H, t, J=8.8 Hz), 2.99 (2H, q, J=7.3 Hz), 1.42 (3H, t, J=7.3 Hz).

Step 2: Synthesis of ethyl(2-ethynyl-3-fluorophenyl)sulfane

The title compound was obtained as in step 1 of Example 51, except that 2-(ethylthio)-6-fluorobenzaldehyde was used in place of 2-fluoro-6-methoxybenzaldehyde.

$^1$H-NMR (CDCl$_3$) δ: 7.30-7.24 (1H, m), 7.03 (1H, d, J=8.1 Hz), 6.89 (1H, dd, J=8.8, 8.1 Hz), 3.71 (1H, s), 3.03 (2H, q, J=7.3 Hz), 1.40 (3H, t, J=7.3 Hz).

Step 3: Synthesis of Example Compound 66

The title compound was obtained as in step 4 of Example 1, except that ethyl (2-ethynyl-3-fluorophenyl)sulfane was used in place of 2-ethynyl-1,3-difluorobenzene.

$^1$H-NMR (DMSO-D$_6$) δ: 8.16 (1H, s), 7.95 (1H, s), 7.91 (1H, d, J=7.0 Hz), 7.46 (1H, t, J=7.7 Hz), 7.41-7.32 (2H, m), 7.22 (1H, d, J=8.1 Hz), 7.12 (1H, t, J=8.8 Hz), 6.57 (2H, s), 5.91 (1H, d, J=7.0 Hz), 5.37 (1H, brs), 5.21 (1H, brs), 4.57 (1H, brs), 4.09-4.06 (1H, brm), 4.04-4.01 (1H, brm), 3.23-3.05 (2H, m), 1.28 (3H, t, J=7.0 Hz). LCMS (ESI) m/z 523 [M+H]$^+$.

Example 67

4-Amino-5-[2-[2,6-difluoro-4-(triazol-2-ylmethoxy)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine

Step 1: Synthesis of 4-((2H-1,2,3-triazol-2-yl)methoxy)-2,6-difluorobenzaldehyde The title compound was obtained as in step 1 of Example 55, except that 2,6-difluoro-4-hydroxybenzaldehyde was used in place of 2-fluoro-6-hydroxybenzaldehyde, and that 2-(chloromethyl)triazole was used in place of iodoethane.

$^1$H-NMR (CDCl$_3$) δ: 10.21 (1H, s), 7.76 (2H, s), 6.88 (2H, d, J=10.0 Hz), 6.30 (2H, s). LCMS (ESI) m/z 240 [M+H]$^+$

Step 2: Synthesis of 2-((4-ethynyl-3,5-difluorophenoxy)methyl)-2H-1,2,3-triazole The title compound was obtained as in step 1 of Example 51, except that 4-((2H-1,2,3-triazol-2-yl)methoxy)-2,6-difluorobenzaldehyde was used in place of 2-fluoro-6-methoxybenzaldehyde.

$^1$H-NMR (CDCl$_3$) δ: 7.74 (2H, s), 7.26 (2H, s), 6.82 (1H, d, J=8.5 Hz), 6.24 (1H, s), 3.43 (1H, s). LCMS (ESI) m/z 236 [M+H]$^+$

Step 3: Synthesis of Example Compound 67

The title compound was obtained as in step 4 of Example 1, except that 2-((4-ethynyl-3,5-difluorophenoxy)methyl)-2H-1,2,3-triazole was used in place of 2-ethynyl-1,3-difluorobenzene.

$^1$H-NMR (DMSO-D$_6$) δ: 8.17 (1H, s), 7.99 (2H, s), 7.96 (1H, s), 7.36-7.31 (1H, brs), 7.19 (2H, d, J=9.5 Hz), 6.61-6.57 (2H, s), 6.52 (2H, s), 5.91 (1H, d, J=7.1 Hz), 5.40 (1H, d, J=6.6 Hz), 5.23 (1H, d, J=4.1 Hz), 4.59-4.54 (1H, m), 4.10-4.06 (1H, m), 4.05-4.02 (1H, m), 3.22-3.16 (1H, m), 3.10-3.06 (1H, m). LCMS (ESI) m/z 578 [M+H]$^+$.

Example 68

4-Amino-7-[(2R,3R,4S,5R)-3,4-dihydroxy-5-[(sulfamoylamino)methyl]tetrahydrofuran-2-yl]-5-[2-[2-(ethylamino)-6-fluoro-phenyl]ethynyl]pyrrolo[2,3-d]pyrimidine

Step 1: Synthesis of 2-(ethylamino)-6-fluorobenzaldehyde

The title compound was obtained as in step 1 of Example 23, except that 2,6-difluorobenzaldehyde and ethylamine were used in place of 2-ethynyl-1,3,5-trifluorobenzene and morpholine.

$^1$H-NMR (CDCl$_3$) δ: 10.28 (1H, s), 8.66 (1H, brs), 7.35-7.29 (1H, m), 6.45 (1H, d, J=8.1 Hz), 6.27 (1H, dd, J=11.4, 8.1 Hz), 3.32-3.25 (2H, m), 1.33 (3H, t, J=7.3 Hz). LRMS (ESI) m/z 168 [M+H]$^+$

Step 2: Synthesis of N-ethyl-2-ethynyl-3-fluoroaniline

The title compound was obtained as in step 1 of Example 51, except that 2-(ethylamino)-6-fluorobenzaldehyde was used in place of 2-fluoro-6-methoxybenzaldehyde.

¹H-NMR (CDCl₃) δ: 7.13 (1H, dd, J=14.7, 7.7 Hz), 6.38-6.34 (2H, m), 4.62-4.56 (1H, brm), 3.62 (1H, s), 3.21 (2H, dq, J=7.3, 6.6 Hz), 1.29 (3H, t, J=7.3 Hz). LRMS (ESI) m/z 164 [M+H]⁺

Step 3: Synthesis of Example Compound 68

The title compound was obtained as in step 4 of Example 1, except that N-ethyl-2-ethynyl-3-fluoroaniline was used in place of 2-ethynyl-1,3-difluorobenzene.

¹H-NMR (CD₃OD) δ: 8.22 (1H, s), 7.55 (1H, s), 7.26 (1H, ddd, J=8.4, 8.4, 7.0 Hz), 6.82 (1H, d, J=8.4 Hz), 6.74 (1H, t, J=8.4 Hz), 5.87 (1H, d, J=6.6 Hz), 4.79 (1H, t, J=6.6 Hz), 4.30 (1H, dd, J=5.5, 2.6 Hz), 4.23-4.17 (2H, m), 4.19 (1H, q, J=7.0 Hz), 3.56-3.54 (2H, m), 1.46 (3H, t, J=7.0 Hz). LCMS (ESI) m/z 506 [M+H]⁺.

Example 69

4-Amino-5-[2-(2,4-difluoro-3-pyridyl)ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of 3-ethynyl-2,4-difluoropyridine The title compound was obtained as in step 1 of Example 51, except that 2,4-difluoronicotinaldehyde was used in place of 2-fluoro-6-methoxybenzaldehyde.

¹H-NMR (ACETONE-D₆) δ: 8.38 (1H, dd, J=8.2, 5.7 Hz), 7.44-7.40 (1H, m), 4.46 (1H, s). LCMS (ESI) m/z 140 [M+H]⁺

Step 2: Synthesis of Example Compound 69

The title compound was obtained as in step 4 of Example 1, except that 3-ethynyl-2,4-difluoropyridine was used in place of 2-ethynyl-1,3-difluorobenzene.

¹H-NMR (CD₃OD) δ: 8.25 (1H, s), 8.18 (1H, dd, J=8.2, 5.8 Hz), 7.73 (1H, s), 7.27 (1H, dd, J=8.2, 5.8 Hz), 5.87 (1H, d, J=6.6 Hz), 4.82 (1H, d, J=5.9 Hz), 4.32 (1H, dd, J=5.5, 2.6 Hz), 4.26 (1H, q, J=3.1 Hz), 3.43-3.33 (2H, m). LCMS (ESI) m/z 482 [M+H]⁺.

Example 70

4-Amino-7-[(2R,3R,4S,5R)-3,4-dihydroxy-5-[(sulfamoylamino)methyl]tetrahydrofuran-2-yl]-5-[2-(2-ethylsulfonyl-6-fluoro-4-pyrrolidin-1-yl-phenyl)ethynyl]pyrrolo[2,3-d]pyrimidine Step 1: Synthesis of 2,6-difluoro-4-(pyrrolidin-1-yl)benzaldehyde The title compound was obtained as in step 1 of Example 23, except that 2,4,6-trifluorobenzaldehyde and pyrrolidine were used in place of 2-ethynyl-1,3,5-trifluorobenzene and morpholine.

¹H-NMR (CDCl₃) δ: 10.04 (1H, s), 6.01 (2H, d, J=12.8 Hz), 3.35-3.32 (4H, m), 2.07-2.03 (4H, m). LCMS (ESI) m/z 212 [M+H]⁺

Step 2: Synthesis of 2-(ethylthio)-6-fluoro-4-(pyrrolidin-1-yl)benzaldehyde 2,6-Difluoro-4-(pyrrolidin-1-yl)benzaldehyde (3.7 g, 18 mmol) was dissolved in N,N-dimethylformamide (37 mL), and sodium ethanethiolate (1.6 g, 18 mmol) was added thereto, followed by stirring at room temperature for 30 minutes. Ethyl acetate, water, and a saturated aqueous sodium hydrogen carbonate solution were added to the reaction solution, and the aqueous layer was extracted with ethyl acetate. The organic layer was washed with water and a saturated sodium chloride aqueous solution, and dried over sodium sulfate, followed by distilling off the solvent. The residue was purified by silica gel column chromatography (developing solvent: chloroform), thereby obtaining 2-(ethylthio)-6-fluoro-4-(pyrrolidin-1-yl)benzaldehyde (4.4 g) as a white solid.

¹H-NMR (CDCl₃) δ: 10.18 (1H, s), 6.10 (1H, d, J=2.0 Hz), 5.98 (1H, dd, J=14.3, 2.0 Hz), 3.39-3.35 (4H, m), 2.91 (2H, q, J=7.3 Hz), 2.07-2.04 (4H, m), 1.41 (3H, t, J=7.3 Hz). LCMS (ESI) m/z 254 [M+H]⁺

Step 3: Synthesis of 2-(ethylsulfonyl)-6-fluoro-4-(pyrrolidin-1-yl)benzaldehyde 2-(Ethylthio)-6-fluoro-4-(pyrrolidin-1-yl)benzaldehyde (79 mg, 0.31 mmol) was dissolved in dichloromethane (1.6 mL), and 3-chloroperbenzoic acid (110 mg, 0.65 mmol) was added thereto in an ice bath, followed by stirring for 2 hours in an ice bath. 3-chloroperbenzoic acid (56 mg, 0.32 mmol) was added to the resulting mixture in an ice bath, followed by stirring for 1 hour in an ice bath. Thereafter, 3-chloroperbenzoic acid (10 mg, 0.058 mmol) was further added thereto in an ice bath, followed by stirring for 30 minutes in an ice bath. Chloroform, water, and a saturated aqueous sodium hydrogen carbonate solution were added in an ice bath to the reaction solution, and the aqueous solution was extracted with chloroform. The organic layer was washed with a saturated sodium chloride aqueous solution, and dried over sodium sulfate, followed by distilling off the solvent. The residue was purified by silica gel column chromatography (developing solvent: ethyl acetate/hexane), thereby obtaining 2-(ethylsulfonyl)-6-fluoro-4-(pyrrolidin-1-yl)benzaldehyde (54 mg, 0.19 mmol, 62%) as a yellow solid.

¹H-NMR (CDCl₃) δ: 10.28 (1H, s), 7.19 (1H, d, J=2.6 Hz), 6.33 (1H, dd, J=13.9, 2.6 Hz), 3.62 (2H, q, J=7.5 Hz), 3.50-3.40 (4H, m), 2.11-2.08 (4H, m), 1.31 (3H, t, J=7.5 Hz). LCMS (ESI) m/z 286 [M+H]⁺

Step 4: Synthesis of 1-(3-(ethylsulfonyl)-4-ethynyl-5-fluorophenyl)pyrrolidine

The title compound was obtained as in step 1 of Example 51, except that 2-(ethylsulfonyl)-6-fluoro-4-(pyrrolidin-1-yl)benzaldehyde was used in place of 2-fluoro-6-methoxybenzaldehyde.

¹H-NMR (CDCl₃) δ: 7.01 (1H, d, J=2.3 Hz), 6.38 (1H, dd, J=11.9, 2.3 Hz), 3.63 (1H, s), 3.49 (2H, q, J=7.4 Hz), 3.36-3.32 (4H, m), 2.07-2.04 (4H, m), 1.27 (3H, t, J=7.4 Hz). LCMS (ESI) m/z 282 [M+H]⁺

Step 5: Synthesis of Example Compound 70

The title compound was obtained as in step 4 of Example 1, except that 1-(3-(ethylsulfonyl)-4-ethynyl-5-fluorophenyl)pyrrolidine was used in place of 2-ethynyl-1,3-difluorobenzene.

¹H-NMR (CD₃OD) δ: 8.22 (1H, s), 7.61 (1H, s), 7.01 (1H, d, J=2.3 Hz), 6.66 (1H, dd, J=12.4, 2.3 Hz), 5.86 (1H, d, J=7.1 Hz), 4.85-4.81 (1H, m), 4.32-4.30 (1H, m), 4.27-4.24 (1H, m), 3.49 (2H, q, J=7.3 Hz), 3.40-3.36 (4H, m), 3.31-

3.30 (2H, m), 2.10-2.07 (4H, m), 1.25 (3H, t, J=7.3 Hz). LCMS (ESI) m/z 624 [M+H].

Example 71

4-Amino-7-[(2R,3R,4S,5R)-3,4-dihydroxy-5-[(sulfamoylamino)methyl]tetrahydrofuran-2-yl]-5-[2-(3-fluoro-5-methoxy-4-pyridyl)ethynyl]pyrrolo[2,3-d]pyrimidine Step 1: Synthesis of 4-ethynyl-3-fluoro-5-methoxypyridine The title compound was obtained as in step 1 of Example 51, except that 3-fluoro-5-methoxyisonicotinaldehyde was used in place of 2-fluoro-6-methoxybenzaldehyde.
$^1$H-NMR (CDCl$_3$) δ: 8.21-8.17 (2H, m), 4.03 (3H, s), 3.69 (1H, s).
LCMS (ESI) m/z 152 [M+H]$^+$ Step 2: Synthesis of Example Compound 71

The title compound was obtained as in step 4 of Example 1, except that 4-ethynyl-3-fluoro-5-methoxypyridine was used in place of 2-ethynyl-1,3-difluorobenzene.
$^1$H-NMR (DMSO-D$_6$) δ: 8.38 (1H, d, J=7.8 Hz), 8.37 (1H, s), 8.20 (1H, s), 8.05 (1H, s), 7.32-7.29 (1H, brs), 6.58 (2H, s), 5.93 (1H, d, J=6.8 Hz), 5.41-5.38 (1H, brs), 5.23-5.21 (1H, brs), 4.59-4.57 (1H, m), 4.08-4.04 (2H, m), 4.07 (3H, s), 3.22-3.18 (1H, m), 3.12-3.08 (1H, m). LCMS (ESI) m/z 494 [M+H].

Example 72

4-Amino-7-[(2R,3R,4S,5R)-3,4-dihydroxy-5-[(sulfamoylamino)methyl]tetrahydrofuran-2-yl]-5-[2-[2-ethylsulfonyl-6-fluoro-4-[(3R)-3-hydroxypyrrolidin-1-yl]phenyl]ethynyl]pyrrolo[2,3-d]pyrimidine Step 1: Synthesis of 2,6-difluoro-4-[(3R)-3-hydroxypyrrolidin-1-yl]benzaldehyde The title compound was obtained as in step 1 of Example 23, except that 2,4,6-trifluorobenzaldehyde and (R)-pyrrolidin-3-ol were used in place of 2-ethynyl-1,3,5-trifluorobenzene and morpholine.
$^1$H-NMR (CDCl$_3$) δ: 10.05 (1H, s), 6.03 (2H, d, J=12.4 Hz), 4.70-4.66 (1H, m), 3.60-3.53 (2H, m), 3.48-3.42 (1H, m), 3.36-3.31 (1H, m), 2.21-2.12 (2H, m), 1.79 (1H, d, J=3.9 Hz). LCMS (ESI) m/z 228 [M+H]$^+$ Step 2: Synthesis of 2-ethylsulfanyl-6-fluoro-4-[(3R)-3-hydroxypyrrolidin-1-yl]benzaldehyde The title compound was obtained as in step 2 of Example 70, except that 2,6-difluoro-4-[(3R)-3-hydroxypyrrolidin-1-yl]benzaldehyde was used in place of 2,6-difluoro-4-(pyrrolidin-1-yl)benzaldehyde.
$^1$H-NMR (CDCl$_3$) δ: 10.19 (1H, s), 6.11 (1H, d, J=2.2 Hz), 6.00 (1H, dd, J=14.1, 2.2 Hz), 4.69-4.66 (1H, m), 3.63-3.57 (2H, m), 3.50-3.45 (1H, m), 3.41-3.35 (1H, m), 2.91 (2H, q, J=7.4 Hz), 2.21-2.14 (2H, m), 1.77 (1H, d, J=4.1 Hz), 1.41 (3H, t, J=7.4 Hz). LCMS (ESI) m/z 270 [M+H]$^+$ Step 3: Synthesis of 2-ethylsulfonyl-6-fluoro-4-[(3R)-3-hydroxypyrrolidin-1-yl]benzaldehyde The title compound was obtained as in step 3 of Example 70, except that 2-ethylsulfanyl-6-fluoro-4-[(3R)-3-hydroxypyrrolidin-1-yl]benzaldehyde was used in place of 2-(ethylthio)-6-fluoro-4-(pyrrolidin-1-yl)benzaldehyde.
$^1$H-NMR (CDCl$_3$) δ: 10.30 (1H, s), 7.20 (1H, d, J=2.4 Hz), 6.36 (1H, dd, J=14.0, 2.4 Hz), 4.73-4.71 (1H, m), 3.67-3.42 (4H, m), 3.46-3.42 (1H, m), 3.35-3.32 (1H, m), 2.21-2.17 (2H, m), 1.76 (1H, d, J=3.4 Hz), 1.32 (3H, t, J=7.6 Hz). LCMS (ESI) m/z 302 [M+H]$^+$ Step 4: Synthesis of (3R)-1-(3-(ethylsulfonyl)-4-ethynyl-5-fluorophenyl)pyrrolidin-3-ol The title compound was obtained as in step 1 of Example 51, except that 2-ethylsulfonyl-6-fluoro-4-[(3R)-3-hydroxypyrrolidin-1-yl]benzaldehyde was used in place of 2-fluoro-6-methoxybenzaldehyde.
$^1$H-NMR (CDCl$_3$) δ: 7.03 (1H, d, J=2.4 Hz), 6.41 (1H, dd, J=11.7, 2.4 Hz), 4.69-4.67 (1H, m), 3.65 (1H, s), 3.61-3.43 (5H, m), 3.35 (1H, d, J=11.0 Hz), 2.23-2.12 (2H, m), 1.69 (1H, d, J=3.7 Hz), 1.27 (3H, t, J=7.4 Hz). LCMS (ESI) m/z 298 [M+H]$^+$ Step 5: Synthesis of Example Compound 72

The title compound was obtained as in step 4 of Example 1, except that (3R)-1-(3-(ethylsulfonyl)-4-ethynyl-5-fluorophenyl)pyrrolidin-3-ol was used in place of 2-ethynyl-1,3-difluorobenzene.
$^1$H-NMR (CD$_3$OD) δ: 8.23 (1H, s), 7.62 (1H, s), 7.01 (1H, d, J=2.3 Hz), 6.67 (1H, dd, J=12.2, 2.3 Hz), 5.87 (1H, d, J=7.1 Hz), 4.85-4.79 (1H, m), 4.58-4.54 (1H, m), 4.32-4.30 (1H, m), 4.26-4.24 (1H, m), 3.58-3.43 (6H, m), 3.42-3.33 (2H, m), 2.22-2.14 (1H, m), 2.12-2.05 (1H, m), 1.25 (3H, t, J=7.4 Hz). LCMS (ESI) m/z 640 [M+H].

Example 73

4-Amino-5-[2-(2-chloro-6-fluoro-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of 1-chloro-2-ethynyl-3-fluorobenzene The title compound was obtained as in step 1 of Example 51, except that 2-chloro-6-fluorobenzaldehyde was used in place of 2-fluoro-6-methoxybenzaldehyde.
$^1$H-NMR (CDCl$_3$) δ: 7.29-7.21 (2H, m), 7.05-7.00 (1H, m), 3.61 (1H, s).

Step 2: Synthesis of Example Compound 73

The title compound was obtained as in step 4 of Example 1, except that 1-chloro-2-ethynyl-3-fluorobenzene was used in place of 2-ethynyl-1,3-difluorobenzene.
$^1$H-NMR (CD$_3$OD) δ: 8.23 (1H, s), 7.67 (1H, s), 7.37-7.30 (2H, m), 7.18-7.13 (1H, m), 5.87 (1H, d, J=7.1 Hz), 4.85-4.82 (1H, m), 4.33-4.31 (1H, m), 4.27-4.25 (1H, m), 3.43-3.34 (2H, m). LCMS (ESI) m/z 497 [M+H].

Example 74

4-[4-[2-[4-amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-3,5-difluorophenyl]-1,1-dioxo-1,4-thiazinane

Step 1: Synthesis of 4-(4-ethynyl-3,5-difluorophenyl)thiomorpholine-1,1-dioxide The title compound was obtained as in step 3 of Example 70, except that 4-(4-ethynyl-3,5-difluorophenyl)thiomorpholine was used in place of 2-(ethylthio)-6-fluoro-4-(pyrrolidin-1-yl)benzaldehyde.

$^1$H-NMR (CDCl$_3$) δ: 6.40 (2H, d, J=10.2 Hz), 3.92-3.88 (4H, m), 3.42 (1H, s), 3.11-3.06 (4H, m). LCMS (ESI) m/z 272 [M+H]$^+$

Step 2: Synthesis of Example Compound 74

The title compound was obtained as in step 4 of Example 1, except that 4-(4-ethynyl-3,5-difluorophenyl)thiomorpholine-1,1-dioxide was used in place of 2-ethynyl-1,3-difluorobenzene.

$^1$H-NMR (DMSO-D$_6$) δ: 8.18 (1H, s), 7.90 (1H, s), 7.36-7.32 (1H, m), 6.95 (2H, d, J=11.4 Hz), 6.60 (2H, s), 5.92 (1H, d, J=7.0 Hz), 5.39 (1H, d, J=6.2 Hz), 5.24-5.22 (1H, m), 4.60-4.55 (1H, m), 4.12-4.08 (1H, m), 4.06-4.03 (1H, m), 3.95-3.89 (4H, m), 3.25-3.17 (1H, m), 3.17-3.09 (5H, m). LCMS (ESI) m/z 614 [M+H]$^+$.

Example 75

4-Amino-7-[(2R,3R,4S,5R)-3,4-dihydroxy-5-[(sulfamoylamino)methyl]tetrahydrofuran-2-yl]-5-[2-[2-ethylsulfonyl-6-fluoro-4-[(3R)-3-fluoropyrrolidin-1-yl]phenyl]ethynyl]pyrrolo[2,3-d]pyrimidine

Step 1: Synthesis of 2,6-difluoro-4-[(3R)-fluoropyrrolidin-1-yl]benzaldehyde The title compound was obtained as in step 1 of Example 23, except that 2,4,6-trifluorobenzaldehyde and (R)-3-fluoropyrrolidine were used in place of 2-ethynyl-1,3,5-trifluorobenzene and morpholine.

$^1$H-NMR (CDCl$_3$) δ: 10.07 (1H, s), 6.04 (2H, d, J=12.5 Hz), 5.47-5.32 (1H, m), 3.64-3.51 (4H, m), 2.50-2.41 (1H, m), 2.28-2.08 (1H, m). LCMS (ESI) m/z 230 [M+H]$^+$

Step 2: Synthesis of 2-(ethylthio)-6-fluoro-4-[(3R)-3-fluoropyrrolidin-1-yl]benzaldehyde The title compound was obtained as in step 2 of Example 70, except that 2,6-difluoro-4-[(3R)-fluoropyrrolidin-1-yl]benzaldehyde was used in place of 2,6-difluoro-4-(pyrrolidin-1-yl)benzaldehyde.

$^1$H-NMR (CDCl$_3$) δ: 10.21 (1H, s), 6.11 (1H, d, J=1.8 Hz), 6.01 (1H, dd, J=13.9, 1.8 Hz), 5.47-5.33 (1H, m), 3.70-3.52 (4H, m), 2.92 (2H, q, J=7.3 Hz), 2.49-2.40 (1H, m), 2.28-2.09 (1H, m), 1.41 (3H, t, J=7.3 Hz). LCMS (ESI) m/z 272 [M+H]$^+$

Step 3: Synthesis of 2-(ethylsulfonyl)-6-fluoro-4-[(3R)-3-fluoropyrrolidin-1-yl]benzaldehyde The title compound was obtained as in step 3 of Example 70, except that 2-(ethylthio)-6-fluoro-4-[(3R)-3-fluoropyrrolidin-1-yl]benzaldehyde was used in place of 2-(ethylthio)-6-fluoro-4-(pyrrolidin-1-yl)benzaldehyde.

$^1$H-NMR (CDCl$_3$) δ: 10.31 (1H, s), 7.21 (1H, d, J=2.3 Hz), 6.38 (1H, dd, J=13.7, 2.3 Hz), 5.51-5.35 (1H, m), 3.74-3.60 (6H, m), 2.53-2.45 (1H, m), 2.29-2.14 (1H, m), 1.32 (3H, t, J=7.3 Hz).
LCMS (ESI) m/z 304 [M+H]$^+$

Step 4: Synthesis of (3R)-1-(3-ethylsulfonyl-4-ethynyl-5-fluoro-phenyl)-3-fluoro-pyrrolidine The title compound was obtained as in step 1 of Example 51, except that 2-(ethylsulfonyl)-6-fluoro-4-[(3R)-3-fluoropyrrolidin-1-yl]benzaldehyde was used in place of 2-fluoro-6-methoxybenzaldehyde.

$^1$H-NMR (CDCl$_3$) δ: 7.03 (1H, d, J=2.4 Hz), 6.42 (1H, dd, J=11.7, 2.4 Hz), 5.47-5.33 (1H, m), 3.66-3.64 (2H, m), 3.61-3.46 (5H, m), 2.49-2.40 (1H, m), 2.29-2.11 (1H, m), 1.27 (3H, t, J=7.5 Hz).
LCMS (ESI) m/z 300 [M+H]$^+$

Step 5: Synthesis of Example Compound 75

The title compound was obtained as in step 4 of Example 1, except that (3R)-1-(3-ethylsulfonyl-4-ethynyl-5-fluoro-phenyl)-3-fluoro-pyrrolidine was used in place of 2-ethynyl-1,3-difluorobenzene.

$^1$H-NMR (CD$_3$OD) δ: 8.20 (1H, s), 7.60 (1H, s), 6.99 (1H, d, J=2.6 Hz), 6.66 (1H, dd, J=12, 2.6 Hz), 5.86 (1H, d, J=7.0 Hz), 5.47-5.34 (1H, m), 4.81-4.78 (1H, m), 4.31-4.29 (1H, m), 4.25-4.23 (1H, m), 3.70-3.44 (6H, m), 3.41-3.32 (2H, m), 2.42-2.15 (2H, m), 1.24 (3H, t, J=7.3 Hz). LCMS (ESI) m/z 642 [M+H].

Example 76

4-Amino-5-[2-(5-benzyloxypyrimidin-2-yl)ethynyl]-7-[(2R,3R,4S,5R)-3,4-dihydroxy-5-[(sulfamoylamino)methyl]tetrahydrofuran-2-yl]pyrrolo[2,3-d]pyrimidine

Step 1: Synthesis of 5-(benzyloxy)-2-bromopyrimidine

2-Bromopyrimidin-5-ol (200 mg, 1.1 mmol) was dissolved in a liquid mixture of tetrahydrofuran (1 mL) and N,N-dimethylformamide (1 mL). Then, potassium carbonate (170 mg, 1.3 mmol) and benzyl bromide (0.15 mL, 1.3 mmol) were added thereto at room temperature, followed by stirring at room temperature for 6 hours. The reaction solution was partitioned with ethyl acetate and water, and the organic layer was washed with water and saturated saline. The resulting product was dried over sodium sulfate, followed by filtration and concentration, and the residue was purified by silica gel column chromatography (developing solvent: ethyl acetate/hexane), thereby obtaining 5-(benzyloxy)-2-bromopyrimidine (200 mg, 0.75 mmol, 66%) as a white powder.

$^1$H-NMR (CDCl$_3$) δ: 8.31 (2H, s), 7.45-7.36 (5H, m), 5.15 (2H, s).
LCMS (ESI) m/z 265 [M+H]$^+$

Step 2: Synthesis of 5-(benzyloxy)-2-((triisopropylsilyl)ethynyl)pyrimidine 5-(Benzyloxy)-2-bromopyrimidine (200 mg, 0.75 mmol), ethynyltriisopropylsilane (0.34 mL, 1.5 mmol), bis(triphenylphosphine)palladium (II) dichloride (53 mg, 0.075 mmol), copper iodide (14 mg, 0.075 mmol), and diisopropylethylamine (0.26 mL, 1.5 mmol) were suspended in tetrahydrofuran (2 mL). The reaction solution was stirred at 70° C. for 1 hour and 30 minutes, and filtered through a celite bed, followed by distilling off the solvent. The residue was purified by silica gel column chromatography (developing solvent: ethyl acetate/hexane), thereby obtaining 5-(benzyloxy)-2-((triisopropylsilyl)ethynyl)pyrimidine (120 mg, 0.32 mmol, 43%) as a yellow oil.

$^1$H-NMR (CDCl$_3$) δ: 8.42 (2H, s), 7.43-7.36 (5H, m), 5.18 (2H, s), 1.17-1.13 (21H, m). LCMS (ESI) m/z 367 [M+H]$^+$

Step 3: Synthesis of 5-(benzyloxy)-2-ethynylpyrimidine 5-(Benzyloxy)-2-((triisopropylsilyl)ethynyl)pyrimidine (120 mg, 0.32 mmol) was dissolved in tetrahydrofuran (1 mL), and a tetrabutylammonium fluoride solution (1 M tetrahydrofuran solution, 0.38 mL, 0.38 mmol) was added thereto at room temperature, followed by stirring at room temperature for 30 minutes.

After the solvent was distilled off, the residue was purified by silica gel column chromatography (developing solvent: ethyl acetate/hexane), thereby obtaining 5-(benzyloxy)-2-ethynylpyrimidine (45 mg, 0.21 mmol, 67%) as a yellow powder.

$^1$H-NMR (CDCl$_3$) δ: 8.43 (2H, s), 7.44-7.38 (5H, m), 5.19 (2H, s), 3.04 (1H, s). LCMS (ESI) m/z 211 [M+H]$^+$

Step 4: Synthesis of Example Compound 76

The title compound was obtained as in step 4 of Example 1, except that 5-(benzyloxy)-2-ethynylpyrimidine was used in place of 2-ethynyl-1,3-difluorobenzene.

$^1$H-NMR (CD$_3$OD) δ: 8.57 (2H, s), 8.26 (1H, s), 7.75 (1H, s), 7.49-7.33 (5H, m), 5.87 (1H, d, J=6.8 Hz), 5.30 (2H, s), 4.84-4.79 (1H, m), 4.32-4.27 (1H, m), 4.26-4.24 (1H, m), 3.40-3.35 (2H, m).

LCMS (ESI) m/z 553 [M+H]$^+$.

Example 77

4-Amino-5-[2-(4-benzyloxy-2-fluoro-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of ((4-(benzyloxy)-2-fluorophenyl)ethynyl)trimethylsilane The title compound was obtained as in step 2 of Example 76, except that 4-(benzyloxy)-2-fluoro-1-iodobenzene and ethynyltrimethylsilane were used in place of 5-(benzyloxy)-2-bromopyrimidine and ethynyltriisopropylsilane.

$^1$H-NMR (CDCl$_3$) δ: 7.43-7.33 (6H, m), 6.77 (1H, dd, J=10.4, 2.8 Hz), 6.70-6.67 (1H, m), 5.04 (2H, s), 0.25 (9H, s).

Step 2: Synthesis of 4-(benzyloxy)-1-ethynyl-2-fluorobenzene

The title compound was obtained as in step 3 of Example 76, except that 4((4-(benzyloxy)-2-fluorophenyl)ethynyl)trimethylsilane was used in place of 5-(benzyloxy)-2-((triisopropylsilyl)ethynyl)pyrimidine.

$^1$H-NMR (CDCl$_3$) δ: 7.43-7.29 (6H, m), 6.66-6.79 (2H, m), 5.04 (2H, s), 3.25 (1H, s).

Step 3: Synthesis of Example Compound 77

The title compound was obtained as in step 4 of Example 1, except that 4-(benzyloxy)-1-ethynyl-2-fluorobenzene was used in place of 2-ethynyl-1,3-difluorobenzene.

$^1$H-NMR (CD$_3$OD) δ: 8.22 (1H, s), 7.56 (1H, s), 7.40-7.26 (6H, m), 6.87-6.84 (2H, m), 5.85 (1H, d, J=6.8 Hz), 5.12 (2H, s), 4.83-4.81 (1H, m), 4.33-4.29 (1H, m), 4.27-4.25 (1H, m), 3.40-3.35 (2H, m). LCMS (ESI) m/z 569 [M+H]$^+$.

Example 78

4-Amino-5-[2-[4-(benzylamino)phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of N-benzyl-4-((triisopropylsilyl)ethynyl)aniline The title compound was obtained as in step 2 of Example 76, except that N-benzyl-4-iodoaniline and ethynyltriisopropylsilane were used in place of 5-(benzyloxy)-2-bromopyrimidine and ethynyltriisopropylsilane.

$^1$H-NMR (CDCl$_3$) δ: 7.37-7.25 (7H, m), 6.53 (2H, d, J=8.8 Hz), 4.34 (2H, s), 1.12-1.05 (21H, m). LCMS (ESI) m/z 364 [M+H]$^+$

Step 2: Synthesis of N-benzyl-4-ethynylaniline

The title compound was obtained as in step 3 of Example 76, except that N-benzyl-4-((triisopropylsilyl)ethynyl)aniline was used in place of 5-(benzyloxy)-2-((triisopropylsilyl)ethynyl)pyrimidine.

$^1$H-NMR (CDCl$_3$) δ: 7.39-7.25 (7H, m), 6.55 (2H, d, J=8.0 Hz), 4.35 (2H, s), 4.28-4.19 (1H, brs), 2.96 (1H, s). LCMS (ESI) m/z 208 [M+H]$^+$ Step 3: Synthesis of Example Compound 78

The title compound was obtained as in step 4 of Example 1, except that N-benzyl-4-ethynylaniline was used in place of 2-ethynyl-1,3-difluorobenzene.

$^1$H-NMR (CD$_3$OD) δ: 8.25 (1H, s), 7.60 (1H, s), 7.36-7.20 (7H, m), 6.60 (2H, d, J=8.8 Hz), 5.93 (1H, d, J=6.6 Hz), 4.73-4.70 (1H, m), 4.35 (2H, s), 4.31-4.29 (1H, m), 4.25-4.22 (1H, m), 3.40-3.35 (2H, m). LCMS (ESI) m/z 550 [M+H]$^+$.

Example 79

2-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-3-fluorobenzamide Step 1: Synthesis of 3-fluoro-2-((trimethylsilyl)ethynyl)benzamide The title compound was obtained as in step 2 of Example 76, except that 3-fluoro-2-iodobenzamide and ethynyltrimethylsilane were used in place of 5-(benzyloxy)-2-bromopyrimidine and ethynyltriisopropylsilane.

¹H-NMR (CDCl₃) δ: 7.96 (1H, d, J=7.8 Hz), 7.83-7.55 (1H, brs), 7.45-7.40 (1H, m), 7.28-7.22 (1H, m), 6.19-5.72 (1H, brs), 0.31 (9H, s). LCMS (ESI) m/z 236 [M+H]⁺

Step 2: Synthesis of 2-ethynyl-3-fluorobenzamide

The title compound was obtained as in step 3 of Example 76, except that 3-fluoro-2-((trimethylsilyl)ethynyl)benzamide was used in place of 5-(benzyloxy)-2-((triisopropylsilyl)ethynyl)pyrimidine.

¹H-NMR (CDCl₃) δ: 7.89-7.86 (1H, m), 7.46 (1H, dt, J=5.4, 8.0 Hz), 7.30-7.21 (2H, m), 6.29-5.45 (1H, brs), 3.77 (1H, s). LCMS (ESI) m/z 164 [M+H]⁺

Step 3: Synthesis of Example Compound 79

The title compound was obtained as in step 4 of Example 1, except that 2-ethynyl-3-fluorobenzamide was used in place of 2-ethynyl-1,3-difluorobenzene.

¹H-NMR (CD₃OD) δ: 8.23 (1H, s), 7.66 (1H, s), 7.47-7.41 (2H, m), 7.35-7.30 (1H, m), 5.87 (1H, d, J=6.8 Hz), 4.82-4.75 (1H, m), 4.32-4.29 (1H, m), 4.26-4.24 (1H, m), 3.40-3.35 (2H, m). LCMS (ESI) m/z 506 [M+H]⁺.

Example 80

4-Amino-5-[2-(3,5-difluoro-2-methoxy-4-pyridyl)ethynyl]-7-[(2R,3R,4S,5R)-3,4-dihydroxy-5-[(sulfamoylamino)methyl]tetrahydrofuran-2-yl]pyrrolo[2,3-d]pyrimidine Step 1: Synthesis of 4-ethynyl-3,5-difluoro-2-methoxypyridine 2,3,5-Trifluoro-4-iodopyridine (500 mg, 1.93 mmol) was dissolved in methanol (3 mL), and sodium methoxide (a 5 M methanol solution, 1.15 mL) was added thereto at room temperature, followed by stirring at room temperature overnight. The reaction solution was partitioned between ethyl acetate and water, and the organic layer was separated and sequentially washed with water and brine. The solvent was distilled off, and the residue was purified by silica gel column chromatography (developing solvent: ethyl acetate/hexane), thereby obtaining the target product (376 mg) as an oil mixture of 4-ethynyl-3,5-difluoro-2-methoxypyridine and 4-ethynyl-3-fluoro-2,5-dimethoxypyridine.

The synthesis was performed as in steps 2 and 3 of Example 76 by using the obtained mixture, followed by separation and purification by silica gel column chromatography (developing solvent: ethyl acetate/hexane) to give the title compound.

¹H-NMR (CDCl₃) δ: 7.87 (1H, s), 4.02 (3H, s), 3.73 (1H, s).

Step 2: Synthesis of Example Compound 80

The title compound was obtained as in step 4 of Example 1, except that 4-ethynyl-3,5-difluoro-2-methoxypyridine was used in place of 2-ethynyl-1,3-difluorobenzene.

¹H-NMR (DMSO-D₆) δ: 8.20 (1H, s), 8.19 (1H, s), 8.14 (1H, s), 7.32-7.29 (1H, m), 6.59 (2H, s), 5.94 (1H, d, J=6.6 Hz), 5.41 (1H, d, J=6.6 Hz), 5.24 (1H, d, J=4.4 Hz), 4.58 (1H, ddd, J=7.3, 6.2, 4.4 Hz), 4.11-4.04 (2H, m), 3.96 (3H, s). LCMS (ESI) m/z 512 [M+H]⁺.

Example 81

4-Amino-7-[(2R,3R,4S,5R)-3,4-dihydroxy-5-[(sulfamoylamino)methyl]tetrahydrofuran-2-yl]-5-[2-(3-fluoro-2,5-dimethoxy-4-pyridyl)ethynyl]pyrrolo[2,3-d]pyrimidine Step 1: Synthesis of 4-ethynyl-3-fluoro-2,5-dimethoxypyridine In accordance with step 1 of Example 80, the title compound was obtained.

¹H-NMR (CDCl₃) δ: 7.76 (1H, s), 4.01 (3H, s), 3.97 (3H, s), 3.66 (1H, s).

Step 2: Synthesis of Example Compound 81

The title compound was obtained as in step 4 of Example 1, except that 4-ethynyl-3-fluoro-2,5-dimethoxypyridine was used in place of 2-ethynyl-1,3-difluorobenzene.

¹H-NMR (CD₃OD) δ: 8.26 (1H, s), 7.83 (1H, s), 7.75 (1H, s), 5.89 (1H, d, J=6.6 Hz), 4.85-4.82 (3H, m), 4.34-4.32 (1H, m), 4.29-4.26 (1H, m), 4.04 (3H, s), 3.99 (3H, s), 3.70-3.67 (1H, m), 3.58-3.56 (1H, m), 3.42 (1H, dd, J=12.5, 4.4 Hz), 3.37 (1H, dd, J=12.5, 3.7 Hz). LCMS (ESI) m/z 524 [M+H]⁺.

Example 82

4-Amino-7-[(2R,3R,4S,5R)-3,4-dihydroxy-5-[(sulfamoylamino)methyl]tetrahydrofuran-2-yl]-5-[2-(2-ethylsulfanylphenyl)ethynyl]pyrrolo[2,3-d]pyrimidine Step 1: Synthesis of 1-ethylsulfanyl-2-ethynyl-benzene The title compound was obtained as in step 2 and step 3 of Example 76, except that 1-bromo-2-ethylsulfanyl-benzene was used in place of 5-(benzyloxy)-2-bromopyrimidine.

¹H-NMR (CDCl₃) δ: 7.49 (1H, dd, J=7.5, 1.3 Hz), 7.33-7.25 (2H, m), 7.12 (1H, dt, J=1.5, 7.3 Hz), 3.47 (1H, s), 3.01 (2H, q, J=7.5 Hz), 1.37 (3H, dd, J=9.5, 5.1 Hz).

Step 2: Synthesis of Example Compound 82

The title compound was obtained as in step 4 of Example 1, except that 1-ethylsulfanyl-2-ethynyl-benzene was used in place of 2-ethynyl-1,3-difluorobenzene.

¹H-NMR (DMSO-D₆) δ: 8.18 (1H, s), 7.91 (1H, s), 7.52 (1H, dd, J=7.7, 1.1 Hz), 7.44-7.36 (3H, m), 7.23 (1H, dt, J=1.5, 7.3 Hz), 6.61 (2H, s), 5.93 (1H, d, J=7.0 Hz), 5.41 (1H, d, J=6.6 Hz), 5.25 (1H, d, J=4.4 Hz), 4.59 (1H, q, J=6.2 Hz), 4.12-4.03 (2H, m), 3.23-3.19 (1H, m), 3.13 (1H, dd,

J=8.1, 5.1 Hz), 3.05 (2H, q, J=7.5 Hz), 1.29 (3H, t, J=7.3 Hz). LCMS (ESI) m/z 505.3 [M+H]$^+$.

Example 83

4-Amino-7-[(2R,3R,4S,5R)-3,4-dihydroxy-5-[(sulfamoylamino)methyl]tetrahydrofuran-2-yl]-5-[2-(1,1-dioxo-3,4-dihydro-2H-thiochromen-8-yl)ethynyl]pyrrolo[2,3-d]pyrimidine

Step 1: Synthesis of triisopropyl(thiochroman-8-ylethynyl)silane

The title compound was obtained as in step 2 of Example 76, except that 8-iodothiochroman was used in place of 5-(benzyloxy)-2-bromopyrimidine.

$^1$H-NMR (CDCl$_3$) δ: 7.27-7.25 (1H, m), 6.97-6.93 (1H, m), 6.89 (1H, t, J=7.6 Hz), 3.07-3.04 (2H, m), 2.80 (2H, t, J=6.1 Hz), 2.12-2.06 (2H, m), 1.26-1.04 (21H, m).

Step 2: Synthesis of 8-Ethynyl Thiochroman

The title compound was obtained as in step 3 of Example 76, except that triisopropyl(thiochroman-8-ylethynyl)silane was used in place of 5-(benzyloxy)-2-((triisopropylsilyl)ethynyl)pyrimidine.

$^1$H-NMR (CDCl$_3$) δ: 7.31-7.26 (1H, m), 7.02-6.98 (1H, m), 6.92 (1H, t, J=7.6 Hz), 3.45 (1H, s), 3.09-3.06 (2H, m), 2.82 (2H, t, J=6.1 Hz), 2.13-2.07 (2H, m).

Step 3: Synthesis of 8-ethynyl thiochroman 1,1-dioxide 1,4-Dioxane (1 mL) and water (0.50 mL) were added to 8-ethynyl thiochroman (59 mg, 0.34 mmol). Then, oxone (420 mg, 0.68 mmol) was added thereto under ice-cooling, and the resulting mixture was allowed to warm to room temperature overnight. The reaction solution was partitioned at room temperature with the addition of ethyl acetate, a saturated aqueous sodium hydrogen carbonate solution, and water, and the aqueous layer was extracted with ethyl acetate. The organic layer was washed with saturated saline, and dried over sodium sulfate, followed by filtration and concentration. The residue was purified by silica gel column chromatography (developing solvent: ethyl acetate/hexane), thereby obtaining the title compound (51 mg, 0.25 mmol, 73%) as a white solid.

$^1$H-NMR (CDCl$_3$) δ: 7.55 (1H, d, J=7.8 Hz), 7.38 (1H, t, J=7.8 Hz), 7.21 (1H, dd, J=7.8, 1.0 Hz), 3.59 (1H, s), 3.44-3.41 (2H, m), 3.01 (2H, t, J=6.2 Hz), 2.48-2.42 (2H, m). LCMS (ESI) m/z 207 [M+H]$^+$

Step 4: Synthesis of Example Compound 83

The title compound was obtained as in step 4 of Example 1, except that 8-ethynyl thiochroman 1,1-dioxide was used in place of 2-ethynyl-1,3-difluorobenzene.

$^1$H-NMR (CD$_3$OD) δ: 8.22 (1H, s), 7.69 (1H, s), 7.57 (1H, d, J=7.6 Hz), 7.48 (1H, t, J=7.6 Hz), 7.30 (1H, d, J=7.6 Hz), 5.87 (1H, d, J=6.8 Hz), 4.83-4.79 (1H, m), 4.32-4.30 (1H, m), 4.27-4.25 (1H, m), 3.54-3.51 (2H, m), 3.43-3.33 (2H, m), 3.07 (2H, t, J=6.0 Hz), 2.43-2.38 (2H, m). LCMS (ESI) m/z 549 [M+H].

Example 84

2-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-3-fluoro-benzenesulfonamide

Step 1: Synthesis of 3-fluoro-2-((trimethylsilyl)ethynyl)benzenesulfonamide

The title compound was obtained as in step 2 of Example 76, except that 3-fluoro-2-iodobenzenesulfonamide and ethynyltrimethylsilane were used in place of 5-(benzyloxy)-2-bromopyrimidine and ethynyltriisopropylsilane.

$^1$H-NMR (CDCl$_3$) δ: 7.85 (1H, d, J=7.8 Hz), 7.45-7.41 (1H, m), 7.31-7.27 (1H, m), 5.24 (2H, s), 0.33 (9H, s). LCMS (ESI) m/z 272 [M+H]$^+$

Step 2: Synthesis of 2-ethynyl-3-fluorobenzenesulfonamide

The title compound was obtained as in step 3 of Example 76, except that 3-fluoro-2-((trimethylsilyl)ethynyl)benzenesulfonamide was used in place of 5-(benzyloxy)-2-((triisopropylsilyl)ethynyl)pyrimidine.

$^1$H-NMR (CDCl$_3$) δ: 7.88 (1H, d, J=7.8 Hz), 7.52-7.47 (1H, m), 7.37-7.31 (1H, m), 5.21 (2H, s), 3.90 (1H, s). LCMS (ESI) m/z 200 [M+H]$^+$

Step 3: Synthesis of Example Compound 84

The title compound was obtained as in step 4 of Example 1, except that 2-ethynyl-3-fluorobenzenesulfonamide was used in place of 2-ethynyl-1,3-difluorobenzene.

$^1$H-NMR (CD3OD) δ: 8.30 (1H, s), 7.85 (1H, d, J=7.8 Hz), 7.74 (1H, s), 7.54-7.49 (1H, m), 7.46-7.41 (1H, m), 5.88 (1H, d, J=6.8 Hz), 4.84-4.81 (1H, m), 4.33-4.30 (1H, m), 4.27-4.25 (1H, m), 3.43-3.33 (2H, m). LCMS (ESI) m/z 542 [M+H].

Example 85

4-Amino-5-[2-(2-cyano-6-fluoro-phenyl)ethynyl]-7-[(2R,3R,4S,5R)-3,4-dihydroxy-5-[(sulfamoylamino)methyl]tetrahydrofuran-2-yl]pyrrolo[2,3-d]pyrimidine

Step 1: Synthesis of 3-fluoro-2-((trimethylsilyl)ethynyl)benzonitrile

The title compound was obtained as in step 2 of Example 76, except that 3-fluoro-2-iodobenzonitrile and ethynyltrimethylsilane were used in place of 5-(benzyloxy)-2-bromopyrimidine and ethynyltriisopropylsilane.

$^1$H-NMR (CDCl$_3$) δ: 7.46-7.44 (1H, m), 7.41-7.35 (1H, m), 7.33-7.29 (1H, m), 0.31 (9H, s). LCMS (ESI) m/z 218 [M+H]$^+$

Step 2: Synthesis of 2-ethynyl-3-fluorobenzonitrile

The title compound was obtained as in step 3 of Example 76, except that 3-fluoro-2-((trimethylsilyl)ethynyl)benzonitrile was used in place of 5-(benzyloxy)-2-((triisopropylsilyl)ethynyl)pyrimidine.

$^1$H-NMR (CDCl$_3$) δ: 7.51 (1H, dd, J=7.7, 1.5 Hz), 7.49-7.44 (1H, m), 7.39-7.35 (1H, m), 3.72 (1H, s).

Step 3: Synthesis of Example Compound 85

The title compound was obtained as in step 4 of Example 1, except that 2-ethynyl-3-fluorobenzonitrile was used in place of 2-ethynyl-1,3-difluorobenzene.

$^1$H-NMR (CD$_3$OD) δ: 8.27 (1H, s), 7.79 (1H, s), 7.66-7.64 (1H, m), 7.57-7.53 (2H, m), 5.88 (1H, d, J=6.8 Hz), 4.84-4.80 (1H, m), 4.33-4.31 (1H, m), 4.28-4.26 (1H, m), 3.45-3.35 (2H, m). LCMS (ESI) m/z 488 [M+H].

Example 86

4-Amino-5-[2-[2-(cyclopropylmethoxy)-6-fluorophenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine

Step 1: Synthesis of 1-(cyclopropylmethoxy)-3-fluoro-2-iodobenzene

3-Fluoro-2-iodophenol (200 mg, 0.84 mmol) was dissolved in tetrahydrofuran (2 mL). Then, cyclopropylmethanol (0.14 mL, 1.7 mmol) and triphenylphosphine (440 mg, 1.7 mmol) were added thereto at room temperature, and diisopropyl azodicarboxylate (0.33 ml, 1.7 mmol) was added thereto in an ice bath, followed by stirring for 2 hours in an ice bath. The reaction solution was concentrated, and the residue was purified by silica gel column chromatography (developing solvent: ethyl acetate/hexane), thereby obtaining 1-(cyclopropylmethoxy)-3-fluoro-2-iodobenzene (192 mg) as a yellow oil.

$^1$H-NMR (CDCl$_3$) δ: 7.26-7.19 (1H, m), 6.72-6.67 (1H, m), 6.57 (1H, d, J=8.3 Hz), 3.91 (2H, d, J=6.6 Hz), 1.33-1.28 (1H, m), 0.68-0.63 (2H, m), 0.44-0.41 (2H, m).

Step 2: Synthesis of ((2-(cyclopropylmethoxy)-6-fluorophenyl)ethynyl)trimethylsilane The title compound was obtained as in step 2 of Example 76, except that 1-(cyclopropylmethoxy)-3-fluoro-2-iodobenzene and ethynyltrimethylsilane were used in place of 5-(benzyloxy)-2-bromopyrimidine and ethynyltriisopropylsilane.

$^1$H-NMR (CDCl$_3$) δ: 7.17 (1H, dt, J=6.6, 8.4 Hz), 6.69-6.64 (1H, m), 6.61 (1H, d, J=8.5 Hz), 3.91 (2H, d, J=6.3 Hz), 1.31-1.24 (1H, m), 0.64-0.60 (2H, m), 0.45-0.41 (2H, m), 0.28 (9H, s).

Step 3: Synthesis of 1-(cyclopropylmethoxy)-2-ethynyl-3-fluorobenzene

The title compound was obtained as in step 3 of Example 76, except that ((2-(cyclopropylmethoxy)-6-fluorophenyl)ethynyl)trimethylsilane was used in place of 5-(benzyloxy)-2-((triisopropylsilyl)ethynyl)pyrimidine.

$^1$H-NMR (CDCl$_3$) δ: 7.24 (1H, dt, J=6.6, 8.4 Hz), 6.72 (1H, t, J=8.4 Hz), 6.67 (1H, J=8.4 Hz), 3.93 (2H, d, J=6.6 Hz), 3.52 (1H, s), 1.36-1.30 (1H, m), 0.68-0.63 (2H, m), 0.43-0.39 (2H, m).

Step 4: Synthesis of Example Compound 86

The title compound was obtained as in step 4 of Example 1, except that 1-(cyclopropylmethoxy)-2-ethynyl-3-fluorobenzene was used in place of 2-ethynyl-1,3-difluorobenzene.

$^1$H-NMR (CD$_3$OD) δ: 8.25 (1H, s), 7.59 (1H, s), 7.33-7.27 (1H, m), 6.88 (1H, d, J=8.5 Hz), 6.79 (1H, t, J=8.5 Hz), 5.88 (1H, d, J=7.0 Hz), 4.86-4.83 (1H, m), 4.34-4.32 (1H, m), 4.28-4.26 (1H, m), 4.01 (2H, d, J=7.0 Hz), 3.44-3.34 (2H, m), 1.40-1.32 (1H, m), 0.73-0.68 (2H, m), 0.43 (2H, m). LCMS (ESI) m/z 533 [M+H].

Example 87

4-Amino-7-[(2R,3R,4S,5R)-3,4-dihydroxy-5-[(sulfamoylamino)methyl]tetrahydrofuran-2-yl]-5-[2-[4-(3-pyridylmethoxy)phenyl]ethynyl]pyrrolo[2,3-d]pyrimidine

Step 1: Synthesis of tert-butyl N-(((3aR,4R,6R,6aR)-6-(4-amino-5-((trimethylsilyl)ethynyl)-7H-pyrrolo[2,3-d]pyrimidin-7-yl)-2,2-dimethyltetrahydrofuro[3,4-d][1,3]dioxol-4-yl)methyl)sulfamoyl carbamate tert-Butyl N-(((3aR,4R,6R,6aR)-6-(4-amino-5-iodo-7H-pyrrolo[2,3-d]pyrimidin-7-yl)-2,2-dimethyltetrahydrofuro[3,4-d][1,3]dioxol-4-yl)methyl)sulfamoyl carbamate (500 mg, 0.82 mmol), ethynyltrimethylsilane (240 mg, 2.5 mmol), bis(triphenylphosphine)palladium (II) dichloride (58 mg, 0.082 mmol), copper iodide (16 mg, 0.082 mmol), and diisopropylethylamine (0.28 mL, 1.6 mmol) were suspended in tetrahydrofuran (5 mL). The reaction solution was stirred at 70° C. overnight and filtered through a celite bed, followed by distilling off the solvent. The residue was purified by silica gel column chromatography (developing solvent: methanol/chloroform), thereby obtaining the title compound (339 mg, 0.58 mmol, 71%) as a yellow amorphous substance.

$^1$H-NMR (CDCl$_3$) δ: 9.41 (1H, brs), 8.50 (1H, s), 7.16 (1H, s), 5.98 (2H, brs), 5.63 (1H, d, J=4.6 Hz), 5.25-5.21 (1H, m), 5.07-5.03 (1H, m), 4.51-4.49 (1H, m), 3.59-3.50 (2H, m), 1.59 (3H, s), 1.43 (9H, s), 1.34 (3H, s), 0.26 (9H, s). LCMS (ESI) m/z 581 [M+H]$^+$

Step 2: Synthesis of tert-butyl N-(((3aR,4R,6R,6aR)-6-(4-amino-5-ethynyl-7H-pyrrolo[2,3-d]pyrimidin-7-yl)-2,2-dimethyltetrahydrofuro[3,4-d][1,3]dioxol-4-yl)methyl)sulfamoyl carbamate tert-Butyl N-(((3aR,4R,6R,6aR)-6-(4-amino-5-((trimethylsilyl)ethynyl)-7H-pyrrolo[2,3-d]pyrimidin-7-yl)-2,2-dimethyltetrahydrofuro[3,4-d][1,3]dioxol-4-yl)methyl)sulfamoyl carbamate (339 mg, 0.58 mmol) was dissolved in tetrahydrofuran (6.8 mL), and a tetrabutylammonium fluoride solution (1 M tetrahydrofuran solution, 0.70 mL, 0.70 mmol) was added thereto at room temperature, followed by stirring at room temperature for 25 minutes. After the solvent was distilled off, the residue was purified by silica gel column chromatography (developing solvent: methanol/chloroform), thereby obtaining the title compound (260 mg, 0.51 mmol, 88%) as a yellow powder.

$^1$H-NMR (CDCl$_3$) δ: 9.25 (1H, brs), 8.51 (1H, s), 7.20 (1H, s), 6.11 (2H, brs), 5.65 (1H, d, J=4.6 Hz), 5.29-5.25 (1H, m), 5.10-5.06 (1H, m), 4.52-4.49 (1H, m), 3.66-3.53 (2H, m), 3.25 (1H, s), 1.61 (3H, s), 1.44 (9H, s), 1.35 (3H, s). LCMS (ESI) m/z 509 [M+H]$^+$

Step 3: Synthesis of Example Compound 87 tert-Butyl N-(((3aR,4R,6R,6aR)-6-(4-amino-5-ethynyl-7H-pyrrolo[2,3-d]pyrimidin-7-yl)-2,2-dimethyltetrahydrofuro[3,4-d][1,3]dioxol-4-yl)methyl)sulfamoyl carbamate (20 mg, 0.039 mmol), 3-((4-iodophenoxy)methyl)pyridine (24 mg, 0.079 mmol), bis(triphenylphosphine)palladium (II) dichloride (3 mg, 0.0043 mmol), copper iodide (1 mg, 0.0053 mmol), and diisopropylethylamine (0.013 mL, 0.079 mmol) were suspended in tetrahydrofuran (0.30 mL). The reaction solution was stirred at 70° C. overnight, and a mixed solution (0.60 mL) of trifluoroacetic acid/water=4/1 was added thereto at room temperature, followed by stirring at room temperature overnight. After the solvent was distilled off, the residue was purified by basic silica gel column chromatography (developing solvent: methanol/chloroform), thereby obtaining the title compound (2.1 mg, 0.0039 mmol, 10%) as a yellow powder.

$^1$H-NMR (CD$_3$OD) δ: 8.65-8.60 (1H, m), 8.55-8.50 (1H, m), 8.24 (1H, s), 7.95-7.90 (1H, m), 7.50-7.40 (4H, m), 7.05-7.00 (2H, brs), 5.84-5.82 (1H, brs), 5.19 (2H, s), 4.80-4.70 (1H, m), 4.35-4.20 (2H, m), 3.40-3.30 (2H, m). LCMS (ESI) m/z 552 [M+H]$^+$.

Example 88

4-Amino-7-[(2R,3R,4S,5R)-3,4-dihydroxy-5-[(sulfamoylamino)methyl]tetrahydrofuran-2-yl]-5-[2-(3-fluoro-2-pyridyl)ethynyl]pyrrolo[2,3-d]pyrimidine The title compound was obtained as in step 3 of Example 87, except that 3-fluoro-2-iodopyridine was used in place of 3-((4-iodophenoxy)methyl)pyridine.

$^1$H-NMR (CD$_3$OD) δ: 8.43-8.39 (1H, m), 8.26 (1H, s), 7.78 (1H, s), 7.78-7.71 (1H, m), 7.50-7.46 (1H, m), 5.88 (1H, d, J=7.1 Hz), 4.90-4.60 (1H, m), 4.33-4.31 (1H, m), 4.28-4.25 (1H, m), 3.40-3.31 (2H, m). LCMS (ESI) m/z 464 [M+H]$^+$.

Example 89

4-Amino-7-[(2R,3R,4S,5R)-3,4-dihydroxy-5-[(sulfamoylamino)methyl]tetrahydrofuran-2-yl]-5-[2-(2-methylsulfanylphenyl)ethynyl]pyrrolo[2,3-d]pyrimidine The title compound was obtained as in step 3 of Example 87, except that (2-iodophenyl)(methyl)sulfane was used in place of 3-((4-iodophenoxy)methyl)pyridine.

$^1$H-NMR (CD$_3$OD) δ: 8.24 (1H, s), 7.62 (1H, s), 7.48-7.46 (1H, m), 7.37-7.34 (2H, m), 7.22-7.16 (1H, m), 5.86 (1H, d, J=8.0 Hz), 4.83-4.81 (1H, m), 4.33-4.29 (1H, m), 4.27-4.25 (1H, m), 3.40-3.35 (2H, m), 2.55 (3H, s). LCMS (ESI) m/z 491 [M+H]$^+$.

Example 90

2-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]benzenesulfonamide The title compound was obtained as in step 3 of Example 87, except that 2-iodobenzenesulfonamide was used in place of 3-((4-iodophenoxy)methyl)pyridine.

$^1$H-NMR (CD$_3$OD) δ: 8.23 (1H, s), 8.02 (1H, dd, J=8.0, 4.0 Hz), 7.74 (1H, dd, J=7.8, 4.0 Hz), 7.71 (1H, s), 7.85-7.79 (1H, m), 7.53-7.49 (1H, m), 5.87 (1H, d, J=6.8 Hz), 4.83-4.81 (1H, m), 4.33-4.29 (1H, m), 4.27-4.25 (1H, m), 3.40-3.35 (2H, m). LCMS (ESI) m/z 524 [M+H]$^+$.

Example 91

3-[[4-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]phenoxy]methyl]benzamide The title compound was obtained as in step 3 of Example 87, except that 3-((4-iodophenoxy)methyl)benzamide was used in place of 3-((4-iodophenoxy)methyl)pyridine.

$^1$H-NMR (CD$_3$OD) δ: 8.23 (1H, s), 7.98 (1H, s), 7.84 (1H, d, J=8.1 Hz), 7.65 (1H, d, J=8.0 Hz), 7.54 (1H, s), 7.54-7.49 (1H, m), 7.48 (2H, d, J=8.0 Hz), 7.05 (2H, d, J=8.0 Hz), 5.85 (1H, d, J=7.1 Hz), 5.19 (2H, s), 4.83-4.81 (1H, m), 4.33-4.29 (1H, m), 4.27-4.25 (1H, m), 3.40-3.35 (2H, m). LCMS (ESI) m/z 594 [M+H]$^+$.

Example 92

4-[2-[4-Amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]isoquinoline The title compound was obtained as in step 3 of Example 87, except that 4-iodoisoquinoline was used in place of 3-((4-iodophenoxy)methyl)pyridine.

$^1$H-NMR (CD$_3$OD) δ: 9.20 (1H, s), 8.69 (1H, s), 8.34 (1H, d, J=8.3 Hz), 8.26 (1H, s), 8.16 (1H, d, J=8.3 Hz), 7.95-7.90 (1H, m), 7.81 (1H, s), 7.80-7.74 (1H, m), 5.92 (1H, d, J=6.8 Hz), 4.87-4.81 (1H, m), 4.36-4.33 (1H, m), 4.29-4.25 (1H, m), 3.43-3.39 (2H, m). LCMS (ESI) m/z 496 [M+H]$^+$.

Example 93

4-Amino-7-[(1R,2S,3R,4R)-2,3-dihydroxy-4-[(sulfamoylamino)methyl]cyclopentyl]-5-[2-(1-naphthyl)ethynyl]pyrrolo[2,3-d]pyrimidine Step 1: Synthesis of ((3aR,4R,6R,6aS)-6-amino-2,2-dimethyltetrahydro-3aH-cyclopenta[d][1,3]dioxol-4-yl)methanol and (4aR,6R,7S,7aR)-6-amino-2,2-dimethylhexahydrocyclopenta[d][1,3]dioxin-7-ol (1R,2S,3R,5R)-3-Amino-5-(hydroxymethyl)cyclopentane-1,2-diol hydrochloride (40 g, 218 mmol) was dissolved at room temperature in methanol (400 mL) and 2,2-dimethoxypropane (54 mL, 436 mmol), and methanesulfonic acid (14 mL, 218 mmol) was added thereto dropwise in an ice bath with stirring so as to keep the internal temperature at 7° C. or lower. After the mixture was stirred in an ice bath for 5 minutes and at room temperature overnight, triethylamine (122 mL, 872 mmol) was added thereto dropwise in an ice bath so as to keep the internal temperature at 10° C. or lower. After the mixture was stirred in an ice bath for 5 minutes and at room temperature for 30 minutes, the solvent was distilled off under reduced pressure, thereby obtaining the title compound as a crude isomeric mixture (102 g).

LCMS (ESI) m/z 188 [M+H]$^+$

Step 2: Synthesis of ((3aR,4R,6R,6aS)-6-(4-chloro-7H-pyrrolo[2,3-d]pyrimidin-7-yl)-2,2-dimethyltetrahydro-3aH-cyclopenta[d][1,3]dioxol-4-yl)methanol and (4aR,6R,7S,7aR)-6-(4-chloro-7H-pyrrolo[2,3-d]pyrimidin-7-yl)-2,2-dimethylhexahydrocyclopenta[d][1,3]dioxin-7-ol The crude isomeric mixture (102 g) of ((3aR,4R,6R,6aS)-6-amino-2,2-dimethyltetrahydro-3aH-cyclopenta[d][1,3]dioxol-4-yl)methanol and (4aR,6R,7S,7aR)-6-amino-2,2-dimethylhexahydrocyclopenta[d][1,3]dioxin-7-ol obtained in step 1 of Example 93, and 2-(4,6-dichloropyrimidin-5-yl) acetaldehyde (46 g, 240 mmol) was suspended in 2-butanol (400 mL). Then, triethylamine (61 mL, 436 mmol) was added thereto at room temperature, and the reaction solution was stirred at 80° C. overnight. After the reaction solvent was distilled off under reduced pressure, the residue was partitioned with the addition of ethyl acetate and an aqueous sodium hydrogen carbonate solution, followed by extraction with ethyl acetate. The organic layer was washed with saturated saline, and dried over sodium sulfate, followed by distilling off the solvent, thereby obtaining the title compound as a crude isomeric mixture (72 g).

LCMS (ESI) m/z 324 [M+H]$^+$

Step 3: Synthesis of ((3aR,4R,6R,6aS)-6-(4-chloro-7H-pyrrolo[2,3-d]pyrimidin-7-yl)-2,2-dimethyltetrahydro-3aH-cyclopenta[d][1,3]dioxol-4-yl)methanol The crude isomeric mixture (72 g) of ((3aR,4R,6R,6aS)-6-(4-chloro-7H-pyrrolo[2,3-d]pyrimidin-7-yl)-2,2-dimethyltetrahydro-3aH-cyclopenta[d][1,3]dioxol-4-yl)methanol and (4aR,6R,7S,7aR)-6-(4-chloro-7H-pyrrolo[2,3-d]pyrimidin-7-yl)-2,2-dimethylhexahydrocyclopenta[d][1,3]dioxin-7-ol, obtained in step 2 of Example 93, was suspended in acetone (720 mL), and methanesulfonic acid (14.2 mL, 218 mmol) was added thereto in an ice bath. After the reaction solution was stirred in an ice bath for 40 minutes and at room temperature overnight, triethylamine (122 mL, 872 mmol) was added thereto dropwise in an ice bath so as to keep the internal temperature at 10° C. or lower. After the mixture was stirred in an ice bath for 10 minutes and at room temperature for 30 minutes, the solvent was distilled off under reduced pressure. The residue was partitioned with the addition of ethyl acetate and a sodium bicarbonate solution, followed by extraction with ethyl acetate. The organic layer was washed with saturated saline, and dried over sodium sulfate. The solvent was distilled off, thereby giving a crude product of the title compound (77 g) as a brown oil.

$^1$H-NMR (CDCl$_3$) δ: 8.63 (1H, s), 7.33 (1H, d, J=3.7 Hz), 6.63 (1H, d, J=3.7 Hz), 5.03-4.95 (2H, m), 4.73-4.70 (1H, m), 3.90-3.86 (1H, m), 3.83-378 (1H, m), 2.52-2.43 (2H, m), 2.38-2.32 (1H, m), 2.18-2.16 (1H, m), 1.60 (3H, s), 1.32 (3H, s). LCMS (ESI) m/z 324 [M+H]$^+$

Step 4: Synthesis of 7-((3aS,4R,6R,6aR)-6-(((tert-butyldimethylsilyl)oxy)methyl)-2,2-dimethyltetrahydro-3aH-cyclopenta[d][1,3]dioxol-4-yl)-4-chloro-7H-pyrrolo[2,3-d]pyrimidine The crude product (77 g), i.e., ((3aR,4R,6R,6aS)-6-(4-chloro-7H-pyrrolo[2,3-d]pyrimidin-7-yl)-2,2-dimethyltetrahydro-3aH-cyclopenta[d][1,3]dioxol-4-yl)methanol, obtained in step 3 of Example 93 was dissolved in N,N-dimethylformamide (770 mL). Then, imidazole (37 g, 545 mmol) was added thereto at room temperature, and tert-butyldimethylchlorosilicane (58 g, 382 mmol) was added in a water bath (25° C.), followed by stirring for 40 minutes in a water bath (29° C.). The reaction solution was partitioned with the addition of ethyl acetate (800 mL) and water (800 mL) in an ice bath, and the organic layer was washed with water (400 mL). After the aqueous layer (about 300 mL) was removed, saturated saline (100 mL) was added to the organic layer and washed, followed by further washing with saturated saline (400 mL). After the resulting product was dried over sodium sulfate, the solvent was distilled off under reduced pressure, and the residue was purified by silica gel column chromatography (developing solvent: ethyl acetate/hexane), thereby obtaining the title compound (79 g, four steps: 83%) as a yellow oil.

$^1$H-NMR (CDCl$_3$) δ: 8.62 (1H, s), 7.31 (1H, d, J=3.7 Hz), 6.63 (1H, d, J=3.7 Hz), 5.09-5.04 (1H, m), 4.88 (1H, t, J=6.3 Hz), 4.67-4.64 (1H, m), 3.82-3.74 (2H, m), 2.39-2.37 (3H, m), 1.59 (3H, s), 1.31 (3H, s), 0.93 (9H, s), 0.087 (3H, s), 0.074 (3H, s).

LCMS (ESI) m/z 438 [M+H]$^+$

Step 5: Synthesis of 7-((3aS,4R,6R,6aR)-6-(((tert-butyldimethylsilyl)oxy)methyl)-2,2-dimethyltetrahydro-3aH-cyclopenta[d][1,3]dioxol-4-yl)-4-chloro-5-iodo-7H-pyrrolo [2,3-d]pyrimidine 7-((3aS,4R,6R,6aR)-6-(((tert-Butyldimethylsilyl)oxy) methyl)-2,2-dimethyltetrahydro-3aH-cyclopenta[d][1,3]dioxol-4-yl)-4-chloro-7H-pyrrolo[2,3-d]pyrimidine (79 g, 180 mmol) was dissolved in N,N-dimethylformamide (790 mL), and N-iodosuccinimide (45 g, 198 mmol) was added thereto at room temperature, followed by stirring at 50° C. for 11 hours and at room temperature for 12 hours. Ethyl acetate (600 mL), a saturated sodium hydrogen sulphite solution (300 mL), and water (600 mL) were added in an ice bath to the reaction solution, followed by stirring at room temperature for 10 minutes. After partition, the organic layer was sequentially washed with a liquid mixture of water (600 mL) and saturated saline (100 mL), and saturated saline (500 mL). After the resulting product was dried over sodium sulfate, the solvent was distilled off under reduced pressure, thereby giving a crude product of the title compound (95 g) as a brown oil.

$^1$H-NMR (CDCl$_3$) δ: 8.61 (1H, s), 7.46 (1H, s), 5.08-5.04 (1H, m), 4.85 (1H, t, J=6.3 Hz), 4.64-4.62 (1H, m), 3.81-3.73 (2H, m), 2.42-2.32 (3H, m), 1.58 (3H, s), 1.30 (3H, s), 0.94 (9H, s), 0.095 (3H, s), 0.082 (3H, s). LCMS (ESI) m/z 564 [M+H]$^+$

Step 6: Synthesis of ((3aR,4R,6R,6aS)-6-(4-chloro-5-iodo-7H-pyrrolo[2,3-d]pyrimidin-7-yl)-2,2-dimethyltetrahydro-3aH-cyclopenta[d][1,3]dioxol-4-yl) methanol The crude product (95 g), i.e., 7-((3aS,4R,6R,6aR)-6-(((tert-butyldimethylsilyl)oxy)methyl)-2,2-dimethyltetrahydro-3aH-cyclopenta[d][1,3]dioxol-4-yl)-4-chloro-5-iodo-7H-pyrrolo[2,3-d]pyrimidine, obtained in step 5 of Example 93 was dissolved in tetrahydrofuran (950 mL), and a tetrabutylammonium fluoride solution (1 M tetrahydrofuran solution, 180 mL) was added thereto at room temperature, followed by stirring at room temperature for 1 hour. The resulting mixture was partitioned in an ice bath with the addition of ethyl acetate (500 mL), water (500 mL), and a saturated sodium bicarbonate solution (300 mL), and the aqueous layer was extracted with ethyl acetate (500 mL). The organic layer was washed with saturated saline (500 mL), and dried over sodium sulfate, followed by distilling off the solvent under reduced pressure. The residue was purified by silica gel column chromatography (developing solvent: ethyl acetate/hexane), thereby obtaining the title compound (70 g, two steps: 86%) as a light-green amorphous substance.

$^1$H-NMR (CDCl$_3$) δ: 8.62 (1H, s), 7.48 (1H, s), 5.05-4.99 (1H, m), 4.91 (1H, t, J=6.5 Hz), 4.71-4.68 (1H, m), 3.89-3.85 (1H, m), 3.82-3.78 (1H, m), 2.50-2.45 (2H, m), 2.31-

2.27 (1H, m), 1.90-1.88 (1H, m), 1.59 (3H, s), 1.31 (3H, s). LCMS (ESI) m/z 450 [M+H]$^+$

Step 7: Synthesis of ((3aR,4R,6R,6aS)-6-(4-amino-5-iodo-7H-pyrrolo[2,3-d]pyrimidin-7-yl)-2,2-dimethyltetrahydro-3aH-cyclopenta[d][1,3]dioxol-4-yl)methanol ((3aR,4R,6R,6aS)-6-(4-Chloro-5-iodo-7H-pyrrolo[2,3-d]pyrimidin-7-yl)-2,2-dimethyltetrahydro-3aH-cyclopenta[d][1,3]dioxol-4-yl)methanol (70 g) was dissolved in 1,4-dioxane (350 mL), and 28% aqueous ammonia (350 mL) was added thereto at room temperature, followed by stirring at 100° C. overnight in a pressure-resistant container. After the solvent was distilled off under reduced pressure, the resulting product was suspended in water (700 mL), followed by stirring at room temperature overnight. The precipitate was collected by filtration and washed with water (420 mL), followed by drying to give the title compound (67 g, 99%) as a light-brown powder.

$^1$H-NMR (CDCl$_3$) δ: 8.26 (1H, s), 7.12 (1H, s), 5.69-5.67 (2H, brs), 4.94 (1H, t, J=6.2 Hz), 4.90-4.84 (1H, m), 4.72-4.70 (1H, m), 3.89-3.85 (1H, m), 3.81-3.77 (1H, m), 3.06-3.04 (1H, brs), 2.58-2.46 (2H, m), 2.35-2.27 (1H, m), 1.59 (3H, s), 1.33 (3H, s) LCMS (ESI) m/z 431 [M+H]$^+$.

Step 8: Synthesis of 7-((3aS,4R,6R,6aR)-6-(aminomethyl)-2,2-dimethyltetrahydro-3aH-cyclopenta[d][1,3]dioxol-4-yl)-5-iodo-7H-pyrrolo[2,3-d]pyrimidin-4-amine ((3aR,4R,6R,6aS)-6-(4-Amino-5-iodo-7H-pyrrolo[2,3-d]pyrimidin-7-yl)-2,2-dimethyltetrahydro-3aH-cyclopenta[d][1,3]dioxol-4-yl)methanol (51 g, 118 mmol) and phthalimide (35 g, 236 mmol) were dissolved in tetrahydrofuran (1000 mL). Then, triphenylphosphine (93 g, 354 mmol) was added thereto with stirring under ice-cooling. After triphenylphosphine was dissolved, diisopropyl azodicarboxylate (70 mL, 354 mmol) was added thereto dropwise with stirring under ice-cooling. After the reaction solution was stirred for 30 minutes under ice-cooling, the resulting product was stirred at room temperature for 90 minutes, and the reaction solution was distilled off under reduced pressure. Ethanol (750 mL), hydrazine monohydrate (25 mL, 519 mmol), and water (150 mL) were added to the residue, followed by stirring at 80° C. overnight. After the solvent was distilled off under reduced pressure, the resulting product was partitioned with the addition of chloroform, water, and a saturated aqueous sodium hydrogen carbonate solution. The aqueous layer was then separated and extracted with chloroform. All of the organic layers were combined and dried over sodium sulfate, followed by distilling off the solvent. The residue was purified by basic silica gel column chromatography (developing solvent: methanol/chloroform), thereby obtaining the title compound (52 g, 89 wt %) as a yellow amorphous substance.

$^1$H-NMR (CDCl$_3$) δ: 8.27 (1H, s), 7.13 (1H, s), 5.62-5.60 (2H, brs), 4.96-4.90 (2H, m), 4.56 (1H, t, J=6.0 Hz), 2.90 (2H, d, J=6.6 Hz), 2.46-2.40 (1H, m), 2.27-2.21 (1H, m), 2.17-2.08 (1H, m), 1.58 (3H, s), 1.32 (3H, s). LCMS (ESI) m/z 430 [M+H]$^+$.

Step 9: Synthesis of tert-butyl N-(((3aR,4R,6R,6aS)-6-(4-amino-5-iodo-7H-pyrrolo[2,3-d]pyrimidin-7-yl)-2,2-dimethyltetrahydro-3aH-cyclopenta[d][1,3]dioxol-4-yl)methyl)sulfamoyl carbamate 7-((3aS,4R,6R,6aR)-6-(Aminomethyl)-2,2-dimethyltetrahydro-3aH-cyclopenta[d][1,3]dioxol-4-yl)-5-iodo-7H-pyrrolo[2,3-d]pyrimidin-4-amine (51.5 g, 89 wt %, ca. 107 mmol) obtained in step 8 of Example 93 was dissolved in acetonitrile (515 mL). Then, 1-aza-4-azoniabicyclo[2.2.2]octan-4-ylsulfonyl(tert-butoxycarbonyl)azanido: 1,4-diazabicyclo[2.2.2]octane monohydrochloride (Reference: Organic Letters, 2012, 10, 2626-2629) (70.5 g, 160 mmol) was added thereto at room temperature. After the reaction solution was stirred at room temperature for 30 minutes, water (1030 mL) and a saturated aqueous ammonium chloride solution (258 mL) were added to the reaction solution, followed by stirring at room temperature for 5 hours. The precipitate was collected by filtration and washed with water (1545 mL), followed by drying to give the title compound (57.1 g, 88%) as a yellowish white powder.

$^1$H-NMR (CDCl$_3$) δ: 8.33 (1H, s), 7.05 (1H, s), 6.62-6.60 (1H, brs), 5.73-5.71 (2H, brs), 4.99 (1H, t, J=5.9 Hz), 4.78-4.72 (1H, m), 4.64-4.62 (1H, m), 3.36-3.32 (1H, m), 3.24-3.25 (1H, m), 2.57-2.46 (2H, m), 2.38-2.32 (1H, m), 1.56 (3H, s), 1.48 (9H, s), 1.29 (3H, s). LCMS (ESI) m/z 609 [M+H]$^+$.

Step 10: Synthesis of Example Compound 93 tert-Butyl N-(((3aR,4R,6R,6aS)-6-(4-amino-5-iodo-7H-pyrrolo[2,3-d]pyrimidin-7-yl)-2,2-dimethyltetrahydro-3aH-cyclopenta[d][1,3]dioxol-4-yl)methyl)sulfamoyl carbamate (20 mg, 0.033 mmol), 1-ethynylnaphthalene (10 mg, 0.066 mmol), bis(triphenylphosphine)palladium (II) dichloride (3 mg, 0.0043 mmol), copper iodide (1 mg, 0.0053 mmol), and diisopropylethylamine (0.011 mL, 0.066 mmol) were suspended in tetrahydrofuran (0.30 mL). After the reaction solution was stirred at 70° C. for 1 hour, a mixed solution (0.60 mL) of trifluoroacetic acid/water=4/1 was added thereto at room temperature, followed by stirring at room temperature overnight. After the solvent was distilled off, the residue was purified by silica gel column chromatography (developing solvent: methanol/chloroform), thereby obtaining the title compound (8.2 mg, 50%) as a yellow powder.

$^1$H-NMR (CD$_3$OD) δ: 8.36 (1H, d, J=8.5 Hz), 8.17 (1H, s), 7.93-7.89 (2H, m), 7.78-7.75 (1H, m), 7.74 (1H, s), 7.64-7.47 (3H, m), 5.02-4.95 (1H, m), 4.47-4.44 (1H, m), 4.05-4.03 (1H, m), 3.30-3.16 (2H, m), 2.52-2.44 (1H, m), 2.37-2.28 (1H, m), 1.90-1.82 (1H, m). LCMS (ESI) m/z 493 [M+H]$^+$.

Example 94

4-Amino-7-[(1R,2S,3R,4R)-2,3-dihydroxy-4-[(sulfamoylamino)methyl]cyclopentyl]-5-[2-(2,6-dimethoxyphenyl)ethynyl]pyrrolo[2,3-d]pyrimidine The title compound was obtained as in step 10 of Example 93, except that 2-ethynyl-1,3-dimethoxybenzene was used in place of 1-ethynylnaphthalene.

$^1$H-NMR (CD$_3$OD) δ: 8.12 (1H, s), 7.52 (1H, s), 7.27 (1H, t, J=8.5 Hz), 6.68 (2H, d, J=8.5 Hz), 4.95-4.86 (1H, m), 4.40-4.35 (1H, m), 4.05-3.95 (1H, m), 3.91 (6H, s), 3.30-3.13 (2H, m), 2.50-2.40 (1H, m), 2.34-2.28 (1H, m), 1.85-1.73 (1H, m). LCMS (ESI) m/z 503 [M+H]$^+$.

Example 95

4-Amino-7-[(1R,2S,3R,4R)-2,3-dihydroxy-4-[(sulfamoylamino)methyl]cyclopentyl]-5-[2-(2-fluoro-6-methoxy-phenyl)ethynyl]pyrrolo[2,3-d]pyrimidine The title compound was obtained as in step 10 of Example 93, except that 2-ethynyl-1-fluoro-3-methoxybenzene was used in place of 1-ethynylnaphthalene.

¹H-NMR (CD₃OD) δ: 8.13 (1H, s), 7.59 (1H, s), 7.34-7.28 (1H, m), 6.88 (1H, d, J=8.5 Hz), 6.78-6.74 (1H, m), 4.97-4.86 (1H, m), 4.43-4.39 (1H, m), 4.03-4.00 (1H, m), 3.96 (3H, s), 3.30-3.23 (1H, m), 3.22-3.14 (1H, m), 2.50-2.40 (1H, m), 2.34-2.28 (1H, m), 1.85-1.73 (1H, m). LCMS (ESI) m/z 491 [M+H]⁺.

Example 96

8-[2-[4-Amino-7-[(1R,2S,3R,4R)-2,3-dihydroxy-4-[(sulfamoylamino)methyl]cyclopentyl]pyrrolo[2,3-d]pyrimidin-5-yl]ethynyl]quinoline The title compound was obtained as in step 10 of Example 93, except that 8-ethynylquinoline was used in place of 1-ethynylnaphthalene.
¹H-NMR (CD₃OD) δ: 9.04-9.02 (1H, m), 8.40-8.35 (1H, m), 8.16 (1H, s), 7.94-7.85 (2H, m), 7.63 (1H, s), 7.61-7.57 (2H, m), 5.00-4.91 (1H, m), 4.46-4.42 (1H, m), 4.05-4.00 (1H, m), 3.30-3.14 (2H, m), 2.50-2.38 (1H, m), 2.34-2.28 (1H, m), 1.87-1.81 (1H, m). LCMS (ESI) m/z 494 [M+H]⁺.

Example 97

4-Amino-7-[(1R,2S,3R,4R)-2,3-dihydroxy-4-[(sulfamoylamino)methyl]cyclopentyl]-5-[2-(2-ethoxy-6-fluoro-phenyl)ethynyl]pyrrolo[2,3-d]pyrimidine Step 1: the Title Compound was Obtained as in Step 10 of Example 93, Except that 1-ethoxy-2-ethynyl-3-fluorobenzene was Used in Place of 1-ethynylnaphthalene ¹H-NMR (CD₃OD) δ: 8.14 (1H, s), 7.60 (1H, s), 7.32-7.26 (1H, m), 6.86 (1H, d, J=8.5 Hz), 6.79-6.74 (1H, m), 5.00-4.91 (1H, m), 4.45-4.42 (1H, m), 4.23 (2H, q, J=7.1 Hz), 4.05-4.00 (1H, m), 3.30-3.24 (1H, m), 3.21-3.15 (1H, m), 2.50-2.40 (1H, m), 2.34-2.28 (1H, m), 1.87-1.81 (1H, m), 1.47 (3H, t, J=7.1 Hz). LCMS (ESI) m/z 505 [M+H]⁺.

Step 2: Synthesis of 4-amino-7-[(1R,2S,3R,4R)-2,3-dihydroxy-4-[(sulfamoylamino)methyl]cyclopentyl]-5-[2-(2-ethoxy-6-fluoro-phenyl)ethynyl]pyrrolo[2,3-d]pyrimidine hydrochloride The title compound hydrochloride was obtained in accordance with step 5 of Example 1.
¹H-NMR (CD₃OD) δ: 8.32 (1H, s), 7.95 (1H, s), 7.38-7.34 (1H, m), 6.93 (1H, d, J=8.5 Hz), 6.84-6.80 (1H, m), 5.13-5.09 (1H, m), 4.41-4.37 (1H, m), 4.27 (2H, q, J=7.0 Hz), 4.02-4.00 (1H, m), 3.28-3.23 (1H, m), 3.19-3.13 (1H, m), 2.47-2.42 (1H, m), 2.32-2.80 (1H, m), 1.87-1.79 (1H, m), 1.48 (3H, t, J=7.0 Hz). LCMS (ESI) m/z 505 [M+H]⁺

Example 98

4-Amino-7-[(1R,2S,3R,4R)-2,3-dihydroxy-4-[(sulfamoylamino)methyl]cyclopentyl]-5-[2-(2-fluoro-6-methylsulfanyl-phenyl)ethynyl]pyrrolo[2,3-d]pyrimidine The title compound was obtained as in step 10 of Example 93, except that 2-ethynyl-1-fluoro-3-methylsulfanyl-benzene was used in place of 1-ethynylnaphthalene.
¹H-NMR (CD₃OD) δ: 8.15 (1H, s), 7.67 (1H, s), 7.35-7.30 (1H, m), 7.10 (1H, d, J=7.8 Hz), 6.98-6.92 (1H, m), 5.00-4.91 (1H, m), 4.45-4.40 (1H, m), 4.05-4.00 (1H, m), 3.30-3.24 (1H, m), 3.21-3.15 (1H, m), 2.56 (3H, s), 2.50-2.41 (1H, m), 2.34-2.28 (1H, m), 1.87-1.78 (1H, m). LCMS (ESI) m/z 507 [M+H]⁺.

Example 99

4-Amino-7-[(1R,2S,3R,4R)-2,3-dihydroxy-4-[(sulfamoylamino)methyl]cyclopentyl]-5-[2-(2-ethylsulfanyl-6-fluoro-phenyl)ethynyl]pyrrolo[2,3-d]pyrimidine The title compound was obtained as in step 10 of Example 93, except that 1-ethylsulfanyl-2-ethynyl-3-fluorobenzene was used in place of 1-ethynylnaphthalene.
¹H-NMR (DMSO-D₆) δ: 8.15 (1H, s), 7.93 (1H, s), 7.42-7.36 (1H, m), 7.23 (1H, d, J=8.8 Hz), 7.13 (1H, t, J=8.8 Hz), 6.65 (1H, dd, J=6.6, 5.9 Hz), 6.53 (2H, brs), 4.90 (1H, ddd, J=10.3, 9.9, 8.4 Hz), 4.71 (1H, brs), 4.24 (1H, dd, J=8.8, 5.5 Hz), 3.79 (1H, dd, J=5.5, 3.7 Hz), 3.10-3.05 (1H, m), 3.09 (2H, q, J=7.3 Hz), 2.96-2.89 (1H, m), 2.22 (1H, dt, J=13.2, 8.1 Hz), 2.15-2.06 (1H, m), 1.61-1.53 (1H, m), 1.30 (3H, t, J=7.3 Hz). LCMS (ESI) m/z 521 [M+H]⁺.

Example 100

4-Amino-7-[(1R,2S,3R,4R)-2,3-dihydroxy-4-[(sulfamoylamino)methyl]cyclopentyl]-5-[2-(2-ethoxy-6-methoxy-phenyl)ethynyl]pyrrolo[2,3-d]pyrimidine The title compound was obtained as in step 10 of Example 93, except that 1-ethoxy-2-ethynyl-3-methoxybenzene was used in place of 1-ethynylnaphthalene.
¹H-NMR (DMSO-D₆) δ: 8.12 (1H, s), 7.72 (1H, s), 7.27 (1H, t, J=8.4 Hz), 6.72-6.65 (3H, m), 6.53 (2H, s), 4.92-4.85 (2H, m), 4.68 (1H, d, J=4.4 Hz), 4.25-4.20 (1H, m), 4.16 (2H, q, J=7.0 Hz), 3.87 (3H, s), 3.82-3.78 (1H, m), 3.12-3.06 (1H, m), 2.96-2.90 (1H, m), 2.23-2.18 (1H, m), 2.15-2.07 (1H, m), 1.61-1.53 (1H, m), 1.37 (3H, t, J=7.0 Hz). LCMS (ESI) m/z 517.3 [M+H]⁺.

Example 101

4-[4-[2-[4-amino-7-[(1R,2S,3R,4R)-2,3-dihydroxy-4-[(sulfamoylamino)methyl]cyclopentyl]pyrrolo[2,3-d]pyrimidin-5-yl]ethynyl]-3,5-difluoro-phenyl]morpholine The title compound was obtained as in step 10 of Example 93, except that 4-(4-ethynyl-3,5-difluorophenyl)morpholine was used in place of 1-ethynylnaphthalene.
¹H-NMR (CD₃OD) δ: 8.14 (1H, s), 7.59 (1H, s), 6.63 (2H, d, J=11.5 Hz), 4.97-4.93 (1H, m), 4.41 (1H, dd, J=8.4, 5.7 Hz), 4.01 (1H, dd, J=5.7, 3.8 Hz), 3.80 (4H, t, J=4.9 Hz), 3.27-3.11 (6H, m), 2.48-2.40 (1H, m), 2.35-2.25 (1H, m), 1.84-1.76 (1H, m).
LCMS (ESI) m/z 564 [M+H]⁺.

Example 102

4-Amino-5-[2-[2,6-difluoro-4-(1-piperidyl)phenyl]ethynyl]-7-[(1R,2S,3R,4R)-2,3-dihydroxy-4-[(sulfamoylamino)methyl]cyclopentyl]pyrrolo[2,3-d]pyrimidine Step 1: Synthesis of 1-(4-ethynyl-3,5-difluorophenyl)piperidine The title compound was obtained as in step 1 of Example 23, except that piperidine was used in place of morpholine.

¹H-NMR (CDCl₃) δ: 6.34 (2H, d, J=11.4 Hz), 3.37 (1H, s), 3.26-3.20 (4H, m), 1.68-1.60 (6H, m). LCMS (ESI) m/z 222 [M+H]⁺

Step 2: Synthesis of Example Compound 102

The title compound was obtained as in step 10 of Example 93, except that 1-(4-ethynyl-3,5-difluorophenyl)piperidine was used in place of 1-ethynylnaphthalene.
¹H-NMR (CD₃OD) δ: 8.13 (1H, s), 7.57 (1H, s), 6.54 (2H, d, J=11.7 Hz), 4.98-4.91 (1H, m), 4.40 (1H, dd, J=8.4, 5.6 Hz), 4.01 (1H, dd, J=5.6, 3.8 Hz), 3.31-3.30 (4H, m), 3.28-3.14 (2H, m), 2.48-2.39 (1H, m), 2.35-2.26 (1H, m), 1.85-1.75 (1H, m), 1.70-1.63 (6H, m). LCMS (ESI) m/z 562 [M+H]⁺.

Example 103

4-Amino-5-[2-[2,6-difluoro-4-(4-methylpiperazin-1-yl)phenyl]ethynyl]-7-[(1R,2S,3R,4R)-2,3-dihydroxy-4-[(sulfamoylamino)methyl]cyclopentyl]pyrrolo[2,3-d]pyrimidine Step 1: Synthesis of 1-(4-ethynyl-3,5-difluorophenyl)-4-methylpiperazine The title compound was obtained as in step 1 of Example 23, except that 4-methylpiperazine was used in place of morpholine.
¹H-NMR (CDCl₃) δ: 6.36 (2H, d, J=11.0 Hz), 3.39 (1H, s), 3.27-3.23 (4H, m), 2.54-2.50 (4H, m), 2.34 (3H, s). LCMS (ESI) m/z 237 [M+H]⁺

Step 2: Synthesis of Example Compound 103

The title compound was obtained as in step 10 of Example 93, except that 1-(4-ethynyl-3,5-difluorophenyl)-4-methylpiperazine was used in place of 1-ethynylnaphthalene.
¹H-NMR (CD₃OD) δ: 8.23 (1H, s), 7.76 (1H, s), 6.76 (2H, d, J=10.6 Hz), 5.06-4.97 (1H, m), 4.40 (1H, dd, J=8.6, 5.6 Hz), 4.01 (1H, dd, J=5.6, 3.7 Hz), 3.49-3.11 (10H, m), 2.97 (3H, s), 2.48-2.40 (1H, m), 2.34-2.26 (1H, m), 1.87-1.77 (1H, m). LCMS (ESI) m/z 577 [M+H]⁺.

Example 104

4-Amino-5-[2-[2,6-difluoro-4-(pyrazol-1-ylmethoxy)phenyl]ethynyl]-7-[(1R,2S,3R,4R)-2,3-dihydroxy-4-[(sulfamoylamino)methyl]cyclopentyl]pyrrolo[2,3-d]pyrimidine Step 1: Synthesis of 4-((1H-pyrazol-1-yl)methoxy)-2,6-difluorobenzaldehyde The title compound was obtained as in step 1 of Example 55, except that 2,6-difluoro-4-hydroxybenzaldehyde and 1-(chloromethyl)pyrazole hydrochloride were used in place of 2-fluoro-6-hydroxybenzaldehyde and iodoethane.
¹H-NMR (CDCl₃) δ: 10.20 (1H, s), 7.65-7.62 (2H, m), 6.81 (2H, d, J=10.0 Hz), 6.39 (1H, t, J=2.1 Hz), 6.05 (2H, s). LCMS (ESI) m/z 239 [M+H]⁺

Step 2: Synthesis of 1-((4-ethynyl-3,5-difluorophenoxy)methyl)-1H-pyrazole

The title compound was obtained as in step 1 of Example 51, except that 4-((1H-pyrazol-1-yl)methoxy)-2,6-difluorobenzaldehyde was used in place of 2-fluoro-6-methoxybenzaldehyde.

¹H-NMR (CDCl₃) δ: 7.64-7.60 (2H, m), 6.73 (2H, d, J=8.8 Hz), 6.37 (1H, t, J=2.2 Hz), 5.99 (2H, s), 3.42 (1H, s). LCMS (ESI) m/z 235 [M+H]⁺

Step 3: Synthesis of Example Compound 104

The title compound was obtained as in step 10 of Example 93, except that 1-((4-ethynyl-3,5-difluorophenoxy)methyl)-1H-pyrazole was used in place of 1-ethynylnaphthalene.
¹H-NMR (DMSO-D₆) δ: 8.14 (1H, s), 8.04 (1H, d, J=2.0 Hz), 7.91 (1H, s), 7.61 (1H, d, J=1.5 Hz), 7.15 (2H, d, J=9.5 Hz), 6.64 (1H, t, J=6.3 Hz), 6.51 (2H, s), 6.37-6.36 (1H, m), 6.18 (2H, s), 4.91-4.86 (2H, m), 4.69-4.66 (1H, m), 4.23-4.19 (1H, m), 3.80-3.77 (1H, brs), 3.09-3.04 (1H, m), 2.95-2.88 (1H, m), 2.26-2.18 (1H, m), 2.14-2.10 (1H, m), 1.59-1.51 (1H, m). LCMS (ESI) m/z 575 [M+H]⁺.

Example 105

4-Amino-5-[2-(2,6-difluoro-4-pyrrolidin-1-yl-phenyl)ethynyl]-7-[(1R,2S,3R,4R)-2,3-dihydroxy-4-[(sulfamoylamino)methyl]cyclopentyl]pyrrolo[2,3-d]pyrimidine Step 1: Synthesis of 1-(4-ethynyl-3,5-difluorophenyl)pyrrolidine The title compound was obtained as in step 1 of Example 23, except that pyrrolidine was used in place of morpholine.
¹H-NMR (CDCl₃) δ: 6.02 (2H, d, J=10.6 Hz), 3.38 (1H, s), 3.28-3.22 (4H, m), 2.04-2.00 (4H, m). LCMS (ESI) m/z 208 [M+H]⁺

Step 2: Synthesis of Example Compound 105

The title compound was obtained as in step 10 of Example 93, except that 1-(4-ethynyl-3,5-difluorophenyl)pyrrolidine was used in place of 1-ethynylnaphthalene.
¹H-NMR (CD₃OD) δ: 8.13 (1H, s), 7.54 (1H, s), 6.21 (2H, d, J=11.0 Hz), 4.40 (1H, dd, J=8.6, 5.7 Hz), 4.00 (1H, t, J=4.6 Hz), 3.67-3.62 (1H, m), 3.29-3.05 (6H, m), 2.48-2.39 (1H, m), 2.35-2.25 (1H, m), 2.08-2.02 (4H, m), 1.85-1.75 (1H, m). LCMS (ESI) m/z 548 [M+H]⁺.

Example 106

4-Amino-7-[(1R,2S,3R,4R)-2,3-dihydroxy-4-[(sulfamoylamino)methyl]cyclopentyl]-5-[2-[2-ethoxy-6-fluoro-4-(1-piperidyl)phenyl]ethynyl]pyrrolo[2,3-d]pyrimidine Step 1: Synthesis of 1-(3-ethoxy-4-ethynyl-5-fluorophenyl)piperidine The title compound was obtained as in step 1 of Example 34, except that 1-(4-ethynyl-3,5-difluorophenyl)piperidine was used in place of 4-(4-ethynyl-3,5-difluorophenyl)morpholine.
¹H-NMR (CDCl₃) δ: 6.24 (1H, dd, J=12.8, 2.2 Hz), 6.18-6.16 (1H, m), 4.12 (2H, q, J=7.0 Hz), 3.42 (1H, s), 3.27-3.22 (4H, m), 1.73-1.60 (6H, m), 1.48 (3H, t, J=7.0 Hz). LCMS (ESI) m/z 248 [M+H]⁺

Step 2: Synthesis of Example Compound 106

The title compound was obtained as in step 10 of Example 93, except that 1-(3-ethoxy-4-ethynyl-5-fluorophenyl)piperidine was used in place of 1-ethynylnaphthalene.

¹H-NMR (CD₃OD) δ: 8.13 (1H, s), 7.50 (1H, s), 6.33-6.30 (2H, m), 4.97-4.90 (1H, m), 4.39 (1H, dd, J=8.4, 5.5 Hz), 4.17 (2H, q, J=7.1 Hz), 4.00 (1H, dd, J=5.7, 3.8 Hz), 3.29-3.13 (6H, m), 2.47-2.40 (1H, m), 2.34-2.26 (1H, m), 1.84-1.75 (1H, m), 1.71-1.61 (6H, m), 1.45 (3H, t, J=7.1 Hz). LCMS (ESI) m/z 588 [M+H]⁺.

Example 107

4-Amino-5-[2-(4-benzyloxy-2,6-difluoro-phenyl)ethynyl]-7-[(1R,2S,3R,4R)-2,3-dihydroxy-4-[(sulfamoylamino)methyl]cyclopentyl]pyrrolo[2,3-d]pyrimidine Step 1: Synthesis of 4-(benzyloxy)-2,6-difluorobenzaldehyde The title compound was obtained as in step 1 of Example 55, except that 2,6-difluoro-4-hydroxybenzaldehyde and benzylbromide were used in place of 2-fluoro-6-hydroxybenzaldehyde and iodoethane.

¹H-NMR (CDCl₃) δ: 10.20 (1H, s), 7.49-7.36 (5H, m), 6.57 (2H, d, J=10.5 Hz), 5.11 (2H, s). LCMS (ESI) m/z 249 [M+H]⁺

Step 2: Synthesis of 5-(benzyloxy)-2-ethynyl-1,3-difluorobenzene

The title compound was obtained as in step 1 of Example 51, except that 4-(benzyloxy)-2,6-difluorobenzaldehyde was used in place of 2-fluoro-6-methoxybenzaldehyde.

¹H-NMR (CDCl₃) δ: 7.41-7.36 (5H, m), 6.54 (2H, d, J=9.0 Hz), 5.04 (2H, s), 3.42 (1H, s). LCMS (ESI) m/z 245 [M+H]⁺

Step 3: Synthesis of Example Compound 107

The title compound was obtained as in step 10 of Example 93, except that 5-(benzyloxy)-2-ethynyl-1,3-difluorobenzene was used in place of 1-ethynylnaphthalene.

¹H-NMR (CD₃OD) δ: 8.15 (1H, s), 7.63 (1H, s), 7.45-7.34 (5H, m), 6.78 (2H, d, J=9.5 Hz), 5.13 (2H, s), 4.92-4.88 (1H, m), 4.43-4.40 (1H, m), 4.02-3.98 (1H, m), 3.30-3.13 (2H, m), 2.46-2.40 (1H, m), 2.31-2.28 (1H, m), 1.83-1.78 (1H, m). LCMS (ESI) m/z 585 [M+H]⁺.

Example 108

3-[4-[2-[4-Amino-7-[(1R,2S,3R,4R)-2,3-dihydroxy-4-[(sulfamoylamino)methyl]cyclopentyl]pyrrolo[2,3-d]pyrimidin-5-yl]ethynyl]-3-ethoxy-5-fluoro-phenyl]-8-oxa-3-azabicyclo[3,2,1]octane Step 1: Synthesis of 3-(4-ethynyl-3,5-difluorophenyl)-8-oxa-3-azabicyclo[3.2.1]octane The title compound was obtained as in step 1 of Example 23, except that 8-oxa-3-azabicyclo[3.2.1]octane was used in place of morpholine.

¹H-NMR (CDCl₃) δ: 6.28 (2H, dd, J=13.9, 2.9 Hz), 4.52-4.49 (2H, m), 3.40 (1H, s), 3.26 (2H, d, J=11.3 Hz), 3.08 (2H, dd, J=11.3, 2.7 Hz), 2.04-1.96 (2H, m), 1.89-1.82 (2H, m). LCMS (ESI) m/z 250 [M+H]⁺

Step 2: Synthesis of 3-(3-ethoxy-4-ethynyl-5-fluorophenyl)-8-oxa-3-azabicyclo[3.2.1]octane The title compound was obtained as in step 1 of Example 34, except that 3-(4-ethynyl-3,5-difluorophenyl)-8-oxa-3-azabicyclo[3.2.1]octane was used in place of 4-(4-ethynyl-3,5-difluorophenyl)morpholine.

¹H-NMR (CDCl₃) δ: 6.12 (1H, dd, J=12.6, 2.4 Hz), 6.03 (1H, s), 4.51-4.47 (2H, m), 4.09 (2H, q, J=7.0 Hz), 3.40 (1H, s), 3.28 (2H, d, J=11.3 Hz), 3.06 (2H, dd, J=11.3, 2.7 Hz), 2.03-1.92 (2H, m), 1.92-1.84 (2H, m), 1.46 (3H, t, J=7.0 Hz). LCMS (ESI) m/z 276 [M+H]⁺

Step 3: Synthesis of Example Compound 108

The title compound was obtained as in step 10 of Example 93, except that 3-(3-ethoxy-4-ethynyl-5-fluorophenyl)-8-oxa-3-azabicyclo[3.2.1]octane was used in place of 1-ethynylnaphthalene.

¹H-NMR (CD₃OD) δ: 8.12 (1H, s), 7.49 (1H, s), 6.29 (1H, d, J=1.8 Hz), 6.25 (1H, s), 4.94-4.90 (1H, m), 4.47 (2H, s), 4.39 (1H, dd, J=8.4, 5.9 Hz), 4.18 (2H, q, J=7.1 Hz), 4.00 (1H, dd, J=5.7, 3.8 Hz), 3.45 (2H, d, J=11.0 Hz), 3.26 (1H, dd, J=12.8, 6.2 Hz), 3.17 (1H, dd, J=12.6, 6.8 Hz), 2.97 (2H, dd, J=11.5, 2.4 Hz), 2.48-2.39 (1H, m), 2.35-2.25 (1H, m), 2.00-1.87 (4H, m), 1.84-1.74 (1H, m), 1.45 (3H, t, J=7.0 Hz). LCMS (ESI) m/z 616 [M+H]⁺.

Example 109

4-Amino-5-[2-(2,3-dihydrobenzothiophen-7-yl)ethynyl]-7-[(1R,2S,3R,4R)-2,3-dihydroxy-4-[(sulfamoylamino)methyl]cyclopentyl]pyrrolo[2,3-d]pyrimidine Step 1: Synthesis of 2,3-dihydrobenzo[b]thiophene-7-carbaldehyde 7-Bromo-2,3-dihydrobenzo[b]thiophene (200 mg, 0.93 mmol) was dissolved in tetrahydrofuran (2 mL), and an n-butyllithium solution (1.6 M hexane solution, 1.4 mL, 2.2 mmol) was added thereto at −78° C., followed by stirring at −78° C. for 30 minutes. Thereafter, N,N-dimethylformamide (0.22 mL, 2.8 mmol) was added thereto at −78° C., followed by stirring at −78° C. for 20 minutes and at room temperature for 1 hour. A saturated aqueous ammonium chloride solution, water, and ethyl acetate were added to the reaction solution, and the aqueous layer was extracted with ethyl acetate. The organic layer was washed with a saturated sodium chloride aqueous solution, and dried over sodium sulfate, followed by distilling off the solvent. The residue was purified by silica gel column chromatography (developing solvent: ethyl acetate/hexane), thereby obtaining the title compound (74 mg, 49%) as a yellow oil.

¹H-NMR (CDCl₃) δ: 10.05 (1H, s), 7.62 (1H, d, J=7.5 Hz), 7.39 (1H, dd, J=7.5, 1.0 Hz), 7.18 (1H, t, J=7.5 Hz), 3.42-3.37 (2H, m), 3.31 (2H, t, J=7.6 Hz). LCMS (ESI) m/z 165 [M+H]⁺

Step 2: Synthesis of 7-ethynyl-2,3-dihydrobenzo[b]thiophene

The title compound was obtained as in step 1 of Example 51, except that 2,3-dihydrobenzo[b]thiophene-7-carbaldehyde was used in place of 2-fluoro-6-methoxybenzaldehyde.

¹H-NMR (CDCl₃) δ: 7.25 (1H, d, J=7.6 Hz), 7.15 (1H, dd, J=7.6, 1.0 Hz), 6.96 (1H, t, J=7.6 Hz), 3.40-3.31 (5H, m).

Step 3: Synthesis of Example Compound 109

The title compound was obtained as in step 10 of Example 93, except that 7-ethynyl-2,3-dihydrobenzo[b]thiophene was used in place of 1-ethynylnaphthalene.

¹H-NMR (CD₃OD) δ: 8.15 (1H, s), 7.60 (1H, s), 7.23 (1H, d, J=7.6 Hz), 7.20-7.17 (1H, m), 7.02 (1H, dd, J=7.6, 7.6 Hz), 4.97-4.88 (1H, m), 4.43-4.40 (1H, m), 4.02-4.00 (1H, m), 3.44-3.34 (4H, m), 3.29-3.23 (1H, m), 3.20-3.15 (1H, m), 2.48-2.41 (1H, m), 2.32-2.28 (1H, m), 1.86-1.78 (1H, m). LCMS (ESI) m/z 501 [M+H].

Example 110

8-[4-[2-[4-Amino-7-[(1R,2S,3R,4R)-2,3-dihydroxy-4-[(sulfamoylamino)methyl]cyclopentyl]pyrrolo[2,3-d]pyrimidin-5-yl]ethynyl]-3-ethoxy-5-fluoro-phenyl]-3-oxa-8-azabicyclo[3,2,1]octane Step 1: Synthesis of 8-(4-ethynyl-3,5-difluorophenyl)-3-oxa-8-azabicyclo[3.2.1]octane The title compound was obtained as in step 1 of Example 23, except that 3-oxa-8-azabicyclo[3.2.1]octane was used in place of morpholine.

¹H-NMR (CDCl₃) δ: 6.23 (2H, dd, J=13.6, 3.3 Hz), 4.01-3.98 (2H, m), 3.81 (2H, d, J=11.2 Hz), 3.53 (2H, d, J=11.2 Hz), 3.39 (1H, s), 2.16-2.01 (4H, m). LCMS (ESI) m/z 250 [M+H]⁺

Step 2: Synthesis of 8-(3-ethoxy-4-ethynyl-5-fluorophenyl)-3-oxa-8-azabicyclo[3.2.1]octane The title compound was obtained as in step 1 of Example 34, except that 8-(4-ethynyl-3,5-difluorophenyl)-3-oxa-8-azabicyclo[3.2.1]octane was used in place of 4-(4-ethynyl-3,5-difluorophenyl)morpholine.

¹H-NMR (CDCl₃) δ: 6.08 (1H, dd, J=12.1, 2.2 Hz), 6.00 (1H, s), 4.08 (2H, q, J=7.0 Hz), 4.01 (2H, d, J=2.6 Hz), 3.85 (2H, d, J=11.0 Hz), 3.52 (2H, d, J=11.0 Hz), 3.39 (1H, d, J=5.9 Hz), 2.13-2.00 (4H, m), 1.45 (3H, t, J=7.0 Hz). LCMS (ESI) m/z 276 [M+H]⁺

Step 3: Synthesis of Example Compound 110

The title compound was obtained as in step 10 of Example 93, except that 8-(3-ethoxy-4-ethynyl-5-fluorophenyl)-3-oxa-8-azabicyclo[3.2.1]octane was used in place of 1-ethynylnaphthalene.

¹H-NMR (CD₃OD) δ: 8.13 (1H, s), 7.50 (1H, s), 6.29 (1H, d, J=2.2 Hz), 6.25 (1H, d, J=2.2 Hz), 4.97-4.92 (1H, m), 4.39 (1H, dd, J=8.4, 5.8 Hz), 4.21-4.14 (4H, m), 4.01 (1H, dd, J=5.8, 3.8 Hz), 3.83 (2H, d, J=10.8 Hz), 3.52 (2H, d, J=10.8 Hz), 3.30-3.12 (2H, m), 2.49-2.39 (1H, m), 2.35-2.26 (1H, m), 2.10-1.99 (4H, m), 1.85-1.75 (1H, m), 1.45 (3H, t, J=7.0 Hz). LCMS (ESI) m/z 616 [M+H]⁺.

Example 111

4-Amino-7-[(1R,2S,3R,4R)-2,3-dihydroxy-4-[(sulfamoylamino)methyl]cyclopentyl]-5-[2-[2-methylsulfanyl-4-(1-piperidyl)phenyl]ethynyl]pyrrolo[2,3-d]pyrimidine Step 1: Synthesis of 4-fluoro-2-(methylthio)benzaldehyde Sodium thiomethoxide (680 mg, 9.6 mmol) was suspended in toluene (10 mL), and 2,4-difluorobenzaldehyde (1 g, 7.0 mmol) was added thereto, followed by stirring at 80° C. for 2 days. Ethyl acetate and water were added to the reaction solution. Then, the organic layer was washed with a saturated aqueous sodium hydrogen carbonate solution and saturated saline, and dried over sodium sulfate, followed by distilling off the solvent. The residue was purified by silica gel column chromatography (developing solvent: ethyl acetate/hexane), thereby obtaining the title compound (499 mg, 42%) as a white solid.

¹H-NMR (CDCl₃) δ: 10.15 (1H, s), 7.82 (1H, dd, J=8.3, 6.1 Hz), 7.01 (1H, dd, J=10.1, 2.3 Hz), 6.95 (1H, dt, J=2.3, 8.3 Hz), 2.49 (3H, s). LCMS (ESI) m/z 171 [M+H]⁺

Step 2: Synthesis of 2-(methylthio)-4-(piperidin-1-yl)benzaldehyde

4-Fluoro-2-(methylthio)benzaldehyde (200 mg, 1.2 mmol) and potassium carbonate (220 mg, 1.6 mmol) were suspended in dimethylsulfoxide (2 mL), and piperidine (0.16 ml, 1.6 mmol) was added thereto at room temperature, followed by stirring at 80° C. for 2 hours and 30 minutes. Ethyl acetate and water were added at room temperature to the reaction solution, and the aqueous layer was extracted with ethyl acetate. The organic layer was washed with a saturated sodium chloride aqueous solution, and dried over sodium sulfate, followed by distilling off the solvent. The residue was purified by silica gel column chromatography (developing solvent: ethyl acetate/hexane), thereby obtaining the title compound (345 mg) as a yellow oil.

¹H-NMR (CDCl₃) δ: 9.99 (1H, s), 7.64 (1H, d, J=8.7 Hz), 6.68 (1H, dd, J=8.7, 2.3 Hz), 6.64 (1H, d, J=2.3 Hz), 3.43-3.40 (4H, m), 2.47 (3H, s), 1.80-1.70 (6H, m). LCMS (ESI) m/z 236 [M+H]⁺

Step 3: Synthesis of 1-(4-ethynyl-3-(methylthio)phenyl)piperidine

The title compound was obtained as in step 1 of Example 51, except that 2-(methylthio)-4-(piperidin-1-yl)benzaldehyde was used in place of 2-fluoro-6-methoxybenzaldehyde.

¹H-NMR (CDCl₃) δ: 7.32 (1H, d, J=8.6 Hz), 6.68 (1H, d, J=2.5 Hz), 6.63 (1H, dd, J=8.6, 2.5 Hz), 3.35 (1H, s), 3.24-3.21 (4H, m), 2.49 (3H, s), 1.72-1.58 (6H, m). LCMS (ESI) m/z 232 [M+H]⁺

Step 4: Synthesis of Example Compound 111

The title compound was obtained as in step 10 of Example 93, except that 1-(4-ethynyl-3-(methylthio)phenyl)piperidine was used in place of 1-ethynylnaphthalene.

¹H-NMR (CD₃OD) δ: 8.13 (1H, s), 7.53 (1H, s), 7.29 (1H, d, J=8.8 Hz), 6.81 (1H, d, J=2.3 Hz), 6.75 (1H, dd, J=8.8, 2.3 Hz), 4.96-4.87 (1H, m), 4.42-4.38 (1H, m), 4.02-4.00 (1H, m), 3.29-3.15 (6H, m), 2.52 (3H, s), 2.48-2.40 (1H, m), 2.28-2.32 (1H, m), 1.85-1.77 (1H, m), 1.72-1.61 (6H, m). LCMS (ESI) m/z 572 [M+H].

Example 112

4-[4-[2-[4-Amino-7-[(1R,2S,3R,4R)-2,3-dihydroxy-4-[(sulfamoylamino)methyl]cyclopentyl]pyrrolo[2,3-d]pyrimidin-5-yl]ethynyl]-3-ethoxy-5-fluoro-phenyl]morpholine The title compound was obtained as in step 10 of Example 93, except that 4-(3-ethoxy-4-ethynyl-5-fluorophenyl)morpholine was used in place of 1-ethynylnaphthalene.

¹H-NMR (DMSO-D₆) δ: 8.12 (1H, s), 7.73 (1H, s), 6.65 (1H, t, J=6.0 Hz), 6.56-6.39 (4H, m), 4.91-4.84 (2H, m), 4.69 (1H, d, J=4.4 Hz), 4.23-4.16 (2H, m), 3.79 (1H, dd,

J=8.4, 4.4 Hz), 3.74-3.68 (4H, m), 3.26-3.21 (4H, m), 3.12-3.04 (1H, m), 2.98-2.88 (1H, m), 2.27-2.17 (1H, m), 2.15-2.07 (2H, m), 1.60-1.51 (1H, m), 1.36 (3H, t, J=7.0 Hz). LCMS (ESI) m/z 590 [M+H]+.

Example 113

4-Amino-7-[(1R,2S,3R,4R)-2,3-dihydroxy-4-[(sulfamoylamino)methyl]cyclopentyl]-5-[2-(4-methoxy-2-methylsulfonyl-phenyl)ethynyl]pyrrolo[2,3-d]pyrimidine Step 1: Synthesis of triisopropyl((4-methoxy-2-(methylsulfonyl)phenyl)ethynyl)silane The title compound was obtained as in step 2 of Example 76, except that 1-bromo-2-methanesulfonyl-4-methoxybenzene was used in place of 5-(benzyloxy)-2-bromopyrimidine.

$^1$H-NMR (CDCl$_3$) δ: 7.61-7.59 (2H, m), 7.06 (1H, dd, J=8.5, 2.7 Hz), 3.88 (3H, s), 3.33 (3H, s), 1.19-1.12 (21H, m). LCMS (ESI) m/z 367 [M+H]+

Step 2: Synthesis of 1-ethynyl-4-methoxy-2-(methylsulfonyl)benzene

The title compound was obtained as in step 3 of Example 76, except that triisopropyl((4-methoxy-2-(methylsulfonyl)phenyl)ethynyl)silane was used in place of 5-(benzyloxy)-2-((triisopropylsilyl)ethynyl)pyrimidine.

$^1$H-NMR (CDCl$_3$) δ: 7.64-7.62 (2H, m), 7.09 (1H, dd, J=8.5, 2.7 Hz), 3.90 (3H, s), 3.53 (1H, s), 3.31 (3H, s). LCMS (ESI) m/z 211 [M+H]+

Step 3: Synthesis of Example Compound 113

The title compound was obtained as in step 10 of Example 93, except that 1-ethynyl-4-methoxy-2-(methylsulfonyl)benzene was used in place of 1-ethynylnaphthalene.

$^1$H-NMR (CD$_3$OD) δ: 8.16 (1H, s), 7.72 (1H, s), 7.70 (1H, d, J=8.6 Hz), 7.57 (1H, d, J=2.8 Hz), 7.26 (1H, dd, J=8.6, 2.8 Hz), 4.99-4.91 (1H, m), 4.44-4.40 (1H, m), 4.03-4.01 (1H, m), 3.91 (3H, s), 3.30 (3H, s), 3.39-3.24 (1H, m), 3.21-3.16 (1H, m), 2.50-2.42 (1H, m), 2.35-2.28 (1H, m), 1.87-1.79 (1H, m). LCMS (ESI) m/z 551 [M+H].

Example 114

4-Amino-7-[(1R,2S,3R,4R)-2,3-dihydroxy-4-[(sulfamoylamino)methyl]cyclopentyl]-5-[2-(2-ethylsulfonyl-6-fluoro-4-pyrrolidin-1-yl-phenyl) ethynyl]pyrrolo [2, 3-d]pyrimidine The title compound was obtained as in step 10 of Example 93, except that 1-(3-(ethylsulfonyl)-4-ethynyl-5-fluorophenyl)pyrrolidine was used in place of 1-ethynylnaphthalene.

$^1$H-NMR (CD$_3$OD) δ: 8.13 (1H, s), 7.62 (1H, s), 6.99 (1H, d, J=2.6 Hz), 6.64 (1H, dd, J=12.4, 2.6 Hz), 4.98-4.90 (1H, m), 4.43-4.39 (1H, m), 4.02-4.00 (1H, m), 3.49 (2H, q, J=7.4 Hz), 3.39-3.34 (4H, m), 3.28-3.24 (1H, m), 3.20-3.15 (1H, m), 2.48-2.40 (1H, m), 2.34-2.28 (1H, m), 2.09-2.06 (4H, m), 1.85-1.77 (1H, m), 1.24 (3H, t, J=7.4 Hz). LCMS (ESI) m/z 622 [M+H].

Example 115

4-Amino-5-[2-[2,6-difluoro-4-[(3R)-3-fluoropyrrolidin-1-yl]phenyl]ethynyl]-7-[(1R,2S,3R,4R)-2,3-dihydroxy-4-[(sulfamoylamino)methyl]cyclopentyl] pyrrolo[2,3-d]pyrimidine The title compound was obtained as in step 10 of Example 93, except that (3R)-1-(4-ethynyl-3,5-difluorophenyl)-3-fluoropyrrolidine was used in place of 1-ethynylnaphthalene.

$^1$H-NMR (CD$_3$OD) δ: 8.12 (1H, s), 7.54 (1H, s), 6.25 (2H, d, J=10.6 Hz), 5.38 (1H, d, J=53.2 Hz), 5.04-4.95 (1H, m), 4.40 (1H, dd, J=8.4, 5.9 Hz), 4.01 (1H, dd, J=5.5, 3.7 Hz), 3.64-3.10 (6H, m), 2.49-2.38 (1H, m), 2.37-2.26 (2H, m), 2.22-2.12 (1H, m), 1.84-1.75 (1H, m). LCMS (ESI) m/z 566 [M+H]+.

Example 116

4-Amino-5-[2-[2,6-difluoro-4-[(3S)-3-fluoropyrrolidin-1-yl]phenyl]ethynyl]-7-[(1R,2S,3R,4R)-2,3-dihydroxy-4-[(sulfamoylamino)methyl]cyclopentyl] pyrrolo[2,3-d]pyrimidine Step 1: Synthesis of (3S)-1-(4-ethynyl-3,5-difluorophenyl)-3-fluoropyrrolidine The title compound was obtained as in step 1 of Example 23, except that (S)-3-fluoropyrrolidine was used in place of morpholine.

$^1$H-NMR (CDCl$_3$) δ: 6.06 (2H, d, J=10.3 Hz), 5.38 (1H, d, J=53.5 Hz), 3.62-3.39 (5H, m), 2.47-2.36 (1H, m), 2.28-2.07 (1H, m).
LCMS (ESI) m/z 226 [M+H]+

Step 2: Synthesis of Example Compound 116

The title compound was obtained as in step 10 of Example 93, except that (3S)-1-(4-ethynyl-3,5-difluorophenyl)-3-fluoropyrrolidine was used in place of 1-ethynylnaphthalene.

$^1$H-NMR (CD$_3$OD) δ: 8.11 (1H, s), 7.53 (1H, s), 6.22 (2H, d, J=10.6 Hz), 5.38 (1H, d, J=53.2 Hz), 4.93-4.90 (1H, m), 4.42-4.37 (1H, m), 4.01 (1H, dd, J=5.5, 4.0 Hz), 3.62-3.15 (6H, m), 2.49-2.40 (1H, m), 2.34-2.27 (2H, m), 2.22-2.08 (1H, m), 1.84-1.76 (1H, m). LCMS (ESI) m/z 566 [M+H]+.

Example 117

4-Amino-7-[(1R,2S,3R,4R)-2,3-dihydroxy-4-[(sulfamoylamino)methyl]cyclopentyl]-5-[2-(1,1-dioxo-2,3-dihydrobenzothiophen-7-yl)ethynyl]pyrrolo[2,3-d] pyrimidine Step 1: Synthesis of 7-ethynyl-2,3-dihydrobenzo[b]thiophene 1,1-dioxide The title compound was obtained as in step 3 of Example 70, except that 7-ethynyl-2,3-dihydrobenzo[b]thiophene was used in place of 2-(ethylthio)-6-fluoro-4-(pyrrolidin-1-yl)benzaldehyde.

$^1$H-NMR (CDCl$_3$) δ: 7.57-7.51 (2H, m), 7.36 (1H, d, J=7.1 Hz), 3.57-3.52 (3H, m), 3.35 (2H, t, J=7.2 Hz). LCMS (ESI) m/z 193 [M+H]+

Step 2: Synthesis of Example Compound 117

The title compound was obtained as in step 10 of Example 93, except that 7-ethynyl-2,3-dihydrobenzo[b]thiophene 1,1-dioxide was used in place of 1-ethynylnaphthalene.

$^1$H-NMR (CD$_3$OD) δ: 8.15 (1H, s), 7.74 (1H, s), 7.64 (1H, t, J=7.6 Hz), 7.58 (1H, d, J=7.6 Hz), 7.45 (1H, d, J=7.6 Hz), 5.00-4.89 (1H, m), 4.44-4.40 (1H, m), 4.03-4.00 (1H, m), 3.62 (2H, t, J=7.1 Hz), 3.41 (2H, t, J=7.1 Hz), 3.22-3.11 (2H, m), 2.48-2.42 (1H, m), 2.32-2.26 (1H, m), 1.87-1.77 (1H, m). LCMS (ESI) m/z 533 [M+H].

Example 118

4-Amino-5-[2-[4-(azetidin-1-yl)-2,6-difluoro-phenyl]ethynyl]-7-[(1R,2S,3R,4R)-2,3-dihydroxy-4-[(sulfamoylamino)methyl]cyclopentyl]pyrrolo[2,3-d]pyrimidine The title compound was obtained as in step 10 of Example 93, except that 1-(4-ethynyl-3,5-difluorophenyl)azetidine was used in place of 1-ethynylnaphthalene.

$^1$H-NMR (CD$_3$OD) δ: 8.14 (1H, s), 7.56 (1H, s), 6.03 (2H, d, J=10.0 Hz), 4.99-4.89 (1H, m), 4.40 (1H, dd, J=8.5, 5.6 Hz), 4.01 (1H, dd, J=5.6, 3.7 Hz), 3.94 (4H, t, J=7.4 Hz), 3.28-3.09 (2H, m), 2.46-2.36 (3H, m), 2.34-2.24 (1H, m), 1.85-1.72 (1H, m).
LCMS (ESI) m/z 534 [M+H]$^+$.

Example 119

4-Amino-5-[2-[2,6-difluoro-4-(4-hydroxy-1-piperidyl)phenyl]ethynyl]-7-[(1R,2S,3R,4R)-2,3-dihydroxy-4-[(sulfamoylamino)methyl]cyclopentyl]pyrrolo[2,3-d]pyrimidine

Step 1: Synthesis of 1-(4-ethynyl-3,5-difluorophenyl)piperidin-4-ol

The title compound was obtained as in step 1 of Example 23, except that piperidin-4-ol was used in place of morpholine.

$^1$H-NMR (CDCl$_3$) δ: 6.36 (2H, d, J=11.2 Hz), 3.93-3.87 (1H, m), 3.58 (2H, dt, J=13.0, 4.9 Hz), 3.40 (1H, s), 3.06-3.00 (2H, m), 2.21-2.10 (1H, m), 1.99-1.91 (2H, m), 1.65-1.55 (2H, m). LCMS (ESI) m/z 238 [M+H]$^+$

Step 2: Synthesis of Example Compound 119

The title compound was obtained as in step 10 of Example 93, except that 1-(4-ethynyl-3,5-difluorophenyl)piperidin-4-ol was used in place of 1-ethynylnaphthalene.

$^1$H-NMR (CD$_3$OD) δ: 8.19 (1H, s), 7.57 (1H, s), 6.57 (2H, d, J=11.5 Hz), 4.98-4.89 (1H, m), 4.40 (1H, t, J=6.3 Hz), 4.01 (1H, dd, J=5.5, 3.8 Hz), 3.85-3.78 (1H, m), 3.70-3.65 (2H, m), 3.30-3.14 (2H, m), 3.08-3.00 (2H, m), 2.49-2.40 (1H, m), 2.36-2.25 (1H, m), 1.97-1.88 (2H, m), 1.85-1.75 (1H, m), 1.60-1.50 (2H, m). LCMS (ESI) m/z 578 [M+H]$^+$.

Example 120

4-Amino-5-[2-[2,6-difluoro-4-[(3R)-3-hydroxypyrrolidin-1-yl]phenyl]ethynyl]-7-[(1R,2S,3R,4R)-2,3-dihydroxy-4-[(sulfamoylamino)methyl]cyclopentyl]pyrrolo[2,3-d]pyrimidine The title compound was obtained as in step 10 of Example 93, except that (3R)-1-(4-ethynyl-3,5-difluorophenyl)-pyrrolidin-3-ol was used in place of 1-ethynylnaphthalene.

$^1$H-NMR (CD$_3$OD) δ: 8.22 (1H, s), 7.55 (1H, s), 6.20 (2H, d, J=11.0 Hz), 4.98-4.90 (1H, m), 4.55-4.51 (1H, m), 4.43-4.36 (1H, m), 4.01 (1H, dd, J=5.5, 3.8 Hz), 3.51-3.42 (2H, m), 3.40-3.33 (1H, m), 3.27-3.14 (3H, m), 2.48-2.40 (1H, m), 2.34-2.26 (1H, m), 2.20-2.09 (1H, m), 2.08-2.00 (1H, m), 1.84-1.75 (1H, m). LCMS (ESI) m/z 564 [M+H]$^+$.

Example 121

4-Amino-5-[2-[2,6-difluoro-4-[(3S)-3-hydroxypyrrolidin-1-yl]phenyl]ethynyl]-7-[(1R,2S,3R,4R)-2,3-dihydroxy-4-[(sulfamoylamino)methyl]cyclopentyl]pyrrolo[2,3-d]pyrimidine

Step 1: Synthesis of (3S)-1-(4-ethynyl-3,5-difluorophenyl)-pyrrolidin-3-ol

The title compound was obtained as in step 1 of Example 23, except that (S)-pyrrolidin-3-ol was used in place of morpholine.

$^1$H-NMR (CDCl$_3$) δ: 6.03 (2H, d, J=10.5 Hz), 4.64-4.60 (1H, m), 3.51-3.43 (2H, m), 3.39 (1H, s), 3.34 (1H, dt, J=3.2, 9.0 Hz), 3.22 (1H, d, J=10.7 Hz), 2.22-2.12 (1H, m), 2.12-2.05 (1H, m). LCMS (ESI) m/z 224 [M+H]$^+$

Step 2: Synthesis of Example Compound 121

The title compound was obtained as in step 10 of Example 93, except that (3S)-1-(4-ethynyl-3,5-difluorophenyl)-pyrrolidin-3-ol was used in place of 1-ethynylnaphthalene.

$^1$H-NMR (CD$_3$OD) δ: 8.23 (1H, s), 7.55 (1H, s), 6.20 (2H, d, J=10.7 Hz), 4.97-4.89 (1H, m), 4.54-4.49 (1H, m), 4.46-4.35 (1H, m), 4.03-3.96 (1H, m), 3.51-3.41 (2H, m), 3.40-3.33 (1H, m), 3.27-3.12 (3H, m), 2.48-2.39 (1H, m), 2.35-2.25 (1H, m), 2.19-2.09 (1H, m), 2.08-2.00 (1H, m), 1.84-1.74 (1H, m). LCMS (ESI) m/z 564 [M+H]$^+$.

Example 122

8-[2-[4-amino-7-[(1R,2S,3R,4R)-2,3-dihydroxy-4-[(sulfamoylamino)methyl]cyclopentyl]pyrrolo[2,3-d]pyrimidin-5-yl]ethynyl]-7-fluoro-4-methyl-2,3-dihydro-1,4-benzoxazine

Step 1: The Title Compound was Obtained as in Step 10 of Example 93, except that 8-ethynyl-7-fluoro-4-methyl-2,3-dihydro-1,4-benzoxazine was used in place of 1-ethynylnaphthalene $^1$H-NMR (DMSO-D$_6$) δ: 8.17-8.12 (2H, m), 7.84 (1H, s), 6.77-6.64 (3H, m), 6.53 (2H, s), 4.88 (1H, dd, J=18.7, 8.4 Hz), 4.43 (2H, t, J=4.2 Hz), 4.21 (1H, dd, J=8.6, 5.3 Hz), 3.80 (1H, dd, J=5.1, 3.3 Hz), 3.25 (2H, t, J=4.2 Hz), 3.12-3.04 (1H, m), 2.96-2.89 (1H, m), 2.82 (3H, s), 2.24-2.19 (1H, m), 2.15-2.08 (1H, m), 1.56 (1H, dd, J=20.9, 11.0 Hz). LCMS (ESI) m/z 532.3 [M+H]$^+$.

Step 2: Synthesis of 8-[2-[4-amino-7-[(1R,2S,3R,4R)-2,3-dihydroxy-4-[(sulfamoylamino)methyl]cyclopentyl]pyrrolo[2,3-d]pyrimidin-5-yl]ethynyl]-7-fluoro-4-methyl-2,3-dihydro-1,4-benzoxazine hydrochloride The title compound hydrochloride was obtained as in step 5 of Example 1.

$^1$H-NMR (DMSO-D$_6$) δ: 8.45 (1H, s), 8.24 (1H, s), 6.81-6.74 (2H, m), 4.98 (1H, dd, J=19.1, 8.8 Hz), 4.47 (2H, t, J=4.2 Hz), 4.20 (1H, dd, J=9.0, 5.3 Hz), 3.80 (1H, dd, J=5.1, 2.9 Hz), 3.27 (2H, t, J=4.4 Hz), 3.08 (1H, dd, J=12.8, 6.6 Hz), 2.93 (1H, dd, J=12.5, 7.3 Hz), 2.84 (3H, s), 2.29-2.22 (1H, m), 2.17-2.10 (1H, m), 1.58 (1H, dd, J=20.7, 10.8 Hz). LCMS (ESI) m/z 532.4 [M+H]$^+$

Example 123

4-Amino-7-[(1R,2S,3R,4R)-2,3-dihydroxy-4-[(sulfamoylamino)methyl]cyclopentyl]-5-[2-(1,1-dioxo-3,4-dihydro-2H-thiochromen-8-yl)ethynyl]pyrrolo[2,3-d]pyrimidine The title compound was obtained as in step 10 of Example 93, except that 8-ethynyl thiochroman 1,1-dioxide was used in place of 1-ethynylnaphthalene.
$^1$H-NMR (CD$_3$OD) δ: 8.16 (1H, s), 7.73 (1H, s), 7.57 (1H, d, J=7.7 Hz), 7.50 (1H, t, J=7.7 Hz), 7.31 (1H, d, J=7.7 Hz), 5.03-4.89 (1H, m), 4.44-4.40 (1H, m), 4.04-4.02 (1H, m), 3.56-3.53 (2H, m), 3.30-3.25 (1H, m), 3.22-3.17 (1H, m), 3.09 (2H, t, J=6.0 Hz), 2.50-2.39 (3H, m), 2.36-2.27 (1H, m), 1.87-1.79 (1H, m). LCMS (ESI) m/z 547 [M+H].

Example 124

4-Amino-5-[2-(2,6-difluorophenyl)ethynyl]-7-[(2R,4S,5R)-4-hydroxy-5-[(sulfamoylamino)methyl]tetrahydrofuran-2-yl]pyrrolo[2,3-d]pyrimidine Step 1: Synthesis of (2R,3S,5R)-5-(4-amino-5-iodo-7H-pyrrolo[2,3-d]pyrimidin-7-yl)-2-(aminoethyl)tetrahydrofuran-3-ol The title compound was obtained as in step 2 of Example 1, except that (2R,3S,5R)-5-(4-amino-5-iodo-7H-pyrrolo[2,3-d]pyrimidin-7-yl)-2-(hydroxymethyl)tetrahydrofuran-3-ol was used in place of [(3aR,4R,6R,6aR)-4-(4-amino-5-iodo-pyrrolo[2,3-d]pyrimidin-7-yl)-2,2-dimethyl-3a,4,6,6a-tetrahydrofuro[3,4-d][1,3]dioxol-6-yl]methanol.
$^1$H-NMR (CD$_3$OD) δ: 8.09 (1H, s), 7.48 (1H, s), 6.52 (1H, t, J=7.0 Hz), 4.37 (1H, dt, J=6.6, 4.0 Hz), 3.89 (1H, dt, J=7.0, 4.0 Hz), 2.91 (1H, dd, J=13.2, 4.0 Hz), 2.83 (1H, dd, J=13.2, 7.0 Hz), 2.66-2.59 (1H, m), 2.33 (1H, ddd, J=13.9, 7.0, 3.7 Hz). LCMS (ESI) m/z 376 [M+H]$^+$ Step 2: Synthesis of tert-butyl-N-[[(2R,3S,5R)-5-(4-amino-5-iodo-pyrrolo[2,3-d]pyrimidin-7-yl)-3-hydroxy-tetrahydrofuran-2-yl]methyl sulfamoyl]carbamate The title compound was obtained as in step 3 of Example 1, except that (2R,3S,5R)-5-(4-amino-5-iodo-7H-pyrrolo[2,3-d]pyrimidin-7-yl)-2-(aminoethyl)tetrahydrofuran-3-ol was used in place of 7-((3aR,4R,6R,6aR)-6-(aminomethyl)-2,2-dimethyltetrahydrofuro[3,4-d][1,3]dioxol-4-yl)-5-iodo-7H-pyrrolo[2,3-d]pyrimidin-4-amine.
$^1$H-NMR (DMSO-D$_6$) δ: 10.84 (1H, s), 8.09 (1H, s), 7.61 (1H, s), 6.76-6.61 (2H, brm), 6.35 (1H, dd, J=8.8, 5.9 Hz), 5.33 (1H, d, J=4.0 Hz), 4.28-4.26 (1H, brm), 3.90-3.87 (1H, m), 3.16-3.10 (2H, m), 2.59-2.52 (1H, m), 2.11-2.06 (1H, m), 1.36 (9H, s). LCMS (ESI) m/z 555 [M+H]$^+$ Step 3: Synthesis of Example Compound 124 tert-Butyl-N-[[(2R,3S,5R)-5-(4-amino-5-iodo-pyrrolo[2,3-d]pyrimidin-7-yl)-3-hydroxy-tetrahydrofuran-2-yl]methyl sulfamoyl]carbamate (40 mg, 0.072 mmol), 2-ethynyl-1,3-difluorobenzene (15 mg, 0.11 mmol), bis(triphenylphosphine)palladium (II) dichloride (10 mg, 0.014 mmol), copper iodide (2.7 mg, 0.014 mmol), and diisopropylethylamine (0.030 mL, 0.18 mmol) were suspended in tetrahydrofuran (0.5 mL). The reaction solution was stirred at 70° C. overnight. Thereafter, trifluoroacetic acid (0.5 mL) was added thereto at room temperature, followed by stirring at room temperature overnight. After the solvent was distilled off, the residue was purified by silica gel column chromatography (developing solvent: methanol/chloroform), thereby obtaining the title compound (1.2 mg, 4%) as a white powder.
$^1$H-NMR (DMSO-D$_6$) δ: 8.18 (1H, s), 8.00 (1H, s), 7.53-7.47 (1H, m), 7.29-7.24 (1H, m), 7.18-7.15 (1H, m), 6.58 (2H, s), 6.43 (1H, dd, J=8.8, 5.6 Hz), 5.35 (1H, d, J=4.1 Hz), 4.39-4.35 (1H, brm), 3.98-3.94 (1H, brm), 3.18-3.03 (2H, brm), 2.66-2.59 (1H, m). LCMS (ESI) m/z 465 [M+H]$^+$.

Example 125

4-Amino-7-[(2R,4S,5R)-4-hydroxy-5-[(sulfamoylamino)methyl]tetrahydrofuran-2-yl]-5-[2-(1-naphthyl)ethynyl]pyrrolo[2,3-d]pyrimidine The title compound was obtained as in step 3 of Example 124, except that 1-ethynylnaphthalene was used in place of 2-ethynyl-1,3-difluorobenzene.
$^1$H-NMR (CD$_3$OD) δ: 8.39 (1H, d, J=8.4 Hz), 8.35 (1H, s), 8.07 (1H, s), 7.96 (1H, brs), 7.94 (1H, brs), 7.85 (1H, d, J=7.3 Hz), 7.67-7.46 (3H, m), 6.59 (1H, dd, J=7.7, 6.2 Hz), 4.62-4.59 (1H, m), 4.18-4.15 (1H, m), 3.41-3.34 (2H, m), 2.77 (1H, ddd, J=13.9, 7.7, 6.2 Hz), 2.45 (1H, ddd, J=13.9, 6.2, 2.9 Hz). LCMS (ESI) m/z 479 [M+H]$^+$.

Example 126

4-[4-Amino-7-[(2R,4S,5R)-4-hydroxy-5-[(sulfamoylamino)methyl]tetrahydrofuran-2-yl]pyrrolo[2,3-d]pyrimidin-5-yl]-2-(o-tolyl)thiazole The title compound was obtained as in Example 2, except that tert-butyl-N-[[(2R,3S,5R)-5-(4-amino-5-iodo-pyrrolo[2,3-d]pyrimidin-7-yl)-3-hydroxy-tetrahydrofuran-2-yl]methyl sulfamoyl]carbamate was used in place of tert-butyl N-(((3aR,4R,6R,6aR)-6-(4-amino-5-iodo-7H-pyrrolo[2,3-d]pyrimidin-7-yl)-2,2-dimethyltetrahydrofuro[3,4-d][1,3]dioxol-4-yl)methyl)sulfamoyl carbamate.
$^1$H-NMR (CD$_3$OD) δ: 8.37 (1H, s), 8.26 (1H, s), 8.15 (1H, s), 8.04-8.01 (1H, m), 7.66 (1H, d, J=7.7 Hz), 7.49-7.35 (3H, m), 6.68 (1H, dd, J=7.7, 6.2 Hz), 4.61-4.58 (1H, m), 4.16 (1H, dt, J=5.9, 3.3 Hz), 3.44 (1H, dd, J=13.6, 4.0 Hz), 3.39 (1H, dd, J=13.6, 4.8 Hz), 2.72-2.65 (1H, m), 2.55 (3H, s), 2.47 (1H, ddd, J=13.6, 6.2, 3.3 Hz). LCMS (ESI) m/z 502 [M+H]$^+$.

Example 127

4-Amino-5-[2-(2-ethoxy-6-fluoro-phenyl)ethynyl]-7-[(2R,4S,5R)-4-hydroxy-5-[(sulfamoylamino)methyl]tetrahydrofuran-2-yl]pyrrolo[2,3-d]pyrimidine The title compound was obtained as in step 3 of Example 124, except that 1-ethoxy-2-ethynyl-3-fluorobenzene was used in place of 2-ethynyl-1,3-difluorobenzene.
$^1$H-NMR (DMSO-D$_6$) δ: 8.17 (1H, s), 7.88 (1H, s), 7.37 (1H, ddd, J=8.8, 8.4, 7.0 Hz), 7.19 (1H, dd, J=7.0, 5.5 Hz), 6.97 (1H, d, J=8.4 Hz), 6.91 (1H, t, J=8.8 Hz), 6.57 (2H, s), 6.42 (1H, dd, J=8.4, 5.5 Hz), 5.37 (1H, d, J=4.0 Hz), 4.37 (1H, brs), 4.22 (2H, q, J=7.0 Hz), 3.99-3.93 (1H, m), 3.22-3.04 (2H, m), 2.67-2.61 (1H, m), 2.17 (1H, dd, J=13.6, 5.5 Hz), 1.37 (3H, t, J=7.0 Hz). LCMS (ESI) m/z 491 [M+H]$^+$.

Example 128

4-Amino-5-[2-(2,6-difluorophenyl)ethynyl]-7-[(1R,4R,5S)-4,5-dihydroxy-3-[(sulfamoylamino)methyl]cyclopent-2-en-1-yl]pyrrolo[2,3-d]pyrimidine

Step 1: Synthesis of ((3aS,4R,6aR)-6-(((tert-butyldiphenylsilyl)oxy)methyl)-2,2-dimethyl-4,6a-dihydro-3aH-cyclopenta[d][1,3]dioxol-4-ol (3aR,6aR)-6-(((tert-Butyldiphenylsilyl)oxy)methyl)-2,2-dimethyl-3aH-cyclopenta[d][1,3]dioxol-4(6aH)-one (1.0 g, 2.36 mmol) and cerium chloride heptahydrate (881 mg, 2.36 mmol) were suspended in methanol (5 mL), and sodium borohydride (92%, 146 mg, 3.54 mmol) was added thereto with stirring at 0° C. After the mixture was stirred at 0° C. for 2 hours, water (20 mL) was added thereto. Acetic acid was then added thereto until the pH of the reaction liquid became about 5. After the reaction liquid was partitioned between ethyl acetate and water, the organic layer was separated. The obtained organic layer was sequentially washed with a saturated aqueous ammonium chloride solution and saturated saline, and dried over magnesium sulfate, followed by distilling off the solvent. The residue was purified by silica gel column chromatography (developing solvent: ethyl acetate/hexane), thereby obtaining the title compound (960 mg) as a colorless oil.

$^1$H-NMR (CDCl$_3$) δ: 7.72-7.66 (4H, m), 7.45-7.37 (6H, m), 5.85 (1H, s), 4.88 (1H, d, J=5.5 Hz), 4.76 (1H, dd, J=6.2, 5.9 Hz), 4.58-4.55 (1H, brm), 4.39 (1H, d, J=14.7 Hz), 4.29 (1H, d, J=14.7 Hz), 1.37 (3H, s), 1.34 (3H, s), 1.08 (9H, s). LCMS (ESI) m/z 425 [M+H]$^+$

Step 2: Synthesis of 7-((3aS,4R,6aR)-6-(((tert-butyldiphenylsilyl)oxy)methyl)-2,2-dimethyl-4,6a-dihydro-3aH-cyclopenta[d][1,3]dioxol-4-yl)-4-chloro-5-iodo-7H-pyrrolo[2,3-d]pyrimidine (3aS,4R,6aR)-6-(((tert-Butyldiphenylsilyl)oxy)methyl)-2,2-dimethyl-4,6a-dihydro-3aH-cyclopenta[d][1,3]dioxol-4-ol (960 mg, 2.26 mmol), 4-chloro-5-iodo-7H-pyrrolo[2,3-d]pyrimidine (632 mg, 2.26 mmol), and triphenylphosphine (889 mg, 3.39 mmol) were dissolved in tetrahydrofuran (7 mL). Then, diisopropyl azodicarboxylate (667 μL, 3.39 mmol) was added thereto dropwise with stirring at 0° C. After the reaction liquid was stirred at room temperature for 14 hours, the reaction liquid was concentrated, and the residue was purified by silica gel column chromatography (developing solvent: ethyl acetate/hexane), thereby obtaining the title compound (1.33 g) as a colorless amorphous substance.

$^1$H-NMR (CDCl$_3$) δ: 8.69 (1H, s), 7.72-7.69 (4H, m), 7.49-7.39 (6H, m), 7.15 (1H, s), 5.88-5.86 (1H, brm), 5.84-5.82 (1H, brm), 5.21 (1H, d, J=5.5 Hz), 4.56 (1H, d, J=5.5 Hz), 4.49 (2H, d, J=14.7 Hz), 1.44 (3H, s), 1.31 (3H, s), 1.11 (9H, s). LCMS (ESI) m/z 687 [M+H]$^+$

Step 3: Synthesis of ((3aR,6R,6aS)-6-(4-amino-5-iodo-7H-pyrrolo[2,3-d]pyrimidin-7-yl)-2,2-dimethyl-6,6a-dihydro-3aH-cyclopenta[d][1,3]dioxol-4-yl)methanol 7-((3aS,4R,6aR)-6-(((tert-Butyldiphenylsilyl)oxy)methyl)-2,2-dimethyl-4,6a-dihydro-3aH-cyclopenta[d][1,3]dioxol-4-yl)-4-chloro-5-iodo-7H-pyrrolo[2,3-d]pyrimidine (16.2 g, 23.6 mmol) was suspended in 1,4-dioxane (50 mL) and aqueous ammonia (28%, 50 mL), followed by heating with stirring at 100° C. for 24 hours in a pressure-resistant container. After the solvent was distilled off, tetrahydrofuran (50 mL) was added to the residue, and tetrabutylammonium fluoride (a 1 M tetrahydrofuran solution, 47 mL) was added thereto with stirring at room temperature, followed by stirring at room temperature overnight. After the reaction solution was partitioned between ethyl acetate and water, the aqueous layer was separated, and extracted with ethyl acetate. The organic layers were combined and washed with saturated saline, followed by distilling off the solvent. The residue was purified by silica gel column chromatography (developing solvent: methanol/chloroform), thereby obtaining the title compound (7.4 g) as a milky-white solid.

$^1$H-NMR (DMSO-D$_6$) δ: 8.12 (1H, s), 7.18 (1H, s), 6.63 (2H, brs), 5.63-5.61 (1H, brm), 5.59-5.59 (1H, brm), 5.29 (1H, d, J=5.5 Hz), 5.06 (1H, dd, J=5.7, 5.5 Hz), 4.49 (1H, d, J=5.9 Hz), 4.13 (2H, d, J=5.9 Hz), 1.36 (3H, s), 1.25 (3H, s). LCMS (ESI) m/z 429 [M+H]$^+$

Step 4: Synthesis of tert-butyl(((3aR,6R,6aS)-6-(4-amino-5-iodo-7H-pyrrolo[2,3-d]pyrimidin-7-yl)-2,2-dimethyl-6,6a-dihydro-3aH-cyclopenta[d][1,3]dioxol-4-yl)methyl)(sulfamoyl)carbamate ((3aR,6R,6aS)-6-(4-Amino-5-iodo-7H-pyrrolo[2,3-d]pyrimidin-7-yl)-2,2-dimethyl-6,6a-dihydro-3aH-cyclopenta[d][1,3]dioxol-4-yl)methanol (100 mg, 0.233 mmol), tert-butyl sulfamoylcarbamate (60 mg, 0.30 mmol), and triphenylphosphine (92 mg, 0.35 mmol) were dissolved in tetrahydrofuran (1 mL). Then, diisopropyl azodicarboxylate (69 μL, 0.35 mmol) was added thereto dropwise with stirring at 0° C. After the reaction liquid was stirred for 3 hours under ice-cooling, methanol (1 mL) was added thereto, followed by stirring at room temperature for 10 minutes. The reaction liquid was concentrated, and the residue was purified by silica gel column chromatography (developing solvent: methanol/chloroform), thereby obtaining the title compound (60 mg) as a colorless amorphous substance.

$^1$H-NMR (CDCl$_3$) δ: 8.22 (1H, s), 6.91 (1H, s), 6.36-6.07 (4H, brm), 5.81 (1H, brs), 5.69 (1H, brs), 5.32 (1H, d, J=5.9 Hz), 4.66-4.52 (3H, m), 1.55 (9H, s), 1.48 (3H, s), 1.34 (3H, s). LCMS (ESI) m/z 607 [M+H]$^+$

Step 5: Synthesis of Example Compound 128 tert-Butyl (((3aR,6R,6aS)-6-(4-amino-5-iodo-7H-pyrrolo[2,3-d]pyrimidin-7-yl)-2,2-dimethyl-6,6a-dihydro-3aH-cyclopenta[d][1,3]dioxol-4-yl)methyl)(sulfamoyl)carbamate (60 mg, 0.099 mmol), 2-ethynyl-1,3-difluorobenzene (27.3 mg, 0.198 mmol), bis(triphenylphosphine)palladium (II) dichloride (3.5 mg, 0.005 mmol), copper iodide (1 mg, 0.0053 mmol), and diisopropylethylamine (0.034 mL, 0.19 mmol) were suspended in tetrahydrofuran (0.7 mL). After the reaction solution was stirred at 50° C. for 1 hour, the reaction liquid was concentrated, and the residue was roughly purified by silica gel column chromatography (developing solvent: methanol/chloroform). The obtained residue was dissolved at room temperature in acetonitrile (0.5 mL) and concentrated hydrochloric acid (0.2 mL), followed by stirring at room temperature overnight. After the reaction liquid was concentrated, the residue was purified by basic silica gel column chromatography (developing solvent: methanol/chloroform), thereby obtaining the title compound (5.7 mg, 12%) as a white solid.

$^1$H-NMR (CD$_3$OD) δ: 8.16 (1H, s), 7.56 (1H, s), 7.45-7.38 (1H, m), 7.11-7.05 (2H, m), 5.94 (1H, brs), 5.63 (1H, d, J=5.5 Hz), 4.68 (1H, d, J=5.5 Hz), 4.27 (1H, t, J=5.5 Hz), 3.95 (1H, d, J=16.5 Hz), 3.87 (1H, d, J=16.5 Hz). LCMS (ESI) m/z 477 [M+H]$^+$.

Example 129

4-Amino-7-[(1R,4R,5S)-4,5-dihydroxy-3-[(sulfamoylamino)methyl]cyclopent-2-en-1-yl]-5-[2-(2-ethoxy-6-fluoro-phenyl)ethynyl]pyrrolo[2,3-d]pyrimidine The title compound was obtained as in step 5 of Example 128, except that 1-ethoxy-2-ethynyl-3-fluorobenzene was used in place of 2-ethynyl-1,3-difluorobenzene.

$^1$H-NMR (CD$_3$OD) δ: 8.14 (1H, s), 7.45 (1H, s), 7.30 (1H, ddd, J=8.8, 8.4, 6.6 Hz), 6.88 (1H, d, J=8.4 Hz), 6.78 (1H, t, J=8.8 Hz), 5.94 (1H, brs), 5.61 (1H, d, J=4.8 Hz), 4.68 (1H, d, J=5.5 Hz), 4.27 (1H, dd, J=5.5, 4.8 Hz), 4.24 (2H, q, J=7.0 Hz), 3.94 (1H, d, J=16.1 Hz), 3.91 (1H, d, J=16.1 Hz), 1.48 (3H, t, J=7.0 Hz). LCMS (ESI) m/z 503 [M+H]$^+$.

Example 130

4-Amino-7-[(1R,4R,5S)-4,5-dihydroxy-3-[(sulfamoylamino)methyl]cyclopent-2-en-1-yl]-5-[2-(2-fluoro-6-methylsulfanyl-phenyl)ethynyl]pyrrolo[2,3-d]pyrimidine The title compound was obtained as in step 5 of Example 128, except that 2-ethynyl-1-fluoro-3-methanesulfanyl-benzene was used in place of 2-ethynyl-1,3-difluorobenzene.

$^1$H-NMR (DMSO-D$_6$) δ: 8.17 (1H, s), 7.62 (1H, s), 7.41 (1H, ddd, J=8.8, 8.8, 6.2 Hz), 7.15 (1H, d, J=8.8 Hz), 7.11 (1H, t, J=8.8 Hz), 6.80 (1H, t, J=5.7 Hz), 6.64 (2H, s), 5.74 (1H, s), 5.56 (1H, brs), 5.10 (1H, d, J=6.2 Hz), 5.01 (1H, d, J=6.2 Hz), 4.48 (1H, t, J=6.2 Hz), 4.11-4.06 (1H, m), 3.73-3.59 (2H, m), 2.55 (3H, s). LCMS (ESI) m/z 505 [M+H]$^+$.

Example 131

[(2R,3S,4R,5R)-5-[4-amino-5-(2-phenylethynyl)pyrrolo[2,3-d]pyrimidin-7-yl]-3,4-dihydroxy-tetrahydrofuran-2-yl]methyl sulfamate Step 1: Synthesis of ((3aR,4R,6R,6aR)-6-(4-amino-5-(phenylethynyl)-7H-pyrrolo[2,3-d]pyrimidin-7-yl)-2,2-dimethyltetrahydrofuro[3,4-d][1,3]dioxol-4-yl)methanol

[(3aR,4R,6R,6aR)-4-(4-Amino-5-iodo-pyrrolo[2,3-d]pyrimidin-7-yl)-2,2-dimethyl-3a,4,6,6a-tetrahydrofuro[3,4-d][1,3]dioxol-6-yl]methanol (1 g, 2.3 mmol), phenylacetylene (354 mg, 3.5 mmol), bis(triphenylphosphine)palladium (II) dichloride (161 mg, 0.23 mmol), and copper iodide (44 mg, 0.23 mmol) were suspended in tetrahydrofuran (10 mL), Then, nitrogen purging was performed, and after diisopropylethylamine (0.78 mL, 4.6 mmol) was added thereto, the reaction solution was stirred at 70° C. for 2 hours. The reaction solution was filtered through a celite bed and washed with chloroform, followed by distilling off the solvent. The residue was purified by silica gel column chromatography (developing solvent: ethyl acetate/hexane), thereby obtaining the title compound (800 mg, 85%) as a yellow amorphous substance.

$^1$H-NMR (CDCl$_3$) δ: 8.27 (1H, s), 7.51-7.49 (2H, m), 7.39-7.36 (3H, m), 7.27-7.25 (1H, m), 6.52 (1H, d, J=10.7 Hz), 5.85-5.72 (2H, brs), 5.72 (1H, d, J=5.1 Hz), 5.24 (1H, t, J=5.5 Hz), 5.12-5.09 (1H, m), 4.52-4.50 (1H, brs), 4.00-3.96 (1H, m), 3.83-3.76 (1H, m), 1.64 (3H, s), 1.37 (3H, s). LCMS (ESI) m/z 407 [M+H]$^+$ Step 2: Synthesis of ((3aR,4R,6R,6aR)-6-(4-amino-5-(phenylethynyl)-7H-pyrrolo[2,3-d]pyrimidin-7-yl)-2,2-dimethyltetrahydrofuro[3,4-d][1,3]dioxol-4-yl)methyl sulfamate ((3aR,4R,6R,6aR)-6-(4-Amino-5-(phenylethynyl)-7H-pyrrolo[2,3-d]pyrimidin-7-yl)-2,2-dimethyltetrahydrofuro[3,4-d][1,3]dioxol-4-yl)methanol (50 mg, 0.12 mmol) was dissolved in acetonitrile (0.5 mL). Then, triethylamine (0.084 mL, 0.59 mmol) was added thereto at room temperature, and sulfamoyl chloride (0.5 M acetonitrile solution, 0.27 mL) was added thereto in an ice bath. After the resulting mixture was stirred for 40 minutes in an ice bath, the solvent was distilled off. Then, chloroform and an aqueous sodium hydrogen carbonate solution were added thereto, and the aqueous layer was extracted with a liquid mixture of chloroform/methanol=5/1. The organic layer was washed with saturated saline and dried over sodium sulfate, followed by distilling off the solvent. The residue was purified by silica gel column chromatography (developing solvent: ethyl acetate/hexane), thereby obtaining the title compound (39 mg, 67%) as a yellow amorphous substance.

$^1$H-NMR (CDCl$_3$) δ: 8.29 (1H, s), 7.52-7.49 (2H, m), 7.37-7.36 (3H, m), 7.30 (1H, s), 6.08 (1H, d, J=2.7 Hz), 5.72-5.68 (2H, brs), 5.35 (1H, dd, J=6.3, 2.9 Hz), 5.13-5.11 (1H, m), 4.50-4.43 (3H, m), 1.62 (3H, s), 1.39 (3H, s). LCMS (ESI) m/z 486 [M+H]$^+$ Step 3: Synthesis of Example Compound 131

((3aR,4R,6R,6aR)-6-(4-Amino-5-(phenylethynyl)-7H-pyrrolo[2,3-d]pyrimidin-7-yl)-2,2-dimethyltetrahydrofuro[3,4-d][1,3]dioxol-4-yl)methyl sulfamate (380 mg, 0.79 mmol) was dissolved in tetrahydrofuran (4 mL), and a mixed solution (9.5 mL) of trifluoroacetic acid/water=4/1 was added thereto, followed by stirring at room temperature for 8 hours. After the solvent was distilled off, methanol was added, and the solvent was distilled off again. The residue was purified by basic silica gel column chromatography (developing solvent: methanol/chloroform), thereby obtaining the title compound (323 mg, 92%) as a white powder.

$^1$H-NMR (CD$_3$OD) δ: 8.15 (1H, s), 7.67 (1H, s), 7.55-7.52 (2H, m), 7.39-7.37 (3H, m), 6.22 (1H, d, J=5.6 Hz), 4.90-4.80 (1H, m), 4.47-4.26 (4H, m). LCMS (ESI) m/z 446 [M+H]$^+$.

Example 132

[(2R,3S,4R,5R)-5-[4-Amino-5-[2-(2,6-difluorophenyl)ethynyl]pyrrolo[2,3-d]pyrimidin-7-yl]-3,4-dihydroxy-tetrahydrofuran-2-yl]methyl sulfamate The title compound was obtained as in Example 131, except that 2-ethynyl-1,3-difluorobenzene was used in place of phenylacetylene.

¹H-NMR (DMSO-D₆) δ: 8.20 (1H, s), 7.97 (1H, s), 7.55-7.50 (1H, m), 7.31-7.25 (2H, m), 6.45-6.37 (2H, brs), 6.13 (1H, d, J=5.9 Hz), 4.47-4.43 (1H, m), 4.28-4.23 (1H, m), 4.20-4.09 (5H, m). LCMS (ESI) m/z 482 [M+H]⁺.

Example 133

[(2R,3S,4R,5R)-5-[4-Amino-5-[2-(1-naphthyl)ethynyl]pyrrolo[2,3-d]pyrimidin-7-yl]-3,4-dihydroxytetrahydrofuran-2-yl]methyl sulfamate The title compound was obtained as in Example 131, except that 1-ethynylnaphthalene was used in place of phenylacetylene.

¹H-NMR (CD₃OD) δ: 8.41 (1H, d, J=8.0 Hz), 8.19 (1H, s), 7.94-7.90 (2H, m), 7.86 (1H, s), 7.80 (1H, d, J=4.0 Hz), 7.69-7.48 (3H, m), 6.29 (1H, d, J=5.1 Hz), 4.87-4.80 (1H, m), 4.52-4.26 (4H, m). LCMS (ESI) m/z 496 [M+H]⁺.

Example 134

[(2R,3S,5R)-5-[4-Amino-5-(2-phenylethynyl)pyrrolo[2,3-d]pyrimidin-7-yl]-3-hydroxy-tetrahydrofuran-2-yl]methyl sulfamate The title compound was obtained as in Example 131, except that (2R,3S,5R)-5-(4-amino-5-iodo-7H-pyrrolo[2,3-d]pyrimidin-7-yl)-2-(hydroxymethyl)tetrahydrofuran-3-ol was used in place of [(3aR,4R,6R,6aR)-4-(4-amino-5-iodopyrrolo[2,3-d]pyrimidin-7-yl)-2,2-dimethyl-3a,4,6,6a-tetrahydrofuro[3,4-d][1,3]dioxol-6-yl]methanol.

¹H-NMR (CD₃OD) δ: 8.14 (1H, s), 7.67 (1H, s), 7.54-7.52 (2H, m), 7.39-7.36 (3H, m), 6.65 (1H, dd, J=7.8, 6.1 Hz), 4.57-4.55 (1H, m), 4.32 (1H, dd, J=11.0, 3.9 Hz), 4.29 (1H, dd, J=11.0, 3.9 Hz), 4.18 (1H, dt, J=3.2, 3.9 Hz), 2.60 (1H, ddd, J=13.7, 7.8, 6.1 Hz), 2.39 (1H, ddd, J=13.7, 6.1, 3.2 Hz). LCMS (ESI) m/z 430 [M+H]⁺.

Example 135

[(2R,3S,5R)-5-[4-Amino-5-(1-benzylpyrazol-4-yl)pyrrolo[2,3-d]pyrimidin-7-yl]-3-hydroxy-tetrahydrofuran-2-yl]methyl sulfamate Step 1: Synthesis of (2R,3S,5R)-5-(4-amino-5-(1-benzyl-1H-pyrazol-4-yl)-7H-pyrrolo[2,3-d]pyrimidin-7-yl)-2-(hydroxymethyl)tetrahydrofuran-3-ol (2R,3S,5R)-5-(4-Amino-5-iodo-7H-pyrrolo[2,3-d]pyrimidin-7-yl)-2-(hydroxymethyl)tetrahydrofuran-3-ol (100 mg, 0.265 mmol), tetrakis(triphenylphosphine)palladium(0) (15.3 mg, 0.013 mmol), and 1-benzyl-4-(4,4,5,5-tetramethyl-1,3,2-dioxaborolan-2-yl)-1H-pyrazole (98 mg, 0.34 mmol) were suspended in a 2 M aqueous sodium carbonate solution (0.66 mL) and 1,2-dimethoxyethane (2 mL), followed by stirring at 100° C. for 3 hours. The reaction solution was partitioned between ethyl acetate and water, and the organic layer was washed with water, followed by concentration. The residue was purified by silica gel column chromatography (developing solvent: methanol/chloroform), thereby obtaining the target product (66 mg, 61%) as a yellow oil.

¹H-NMR (CDCl₃) δ: 8.18 (1H, brs), 7.59 (1H, s), 7.44 (1H, s), 7.38-7.32 (3H, m), 7.27-7.23 (2H, m), 6.90 (1H, s), 6.24 (1H, dd, J=8.8, 5.5 Hz), 5.42-5.38 (2H, m), 5.32 (2H, s), 4.71 (1H, d, J=4.0 Hz), 4.15 (1H, s), 3.91 (1H, d, J=12.5 Hz), 3.75 (1H, d, J=12.5 Hz), 3.05-2.98 (1H, m), 2.25 (1H, dd, J=12.8, 5.5 Hz). LRMS (ESI) m/z 407 [M+H]⁺

Step 2: Synthesis of Example Compound 135

(2R,3S,5R)-5-(4-amino-5-(1-benzyl-1H-pyrazol-4-yl)-7H-pyrrolo[2,3-d]pyrimidin-7-yl)-2-(hydroxymethyl)tetrahydrofuran-3-ol (53 mg, 0.13 mmol) was dissolved in acetonitrile (1 mL). Then, 1-aza-4-azoniabicyclo[2.2.2]octan-4-ylsulfonyl(tert-butoxycarbonyl)azanido: 1,4-diazabicyclo[2.2.2]octane monohydrochloride (Reference: Organic Letters, 2012, 10, 2626-2629) (114 mg, 0.26 mmol) was added thereto at room temperature. After the reaction solution was stirred at 40° C. overnight, trifluoroacetic acid (0.3 mL) was added to the reaction liquid, followed by stirring at room temperature overnight. The reaction solution was concentrated, and the residue was purified by silica gel column chromatography (developing solvent: methanol/chloroform), thereby obtaining the title compound (4.7 mg, 7%) as a milky-white solid.

¹H-NMR (CD₃OD) δ: 8.12 (1H, s), 7.88 (1H, s), 7.69 (1H, s), 7.41 (1H, s), 7.37-7.28 (5H, m), 6.71 (1H, t, J=7.0 Hz), 5.39 (2H, s), 4.57-4.52 (1H, brm), 4.29-4.28 (2H, brm), 4.18-4.15 (1H, brm), 2.62-2.55 (1H, m), 2.39-2.35 (1H, m). LCMS (ESI) m/z 486 [M+H]⁺.

Example 136

[(1R,2R,3S,4R)-4-[4-Amino-5-(1-benzylpyrazol-4-yl)pyrrolo[2,3-d]pyrimidin-7-yl]-2,3-dihydroxycyclopentyl]methyl sulfamate The title compound was obtained as in Example 135, except that ((3aR,4R,6R,6aS)-6-(4-amino-5-iodo-7H-pyrrolo[2,3-d]pyrimidin-7-yl)-2,2-dimethyltetrahydro-3aH-cyclopenta[d][1,3]dioxol-4-yl)methanol was used in place of (2R,3S,5R)-5-(4-amino-5-iodo-7H-pyrrolo[2,3-d]pyrimidin-7-yl)-2-(hydroxymethyl)tetrahydrofuran-3-ol.

¹H-NMR (CD₃OD) δ: 8.10 (1H, s), 7.85 (1H, s), 7.66 (1H, s), 7.37-7.21 (6H, m), 5.39 (2H, s), 5.07-4.98 (1H, m), 4.32 (1H, dd, J=8.2, 5.7 Hz), 4.25 (2H, d, J=4.9 Hz), 4.05 (1H, dd, J=5.7, 3.5 Hz), 2.48-2.34 (2H, m), 1.82-1.76 (1H, m). LCMS (ESI) m/z 500 [M+H]⁺.

Example 137

[(2R,3S,5R)-5-[4-Amino-5-[1-[(3,4-dimethylphenyl)methyl]pyrazol-4-yl]pyrrolo[2,3-d]pyrimidin-7-yl]-3-hydroxy-tetrahydrofuran-2-yl]methyl sulfamate Step 1: Synthesis of 1-(3,4-dimethylbenzyl)-4-(4,4,5,5-tetramethyl-1,3,2-dioxaborolan-2-yl)-1H-pyrazole 4-(4,4,5,5-Tetramethyl-1,3,2-dioxaborolan-2-yl)-1H-pyrazole (1.0 g, 5.2 mmol), cesium carbonate (2.18 g, 6.7 mmol), and 3,4-dimethylbenzylchloride (0.98 mL, 6.7 mmol) were suspended in acetonitrile (10 mL). After the mixture was stirred at room temperature overnight, the solid was filtered off through celite, and the filtrate was concentrated. The residue was purified by basic silica gel column chromatography (developing solvent: ethyl acetate/hexane), thereby obtaining the title compound (1.29 g, 80%) as a light-yellow oil.

¹H-NMR (CDCl₃) δ: 7.80 (1H, s), 7.63 (1H, s), 7.14-6.97 (3H, m), 5.21 (2H, s), 2.25 (3H, s), 2.25 (3H, s), 1.29 (12H, s). LRMS (ESI) m/z 313 [M+H]⁺

Step 2: Synthesis of Example Compound 137

The title compound was obtained as in Example 135, except that 1-(3,4-dimethylbenzyl)-4-(4,4,5,5-tetramethyl-1,3,2-dioxaborolan-2-yl)-1H-pyrazole was used in place of 1-benzyl-4-(4,4,5,5-tetramethyl-1,3,2-dioxaborolan-2-yl)-1H-pyrazole.

$^1$H-NMR (CD$_3$OD) δ: 8.12 (1H, s), 7.83 (1H, s), 7.66 (1H, s), 7.39 (1H, s), 7.11 (1H, d, J=7.8 Hz), 7.09 (1H, s), 7.02 (1H, d, J=7.8 Hz), 6.70 (1H, dd, J=7.9, 6.2 Hz), 5.29 (2H, s), 4.57-4.52 (1H, m), 4.28 (2H, m), 4.16 (1H, m), 3.60 (1H, dd, J=14.1, 7.1 Hz), 2.62-2.55 (1H, m), 2.40-2.34 (1H, m), 2.25 (3H, s), 2.23 (3H, s). LCMS (ESI) m/z 514 [M+H]$^+$.

Example 138

[(1R,2S,4R)-4-[4-Amino-5-[1-[(3,4-dimethylphenyl)methyl]pyrazol-4-yl]pyrrolo[2,3-d]pyrimidin-7-yl]-2-hydroxy-cyclopentyl]methyl sulfamate

Step 1: Synthesis of (1S,2R,4R)-4-(4-amino-5-iodo-7H-pyrrolo[2,3-d]pyrimidin-7-yl)-2-(hydroxymethyl)cyclopentanol The title compound was obtained as in step 2, step 5, and step 7 of Example 93, except that (1S,2R,4R)-4-amino-2-(hydroxymethyl)cyclopentanol was used in place of ((3aR,4R,6R,6aS)-6-amino-2,2-dimethyltetrahydro-3aH-cyclopenta[d][1,3]dioxol-4-yl)methanol.

$^1$H-NMR (DMSO-D$_6$) δ: 8.06 (1H, s), 7.54 (1H, s), 6.64 (2H, brs), 5.23-5.14 (1H, m), 4.73 (1H, brs), 4.61 (1H, brs), 4.01 (1H, m), 3.48-3.44 (1H, m), 3.41-3.36 (1H, m), 2.23-2.16 (1H, m), 2.08-2.01 (1H, m), 1.96-1.85 (2H, m), 1.58-1.50 (1H, m). LCMS (ESI) m/z 375 [M+H]$^+$

Step 2: Synthesis of Example Compound 138

The title compound was obtained as in Example 135, except that (1S,2R,4R)-4-(4-amino-5-iodo-7H-pyrrolo[2,3-d]pyrimidin-7-yl)-2-(hydroxymethyl)cyclopentanol and 1-(3,4-dimethylbenzyl)-4-(4,4,5,5-tetramethyl-1,3,2-dioxaborolan-2-yl)-1H-pyrazole were used in place of (2R,3S,5R)-5-(4-amino-5-iodo-7H-pyrrolo[2,3-d]pyrimidin-7-yl)-2-(hydroxymethyl)tetrahydrofuran-3-ol and 1-benzyl-4-(4,4,5,5-tetramethyl-1,3,2-dioxaborolan-2-yl)-1H-pyrazole.

$^1$H-NMR (CD$_3$OD) δ: 8.10 (1H, s), 7.79 (1H, s), 7.64 (1H, s), 7.26 (1H, s), 7.10 (1H, d, J=7.8 Hz), 7.09 (1H, s), 7.02 (1H, d, J=7.8 Hz), 5.39-5.31 (1H, m), 5.29 (2H, s), 4.30-4.20 (3H, m), 2.53-2.46 (1H, m), 2.38-2.15 (3H, m), 2.24 (3H, s), 2.23 (3H, s), 1.87-1.79 (1H, m). LCMS (ESI) m/z 512 [M+H]$^+$.

Example 139

[(2R,3S,5R)-5-[4-Amino-5-[2-(o-tolyl)thiazol-4-yl]pyrrolo[2,3-d]pyrimidin-7-yl]-3-hydroxy-tetrahydrofuran-2-yl]methyl sulfamate The title compound was obtained as in Example 135, except that 4-(4,4,5,5-tetramethyl-1,3,2-dioxaborolan-2-yl)-2-(o-tolyl)thiazole was used in place of 1-benzyl-4-(4,4,5,5-tetramethyl-1,3,2-dioxaborolan-2-yl)-1H-pyrazole.

$^1$H-NMR (CD$_3$OD) δ: 8.07 (1H, s), 8.04 (1H, s), 7.92 (1H, s), 7.67 (1H, d, J=7.3 Hz), 7.42-7.36 (2H, m), 7.34-7.30 (1H, m), 6.75 (1H, t, J=7.0 Hz), 4.62-4.59 (1H, m), 4.39 (1H, dd, J=11.0, 3.2 Hz), 4.35 (1H, dd, J=11.0, 3.2 Hz), 4.22 (1H, dd, J=6.1, 3.2 Hz), 2.59-2.56 (1H, m), 2.56 (3H, s), 2.46-2.41 (1H, m). LCMS (ESI) m/z 503 [M+H]$^+$.

Example 140

4-Amino-7-[(2R,3R,4S,5R)-3,4-dihydroxy-5-[(sulfamoylamino)methyl]tetrahydrofuran-2-yl]-5-[2-(2-ethylsulfonyl-6-fluoro-phenyl)ethynyl]pyrrolo[2,3-d]pyrimidine

Step 1: Synthesis of tert-butyl N-(((3aR,4R,6R,6aR)-6-(4-amino-5-((2-(ethylthio)-6-fluorophenyl)ethynyl)-7H-pyrrolo[2,3-d]pyrimidin-7-yl)-2,2-dimethyltetrahydrofuro[3,4-d][1,3]dioxol-4-yl)methyl)sulfamoylcarbamate tert-Butyl N-(((3aR,4R,6R,6aR)-6-(4-amino-5-iodo-7H-pyrrolo[2,3-d]pyrimidin-7-yl)-2,2-dimethyltetrahydrofuro[3,4-d][1,3]dioxol-4-yl)methyl)sulfamoylcarbamate (39 mg, 0.064 mmol), ethyl(2-ethynyl-3-fluorophenyl)sulfane (23 mg, 0.13 mmol), bis(triphenylphosphine)palladium (II) dichloride (4.5 mg, 0.0064 mmol), copper iodide (1.2 mg, 0.0064 mmol), and diisopropylethylamine (0.022 mL, 0.13 mmol) were suspended in tetrahydrofuran (1 mL). After the reaction solution was stirred at 50° C. for 3 hours, the solvent was distilled off, and the residue was purified by silica gel column chromatography (developing solvent: methanol/chloroform), thereby obtaining the title compound (28 mg, 66%) as a yellow powder.

$^1$H-NMR (CDCl$_3$) δ: 9.15 (1H, d, J=8.1 Hz), 8.52 (1H, s), 7.31 (1H, s), 7.24-7.20 (1H, m), 7.06 (1H, d, J=8.1 Hz), 6.91 (1H, t, J=8.1 Hz), 6.74-6.59 (2H, brm), 5.68 (1H, d, J=4.8 Hz), 5.30 (1H, dd, J=6.2, 4.8 Hz), 5.11 (1H, dd, J=6.2, 2.2 Hz), 4.51 (1H, d, J=2.2 Hz), 3.72-3.66 (1H, m), 3.60 (1H, d, J=12.8 Hz), 3.02 (3H, q, J=7.3 Hz), 1.61 (3H, s), 1.45 (9H, s), 1.37 (3H, t, J=7.3 Hz), 1.35 (3H, s).

Step 2: Synthesis of Example Compound 140 tert-Butyl N-(((3aR,4R,6R,6aR)-6-(4-amino-5-((2-(ethylthio)-6-fluorophenyl)ethynyl)-7H-pyrrolo[2,3-d]pyrimidin-7-yl-2,2-dimethyltetrahydrofuro[3,4-d][1,3]dioxol-4-yl)methyl)sulfamoylcarbamate (55 mg, 0.0829 mmol) was suspended with stirring under ice-cooling in 1,4-dioxane (0.5 mL) and water (0.5 mL) while oxone (102 mg, 0.166 mmol) was added thereto. After the reaction liquid was stirred at room temperature for 3 hours, the reaction solution was partitioned between ethyl acetate and water, and the organic layer was extracted. After the solvent was distilled off, acetonitrile (0.5 mL), water (0.1 mL), and trifluoroacetic acid (0.5 mL) were sequentially added to the residue, and the reaction solution was stirred at room temperature for 3 hours. The reaction liquid was concentrated, and the residue was purified by basic silica gel column chromatography (developing solvent: methanol/chloroform), thereby obtaining the title compound (20 mg) as a light-yellow solid.

$^1$H-NMR (DMSO-D$_6$) δ: 8.16 (1H, s), 8.04 (1H, s), 7.82 (2H, d, J=8.1 Hz), 7.77 (2H, t, J=8.1 Hz), 7.70 (1H, dd, J=8.1, 5.5 Hz), 7.35 (1H, dd, J=7.7, 4.8 Hz), 6.58 (2H, s), 5.92 (1H, d, J=7.0 Hz), 5.38 (1H, d, J=6.2 Hz), 5.22 (1H, brs), 4.62-4.58 (1H, m), 4.09-4.07 (1H, brm), 4.05-4.02 (1H, m), 3.49 (2H, q, J=7.3 Hz), 3.22-3.17 (1H, m), 3.14-3.06 (1H, m), 1.14 (3H, t, J=7.3 Hz). LCMS (ESI) m/z 555 [M+H]$^+$.

Example 141

4-Amino-5-[2-(4-benzyloxy-2-methylsulfonyl-phenyl)ethynyl]-7-[(1R,2S,3R,4R)-2,3-dihydroxy-4-[(sulfamoylamino)methyl]cyclopentyl]pyrrolo[2,3-d]pyrimidine Step 1: (5-(Benzyloxy)-2-iodophenyl)(methyl)sulfane The title compound was obtained as in step 1 of Example 76, except that 4-iodo-3-(methylsulfanyl)phenol was used in place of 2-bromopyrimidin-5-ol.
$^1$H-NMR (CDCl$_3$) δ: 7.63 (1H, d, J=8.6 Hz), 7.43-7.34 (5H, m), 6.74 (1H, d, J=2.9 Hz), 6.51 (1H, dd, J=8.6, 2.8 Hz), 5.06 (2H, s), 3.63 (3H, s). LCMS (ESI) m/z 356 [M+H]$^+$ Step 2: Synthesis of (5-(benzyloxy)-2-ethynylphenyl)(methyl)sulfane The title compound was obtained as in step 2 and step 3 of Example 76, except that (5-(benzyloxy)-2-iodophenyl)(methyl)sulfane was used in place of 5-(benzyloxy)-2-bromopyrimidine.
$^1$H-NMR (CDCl$_3$) δ: 7.41-7.34 (6H, m), 6.76 (1H, d, J=2.3 Hz), 6.69 (1H, dd, J=8.4, 2.3 Hz), 5.08 (2H, s), 3.39 (1H, s), 2.45 (3H, s). LCMS (ESI) m/z 255 [M+H]$^+$ Step 3: Synthesis of Example Compound 141

The title compound was obtained as in Example 140, except that (5-(benzyloxy)-2-ethynylphenyl)(methyl)sulfane was used in place of ethyl(2-ethynyl-3-fluorophenyl)sulfane.
$^1$H-NMR (CD$_3$OD) δ: 8.20 (1H, s), 7.82 (1H, s), 7.73 (1H, d, J=8.4 Hz), 7.67 (1H, d, J=2.8 Hz), 7.47 (2H, d, J=6.8 Hz), 7.42-7.32 (4H, m), 5.23 (2H, s), 5.05-4.95 (1H, m), 4.43-4.39 (1H, m), 4.03-4.00 (1H, m), 3.30 (3H, s), 3.27-3.12 (2H, m), 2.50-2.42 (1H, m), 2.32-2.28 (1H, m), 1.87-1.79 (1H, m). LCMS (ESI) m/z 627 [M+H].

Example 142

4-Amino-7-[(1R,2S,3R,4R)-2,3-dihydroxy-4-[(sulfamoylamino)methyl]cyclopentyl]-5-[2-(2-ethylsulfonyl-6-fluoro-phenyl)ethynyl]pyrrolo[2,3-d]pyrimidine The title compound was obtained as in Example 140, except that tert-butyl N-(((3aR,4R,6R,6aS)-6-(4-amino-5-iodo-7H-pyrrolo[2,3-d]pyrimidin-7-yl)-2,2-dimethyltetrahydro-3aH-cyclopenta[d][1,3]dioxol-4-yl)methyl)sulfamoylcarbamate was used in place of tert-butyl N-(((3aR,4R,6R,6aR)-6-(4-amino-5-iodo-7H-pyrrolo[2,3-d]pyrimidin-7-yl)-2,2-dimethyltetrahydrofuro[3,4-d][1,3]dioxol-4-yl)methyl)sulfamoylcarbamate.
$^1$H-NMR (DMSO-D$_6$) δ: 8.13 (1H, s), 7.99 (1H, s), 7.81 (1H, d, J=8.1 Hz), 7.76 (1H, t, J=8.1 Hz), 7.68 (1H, dd, J=8.1, 5.1 Hz), 6.63 (1H, t, J=6.2 Hz), 6.50 (2H, s), 4.89 (2H, d, J=7.0 Hz), 4.67 (1H, d, J=4.4 Hz), 4.27-4.22 (1H, m), 4.08 (1H, q, J=5.3 Hz), 3.79-3.76 (1H, m), 3.49 (2H, q, J=7.3 Hz), 3.10-3.03 (1H, m), 2.94-2.87 (1H, m), 2.24-2.17 (1H, m), 2.12-2.06 (1H, m), 1.60-1.52 (1H, m), 1.14 (3H, t, J=7.3 Hz). LCMS (ESI) m/z 553 [M+H]$^+$.

Example 143

4-Amino-5-[2-(2-ethylsulfonyl-6-fluoro-phenyl)ethynyl]-7-[(2R,4S,5R)-4-hydroxy-5-[(sulfamoylamino)methyl]tetrahydrofuran-2-yl]pyrrolo[2,3-d]pyrimidine The title compound was obtained as in Example 140, except that tert-butyl N-[[(2R,3S,5R)-5-(4-amino-5-iodo-pyrrolo[2,3-d]pyrimidin-7-yl)-3-hydroxy-tetrahydrofuran-2-yl]methyl sulfamoyl]carbamate was used in place of tert-butyl N-(((3aR,4R,6R,6aR)-6-(4-amino-5-iodo-7H-pyrrolo[2,3-d]pyrimidin-7-yl)-2,2-dimethyltetrahydrofuro[3,4-d][1,3]dioxol-4-yl)methyl)sulfamoylcarbamate.
$^1$H-NMR (DMSO-D$_6$) δ: 8.18 (1H, s), 8.03 (1H, s), 7.87-7.83 (1H, m), 7.80-7.75 (1H, m), 7.73-7.68 (1H, m), 7.16 (1H, t, J=5.9 Hz), 6.56 (2H, s), 6.43 (1H, dd, J=8.7, 5.7 Hz), 4.37 (1H, brs), 3.97 (1H, dt, J=2.0, 4.6 Hz), 3.50 (2H, q, J=7.4 Hz), 3.20-3.14 (1H, m), 3.12-3.05 (1H, m), 2.71-2.62 (1H, m), 2.21-2.16 (1H, m), 1.15 (3H, t, J=7.4 Hz). LCMS (ESI) m/z 539 [M+H]$^+$.

Comparative Example

N-[(1S)-1-indanyl]-7-[(1R)-3α-hydroxy-4α-(sulfamoyloxymethyl)cyclopentyl]-7H-pyrrolo[2,3-d]pyrimidin-4-amine (MLN4924) was obtained by performing the synthesis in accordance with the method disclosed in Patent Document 1.

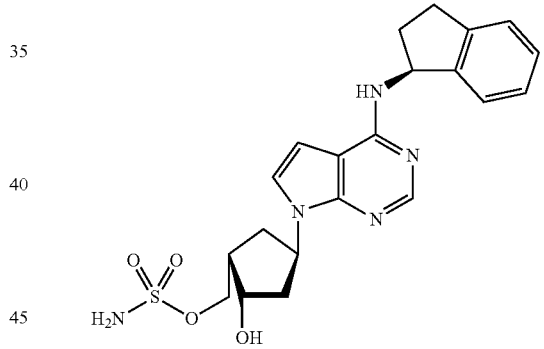

The following tables show the structural formulae of the example compounds of the present application.

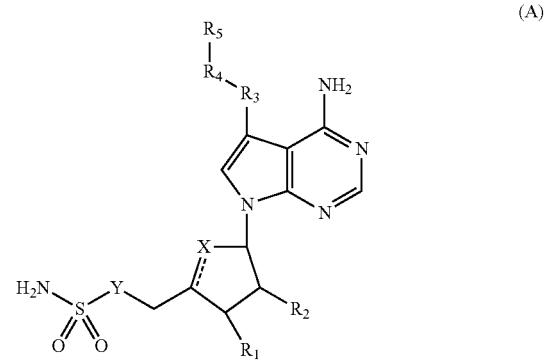

(A)

TABLE 1
| | ----- | X | Y | R₁ | R₂ | R₃ | R₄ | R₅ |
|---|---|---|---|---|---|---|---|---|
| Example 1 | single | O | NH | OH | OH |  | bond | 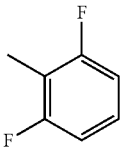 |
| Example 2 | single | O | NH | OH | OH | 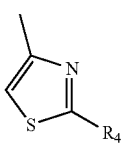 | bond | 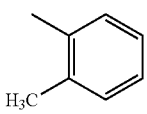 |
| Example 3 | single | O | NH | OH | OH |  | bond | 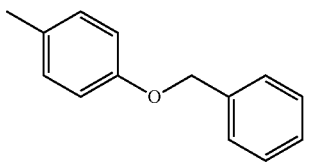 |
| Example 4 | single | O | NH | OH | OH |  | bond | 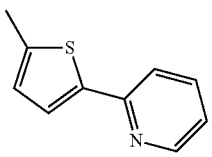 |
| Example 5 | single | O | NH | OH | OH | 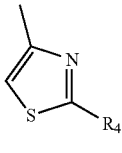 | bond | 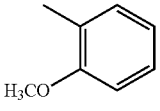 |
| Example 6 | single | O | NH | OH | OH |  | bond | 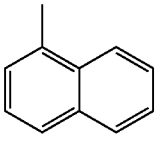 |
| Example 7 | single | O | NH | OH | OH |  | —CH₂— | 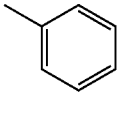 |
| Example 8 | single | O | NH | OH | OH |  | bond | 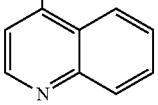 |
| Example 9 | single | O | NH | OH | OH |  | bond | 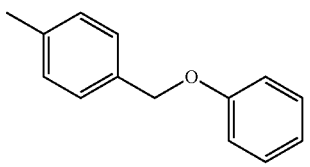 |
| Example 10 | single | O | NH | OH | OH |  | 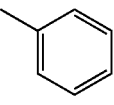 | |

TABLE 2
| | ----- | X | Y | R₁ | R₂ | R₃ | R₄ | R₅ |
|---|---|---|---|---|---|---|---|---|
| Example 11 | single | O | NH | OH | OH | —≡— | bond | 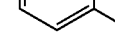 |
| Example 12 | single | O | NH | OH | OH | 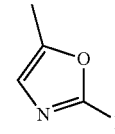 | bond | 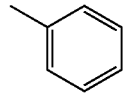 |
| Example 13 | single | O | NH | OH | OH | —≡— | bond | 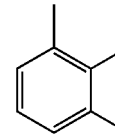 |
| Example 14 | single | O | NH | OH | OH | —≡— | bond | 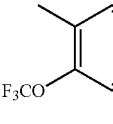 |
| Example 15 | single | O | NH | OH | OH | —≡— | bond | 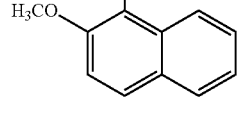 |
| Example 16 | single | O | NH | OH | OH | —≡— | bond | 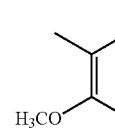 |
| Example 17 | single | O | NH | OH | OH | —≡— | bond | 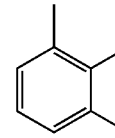 |
| Example 18 | single | O | NH | OH | OH | —≡— | bond | 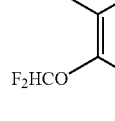 |
| Example 19 | single | O | NH | OH | OH | —≡— | bond | 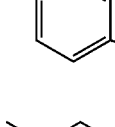 |
| Example 20 | single | O | NH | OH | OH | —≡— | bond | 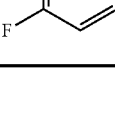 |

TABLE 3

| | ------ | X | Y | R$_1$ | R$_2$ | R$_3$ | R$_4$ | R$_5$ |
|---|---|---|---|---|---|---|---|---|
| Example 21 | single | O | NH | OH | OH | —≡— | bond | 1-methylindane |
| Example 22 | single | O | NH | OH | OH | —≡— | bond | 2-(methylsulfonyl)toluene |
| Example 23 | single | O | NH | OH | OH | —≡— | bond | 4-(3,5-difluoro-4-methylphenyl)morpholine |
| Example 24 | single | O | NH | OH | OH | —≡— | bond | 3,5-difluoro-4-methylaniline |
| Example 25 | single | O | NH | OH | OH | —≡— | bond | 3,5-difluoro-N,4-dimethylaniline |
| Example 26 | single | O | NH | OH | OH | —≡— | bond | N-ethyl-3,5-difluoro-4-methylaniline |
| Example 27 | single | O | NH | OH | OH | —≡— | bond | N-isopropyl-3-methylaniline |
| Example 28 | single | O | NH | OH | OH | —≡— | bond | 4-fluoro-3-methylaniline |
| Example 29 | single | O | NH | OH | OH | —≡— | bond | (S)-1-(3,5-difluoro-4-methylphenyl)-3-fluoropyrrolidine |

TABLE 3-continued

| | ----- | X | Y | R₁ | R₂ | R₃ | R₄ | R₅ |
|---|---|---|---|---|---|---|---|---|
| Example 30 | single | O | NH | OH | OH | —≡— | bond | 3,5-difluoro-4-methylphenyl-N-pyrrolidin-3-ol (R) |

TABLE 4

| | ----- | X | Y | R₁ | R₂ | R₃ | R₄ | R₅ |
|---|---|---|---|---|---|---|---|---|
| Example 31 | single | O | NH | OH | OH | —≡— | —CH₂— | 2,6-difluoro-3-methylphenyl |
| Example 32 | single | O | NH | OH | OH | —≡— | bond | 3,5-difluoro-4-methylphenyl-NH-CH₂CH₂-OH |
| Example 33 | single | O | NH | OH | OH | —≡— | bond | 1-(3,5-difluoro-4-methylphenyl)pyrrolidin-2-one |
| Example 34 | single | O | NH | OH | OH | —≡— | bond | 3-ethoxy-4-methyl-5-fluorophenyl-morpholine |
| Example 35 | single | O | NH | OH | OH | —≡— | bond | 3-ethoxy-4-methyl-5-fluorophenyl (with additional F) |
| Example 36 | single | O | NH | OH | OH | —≡— | —CH₂— | 2-fluoro-6-methylphenyl |
| Example 37 | single | O | NH | OH | OH | —≡— | bond | 4-(3,5-difluoro-4-methylphenyl)thiomorpholine |

TABLE 4-continued

|  | ------ | X | Y | R₁ | R₂ | R₃ | R₄ | R₅ |
|---|---|---|---|---|---|---|---|---|
| Example 38 | single | O | NH | OH | OH | —≡— | bond | 3,5-difluoro-4-methylphenyl-N-(3-hydroxypiperidin-1-yl) |
| Example 39 | single | O | NH | OH | OH | —≡— | bond | 3,5-difluoro-4-methylphenyl-N-(3-hydroxyazetidin-1-yl) |
| Example 40 | single | O | NH | OH | OH | —≡— | bond | 3,5-difluoro-4-methylphenyl-N-((3S)-hydroxypiperidin-1-yl) |

TABLE 5

|  | ------ | X | Y | R₁ | R₂ | R₃ | R₄ | R₅ |
|---|---|---|---|---|---|---|---|---|
| Example 41 | single | O | NH | OH | OH | —≡— | bond | 3,5-difluoro-4-methylphenyl-N-(pyrrolidine-3-carboxylic acid) |
| Example 42 | single | O | NH | OH | OH | —≡— | bond | 3,5-difluoro-4-methylphenyl-N-(4-oxopiperidin-1-yl) |
| Example 43 | single | O | NH | OH | OH | —≡— | bond | 3,5-difluoro-4-methylphenyl-N-azetidinyl |
| Example 44 | single | O | NH | OH | OH | —≡— | bond | 2-methylpyridine |

TABLE 5-continued
| | ----- | X | Y | R₁ | R₂ | R₃ | R₄ | R₅ |
|---|---|---|---|---|---|---|---|---|
| Example 45 | single | O | NH | OH | OH | —≡— | bond | 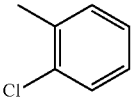 |
| Example 46 | single | O | NH | OH | OH | —≡— | bond | 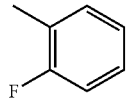 |
| Example 47 | single | O | NH | OH | OH | —≡— | bond | 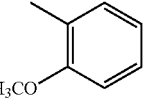 |
| Example 48 | single | O | NH | OH | OH | —≡— | bond | 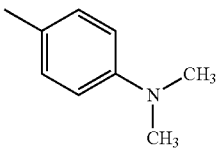 |
| Example 49 | single | O | NH | OH | OH | —≡— | bond | 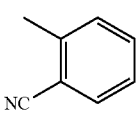 |
| Example 50 | single | O | NH | OH | OH | —≡— | —CH₂— | 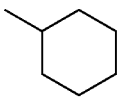 |
TABLE 6
| | ----- | X | Y | R₁ | R₂ | R₃ | R₄ | R₅ |
|---|---|---|---|---|---|---|---|---|
| Example 51 | single | O | NH | OH | OH | —≡— | bond | 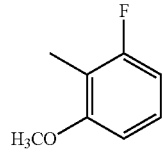 |
| Example 52 | single | O | NH | OH | OH | —≡— | bond | 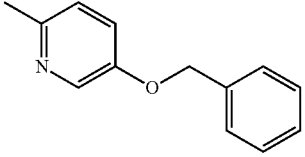 |
| Example 53 | single | O | NH | OH | OH | —≡— | bond | 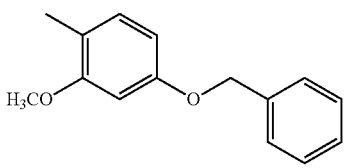 |
| Example 54 | single | O | NH | OH | OH | —≡— | bond | 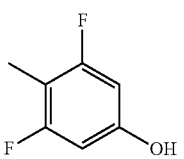 |

TABLE 6-continued
| | ----- | X | Y | R₁ | R₂ | R₃ | R₄ | R₅ |
|---|---|---|---|---|---|---|---|---|
| Example 55 | single | O | NH | OH | OH | —≡— | bond | 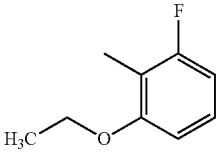 |
| Example 56 | single | O | NH | OH | OH | —≡— | bond | 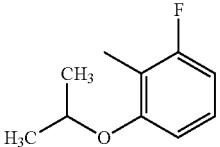 |
| Example 57 | single | O | NH | OH | OH | —≡— | bond | 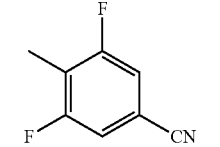 |
| Example 58 | single | O | NH | OH | OH | —≡— | bond | 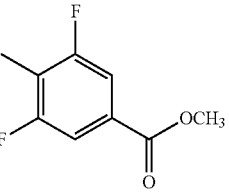 |
| Example 59 | single | O | NH | OH | OH | —≡— | bond | 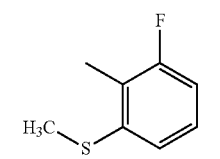 |
| Example 60 | single | O | NH | OH | OH | —≡— | bond | 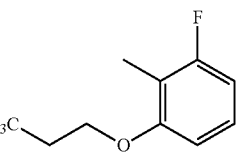 |
TABLE 7
| | ----- | X | Y | R₁ | R₂ | R₃ | R₄ | R₅ |
|---|---|---|---|---|---|---|---|---|
| Example 61 | single | O | NH | OH | OH | —≡— | bond | 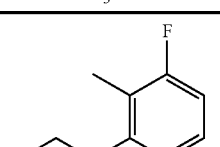 |
| Example 62 | single | O | NH | OH | OH | —≡— | bond | 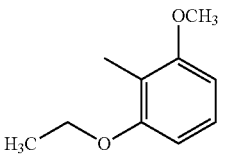 |

TABLE 7-continued
| | ----- | X | Y | R₁ | R₂ | R₃ | R₄ | R₅ |
|---|---|---|---|---|---|---|---|---|
| Example 63 | single | O | NH | OH | OH | —≡— | bond |  |
| Example 64 | single | O | NH | OH | OH | —≡— | bond | 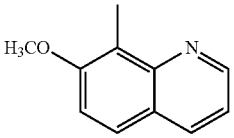 |
| Example 65 | single | O | NH | OH | OH | —≡— | bond |  |
| Example 66 | single | O | NH | OH | OH | —≡— | bond | 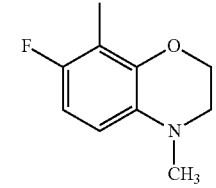 |
| Example 67 | single | O | NH | OH | OH | —≡— | bond |  |
| Example 68 | single | O | NH | OH | OH | —≡— | bond | 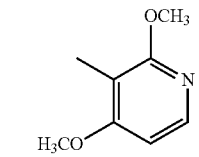 |
| Example 69 | single | O | NH | OH | OH | —≡— | bond |  |
| Example 70 | single | O | NH | OH | OH | —≡— | bond | 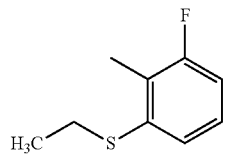 |

TABLE 8

| | ----- | X | Y | R₁ | R₂ | R₃ | R₄ | R₅ |
|---|---|---|---|---|---|---|---|---|
| Example 71 | single | O | NH | OH | OH | —≡— | bond | 5-fluoro-3-methoxy-4-methylpyridine |
| Example 72 | single | O | NH | OH | OH | —≡— | bond | 3-(ethylsulfonyl)-5-fluoro-4-methylphenyl-(3S)-3-hydroxypyrrolidine |
| Example 73 | single | O | NH | OH | OH | —≡— | bond | 3-chloro-2-fluoro-6-methylphenyl (reading: 1-chloro-3-fluoro-2-methylbenzene) |
| Example 74 | single | O | NH | OH | OH | —≡— | bond | 4-(3,5-difluoro-4-methylphenyl)thiomorpholine 1,1-dioxide |
| Example 75 | single | O | NH | OH | OH | —≡— | bond | 3-(ethylsulfonyl)-5-fluoro-4-methylphenyl-(3S)-3-fluoropyrrolidine |
| Example 76 | single | O | NH | OH | OH | —≡— | bond | 5-(benzyloxy)-2-methylpyrimidine |
| Example 77 | single | O | NH | OH | OH | —≡— | bond | 1-(benzyloxy)-3-fluoro-4-methylbenzene |
| Example 78 | single | O | NH | OH | OH | —≡— | bond | N-benzyl-4-methylaniline |

TABLE 8-continued
|  | ------ | X | Y | R₁ | R₂ | R₃ | R₄ | R₅ |
|---|---|---|---|---|---|---|---|---|
| Example 79 | single | O | NH | OH | OH | —≡— | bond | 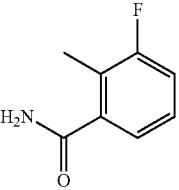 |
| Example 80 | single | O | NH | OH | OH | —≡— | bond | 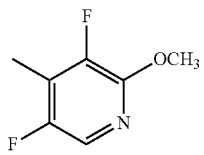 |
TABLE 9
|  | ------ | X | Y | R₁ | R₂ | R₃ | R₄ | R₅ |
|---|---|---|---|---|---|---|---|---|
| Example 81 | single | O | NH | OH | OH | —≡— | bond | 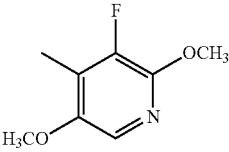 |
| Example 82 | single | O | NH | OH | OH | —≡— | bond | 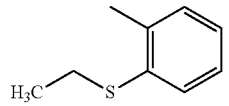 |
| Example 83 | single | O | NH | OH | OH | —≡— | bond | 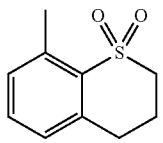 |
| Example 84 | single | O | NH | OH | OH | —≡— | bond | 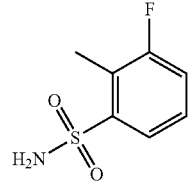 |
| Example 85 | single | O | NH | OH | OH | —≡— | bond | 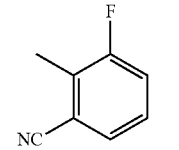 |
| Example 86 | single | O | NH | OH | OH | —≡— | bond | 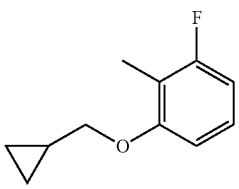 |

TABLE 9-continued
| | ----- | X | Y | R₁ | R₂ | R₃ | R₄ | R₅ |
|---|---|---|---|---|---|---|---|---|
| Example 87 | single | O | NH | OH | OH | —≡— | bond |  |
| Example 88 | single | O | NH | OH | OH | —≡— | bond | 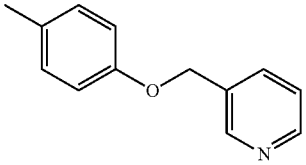 |
| Example 89 | single | O | NH | OH | OH | —≡— | bond |  |
| Example 90 | single | O | NH | OH | OH | —≡— | bond | 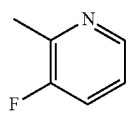 |
TABLE 10
| | ----- | X | Y | R₁ | R₂ | R₃ | R₄ | R₅ |
|---|---|---|---|---|---|---|---|---|
| Example 91 | single | O | NH | OH | OH | —≡— | bond |  |
| Example 92 | single | O | NH | OH | OH | —≡— | bond | 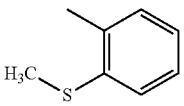 |
| Example 93 | single | C | NH | OH | OH | —≡— | bond |  |
| Example 94 | single | C | NH | OH | OH | —≡— | bond | 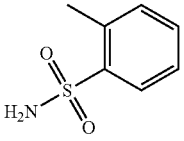 |
| Example 95 | single | C | NH | OH | OH | —≡— | bond |  |

TABLE 10-continued
| | ----- | X | Y | R₁ | R₂ | R₃ | R₄ | R₅ |
|---|---|---|---|---|---|---|---|---|
| Example 96 | single | C | NH | OH | OH | —≡— | bond | 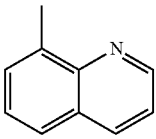 |
| Example 97 | single | C | NH | OH | OH | —≡— | bond | 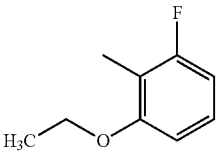 |
| Example 98 | single | C | NH | OH | OH | —≡— | bond | 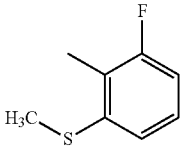 |
| Example 99 | single | C | NH | OH | OH | —≡— | bond | 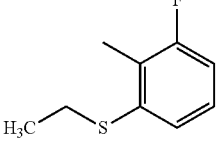 |
| Example 100 | single | C | NH | OH | OH | —≡— | bond | 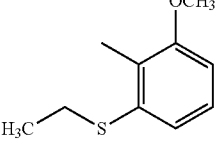 |
TABLE 11
| | ----- | X | Y | R₁ | R₂ | R₃ | R₄ | R₅ |
|---|---|---|---|---|---|---|---|---|
| Example 101 | single | C | NH | OH | OH | —≡— | bond | 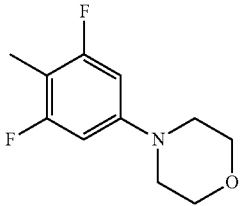 |
| Example 102 | single | C | NH | OH | OH | —≡— | bond | 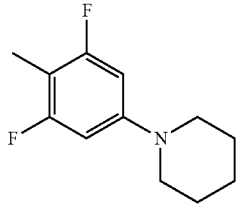 |
| Example 103 | single | C | NH | OH | OH | —≡— | bond | 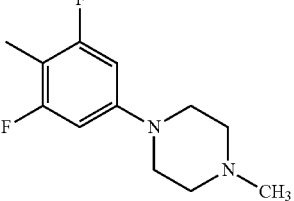 |

TABLE 11-continued
| | ===== | X | Y | R₁ | R₂ | R₃ | R₄ | R₅ |
|---|---|---|---|---|---|---|---|---|
| Example 104 | single | C | NH | OH | OH | —≡— | bond | 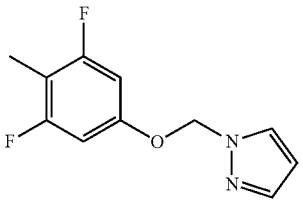 |
| Example 105 | single | C | NH | OH | OH | —≡— | bond | 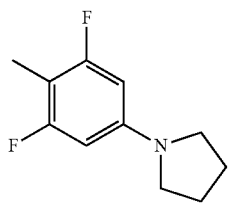 |
| Example 106 | single | C | NH | OH | OH | —≡— | bond | 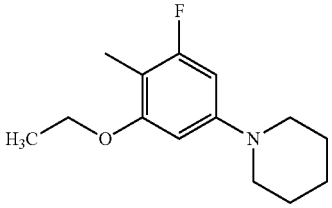 |
| Example 107 | single | C | NH | OH | OH | —≡— | bond | 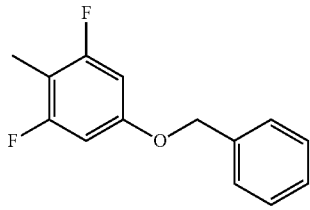 |
| Example 108 | single | C | NH | OH | OH | —≡— | bond | 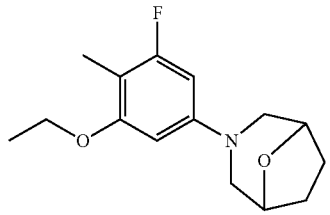 |
| Example 109 | single | C | NH | OH | OH | —≡— | bond | 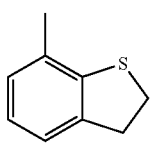 |
| Example 110 | single | C | NH | OH | OH | —≡— | bond | 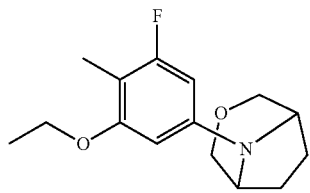 |

TABLE 12

| | --- | X | Y | R₁ | R₂ | R₃ | R₄ | R₅ |
|---|---|---|---|---|---|---|---|---|
| Example 111 | single | C | NH | OH | OH | ─≡─ | bond | |
| Example 112 | single | C | NH | OH | OH | ─≡─ | bond | |
| Example 113 | single | C | NH | OH | OH | ─≡─ | bond | |
| Example 114 | single | C | NH | OH | OH | ─≡─ | bond | |
| Example 115 | single | C | NH | OH | OH | ─≡─ | bond | |
| Example 116 | single | C | NH | OH | OH | ─≡─ | bond | |
| Example 117 | single | C | NH | OH | OH | ─≡─ | bond | |
| Example 118 | single | C | NH | OH | OH | ─≡─ | bond | |

TABLE 12-continued
| | ------ | X | Y | R₁ | R₂ | R₃ | R₄ | R₅ |
|---|---|---|---|---|---|---|---|---|
| Example 119 | single | C | NH | OH | OH | —≡— | bond |  |
| Example 120 | single | C | NH | OH | OH | —≡— | bond | 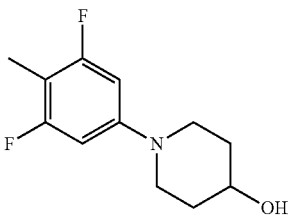 |
TABLE 13
| | ------ | X | Y | R₁ | R₂ | R₃ | R₄ | R₅ |
|---|---|---|---|---|---|---|---|---|
| Example 121 | single | C | NH | OH | OH | —≡— | bond |  |
| Example 122 | single | C | NH | OH | OH | —≡— | bond | 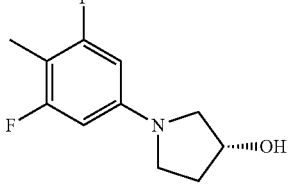 |
| Example 123 | single | C | NH | OH | OH | —≡— | bond |  |
| Example 124 | single | O | NH | OH | H | —≡— | bond | 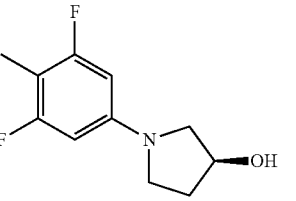 |
| Example 125 | single | O | NH | OH | H | —≡— | bond |  |
| Example 126 | single | O | NH | OH | H | 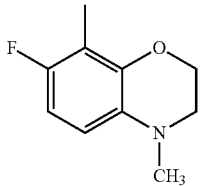 | bond |  |

TABLE 13-continued
| | ------ | X | Y | $R_1$ | $R_2$ | $R_3$ | $R_4$ | $R_5$ |
|---|---|---|---|---|---|---|---|---|
| Example 127 | single | O | NH | OH | H | —≡— | bond |  |
| Example 128 | double | C | NH | OH | OH | —≡— | bond | 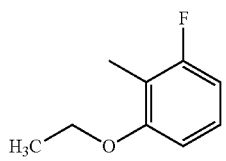 |
| Example 129 | double | C | NH | OH | OH | —≡— | bond |  |
| Example 130 | double | C | NH | OH | OH | —≡— | bond | 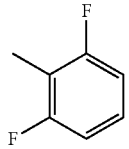 |
TABLE 14
| | ------ | X | Y | $R_1$ | $R_2$ | $R_3$ | $R_4$ | $R_5$ |
|---|---|---|---|---|---|---|---|---|
| Example 131 | single | O | O | OH | OH | —≡— | bond |  |
| Example 132 | single | O | O | OH | OH | —≡— | bond | 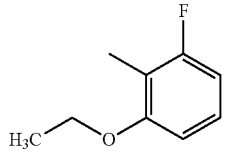 |
| Example 133 | single | O | O | OH | OH | —≡— | bond |  |
| Example 134 | single | O | O | OH | H | —≡— | bond | 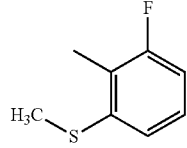 |
| Example 135 | single | O | O | OH | H |  | —CH$_2$— | 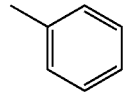 |

TABLE 14-continued
| | ----- | X | Y | R₁ | R₂ | R₃ | R₄ | R₅ |
|---|---|---|---|---|---|---|---|---|
| Example 136 | single | C | O | OH | OH | 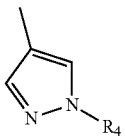 | —CH₂— | 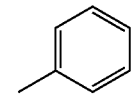 |
| Example 137 | single | O | O | OH | H | 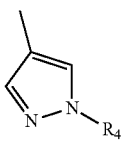 | —CH₂— | 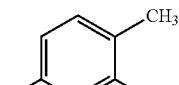 |
| Example 138 | single | C | O | OH | H | 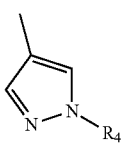 | —CH₂— | 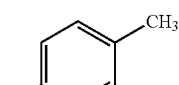 |
| Example 139 | single | O | O | OH | H | 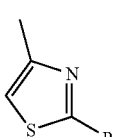 | bond | 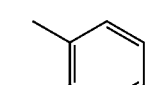 |
| Example 140 | single | O | NH | OH | OH | 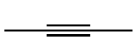 | bond | 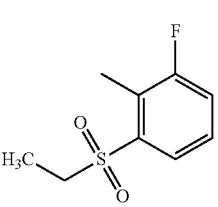 |
TABLE 15
| | ----- | X | Y | R₁ | R₂ | R₃ | R₄ | R₅ |
|---|---|---|---|---|---|---|---|---|
| Example 141 | single | C | NH | OH | OH |  | bond | 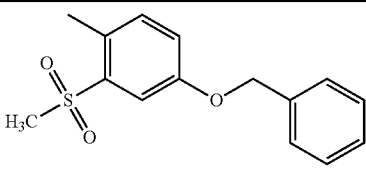 |
| Example 142 | single | C | NH | OH | OH | 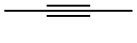 | bond | 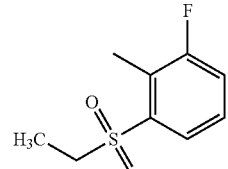 |
| Example 143 | single | O | NH | OH | H |  | bond | 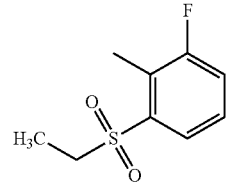 |

Test Example 1: Nedd8 Conjugation Inhibitory Activity

A purified NAE (heterodimer of APPBP1 and UBA3) solution was prepared in the following manner. The human APPBP1 gene (NCBI Reference Sequence number: NM_003905) region corresponding to amino acids 1 to 534 of human APPBP1 protein (NCBI Reference Sequence number: NP_003896, full length: 534 amino acids) was inserted in pBacPAK9 (produced by Clontech) to construct a plasmid pBacPAK9-APPBP1 for expressing APPBP1 full-length protein having a His tag and a TEV protease-recognition sequence at the N-terminus. Next, the human UBA3 gene (NCBI Reference Sequence number: NM_003968) region corresponding to amino acids 1 to 463 of human UBA3 protein (NCBI Reference Sequence number: NP_003959, full length: 463 amino acids) was inserted in pBacPAK9 to construct a plasmid pBacPAK9-UBA3 for expressing UBA3 full-length protein. The pBacPAK9-APPBP1 or pBacPAK9-UBA3, and BacPAK6 DNA were cotransfected into insect cells (Sf9, produced by Clontech) to produce a recombinant baculovirus containing APPBP1 or UBA3 gene. The APPBP1 gene recombinant baculovirus was mixed with the UBA3 gene recombinant baculovirus, and the resulting mixture was used to infect Sf9 cells. The baculovirus-infected Sf9 cells were incubated at 28° C. with shaking for 72 hours in Grace's Insect Medium (produced by Gibco), and the collected cells were suspended in a lysis buffer (50 mM Tris-HCl, 200 mM NaCl, and 10% glycerol (pH 7.4)), followed by sonication. The sonicated cell solution was centrifuged (40,000×g, for 30 minutes) to obtain the supernatant as a crude extract. The crude extract was fractionated on a HisTrap HP column (produced by GE Healthcare) and a TALON Superflow column (produced by Clontech), followed by the addition of a TEV protease. Then, a His-tag cleavage reaction was performed at 4° C. overnight. The resulting solution was subjected to TALON Superflow column chromatography, and the unadsorbed fraction was collected. This fraction was applied to a HiLoad 16/60 Superdex 75 prep grade column equilibrated with 50 mM Tris-HCl, 200 mM NaCl, and 10% glycerol (pH 7.4), and fractionated. A fraction containing an APPBP1/UBA3 complex was concentrated to obtain a purified NAE solution. The purification above was performed entirely at 4° C. The purified NAE solution was stored at −80° C. until use.

A purified GST-UBC12 solution was prepared in the following manner. The human UBC12 gene (NCBI Reference Sequence number: NM_003969) region corresponding to amino acids 1 to 183 of human UBC12 protein (NCBI Reference Sequence number: NP_003960, full length: 183 amino acids) was inserted in pGEX-4T-2 (produced by GE Healthcare) to construct a plasmid pGEX-UBC12 for expressing UBC12 full-length protein having a GST tag at the N-terminus. The pGEX-UBC12 was introduced into *Escherichia coli* (BL21 (DE3), produced by Stratagene), followed by culture at 37° C. for 2 hours in the presence of 1 mM isopropyl-beta-D-thiogalactopyranoside (produced by Sigma-Aldrich). The collected *Escherichia coli* was suspended in PBS, followed by sonication. The sonicated cell solution was centrifuged (40,000×g, for 5 minutes) to obtain the supernatant as a crude extract. A Glutathione Sepharose 4B carrier (produced by GE Healthcare) was added to the crude extract, and eluted with 50 mM Tris-HCl (pH 7.9), 150 mM NaCl, and a 10 mM reduced glutathione solution, followed by dialysis with 50 mM HEPES (pH 7.5) and a 0.05% BSA solution to obtain a purified GST-UBC12 solution. The purified GST-UBC12 solution was divided and stored at −80° C. until use.

The Nedd8 conjugation inhibitory activity was measured using an AlphaScreen assay system. Each of the purified NAE solution and GST-UBC12 solution was diluted with an assay buffer (50 mM HEPES (pH 7.5), 5 mM $MgCl_2$, 1 mM DTT, 0.05% BSA) and added to a 384-well plate (#3673, produced by Corning) containing the test compound. After reaction at room temperature for 30 minutes, a solution obtained by diluting ATP and Biotin-Nedd8 (produced by Boston Biochem) with the assay buffer was added thereto, followed by reaction for 90 minutes.

Detection mix (50 mM HEPES (pH 7.5), 0.05% BSA, 0.04 mg/mL anti-GST Acceptor beads, 0.04 mg/mL Streptavidin Donor beads) (#6760603M, produced by Perkin Elmer) was added to each well in the same amount as that of the reaction solution. Then, after reaction in a dark place at room temperature for 1 hour, the fluorescence intensity was measured using an EnVision (produced by Perkin Elmer) multilabel plate reader. The Neddylation inhibition rate (%) achieved by the compound of the present invention was determined by the equation (equation A) below using the fluorescence signal of a test compound-free group as a positive control, and the fluorescence signal of the test compound- and ATP-free group as a negative control. The concentration at which the Nedd8 conjugation was reduced with the addition of each compound to 50% of the control was calculated ($IC_{50}$ (μM)) and used as a relative index of the Nedd8 conjugation inhibitory activity.

Inhibition rate (%)=100−(T−B)/(C−B)×100    (equation A)

T: Signal in a well to which a test compound was added
C: Signal in a well to which a test compound was not added
B: Signal in a well to which a test compound and ATP were not added Table 16 below show the results.

TABLE 16

|  | IC50 (μM) |
|---|---|
| Example 1 | ≤0.0030 |
| Example 2 | 0.0071 |
| Example 8 | 0.029 |
| Example 10 | 0.024 |
| Example 11 | 0.0078 |
| Example 16 | 0.0096 |
| Example 17 | 0.0054 |
| Example 18 | 0.027 |
| Example 19 | 0.028 |
| Example 20 | 0.0091 |
| Example 21 | 0.015 |
| Example 22 | ≤0.0030 |
| Example 23 | ≤0.0030 |
| Example 24 | ≤0.0030 |
| Example 25 | 0.0048 |
| Example 26 | 0.012 |
| Example 29 | 0.0071 |
| Example 30 | 0.027 |
| Example 33 | ≤0.0030 |
| Example 34 | 0.024 |
| Example 35 | 0.0041 |
| Example 37 | 0.011 |
| Example 38 | 0.0035 |
| Example 39 | ≤0.0030 |
| Example 40 | ≤0.0030 |
| Example 41 | ≤0.0030 |
| Example 42 | 0.0043 |
| Example 43 | 0.0076 |
| Example 44 | 0.029 |
| Example 46 | 0.013 |
| Example 47 | 0.0093 |

TABLE 16-continued

| | IC50 (μM) |
|---|---|
| Example 49 | 0.018 |
| Example 51 | 0.0035 |
| Example 52 | 0.008 |
| Example 54 | 0.0045 |
| Example 55 | ≤0.0030 |
| Example 56 | 0.0053 |
| Example 57 | 0.0058 |
| Example 58 | ≤0.0030 |
| Example 59 | 0.0085 |
| Example 60 | 0.0085 |
| Example 61 | 0.0038 |
| Example 62 | 0.016 |
| Example 63 | 0.011 |
| Example 64 | 0.0094 |
| Example 66 | 0.0071 |
| Example 67 | 0.0085 |
| Example 69 | 0.015 |
| Example 70 | 0.013 |
| Example 71 | 0.014 |
| Example 72 | 0.0044 |
| Example 74 | ≤0.0030 |
| Example 75 | ≤0.0030 |
| Example 76 | 0.0051 |
| Example 79 | 0.0032 |
| Example 80 | 0.014 |
| Example 81 | 0.0056 |
| Example 82 | 0.01 |
| Example 83 | 0.019 |
| Example 84 | 0.0097 |
| Example 86 | 0.0054 |
| Example 88 | 0.018 |
| Example 89 | 0.011 |
| Example 90 | 0.0056 |
| Example 91 | 0.018 |
| Example 94 | 0.021 |
| Example 95 | 0.013 |
| Example 96 | 0.0092 |
| Example 97 | 0.0088 |
| Example 98 | 0.0083 |
| Example 99 | 0.019 |
| Example 101 | 0.0076 |
| Example 103 | 0.013 |
| Example 104 | 0.0089 |
| Example 106 | 0.028 |
| Example 110 | 0.013 |
| Example 112 | 0.015 |
| Example 113 | ≤0.0030 |
| Example 114 | ≤0.0030 |
| Example 115 | 0.004 |
| Example 116 | 0.0051 |
| Example 117 | 0.0043 |
| Example 118 | 0.0068 |
| Example 119 | 0.0042 |
| Example 120 | 0.0043 |
| Example 121 | 0.0062 |
| Example 122 | 0.02 |
| Example 123 | 0.0091 |
| Example 127 | 0.019 |
| Example 128 | 0.0033 |
| Example 129 | ≤0.0030 |
| Example 130 | 0.004 |
| Example 131 | ≤0.0030 |
| Example 132 | ≤0.0030 |
| Example 133 | 0.025 |
| Example 134 | 0.018 |
| Example 136 | 0.012 |
| Example 137 | 0.019 |
| Example 138 | 0.0065 |
| Example 139 | 0.017 |
| Example 142 | 0.009 |
| Example 143 | 0.024 |
| Comp. Example | 0.033 |

These results show that the compounds of the present invention exhibited very excellent Nedd8 conjugation inhibitory activity, compared with the Comparative Example.

Test Example 2: Cell Growth Inhibition 1

The ability of test compounds to inhibit cell growth was determined by quantifying ATP from viable cells using a CellTiter-Glo™ Luminescent Cell Viability Assay (#G7573, produced by Promega, Inc.). The human acute T lymphoblastic leukemia CCRF-CEM cell lines (distributed by Dainippon Pharmaceutical Co., Ltd. (currently Sumitomo Dainippon Pharma Co., Ltd.)) were seeded in a 96-well plate (#165305, produced by Thermo Scientific Nunc) at a concentration of 1,000 cells/100 μL medium per well. The cells were cultured in a 5% $CO_2$ incubator at 37° C. overnight, and the test compound was added thereto, followed by culture for another 72 hours. A CellTiter-Glo™ Luminescent Cell Viability Assay reagent in an amount equal to the medium was added to each well, stirred for 5 minutes on a shaker under shading conditions, and then left to stand at room temperature for about 30 minutes. The luminescence intensity was measured using a microplate reader (EnSpire™ Multimode Plate Reader, produced by PerkinElmer Japan Co., Ltd.), and used as an index of the number of viable cells in each well. The cell growth inhibition rate (%) achieved by the compound of the present invention was determined by the following equation (equation B) by using the luminescence intensity of a drug untreated group (control) as a control. The concentration at which the number of cells are reduced with the addition of each compound to 50% of the control was calculated ($IC_{50}$ (μm)).

$$\text{Inhibition rate (\%)} = (C-T)/C \times 100 \quad \text{(equation B)}$$

T: Luminescence intensity in a well to which a test compound was added
C: Luminescence intensity in a well to which a test substance was not added Table 17 below shows the results.

TABLE 17

| | CCRF-CEM IC50 (μM) |
|---|---|
| Example 1 | 0.0062 |
| Example 24 | 0.0027 |
| Example 25 | 0.0017 |
| Example 29 | 0.004 |
| Example 31 | 0.6 |
| Example 32 | 2.5 |
| Example 33 | 0.037 |
| Example 34 | 0.0061 |
| Example 35 | 0.002 |
| Example 36 | 0.25 |
| Example 37 | 0.006 |
| Example 38 | 0.014 |
| Example 39 | 0.0078 |
| Example 40 | 0.019 |
| Example 43 | 0.0027 |
| Example 55 | 0.0022 |
| Example 60 | 0.0051 |
| Example 61 | 0.003 |
| Example 64 | 0.0058 |
| Example 66 | 0.0043 |
| Example 70 | 0.015 |
| Example 71 | 0.045 |
| Example 72 | 0.088 |
| Example 73 | 0.071 |
| Example 74 | 0.16 |
| Example 83 | 0.056 |
| Example 84 | 0.23 |
| Example 85 | 0.038 |
| Example 86 | 0.0055 |
| Example 97 | 0.0031 |
| Example 98 | 0.0073 |
| Example 120 | 0.035 |

TABLE 17-continued

|  | CCRF-CEM IC50 (μM) |
| --- | --- |
| Example 122 | 0.0088 |
| Example 123 | 0.097 |
| Example 129 | 0.0021 |
| Example 130 | 0.0032 |
| Example 132 | 0.0018 |
| Comp. Example | 0.089 |

These results indicate that the compounds of the present invention inhibited the growth of human leukemia CCRF-CEM cell lines.

Test Example 3: Carbonic Anhydrase II Enzyme Activity Inhibition

The carbonic anhydrase II enzyme activity inhibition was measured by measuring the esterase activity in which carbonic anhydrase II degrades 4-nitrophenyl acetate (4-NPA) (produced by Sigma-Aldrich). A purified carbonic anhydrase II solution (C6624, produced by Sigma-Aldrich) was diluted with an assay buffer (50 mM Tris-HCl (pH 7.5)) to 100 nM, and 50 μL of the resulting solution was added to a 96-well plate (3695, produced by Costar) containing 40 μL of the test substance. After reaction at room temperature for 10 minutes, 10 μL of a 50 mM 4-NPA solution was added to each well, followed by incubation for 30 minutes at room temperature. The 50 mM 4-NPA solution was prepared by 10-fold dilution of a 500 mM 4-NPA solution, which was prepared at the time of use by dissolving the reaction product in DMSO, with the assay buffer. The absorbance at 405 nm was measured using a microplate reader (SpectraMax 250, produced by Molecular Devices). The activity level of the enzymatic hydrolysis reaction of ester was calculated using the following equation (equation C) by subtracting the absorbance in the well to which carbonic anhydrase II was not added.

Inhibition rate (%)=100−(T−B)/(C−B)×100    (equation C)

T: Absorbance in a well to which a test compound was added
C: Absorbance in a well to which a test compound was not added
B: Absorbance in a well to which a test substance and carbonic anhydrase II were not added Table 18 below shows the results.

TABLE 18

|  | IC50 (μM) |
| --- | --- |
| Example 1 | >1.0 |
| Example 2 | >1.0 |
| Example 3 | >1.0 |
| Example 6 | >1.0 |
| Example 10 | >1.0 |
| Example 12 | >1.0 |
| Example 14 | >1.0 |
| Example 24 | 0.4 |
| Example 25 | >1.0 |
| Example 29 | >1.0 |
| Example 35 | >1.0 |
| Example 36 | >1.0 |
| Example 39 | >1.0 |
| Example 43 | >1.0 |
| Example 46 | >1.0 |
| Example 47 | >1.0 |
| Example 49 | >1.0 |
| Example 50 | >1.0 |
| Example 52 | >1.0 |
| Example 55 | >1.0 |
| Example 60 | >1.0 |
| Example 61 | 0.79 |
| Example 64 | >1.0 |
| Example 66 | >1.0 |
| Example 86 | >1.0 |
| Example 88 | >1.0 |
| Example 97 | 0.18 |
| Example 98 | >1.0 |
| Example 120 | >1.0 |
| Example 122 | >1.0 |
| Example 126 | 0.26 |
| Example 127 | 0.34 |
| Example 129 | >1.0 |
| Example 130 | >1.0 |
| Example 134 | >1.0 |
| Example 136 | 0.031 |
| Example 138 | 0.12 |
| Example 139 | 0.41 |
| Example 143 | >1.0 |
| Comp. Example | 0.012 |

These results confirm that the compound of the Comparative Example exhibited inhibitory activity against carbonic anhydrase II, whereas the compounds of the Examples exhibited significantly reduced inhibitory activity.

Test Example 4: Cell Growth Inhibition 2

The ability of test compounds to inhibit cell growth was determined as in Test Example 2, except that the cell lines, the culture plate, and the number of cells seeded per well were as shown in Table 19. For the culture plate, a 384-well plate (#3571, produced by Corning) was used.

Table 20 below shows the results.

TABLE 19

| Cell Name | Origin | Obtained from | Plate | Seeding number (per 1 well) (cells/μL medium) |
| --- | --- | --- | --- | --- |
| HCT116 | Colon cancer | ATCC | 384 wells | 250 cells/20 μL |
| Capan-1 | Pancreatic cancer | ATCC | 384 wells | 500 cells/20 μL |
| A-427 | Lung cancer | ATCC | 384 wells | 250 cells/20 μL |
| MDA-MB-453 | Breast cancer | ATCC | 384 wells | 500 cells/20 μL |
| LNCaP.FGC | Prostate cancer | Dainippon Pharmaceutical Co., Ltd. (currently DS Pharma Biomedical Co., Ltd.) | 384 wells | 500 cells/20 μL |
| SJCRH30 | Osteo- and soft tissue sarcoma | ATCC | 384 wells | 250 cells/20 μL |
| U266B1 | Multiple myeloma | ATCC | 384 wells | 3000 cells/20 μL |
| A-431 | Skin cancer | ATCC | 384 wells | 400 cells/20 μL |
| MV-4-11 | Acute leukemia | ATCC | 384 wells | 400 cells/20 μL |
| DB | B-cell lymphoma | ATCC | 384 wells | 1500 cells/20 μL |

TABLE 20

| Examples | HCT116 IC50 (μM) | Capan-1 IC50 (μM) | A-427 IC50 (μM) | MDA-MB-453 IC50 (μM) | LNCaP.FGC IC50 (μM) |
|---|---|---|---|---|---|
| 1 | 0.016 | 0.73 | 0.022 | 0.46 | 0.65 |
| 25 | 0.0064 | 0.38 | 0.0054 | 0.48 | 0.5 |
| 55 | 0.012 | 0.87 | 0.007 | 0.094 | 0.26 |
| 130 | 0.012 | 0.21 | 0.0064 | 0.032 | 0.46 |
| 29 | 0.014 | 0.56 | 0.049 | 0.64 | 0.28 |
| 122 | 0.018 | 0.89 | 0.022 | 0.076 | 0.51 |
| 64 | 0.014 | 1.2 | 0.091 | 0.14 | 0.68 |
| Comp. Example | 0.089 | 1.5 | 0.18 | 1.9 | 0.41 |

| Examples | SJCRH30 IC50 (μM) | U266B1 IC50 (μM) | A-431 IC50 (μM) | MV-4-11 IC50 (μM) | DB IC50 (μM) |
|---|---|---|---|---|---|
| 1 | >10 | 0.11 | 0.73 | 0.021 | 0.26 |
| 25 | 5.1 | 0.22 | 0.12 | 0.011 | 0.12 |
| 55 | 0.55 | 0.031 | 0.48 | 0.0067 | 0.061 |
| 130 | 0.17 | 0.024 | 0.16 | 0.025 | 0.13 |
| 29 | 6.6 | 0.42 | 0.56 | 0.02 | 0.15 |
| 122 | 0.13 | 0.27 | 1.6 | 0.038 | 0.12 |
| 64 | 0.56 | 0.11 | 0.71 | 0.032 | 0.11 |
| Comp. Example | >10 | 1.4 | 0.75 | 0.11 | 0.56 |

According to the above results, these compounds of the present invention inhibited the growth of human colon cancer HCT116 cell line, human pancreatic cancer Capan-1 cell line, human lung cancer A-427 cell line, human breast cancer MDA-MB-453 cell line, human prostate cancer LNCAP.FGC cell line, human osteo- and soft tissue sarcoma SJCRH30 cell line, human multiple myeloma U266B1 cell line, human skin cancer A-431 cell line, human acute leukemia MV-4-11 cell line, and human diffuse large B-cell lymphoma DB cell line.

Test Example 5: Antitumor Effect on Tumor Cells Transplanted into Mice 1

Human colon cancer HCT-116 cell lines were washed in PBS and suspended at a concentration of $4 \times 10^7$ cells/mL. 0.1 mL of this cell suspension was subcutaneously implanted in the right chest of 6-week-old BALB/cAJcl-nu/nu mice (produced by CLEA Japan, Inc.).

The length and the width of the implanted tumor and the body weight were measured. The tumor volume (TV) was calculated using the following equation (equation D).

$$TV(mm3)=(length \times width^2)/2, \text{ wherein the unit of length and width is mm} \quad \text{(equation D)}$$

When the TV reached 100 to 300 mm3, the animals were assigned to each group in accordance with a stratified randomization procedure. The day was considered day 1, the TV on the day was considered TV1, and the body weight on the day was considered BW1.

A required amount of the test compound was weighed to prepare an administration solution. The compound of Example 1 was intravenously administered in an amount of 5 mL per 1 kg of body weight on days 1, 4, 8, and 11, and the compound of the Comparative Example was intravenously administered in an amount of 10 mL per 1 kg of body weight on days 1, 4, 8, and 11.

Thereafter, the length and the width of the tumor and the body weight (BWn) on day n were measured over time in the same manner, and the TVn of each mouse was calculated. Further, the relative tumor volume (RTVn) was calculated based on the TVn of each mouse using the following equation (equation E); the treatment/control (T/C) value (%) was calculated based on the mean RTVn of each drug administration group using the following equation (equation F); and the weight change rate (BWCn) was calculated using the following equation (equation G).

$$RTVn=TVn/TV1 \quad \text{(equation E)}$$

$$T/Cn(\%)=(\text{mean RTV of each drug administration group on the last day of the test})/(\text{mean RTV of the control group on the last day of the test}) \times 100 \quad \text{(equation F)}$$

$$BWCn\ (\%)=(BWn-BW1)/BW1 \times 100 \quad \text{(equation G)}$$

Figure 2:
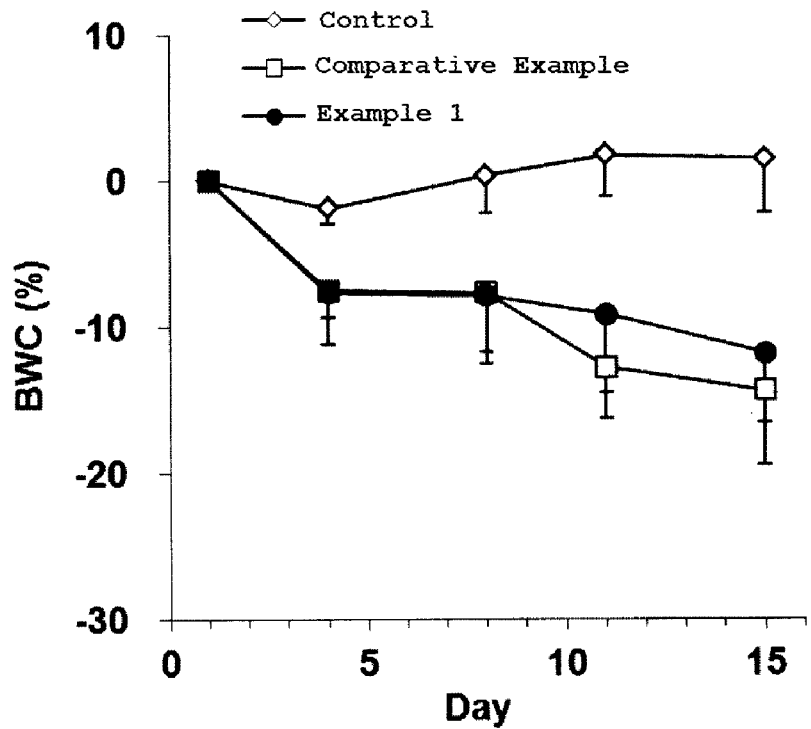
FIG. 2 shows the body weight change caused by the compound obtained in Example 1.

FIGS. 1 and 2, and Table 21 below show the results.

TABLE 21

| Group | Dose (mg/kg/day) | Administration day | Number of mice | T/C15 (%) | BWC15 (%) Mean ± SD |
|---|---|---|---|---|---|
| Control | — | — | 5 | 100 | 1.5 ± 3.7 |
| Comp. Example | 120 | 1, 4, 8, 11 | 5 | 36 | −14.3 ± 5.1 |
| Example 1 | 50 | 1, 4, 8, 11 | 5 | 23 | −11.8 ± 4.7 |

An RTV15 comparison using Dunnett's test revealed that the RTV of the example compound and the comparative example compound was significantly lower than that of the control. Further, a comparison using Aspin-Welch's t-test revealed that the RTV of Example 1 was significantly lower than that of the Comparative Example. The change of the body weight was within an acceptable degree, compared with the control.

These results confirm the excellent tumor growth inhibitory effects of this compound of the present invention on human tumors.

Test Example 6: Antitumor Effect on Tumor Cells Transplanted into Mice 2

The tumor growth inhibitory effects on human tumors were evaluated as in Test Example 5, except that the hydrochloride compound obtained in Example 55 was used, and the animals were assigned to each group in accordance with a stratified randomization procedure when the TV reached 100 to 200 mm3.

Figure 3:
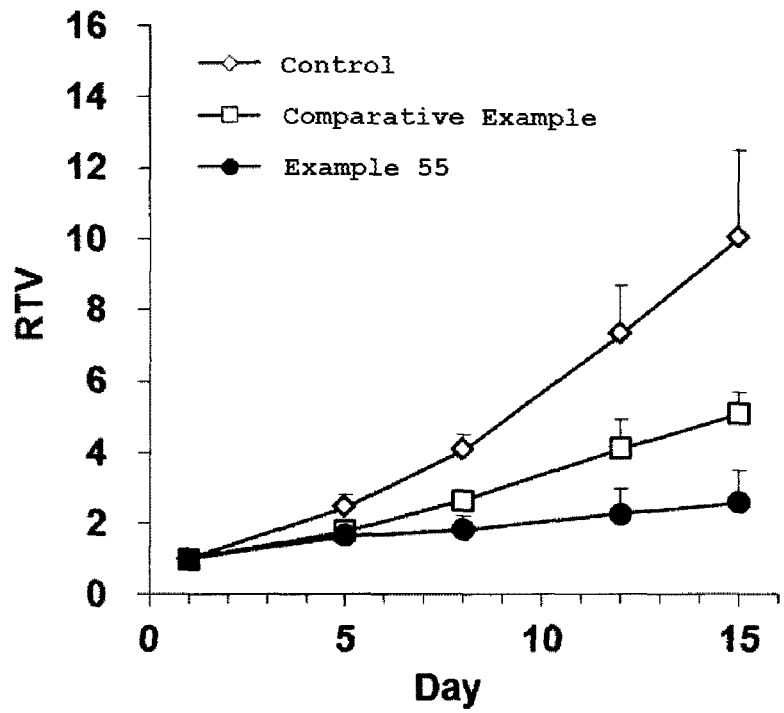
FIG. 3 shows the growth inhibitory effects of the compound obtained in Example 55 on HCT-116.
Figure 4:
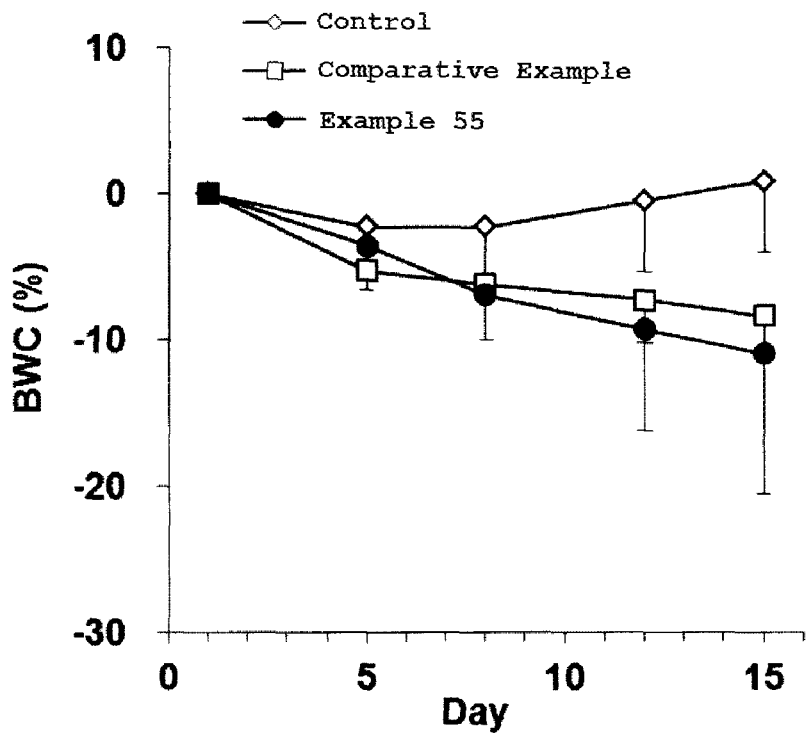
FIG. 4 shows the body weight change caused by the compound obtained in Example 55.

FIGS. 3 and 4, and the following table (Table 22) show the results.

TABLE 22

| Group | Dose (mg/kg/day) | Administration day | Number of mice | T/C15 (%) | BWC15 (%) Mean ± SD |
|---|---|---|---|---|---|
| Control | — | — | 5 | 100 | 0.9 ± 4.9 |
| Comp. Example | 120 | 1, 4, 8, 11 | 5 | 51 | −8.4 ± 3.2 |
| Example 55 | 50 | 1, 4, 8, 11 | 5 | 26 | −11.0 ± 9.6 |

An RTV15 comparison using Dunnett's test revealed that the RTV of the example compound and the comparative example compound was significantly lower than that of the control. Further, a comparison using Aspin-Welch's t-test revealed that the RTV of Example 55 was significantly lower than that of the Comparative Example. The change of the body weight was within an acceptable degree, compared with the control.

These results confirm the excellent tumor growth inhibitory effects of this compound of the present invention on human tumors.

Test Example 7: Antitumor Effect on Tumor Cells Transplanted into Mice 3

The tumor growth inhibitory effects on human tumors were evaluated as in Test Example 5, except that the compound hydrochloride obtained in Example 122, the compound hydrochloride (Example 64), and human acute lymphoblastic leukemia (ALL) CCRF-CEM cell lines were used, and the animals were assigned to each group in accordance with a stratified randomization procedure when the TV reached 140 to 380 mm3.

At this time, the cell lines were washed in PBS, and suspended in 50% PBS and 50% Matrigel basement membrane matrix (#356237; produced by BD Biosciences) at a concentration of $1 \times 10^8$ cells/mL. 0.1 mL of this cell suspension was subcutaneously implanted to the right chest of 6-week-old BALB/cAJcl-nu/nu mice (nude mice) (produced by CLEA Japan, Inc.). The compound hydrochloride (Example 122) was intravenously administered in an amount of 5 mL per 1 kg of body weight on days 1 and 8, and the compound hydrochloride (Example 133) was intravenously administered in an amount of 5 mL per 1 kg of body weight on days 1 and 8. The administration solution of the Comparative Example was intravenously administered in an amount of 5 mL per 1 kg of body weight on days 1, 4, 8, and 11.

Figure 5:
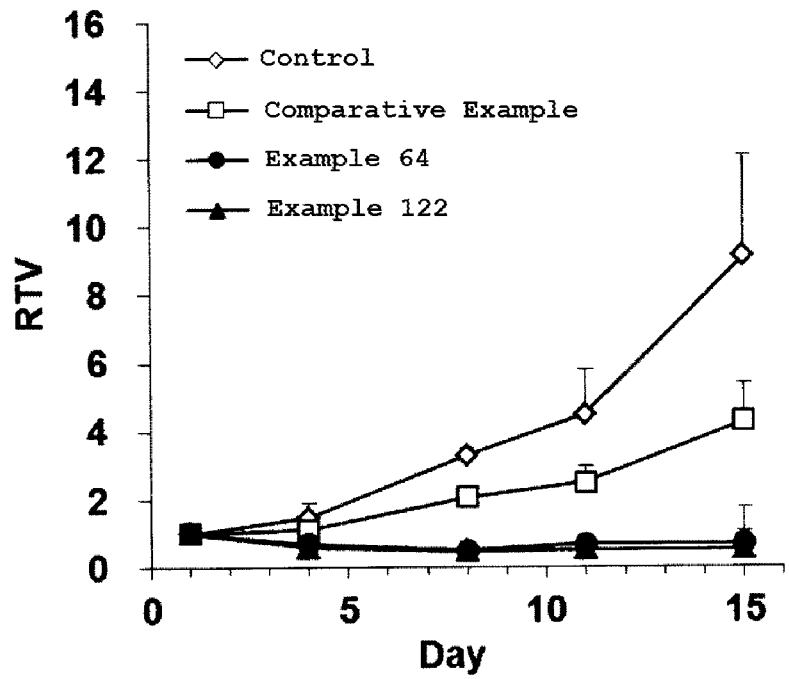
FIG. 5 shows the growth inhibitory effects of the compound obtained in Examples 122 and 64 on CCRF-CEM.
Figure 6:
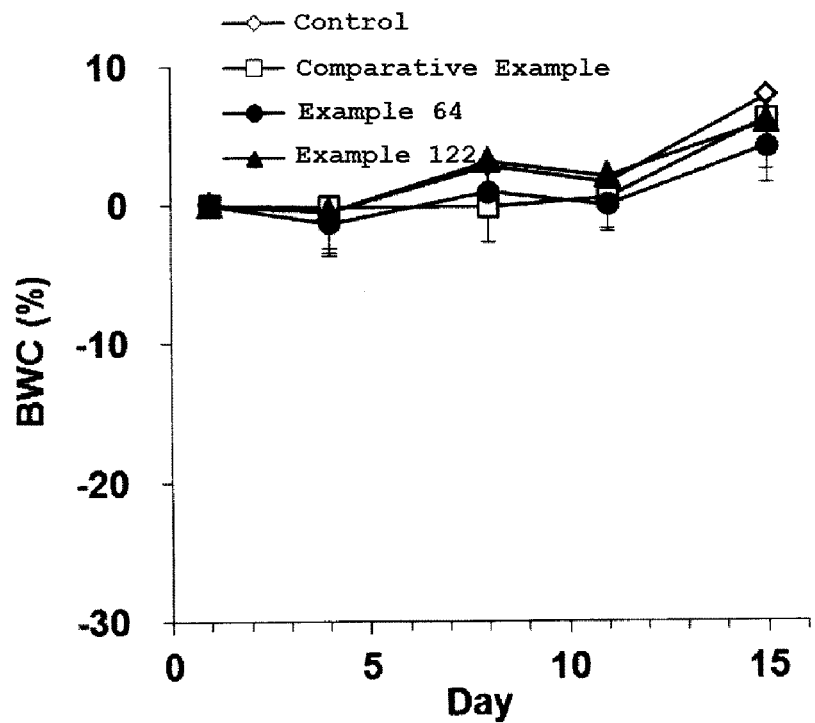
FIG. 6 shows the body weight change caused by the compound obtained in Examples 122 and 64.

FIGS. 5 and 6, and Table 23 below show the results.

TABLE 23

| Group | Dose (mg/kg/day) | Administration day | Number of mice | T/C15 (%) | BWC15 (%) Mean ± SD |
|---|---|---|---|---|---|
| Control | — | — | 5 | 100 | 7.8 ± 3.2 |
| Comp. Example | 120 | 1, 4, 8, 11 | 5 | 47 | 6.1 ± 2.6 |
| Example 64 | 50 | 1, 8 | 5 | 8 | 4.1 ± 1.6 |
| Example 122 | 50 | 1, 8 | 5 | 6 | 6.0 ± 4.5 |

An RTV comparison of Examples 120 and 133 was made using Dunnett's test on day 15. The results reveled that the RTV of Examples 120 and 133 on day 15 was significantly lower than that of the control. The change of the body weight was almost the same as that of the control.

These results confirmed that these compounds of the Examples exhibited antitumor effects.

An RTV15 comparison using Dunnett's test revealed that the RTV of the example compounds and the comparative example compound was significantly lower than that of the control. Further, the RTV of the compounds of Examples 122 and 64 was compared with the RTV of the compound of the Comparative Example using Dunnett's test. The results revealed that the RTV of Example 122 and Example 64 was significantly lower than that of the Comparative Example.

These results confirm the excellent inhibitory effects of the compounds of the present invention on the growth of human tumors.

The invention claimed is:

1. A compound or a salt thereof, represented by Formula (A) below:

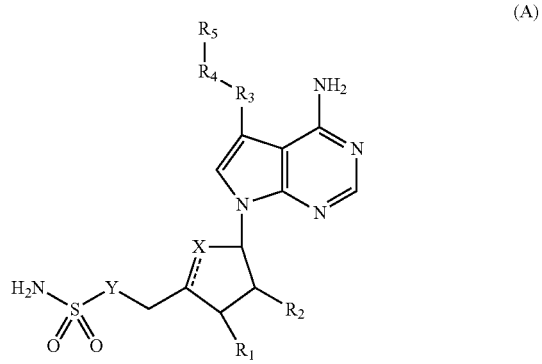

(A)

wherein:

===== is a single bond or a double bond;
X is —O—, —CH$_2$—, or —CH═;
Y is —NH—;
R$_1$ is a hydroxy group;
R$_2$ is a hydroxy group;
R$_3$ is an ethynylene group;
R$_4$ is a bond;
R$_5$ is a phenyl group or a naphthyl group that may have one or more R$^6$;
or a monocyclic or bicyclic unsaturated heterocycloalkyl group that has at least one heteroatom selected from the group consisting of N, S and O, and that may have one or more R$^6$;
R$_6$ is fluorine; a methyl group; a 3-fluoro pyrrolidinyl; a 3-hydroxy azetidinyl; azetidinyl; an amino group; a N-methylamino group; a C1-C6 alkoxy group that may have one or more cyclopropyl group; or a C1-C4 alkylthio group, wherein when two or more R$_6$ are present, the plurality of R$_6$ may be the same or different.

2. A compound or a salt thereof selected from the group consisting of: 4-amino-5-[2-(2,6-difluoro phenyl)ethynyl]-7-[(2R,3R,4S,5R)-3,4-dihydroxy-5-[(sulfamoylamino) methyl]tetrahydrofuran-2-yl]pyrrolo[2,3-d]pyrimidine; 4-amino-5-[2-(4-amino-2,6-difluoro-phenyl)ethynyl]-7-[(2R,3R,4S,5R)-3,4-dihydroxy-5-[(sulfamoylamino) methyl]tetrahydrofuran-2-yl]pyrrolo[2,3-d]pyrimidine; 4-amino-5-[2-[2,6-difluoro-4-(methylamino)phenyl]ethynyl]-7-[(2R,3R,4S,5R)-3,4-dihydroxy-5-[(sulfamoylamino) methyl]tetrahydrofuran-2-yl]pyrrolo[2,3-d]pyrimidine; 4-amino-5-[2-[2,6-difluoro-4-[(3R)-3-fluoro pyrrolidin-1-yl]phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine; 4-amino-7-[(2R,3R,4S,5R)-3,4-dihydroxy-5-[(sulfamoylamino)methyl]tetrahydrofuran-2-yl]-5-[2-(2-ethoxy-4,6-difluoro-phenyl)ethynyl]pyrrolo[2,3-d]pyrimidine; 4-amino-5-[2-[2,6-difluoro-4-(3-hydroxy azetidin-1-yl)phenyl]ethynyl]-7-[(2R,3R,4S,5R)-3,4-dihydroxy-5-[(sulfamoylamino)methyl]tetrahydrofuran-2-yl] pyrrolo[2,3-d]pyrimidine; 4-amino-5-[2-[4-(azetidin-1-yl)-2,6-difluoro-phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine; 4-amino-7-[(2R,3R,4S,5R)-3,4-dihydroxy-5-[(sulfamoylamino)methyl]tetrahydrofuran-2-yl]-5-[2-(2-ethoxy-6-fluoro-phenyl)ethynyl]pyrrolo[2,3- d]pyrimidine; 4-amino-7-[(2R,3R,4S,5R)-3,4-dihydroxy-5-[(sulfamoylamino)methyl]tetrahydrofuran-2-yl]-5-[2-(2-fluoro-6-propoxy-phenyl)ethynyl]pyrrolo[2,3-d]pyrimidine; 8-[2-[4-amino-7-[(2R,3R,4S,5R)-3,4-dihydroxy-5-[(sulfamoylamino)methyl]tetrahydrofuran-2-yl]pyrrolo[2,3-d]pyrimidin-5-yl]ethynyl]-7-fluoro-4-methyl-2,3-dihydro-1,4-benzoxazine; 4-amino-7-[(2R,3R,4S,5R)-3,4-dihydroxy-5-[(sulfamoylamino)methyl]tetrahydrofuran-2-yl]-5-[2-(2-ethylsulfanyl-6-fluoro-phenyl)ethynyl]pyrrolo[2,3-d]pyrimidine; 4-amino-5-[2-[2-(cyclopropyl methoxy)-6-fluoro-phenyl]ethynyl]-7-[(2R,3R,4S,5R)-3,4-dihydroxy-5-[(sulfamoylamino)methyl]tetrahydrofuran-2-yl]pyrrolo[2,3-d]pyrimidine; 4-amino-7-[(1R,2S,3R,4R)-2,3-dihydroxy-4-[(sulfamoylamino)methyl]cyclopentyl]-5-[2-(2-fluoro-6-methylsulfanyl-phenyl)ethynyl]pyrrolo[2,3-d]pyrimidine; 8-[2-[4-amino-7-[(1R,2S,3R,4R)-2,3-dihydroxy-4-[(sulfamoylamino)methyl]cyclopentyl]pyrrolo[2,3-d]pyrimidin-5-yl]ethynyl]-7-fluoro-4-methyl-2,3-dihydro-1,4-benzoxazine; 4-amino-7-[(1R,4R,5S)-4,5-dihydroxy-3-[(sulfamoylamino)methyl]cyclopent-2-en-1-yl]-5-[2-(2-ethoxy-6-fluoro-phenyl)ethynyl]pyrrolo[2,3-d]pyrimidine; and 4-amino-7-[(1R,4R,5S)-4,5-dihydroxy-3-[(sulfamoylamino)methyl]cyclopent-2-en-1-yl]-5-[2-(2-fluoro-6-methylsulfanyl-phenyl)ethynyl]pyrrolo[2,3-d]pyrimidine; and salts of these compounds.

3. A pharmaceutical composition comprising the compound or a salt thereof according to claim 1.

4. A pharmaceutical composition comprising the compound or a salt thereof according to claim 2.

\* \* \* \* \*